US008828408B2

(12) United States Patent
Vilalta et al.

(10) Patent No.: US 8,828,408 B2
(45) Date of Patent: *Sep. 9, 2014

(54) COMPOSITIONS AND METHODS FOR VACCINATING AGAINST HSV-2

(71) Applicants: The University of Washington, Seattle, WA (US); Vical Incorporated, San Diego, CA (US)

(72) Inventors: Adrian Vilalta, San Diego, CA (US); Michal Margalith, Solana Beach, CA (US); Lichun Dong, Seattle, WA (US); David M. Koelle, Seattle, WA (US)

(73) Assignees: Vical Incorporated, San Diego, CA (US); The University of Washington, Seattle, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/843,176

(22) Filed: Mar. 15, 2013

(65) Prior Publication Data

US 2013/0273108 A1   Oct. 17, 2013

Related U.S. Application Data

(60) Continuation of application No. 13/585,668, filed on Aug. 14, 2012, which is a division of application No. 12/604,694, filed on Oct. 23, 2009, now Pat. No. 8,263,087, which is a division of application No. 11/781,153, filed on Jul. 20, 2007, now Pat. No. 7,628,993.

(60) Provisional application No. 60/807,911, filed on Jul. 20, 2006.

(51) Int. Cl.
*A61K 39/245* (2006.01)
*C07K 14/005* (2006.01)
*C12N 15/38* (2006.01)
*C12N 15/00* (2006.01)
*A61K 39/00* (2006.01)

(52) U.S. Cl.
CPC ..... *A61K 39/245* (2013.01); *C12N 2710/16622* (2013.01); *C12N 2710/16634* (2013.01); *A61K 2039/53* (2013.01); *C07K 14/005* (2013.01)
USPC .................. 424/231.1; 424/234.1; 424/184.1; 435/320.1; 536/23.4; 536/23.72

(58) Field of Classification Search
CPC ............ A61K 39/24; A61K 2039/53; C12N 2710/16622; C12N 2710/16634; C07K 14/005
See application file for complete search history.

(56) References Cited

U.S. PATENT DOCUMENTS

| 5,641,665 A | 6/1997 | Hobart et al. |
| 5,654,174 A | 8/1997 | Cohen et al. |
| 5,972,666 A | 10/1999 | Hippenmeyer et al. |
| 5,994,116 A | 11/1999 | Dargan et al. |
| 6,147,055 A | 11/2000 | Hobart et al. |
| 6,375,952 B1 | 4/2002 | Koelle et al. |
| 6,399,588 B1 | 6/2002 | Hobart et al. |
| 6,413,518 B1 | 7/2002 | Koelle et al. |
| 6,586,409 B1 | 7/2003 | Wheeler |
| 6,814,969 B2 | 11/2004 | Koelle et al. |
| 6,821,519 B2 | 11/2004 | Day et al. |
| 6,855,317 B2 | 2/2005 | Koelle et al. |
| 7,037,509 B2 | 5/2006 | Koelle et al. |
| 7,078,041 B2 | 7/2006 | Koelle et al. |
| 7,628,993 B2 | 12/2009 | Vilalta et al. |
| 7,655,235 B2 | 2/2010 | Ertl |
| 7,879,339 B2 | 2/2011 | Vilalta et al. |
| 7,935,352 B2 | 5/2011 | Vilalta et al. |
| 8,263,087 B2 | 9/2012 | Vilalta |
| 8,293,248 B2 | 10/2012 | Vilalta et al. |
| 2002/0045594 A1 | 4/2002 | Volkin et al. |
| 2003/0191082 A1 | 10/2003 | Wheeler |
| 2003/0203863 A1 | 10/2003 | Hobart et al. |
| 2004/0067484 A1 | 4/2004 | Mishkin et al. |
| 2004/0072152 A1 | 4/2004 | Koelle et al. |
| 2004/0185057 A1 | 9/2004 | Kirkby et al. |
| 2004/0253272 A1 | 12/2004 | Kaneda |
| 2005/0064394 A1 | 3/2005 | Liu et al. |
| 2005/0065107 A1 | 3/2005 | Hobart et al. |
| 2005/0163794 A1 | 7/2005 | Koelle et al. |
| 2005/0249705 A1 | 11/2005 | Toda et al. |
| 2005/0287157 A1 | 12/2005 | Glenn et al. |
| 2006/0024670 A1 | 2/2006 | Luke et al. |

(Continued)

FOREIGN PATENT DOCUMENTS

JP  2008131867       6/2008
WO  WO00/57917 A2   10/2000

(Continued)

OTHER PUBLICATIONS

Minke JM, et. al. Vet Immunol Immunopathol. May 15, 2006;111(1-2):47-57. Epub Mar. 31, 2006.*
Bernstein, D., "Glycoprotein D Adjuvant Herpes Simplex Virus Vaccine", Expert Rev Vaccines, Oct. 2005, 4(5):615-27.
Bright H., et al., "The efficacy of HSV-2 vaccines based on gD and gB is enhanced by the addition of ICP27", Vaccine, 30(52):7259-35 (2012).
Chung, E., et al., "The ongoing pursuit of a prophylactic HSV vaccine", Rev. Med. Virol., 22(5):285-300, Sep. 2012 doi: 10.1002/rmv.1709. Epub Mar. 7, 2012.
Cid-Arregui, A, et al., "A synthetic E7 gene of human papillomavirus type 16 that yields enhanced expression of the protein in mammalian cells and is useful for DNA immunization studies", J Virol, Apr. 2003, 77(8):4928-37.

(Continued)

*Primary Examiner* — Benjamin P Blumel
*Assistant Examiner* — Rachel Gill
(74) *Attorney, Agent, or Firm* — Sughrue Mion, PLLC

(57) ABSTRACT

This invention relates to therapeutic polynucleotide compositions and methods for systemic immune activation which are effective for eliciting both a systemic, non-antigen specific immune response and a strong antigen-specific immune response in mammals. The polynucleotide compositions are particularly effective for protecting mammals from herpes simplex virus (HSV), such as HSV VP13/14 polypeptides.

7 Claims, 58 Drawing Sheets

(56) References Cited

U.S. PATENT DOCUMENTS

| | | | |
|---|---|---|---|
| 2006/0110403 | A1 | 5/2006 | Beer et al. |
| 2006/0216304 | A1 | 9/2006 | Koelle et al. |
| 2007/0026015 | A1 | 2/2007 | Braun et al. |
| 2007/0105193 | A1 | 5/2007 | Vilalta et al. |
| 2007/0286869 | A1 | 12/2007 | Luke et al. |
| 2008/0057080 | A1 | 3/2008 | Luke et al. |
| 2008/0102087 | A1 | 5/2008 | Vilalta et al. |
| 2009/0004203 | A1 | 1/2009 | Vilalta et al. |
| 2010/0040651 | A1 | 2/2010 | Vilalta et al. |
| 2010/0160419 | A1 | 6/2010 | Vilalta et al. |
| 2012/0328656 | A1 | 12/2012 | Vilalta et al. |
| 2012/0328657 | A1 | 12/2012 | Vilalta et al. |
| 2012/0328658 | A1 | 12/2012 | Vilalta et al. |

FOREIGN PATENT DOCUMENTS

| | | | |
|---|---|---|---|
| WO | WO01/32221 | A1 | 5/2001 |
| WO | WO03/104400 | A2 | 12/2003 |
| WO | WO2005/011580 | | 2/2005 |

OTHER PUBLICATIONS

Dong, et al., "Cellular and humoral immune responses to HSV-2 tegument proteins in H-2D mice after DNA vaccination", 31st International Herpesvirus Workshop, Seattle, WA Jul. 22-27, 2006, Abstract 9.16.

Dorange, F, et al., Characterization of Marek's disease virus serotype 1 (MDV-1) deletion mutants that lack UL46 to UL49 genes: MDV-1 UL49, encoding VP22, is indispensable for virus growth, J Virol, Feb. 2002, 76(4):1959-70.

Ferrari, M., et al.,"Synergy between cationic lipid and co-lipid determines the macroscopic structure and transfection activity of lipoplexes", Nucleic Acids Research 30(8):1808-1816 (2002).

Flo, J. 2003 "Co-immunization with plasmids coding the full length and a soluble form of glycoprotein D of HSV-2 induces protective cellular and humoral immune response in mice," Vaccine,vol. 21:1239-1245.

Harish, N, et al., "DyNAVacS: an integrative tool for optimized DNA vaccine design", Nucleic Acids Res, Jul. 1, 2006, 34(Web Server issue):W264-6.

Hartikka et al., "Vaxfectin Enhances the Humoral Immune Response to Plasmid DNA-Encoded Antigens", Vaccine, 2001, 19(15-16):1911-23.

Holler, TP, et al., "HIV1 integrase expressed in *Escherichia coli* from a synthetic gene", Gene, Dec. 22, 1993, 136(1-2):323-8.

Hosken, N. et al., 2006 "Diversity of the CD8+ T-Cell Response to Herpes Simplex Virus Type 2 Proteins Among Persons with Genital Herpes." Journal of Virology vol. 80(11) 5509-5515.

Koelle, DM, "Vaccines for Herpes Simplex Virus Infections", Curr Opin Investig Drugs, Feb. 2006, 7(2):136-41.

Koelle, D.M., et al. "Immunogenicity and protective efficacy of plasmid DNA vaccines encoding HSV-2 tegument proteins in a murine intravaginal challenge model", 17th International Society of Sexually Transmitted Diseases Research (ISSTDR), Seattle, WA Jul. 2007, Abstract 317.

Koelle, DM, et al., "Recent progress in herpes simplex virus immunobiology and vaccine research", Clin. Microbiol. Rev., 16(1):96-113 (2003).

Koelle, DM, et al., "CD8 CTL from genital herpes simplex lesions: recognition of viral tegument and immediate early proteins and lysis of infected cutaneous cells", J Immunol Mar. 15, 2001, 166(6):4049-58.

Koide, Y, et al., "DNA vaccines", Jpn J Pharmacol, Jul. 2000, 83(3):167-74.

Kopp, M, et al., "Identification and characterization of the pseudorabies virus tegument proteins UL46 and UL47: role for UL47 in virion morphogenesis in the cytoplasm", J Virol, Sep. 2002, 76(17):8820-33.

Muller, W., et al., "Cellular and humoral immune responses induced by Plasmid DNA vaccines encoding HSV-2 Tegument Proteins", 44th Annual Meeting of the Infectious Diseases Society of America (IDSA), Toronto, Canada, Oct. 12-15, 2006 Abstract 615, p. 166.

Muller, W.J., et al., "HSV-2 tegument directed T-cells develop after vaginal infection in Blab/c mine and tegument-based vaccines partially protect against lethal challenge", 32nd International Herpesvirus Worshop, Asheville, NC, Jul. 2007, Abstract 10.20.

Muller, WJ, et al., "Herpes simplex virus type 2 tegument proteins contain subdominant T-cell epitopes detectable in BALB/c mice after DNA immunization and infection", J Gen Virol, May 2009, 90(Pt 5):1153-63. Epub Mar. 4, 2009.

Nakamura, et al., "Codon usage tabulated from international DNA sequence database: status for the year 2000", Nucleic Acid Research, 28:292 (2000).

Skinner et al., "Prevention of herpes genitalis by the Bulgarian vaccine F.HSV-2V(PRK): preliminary clinical evidence" Croat Med J 41(4):378-83, 2000.

Veselenak, RL, et al., "A VaxfectinÒ-adjuvanted HSV-2 plasmid DNA vaccine is effective for prophylactic and therapeutic use in the guinea pig model of genital herpes", Vaccine, Nov. 19, 2012, 30(49):7046-51.

Wagner, MJ, et al., "Herpes simplex virus requires VP11/12 to induce phosphorylation of the activation loop tyrosine (Y394) of the Src family kinase Lck in T lymphocytes", J Virol, Dec. 2009, 83(23):12452-61. Epub Sep. 23, 2009.

\* cited by examiner

FIGURE 12 gD (VR2139)

Molecule:     VR2139,  5930 bps DNA Circular

Description:  HSV gD2 cloned into VR1012 Not I/BamH I sites

Details:      HSV2 gD2, 14 to 1036,  Draw as Gene
              Translation product   340 aas
              Mol Wt 37333.0, Isoelectric Pt (pI) 6.33

(SEQ ID NO. 1)
Translation: MGRLTSGVGTAALLVVAVGLRVVCAKYALADPSLKMADPNRFRGKNLPVL
DQLTDPPGVKRVYHIQPSLEDPFQPPSIPITVYYAVLERACRSVLLHAPS
EAPQIVRGASDEARKHTYNLTIAWYRMGDNCAIPITVMEYTECPYNKSLG
VCPIRTQPRWSYYDSFSAVSEDNLGFLMHAPAFETAGTYLRLVKINDWTE
ITQFILEHRARASCKYALPLRIPPAACLTSKAYQQGVTVDSIGMLPRFIP
ENQRTVALYSLKIAGWHGPKPPYTSTLLPPELSDTTNATQPELVPEDPED
SALLEDPAGTVSSQIPPNWHIPSIQDVAPHHAPAAPSNPG (SEQ ID NO. 2)
GGCCGCCGCCACCATGGGCAGACTGACTAGCGGAGTGGGCACAGCCGCCC
TGCTCGTGGTGGCTGTGGGCCTGAGAGTGGTGTGTGCTAAGTACGCCCTG
GCTGACCCTAGCCTGAAGATGGCTGATCCTAATAGGTTTAGGGGCAAGAA
CCTGCCCGTGCTGGACCAGCTGACTGACCCCCCTGGCGTGAAGAGAGTGT
ACCACATCCAGCCTAGCCTGGAGGACCCCTTCCAGCCCCCTAGCATCCCT
ATCACCGTGTACTACGCCGTGCTGGAGAGAGCCTGTAGAAGCGTGCTGCT
GCACGCCCCTAGTGAGGCCCCTCAGATTGTGAGAGGCGCTAGTGACGAGG
CTAGGAAGCACACCTATAACCTGACCATCGCCTGGTATAGGATGGGCGAT
AACTGCGCCATCCCCATCACAGTGATGGAGTACACTGAGTGCCCCTATAA
TAAGAGCCTGGGCGTGTGTCCCATTAGGACCCAGCCTAGGTGGAGCTACT
ACGATAGCTTTAGCGCCGTGAGTGAGGATAACCTGGGCTTCCTGATGCAC
GCCCCAGCCTTTGAGACCGCCGGCACCTACCTGAGACTGGTGAAGATTAA
CGACTGGACTGAGATCACCCAGTTCATCCTGGAGCATAGGGCTAGGGCTA
GCTGTAAATACGCCCTGCCCCTGAGAATCCCCCCTGCCGCCTGCCTGACT
AGTAAGGCCTACCAGCAAGGCGTGACCGTGGATAGCATCGGCATGCTGCC
TAGATTCATCCCTGAGAACCAGAGAACCGTGGCCCTGTATAGCCTGAAAA
TCGCCGGCTGGCACGGCCCTAAGCCTCCTTACACTAGCACCCTGCTGCCC
CCTGAGCTGAGTGATACCACTAACGCCACCCAGCCTGAGCTGGTGCCTGA
GGACCCTGAGGATAGCGCTCTGCTGGAAGATCCTGCCGGCACCGTGAGTA
GCCAGATCCCCCCTAACTGGCACATCCCTAGCATTCAGGACGTGGCCCCC
CACCACGCCCCTGCCGCTCCTAGTAACCCTGGCTGATGAGGATCCAGATC
TGCTGTGCCTTCTAGTTGCCAGCCATCTGTTGTTTGCCCCTCCCCCGTGC
CTTCCTTGACCCTGGAAGGTGCCACTCCCACTGTCCTTTCCTAATAAAAT
GAGGAAATTGCATCGCATTGTCTGAGTAGGTGTCATTCTATTCTGGGGGG
TGGGGTGGGGCAGCACAGCAAGGGGGAGGATTGGGAAGACAATAGCAGGC
ATGCTGGGGATGCGGTGGGCTCTATGGGTACCCAGGTGCTGAAGAATTGA
CCCGGTTCCTCCTGGGCCAGAAAGAAGCAGGCACATCCCCTTCTCTGTGA
CACACCCTGTCCACGCCCCTGGTTCTTAGTTCCAGCCCCACTCATAGGAC
ACTCATAGCTCAGGAGGGCTCCGCCTTCAATCCCACCCGCTAAAGTACTT
GGAGCGGTCTCTCCCTCCCTCATCAGCCCACCAAACCAAACCTAGCCTCC
AAGAGTGGGAAGAAATTAAAGCAAGATAGGCTATTAAGTGCAGAGGGAGA
GAAAATGCCTCCAACATGTGAGGAAGTAATGAGAGAAATCATAGAATTTC
TTCCGCTTCCTCGCTCACTGACTCGCTGCGCTCGGTCGTTCGGCTGCGGC
GAGCGGTATCAGCTCACTCAAAGGCGGTAATACGGTTATCCACAGAATCA FIGURE 12 (Cont'd)

```
GGGGATAACGCAGGAAAGAACATGTGAGCAAAAGGCCAGCAAAAGGCCAG
GAACCGTAAAAAGGCCGCGTTGCTGGCGTTTTTCCATAGGCTCCGCCCCC
CTGACGAGCATCACAAAAATCGACGCTCAAGTCAGAGGTGGCGAAACCCG
ACAGGACTATAAAGATACCAGGCGTTTCCCCCTGGAAGCTCCCTCGTGCG
CTCTCCTGTTCCGACCCTGCCGCTTACCGGATACCTGTCCGCCTTTCTCC
CTTCGGGAAGCGTGGCGCTTTCTCAATGCTCACGCTGTAGGTATCTCAGT
TCGGTGTAGGTCGTTCGCTCCAAGCTGGGCTGTGTGCACGAACCCCCCGT
TCAGCCCGACCGCTGCGCCTTATCCGGTAACTATCGTCTTGAGTCCAACC
CGGTAAGACACGACTTATCGCCACTGGCAGCAGCCACTGGTAACAGGATT
AGCAGAGCGAGGTATGTAGGCGGTGCTACAGAGTTCTTGAAGTGGTGGCC
TAACTACGGCTACACTAGAAGGACAGTATTTGGTATCTGCGCTCTGCTGA
AGCCAGTTACCTTCGGAAAAAGAGTTGGTAGCTCTTGATCCGGCAAACAA
ACCACCGCTGGTAGCGGTGGTTTTTTTGTTTGCAAGCAGCAGATTACGCG
CAGAAAAAAAGGATCTCAAGAAGATCCTTTGATCTTTTCTACGGGGTCTG
ACGCTCAGTGGAACGAAAACTCACGTTAAGGGATTTTGGTCATGAGATTA
TCAAAAAGGATCTTCACCTAGATCCTTTTAAATTAAAAATGAAGTTTTAA
ATCAATCTAAAGTATATATGAGTAAACTTGGTCTGACAGTTACCAATGCT
TAATCAGTGAGGCACCTATCTCAGCGATCTGTCTATTTCGTTCATCCATA
GTTGCCTGACTCCGGGGGGGGGGCGCTGAGGTCTGCCTCGTGAAGAAG
GTGTTGCTGACTCATACCAGGCCTGAATCGCCCCATCATCCAGCCAGAAA
GTGAGGGAGCCACGGTTGATGAGAGCTTTGTTGTAGGTGGACCAGTTGGT
GATTTTGAACTTTTGCTTTGCCACGGAACGGTCTGCGTTGTCGGGAAGAT
GCGTGATCTGATCCTTCAACTCAGCAAAAGTTCGATTTATTCAACAAAGC
CGCCGTCCCGTCAAGTCAGCGTAATGCTCTGCCAGTGTTACAACCAATTA
ACCAATTCTGATTAGAAAAACTCATCGAGCATCAAATGAAACTGCAATTT
ATTCATATCAGGATTATCAATACCATATTTTGAAAAAGCCGTTTCTGTA
ATGAAGGAGAAAACTCACCGAGGCAGTTCCATAGGATGGCAAGATCCTGG
TATCGGTCTGCGATTCCGACTCGTCCAACATCAATACAACCTATTAATTT
CCCCTCGTCAAAAATAAGGTTATCAAGTGAGAAATCACCATGAGTGACGA
CTGAATCCGGTGAGAATGGCAAAAGCTTATGCATTTCTTTCCAGACTTGT
TCAACAGGCCAGCCATTACGCTCGTCATCAAAATCACTCGCATCAACCAA
ACCGTTATTCATTCGTGATTGCGCCTGAGCGAGACGAAATACGCGATCGC
TGTTAAAAGGACAATTACAAACAGGAATCGAATGCAACCGGCGCAGGAAC
ACTGCCAGCGCATCAACAATATTTTCACCTGAATCAGGATATTCTTCTAA
TACCTGGAATGCTGTTTTCCCGGGGATCGCAGTGGTGAGTAACCATGCAT
CATCAGGAGTACGGATAAAATGCTTGATGGTCGGAAGAGGCATAAATTCC
GTCAGCCAGTTTAGTCTGACCATCTCATCTGTAACATCATTGGCAACGCT
ACCTTTGCCATGTTTCAGAAACAACTCTGGCGCATCGGGCTTCCCATACA
ATCGATAGATTGTCGCACCTGATTGCCCGACATTATCGCGAGCCCATTTA
TACCCATATAAATCAGCATCCATGTTGGAATTTAATCGCGGCCTCGAGCA
AGACGTTTCCCGTTGAATATGGCTCATAACACCCCTTGTATTACTGTTTA
TGTAAGCAGACAGTTTTATTGTTCATGATGATATATTTTTATCTTGTGCA
ATGTAACATCAGAGATTTTGAGACACAACGTGGCTTTCCCCCCCCCCCCA
TTATTGAAGCATTTATCAGGGTTATTGTCTCATGAGCGGATACATATTTG
AATGTATTTAGAAAAATAAACAAATAGGGGTTCCGCGCACATTTCCCCGA
AAAGTGCCACCTGACGTCTAAGAAACCATTATTATCATGACATTAACCTA
TAAAAATAGGCGTATCACGAGGCCCTTTCGTCTCGCGCGTTTCGGTGATG
ACGGTGAAAACCTCTGACACATGCAGCTCCCGGAGACGGTCACAGCTTGT
CTGTAAGCGGATGCCGGGAGCAGACAAGCCCGTCAGGGCGCGTCAGCGGG
TGTTGGCGGGTGTCGGGGCTGGCTTAACTATGCGGCATCAGAGCAGATTG
TACTGAGAGTGCACCATATGCGGTGTGAAATACCGCACAGATGCGTAAGG
AGAAAATACCGCATCAGATTGGCTATTGGCCATTGCATACGTTGTATCCA
TATCATAATATGTACATTTATATTGGCTCATGTCCAACATTACCGCCATG
TTGACATTGATTATTGACTAGTTATTAATAGTAATCAATTACGGGGTCAT
```

FIGURE 12 (cont'd)

```
TAGTTCATAGCCCATATATGGAGTTCCGCGTTACATAACTTACGGTAAAT
GGCCCGCCTGGCTGACCGCCCAACGACCCCGCCCATTGACGTCAATAAT
GACGTATGTTCCCATAGTAACGCCAATAGGGACTTTCCATTGACGTCAAT
GGGTGGAGTATTTACGGTAAACTGCCCACTTGGCAGTACATCAAGTGTAT
CATATGCCAAGTACGCCCCCTATTGACGTCAATGACGGTAAATGGCCCGC
CTGGCATTATGCCCAGTACATGACCTTATGGGACTTTCCTACTTGGCAGT
ACATCTACGTATTAGTCATCGCTATTACCATGGTGATGCGGTTTTGGCAG
TACATCAATGGGCGTGGATAGCGGTTTGACTCACGGGGATTTCCAAGTCT
CCACCCCATTGACGTCAATGGGAGTTTGTTTTGGCACCAAAATCAACGGG
ACTTTCCAAAATGTCGTAACAACTCCGCCCCATTGACGCAAATGGGCGGT
AGGCGTGTACGGTGGGAGGTCTATATAAGCAGAGCTCGTTTAGTGAACCG
TCAGATCGCCTGGAGACGCCATCCACGCTGTTTTGACCTCCATAGAAGAC
ACCGGGACCGATCCAGCCTCCGCGGCCGGGAACGGTGCATTGGAACGCGG
ATTCCCCGTGCCAAGAGTGACGTAAGTACCGCCTATAGACTCTATAGGCA
CACCCCTTTGGCTCTTATGCATGCTATACTGTTTTTGGCTTGGGGCCTAT
ACACCCCGCTTCCTTATGCTATAGGTGATGGTATAGCTTAGCCTATAGG
TGTGGGTTATTGACCATTATTGACCACTCCCCTATTGGTGACGATACTTT
CCATTACTAATCCATAACATGGCTCTTTGCCACAACTATCTCTATTGGCT
ATATGCCAATACTCTGTCCTTCAGAGACTGACACGGACTCTGTATTTTTA
CAGGATGGGGTCCCATTTATTATTTACAAATTCACATATACAACAACGCC
GTCCCCCGTGCCCGCAGTTTTTATTAAACATAGCGTGGGATCTCCACGCG
AATCTCGGGTACGTGTTCCGGACATGGGCTCTTCTCCGGTAGCGGCGGAG
CTTCCACATCCGAGCCCTGGTCCCATGCCTCCAGCGGCTCATGGTCGCTC
GGCAGCTCCTTGCTCCTAACAGTGGAGGCCAGACTTAGGCACAGCACAAT
GCCCACCACCACCAGTGTGCCGCACAAGGCCGTGGCGGTAGGGTATGTGT
CTGAAAATGAGCGTGGAGATTGGGCTCGCACGGCTGACGCAGATGGAAGA
CTTAAGGCAGCGGCAGAAGAAGATGCAGGCAGCTGAGTTGTTGTATTCTG
ATAAGAGTCAGAGGTAACTCCCGTTGCGGTGCTGTTAACGGTGGAGGGCA
GTGTAGTCTGAGCAGTACTCGTTGCTGCCGCGCGCGCCACCAGACATAAT
AGCTGACAGACTAACAGACTGTTCCTTTCCATGGGTCTTTTCTGCAGTCA
CCGTCGTCGACACGTGTGATCAGATATCGC
```

Molecule:      VR2143,   5817 bps DNA Circular

Description:   UL49 in VR1012 removed   AvrII HSV-Tag 54 bp fragment

Details:       UL49,   9 to 908,   Draw as Gene
               UL49 HSV-2
               Translation product   300 aas
               Mol Wt   31789.8, Isoelectric Pt (pI) 10.99

(SEQ ID NO. 3)
Translation:   MTSRRSVKSCPREAPRGTHEELYYGPVSPADPESPRDDFRRGAGPMRARP
               RGEVRFLHYDEAGYALYRDSSSDDDESRDTARPRRSASVAGSHGPGPARA
               PPPPGGPVGAGGRSHAPPARTPKMTRGAPKASATPATDPARGRRPAQADS
               AVLLDAPAPTASGRTKTPAQGLAKKLHFSTAPPSPTAPWTPRVAGFNKRV
               FCAAVGRLAATHARLAAVQLWDMSRPHTDEDLNELLDLTTIRVTVCEGKN
               LLQRANELVNPDAAQDVDATAAARGRPAGRAAATARAPARSASRPRRPLE (SEQ ID NO. 4)
               ATCCCACCATGACCTCTAGGCGGAGCGTGAAGAGCTGCCCTAGAGAGGCC
               CCTAGAGGCACCCACGAGGAGCTGTACTACGGCCCTGTGTCCCCTGCCGA
               CCCTGAGAGCCCTAGAGATGACTTTAGACGGGGAGCCGGCCCTATGAGAG
               CCAGACCTAGAGGCGAAGTGAGATTCCTGCACTACGACGAGGCCGGCTAC
               GCCCTGTATCGGGATAGCAGCTCTGACGACGACGAGTCTAGGGATACCGC
               CAGGCCTAGAAGAAGCGCCAGCGTGGCCGGCAGCCACGGCCCTGGCCCTG
               CCAGAGCCCCCCCTCCTCCTGGCGGCCCTGTGGGAGCCGGCGGAAGAAGC
               CACGCCCCTCCCGCCCGGACCCCTAAGATGACCAGAGGCGCCCCTAAGGC
               CAGCGCCACCCCCGCCACCGATCCCGCCAGAGGCAGGAGACCCGCCCAGG
               CCGATAGCGCCGTGCTGCTGGACGCCCCTGCCCCCACCGCCTCCGGCAGA
               ACCAAGACCCCTGCCCAGGGCCTGGCCAAGAAGCTGCACTTTAGCACCGC
               CCCTCCTTCCCCCACCGCCCCCTGGACCCCTAGAGTGGCCGGCTTTAATA
               AGCGCGTGTTCTGTGCCGCTGTGGGCAGACTGGCCGCCACCCACGCCAGG
               CTGGCCGCCGTGCAGCTGTGGGATATGAGCAGACCCCACACCGACGAGGA
               CCTGAACGAGCTGCTGGACCTGACCACAATTAGAGTGACCGTGTGTGAGG
               GCAAGAACCTGCTGCAGAGGGCCAACGAGCTGGTGAACCCTGACGCCGCC
               CAGGACGTGGACGCCACCGCCGCCGCCAGGGGCAGACCTGCCGGCAGAGC
               CGCCGCCACAGCCAGGGCCCCTGCCAGAAGCGCCTCTAGGCCAAGACGGC
               CCCTGGAGCCTAGGTAATCTAGACCAGGCCCTGGATCCAGATCTGCTGTG
               CCTTCTAGTTGCCAGCCATCTGTTGTTTGCCCCTCCCCCGTGCCTTCCTT
               GACCCTGGAAGGTGCCACTCCCACTGTCCTTTCCTAATAAAATGAGGAAA
               TTGCATCGCATTGTCTGAGTAGGTGTCATTCTATTCTGGGGGGTGGGGTG
               GGGCAGGACAGCAAGGGGGAGGATTGGGAAGACAATAGCAGGCATGCTGG
               GGATGCGGTGGGCTCTATGGGTACCCAGGTGCTGAAGAATTGACCCGGTT
               CCTCCTGGGCCAGAAAGAAGCAGGCACATCCCCTTCTCTGTGACACACCC
               TGTCCACGCCCTGGTTCTTAGTTCCAGCCCACTCATAGGACACTCATA
               GCTCAGGAGGGCTCCGCCTTCAATCCCACCCGCTAAAGTACTTGGAGCGG
               TCTCTCCCTCCCTCATCAGCCCACCAAACCAAACCTAGCCTCCAAGAGTG
               GGAAGAAATTAAAGCAAGATAGGCTATTAAGTGCAGAGGGAGAGAAAATG
               CCTCCAACATGTGAGGAAGTAATGAGAGAAATCATAGAATTTCTTCCGCT
               TCCTCGCTCACTGACTCGCTGCGCTCGGTCGTTCGGCTGCGGCGAGCGGT
               ATCAGCTCACTCAAAGGCGGTAATACGGTTATCCACAGAATCAGGGGATA
               ACGCAGGAAAGAACATGTGAGCAAAAGGCCAGCAAAAGGCCAGGAACCGT
               AAAAAGGCCGCGTTGCTGGCGTTTTTCCATAGGCTCCGCCCCCCTGACGA FIGURE 13 (cont'd)

```
GCATCACAAAAATCGACGCTCAAGTCAGAGGTGGCGAAACCCGACAGGAC
TATAAAGATACCAGGCGTTTCCCCCTGGAAGCTCCCTCGTGCGCTCTCCT
GTTCCGACCCTGCCGCTTACCGGATACCTGTCCGCCTTTCTCCCTTCGGG
AAGCGTGGCGCTTTCTCATAGCTCACGCTGTAGGTATCTCAGTTCGGTGT
AGGTCGTTCGCTCCAAGCTGGGCTGTGTGCACGAACCCCCCGTTCAGCCC
GACCGCTGCGCCTTATCCGGTAACTATCGTCTTGAGTCCAACCCGGTAAG
ACACGACTTATCGCCACTGGCAGCAGCCACTGGTAACAGGATTAGCAGAG
CGAGGTATGTAGGCGGTGCTACAGAGTTCTTGAAGTGGTGGCCTAACTAC
GGCTACACTAGAAGAACAGTATTTGGTATCTGCGCTCTGCTGAAGCCAGT
TACCTTCGGAAAAGAGTTGGTAGCTCTTGATCCGGCAAACAAACCACCG
CTGGTAGCGGTGGTTTTTTTGTTTGCAAGCAGCAGATTACGCGCAGAAAA
AAAGGATCTCAAGAAGATCCTTTGATCTTTTCTACGGGGTCTGACGCTCA
GTGGAACGAAAACTCACGTTAAGGGATTTTGGTCATGAGATTATCAAAAA
GGATCTTCACCTAGATCCTTTTAAATTAAAAATGAAGTTTTAAATCAATC
TAAAGTATATATGAGTAAACTTGGTCTGACAGTTACCAATGCTTAATCAG
TGAGGCACCTATCTCAGCGATCTGTCTATTTCGTTCATCCATAGTTGCCT
GACTCGGGGGGGGGGGCGCTGAGGTCTGCCTCGTGAAGAAGGTGTTGCT
GACTCATACCAGGCCTGAATCGCCCCATCATCCAGCCAGAAAGTGAGGGA
GCCACGGTTGATGAGAGCTTTGTTGTAGGTGGACCAGTTGGTGATTTTGA
ACTTTTGCTTTGCCACGGAACGGTCTGCGTTGTCGGGAAGATGCGTGATC
TGATCCTTCAACTCAGCAAAAGTTCGATTTATTCAACAAAGCCGCCGTCC
CGTCAAGTCAGCGTAATGCTCTGCCAGTGTTACAACCAATTAACCAATTC
TGATTAGAAAAACTCATCGAGCATCAAATGAAACTGCAATTTATTCATAT
CAGGATTATCAATACCATATTTTTGAAAAAGCCGTTTCTGTAATGAAGGA
GAAAACTCACCGAGGCAGTTCCATAGGATGGCAAGATCCTGGTATCGGTC
TGCGATTCCGACTCGTCCAACATCAATACAACCTATTAATTTCCCCTCGT
CAAAAATAAGGTTATCAAGTGAGAAATCACCATGAGTGACGACTGAATCC
GGTGAGAATGGCAAAAGCTTATGCATTTCTTTCCAGACTTGTTCAACAGG
CCAGCCATTACGCTCGTCATCAAAATCACTCGCATCAACCAAACCGTTAT
TCATTCGTGATTGCGCCTGAGCGAGACGAAATACGCGATCGCTGTTAAAA
GGACAATTACAAACAGGAATCGAATGCAACCGGCGCAGGAACACTGCCAG
CGCATCAACAATATTTTCACCTGAATCAGGATATTCTTCTAATACCTGGA
ATGCTGTTTTCCCGGGGATCGCAGTGGTGAGTAACCATGCATCATCAGGA
GTACGGATAAAATGCTTGATGGTCGGAAGAGGCATAAATTCCGTCAGCCA
GTTTAGTCTGACCATCTCATCTGTAACATCATTGGCAACGCTACCTTTGC
CATGTTTCAGAAACAACTCTGGCGCATCGGGCTTCCCATACAATCGATAG
ATTGTCGCACCTGATTGCCCGACATTATCGCGAGCCCATTTATACCCATA
TAAATCAGCATCCATGTTGGAATTTAATCGCGGCCTCGAGCAAGACGTTT
CCCGTTGAATATGGCTCATAACACCCCTTGTATTACTGTTTATGTAAGCA
GACAGTTTTATTGTTCATGATGATATATTTTTATCTTGTGCAATGTAACA
TCAGAGATTTTGAGACACAACGTGGCTTTCCCCCCCCCCCCATTATTGAA
GCATTTATCAGGGTTATTGTCTCATGAGCGGATACATATTTGAATGTATT
TAGAAAAATAAACAAATAGGGGTTCCGCGCACATTTCCCCGAAAAGTGCC
ACCTGACGTCTAAGAAACCATTATTATCATGACATTAACCTATAAAAATA
GGCGTATCACGAGGCCCTTTCGTCTCGCGCGTTTCGGTGATGACGGTGAA
AACCTCTGACACATGCAGCTCCCGGAGACGGTCACAGCTTGTCTGTAAGC
GGATGCCGGGAGCAGACAAGCCCGTCAGGGCGCGTCAGCGGGTGTTGGCG
GGTGTCGGGGCTGGCTTAACTATGCGGCATCAGAGCAGATTGTACTGAGA
GTGCACCATATGCGGTGTGAAATACCGCACAGATGCGTAAGGAGAAAATA
CCGCATCAGATTGGCTATTGGCCATTGCATACGTTGTATCCATATCATAA
TATGTACATTTATATTGGCTCATGTCCAACATTACCGCCATGTTGACATT
GATTATTGACTAGTTATTAATAGTAATCAATTACGGGGTCATTAGTTCAT
AGCCCATATATGGAGTTCCGCGTTACATAACTTACGGTAAATGGCCCGCC
```

FIGURE 13 (cont'd)

```
TGGCTGACCGCCCAACGACCCCCGCCCATTGACGTCAATAATGACGTATG
TTCCCATAGTAACGCCAATAGGGACTTTCCATTGACGTCAATGGGTGGAG
TATTTACGGTAAACTGCCCACTTGGCAGTACATCAAGTGTATCATATGCC
AAGTACGCCCCCTATTGACGTCAATGACGGTAAATGGCCCGCCTGGCATT
ATGCCCAGTACATGACCTTATGGGACTTTCCTACTTGGCAGTACATCTAC
GTATTAGTCATCGCTATTACCATGGTGATGCGGTTTTGGCAGTACATCAA
TGGGCGTGGATAGCGGTTTGACTCACGGGGATTTCCAAGTCTCCACCCCA
TTGACGTCAATGGGAGTTTGTTTTGGCACCAAAATCAACGGGACTTTCCA
AAATGTCGTAACAACTCCGCCCCATTGACGCAAATGGGCGGTAGGCGTGT
ACGGTGGGAGGTCTATATAAGCAGAGCTCGTTTAGTGAACCGTCAGATCG
CCTGGAGACGCCATCCACGCTGTTTTGACCTCCATAGAAGACACCGGGAC
CGATCCAGCCTCCGCGGCCGGGAACGGTGCATTGGAACGCGGATTCCCCG
TGCCAAGAGTGACGTAAGTACCGCCTATAGACTCTATAGGCACACCCCTT
TGGCTCTTATGCATGCTATACTGTTTTTGGCTTGGGGCCTATACACCCCC
GCTTCCTTATGCTATAGGTGATGGTATAGCTTAGCCTATAGGTGTGGGTT
ATTGACCATTATTGACCACTCCCCTATTGGTGACGATACTTTCCATTACT
AATCCATAACATGGCTCTTTGCCACAACTATCTCTATTGGCTATATGCCA
ATACTCTGTCCTTCAGAGACTGACACGGACTCTGTATTTTTACAGGATGG
GGTCCCATTTATTATTTACAAATTCACATATACAACAACGCCGTCCCCCG
TGCCCGCAGTTTTTATTAAACATAGCGTGGGATCTCCACGCGAATCTCGG
GTACGTGTTCCGGACATGGGCTCTTCTCCGGTAGCGGCGGAGCTTCCACA
TCCGAGCCCTGGTCCCATGCCTCCAGCGGCTCATGGTCGCTCGGCAGCTC
CTTGCTCCTAACAGTGGAGGCCAGACTTAGGCACAGCACAATGCCCACCA
CCACCAGTGTGCCGCACAAGGCCGTGGCGGTAGGGTATGTGTCTGAAAAT
GAGCGTGGAGATTGGGCTCGCACGGCTGACGCAGATGGAAGACTTAAGGC
AGCGGCAGAAGAAGATGCAGGCAGCTGAGTTGTTGTATTCTGATAAGAGT
CAGAGGTAACTCCCGTTGCGGTGCTGTTAACGGTGGAGGGCAGTGTAGTC
TGAGCAGTACTCGTTGCTGCCGCGCGCGCCACCAGACATAATAGCTGACA
GACTAACAGACTGTTCCTTTCCATGGGTCTTTTCTGCAGTCACCGTCGTC
GACACGTGTGATCAGAT
```

Molecule:      VR2144,   7005 bps DNA Circular

Description:   AvrII delition of HSV.Tag   from VR2137

Details:       UL47,   4908 to 6995,   Draw as Gene
               HSV2 UL47
               Translation product    696 aas
               Mol Wt   73527.0, Isoelectric Pt (pI)  9.71

(SEQ ID NO. 5)
Translation: MSVRGHAVRRRRASTRSHAPSAHRADSPVEDEPEGGGGGLMGYLRAVFNV
DDDSEVEAAGEMASEEPPPRRRREARGHPGSRRASEARAAAPPRRASFPR
PRSVTARSQSVRGRRDSAITRAPRGGYLGPMDPRDVLGRVGGSRVVPSPL
FLDELSYEEDDYPAAVAHDDGAGARPPATVEILAGRVSGPELQAAFPLDR
LTPRVAAWDESVRSALALGHPAGFYPCPDSAFGLSRVGVMHFASPADPKV
FFRQTLQQGEALAWYITGDAILDLTDRRAKTSPSRAMGFLVDAIVRVAIN
GWVCGTRLHTEGRGSELDDRAAELRRQFASLTALRPVGAAAVPLLSAGGA
APPHPGPDAAVFRSSLGSLLYWPGVRALLGRDCRVAARYAGRMTYIATGA
LLARFNPGAVKCVLPREAAFAGRVLDVLAVLAEQTVQWLSVVVGARLHPH
SAHPAFADVEQEALFRALPLGSPGVVAAEHEALGDTAARRLLATSGLNAV
LGAAVYALHTALATVTLKYALACGDARRRRDDAAAARAVLATGLILQRLL
GLADTVVACVALAAFDGGSTAPEVGTYTPLRYACVLRATQPLYARTTPAK
FWADVRAAAEHVDLRPASSAPRAPVSGTADPAFLLEDLAAFPPAPLNSES
VLGPRVRVVDIMAQFRKLLMGDEETAALRAHVSGRRATGLGGPPRP (SEQ ID NO. 6)
CTAGACCAGGCCCTGGATCCAGATCTGCTGTGCCTTCTAGTTGCCAGCCA
TCTGTTGTTTGCCCCTCCCCGTGCCTTCCTTGACCCTGGAAGGTGCCAC
TCCCACTGTCCTTTCCTAATAAAATGAGGAAATTGCATCGCATTGTCTGA
GTAGGTGTCATTCTATTCTGGGGGGTGGGGTGGGGCAGGACAGCAAGGGG
GAGGATTGGGAAGACAATAGCAGGCATGCTGGGGATGCGGTGGGCTCTAT
GGGTACCCAGGTGCTGAAGAATTGACCCGGTTCCTCCTGGGCCAGAAAGA
AGCAGGCACATCCCCTTCTCTGTGACACACCCTGTCCACGCCCCTGGTTC
TTAGTTCCAGCCCCACTCATAGGACACTCATAGCTCAGGAGGGCTCCGCC
TTCAATCCCACCCGCTAAAGTACTTGGAGCGGTCTCTCCCTCCCTCATCA
GCCCACCAAACCAAACCTAGCCTCCAAGAGTGGGAAGAAATTAAAGCAAG
ATAGGCTATTAAGTGCAGAGGGAGAGAAAATGCCTCCAACATGTGAGGAA
GTAATGAGAGAAATCATAGAATTTCTTCCGCTTCCTCGCTCACTGACTCG
CTGCGCTCGGTCGTTCGGCTGCGGCGAGCGGTATCAGCTCACTCAAAGGC
GGTAATACGGTTATCCACAGAATCAGGGGATAACGCAGGAAAGAACATGT
GAGCAAAAGGCCAGCAAAAGGCCAGGAACCGTAAAAAGGCCGCGTTGCTG
GCGTTTTTCCATAGGCTCCGCCCCCCTGACGAGCATCACAAAAATCGACG
CTCAAGTCAGAGGTGGCGAAACCCGACAGGACTATAAAGATACCAGGCGT
TTCCCCCTGGAAGCTCCCTCGTGCGCTCTCCTGTTCCGACCCTGCCGCTT
ACCGGATACCTGTCCGCCTTTCTCCCTTCGGGAAGCGTGGCGCTTTCTCA
TAGCTCACGCTGTAGGTATCTCAGTTCGGTGTAGGTCGTTCGCTCCAAGC
TGGGCTGTGTGCACGAACCCCCCGTTCAGCCCGACCGCTGCGCCTTATCC
GGTAACTATCGTCTTGAGTCCAACCCGGTAAGACACGACTTATCGCCACT
GGCAGCAGCCACTGGTAACAGGATTAGCAGAGCGAGGTATGTAGGCGGTG
CTACAGAGTTCTTGAAGTGGTGGCCTAACTACGGCTACACTAGAAGAACA
GTATTTGGTATCTGCGCTCTGCTGAAGCCAGTTACCTTCGGAAAAAGAGT
TGGTAGCTCTTGATCCGGCAAACAAACCACCGCTGGTAGCGGTGGTTTTT FIGURE 14 (cont'd)

```
TTGTTTGCAAGCAGCAGATTACGCGCAGAAAAAAAGGATCTCAAGAAGAT
CCTTTGATCTTTTCTACGGGGTCTGACGCTCAGTGGAACGAAAACTCACG
TTAAGGGATTTTGGTCATGAGATTATCAAAAAGGATCTTCACCTAGATCC
TTTTAAATTAAAAATGAAGTTTTAAATCAATCTAAAGTATATATGAGTAA
ACTTGGTCTGACAGTTACCAATGCTTAATCAGTGAGGCACCTATCTCAGC
GATCTGTCTATTTCGTTCATCCATAGTTGCCTGACTCGGGGGGGGGGGGC
GCTGAGGTCTGCCTCGTGAAGAAGGTGTTGCTGACTCATACCAGGCCTGA
ATCGCCCCATCATCCAGCCAGAAAGTGAGGGAGCCACGGTTGATGAGAGC
TTTGTTGTAGGTGGACCAGTTGGTGATTTTGAACTTTTGCTTTGCCACGG
AACGGTCTGCGTTGTCGGGAAGATGCGTGATCTGATCCTTCAACTCAGCA
AAAGTTCGATTTATTCAACAAAGCCGCCGTCCCGTCAAGTCAGCGTAATG
CTCTGCCAGTGTTACAACCAATTAACCAATTCTGATTAGAAAAACTCATC
GAGCATCAAATGAAACTGCAATTTATTCATATCAGGATTATCAATACCAT
ATTTTTGAAAAAGCCGTTTCTGTAATGAAGGAGAAAACTCACCGAGGCAG
TTCCATAGGATGGCAAGATCCTGGTATCGGTCTGCGATTCCGACTCGTCC
AACATCAATACAACCTATTAATTTCCCCTCGTCAAAAATAAGGTTATCAA
GTGAGAAATCACCATGAGTGACGACTGAATCCGGTGAGAATGGCAAAAGC
TTATGCATTTCTTTCCAGACTTGTTCAACAGGCCAGCCATTACGCTCGTC
ATCAAAATCACTCGCATCAACCAAACCGTTATTCATTCGTGATTGCGCCT
GAGCGAGACGAAATACGCGATCGCTGTTAAAAGGACAATTACAAACAGGA
ATCGAATGCAACCGGCGCAGGAACACTGCCAGCGCATCAACAATATTTTC
ACCTGAATCAGGATATTCTTCTAATACCTGGAATGCTGTTTTCCCGGGGA
TCGCAGTGGTGAGTAACCATGCATCATCAGGAGTACGGATAAAATGCTTG
ATGGTCGGAAGAGGCATAAATTCCGTCAGCCAGTTTAGTCTGACCATCTC
ATCTGTAACATCATTGGCAACGCTACCTTTGCCATGTTTCAGAAACAACT
CTGGCGCATCGGGCTTCCCATACAATCGATAGATTGTCGCACCTGATTGC
CCGACATTATCGCGAGCCCATTTATACCCATATAAATCAGCATCCATGTT
GGAATTTAATCGCGGCCTCGAGCAAGACGTTTCCCGTTGAATATGGCTCA
TAACACCCCTTGTATTACTGTTTATGTAAGCAGACAGTTTTATTGTTCAT
GATGATATATTTTTATCTTGTGCAATGTAACATCAGAGATTTTGAGACAC
AACGTGGCTTTCCCCCCCCCCCCATTATTGAAGCATTTATCAGGGTTATT
GTCTCATGAGCGGATACATATTTGAATGTATTTAGAAAAATAAACAAATA
GGGGTTCCGCGCACATTTCCCCGAAAAGTGCCACCTGACGTCTAAGAAAC
CATTATTATCATGACATTAACCTATAAAAATAGGCGTATCACGAGGCCCT
TTCGTCTCGCGCGTTTCGGTGATGACGGTGAAAACCTCTGACACATGCAG
CTCCCGGAGACGGTCACAGCTTGTCTGTAAGCGGATGCCGGGAGCAGACA
AGCCCGTCAGGGCGCGTCAGCGGGTGTTGGCGGGTGTCGGGGCTGGCTTA
ACTATGCGGCATCAGAGCAGATTGTACTGAGAGTGCACCATATGCGGTGT
GAAATACCGCACAGATGCGTAAGGAGAAAATACCGCATCAGATTGGCTAT
TGGCCATTGCATACGTTGTATCCATATCATAATATGTACATTTATATTGG
CTCATGTCCAACATTACCGCCATGTTGACATTGATTATTGACTAGTTATT
AATAGTAATCAATTACGGGGTCATTAGTTCATAGCCCATATATGGAGTTC
CGCGTTACATAACTTACGGTAAATGGCCCGCCTGGCTGACCGCCCAACGA
CCCCCGCCCATTGACGTCAATAATGACGTATGTTCCCATAGTAACGCCAA
TAGGGACTTTCCATTGACGTCAATGGGTGGAGTATTTACGGTAAACTGCC
CACTTGGCAGTACATCAAGTGTATCATATGCCAAGTACGCCCCCTATTGA
CGTCAATGACGGTAAATGGCCCGCCTGGCATTATGCCCAGTACATGACCT
TATGGGACTTTCCTACTTGGCAGTACATCTACGTATTAGTCATCGCTATT
ACCATGGTGATGCGGTTTTGGCAGTACATCAATGGGCGTGGATAGCGGTT
TGACTCACGGGGATTTCCAAGTCTCCACCCCATTGACGTCAATGGGAGTT
TGTTTTGGCACCAAAATCAACGGGACTTTCCAAAATGTCGTAACAACTCC
GCCCCATTGACGCAAATGGGCGGTAGGCGTGTACGGTGGGAGGTCTATAT
AAGCAGAGCTCGTTTAGTGAACCGTCAGATCGCCTGGAGACGCCATCCAC
GCTGTTTTGACCTCCATAGAAGACACCGGGACCGATCCAGCCTCCGCGGC
```

FIGURE 14 (cont'd)

CGGGAACGGTGCATTGGAACGCGGATTCCCCGTGCCAAGAGTGACGTAAG
TACCGCCTATAGACTCTATAGGCACACCCCTTTGGCTCTTATGCATGCTA
TACTGTTTTTGGCTTGGGGCCTATACACCCCCGCTTCCTTATGCTATAGG
TGATGGTATAGCTTAGCCTATAGGTGTGGGTTATTGACCATTATTGACCA
CTCCCCTATTGGTGACGATACTTTCCATTACTAATCCATAACATGGCTCT
TTGCCACAACTATCTCTATTGGCTATATGCCAATACTCTGTCCTTCAGAG
ACTGACACGGACTCTGTATTTTTACAGGATGGGGTCCCATTTATTATTTA
CAAATTCACATATACAACAACGCCGTCCCCCGTGCCCGCAGTTTTTATTA
AACATAGCGTGGGATCTCCACGCGAATCTCGGGTACGTGTTCCGGACATG
GGCTCTTCTCCGGTAGCGGCGGAGCTTCCACATCCGAGCCCTGGTCCCAT
GCCTCCAGCGGCTCATGGTCGCTCGGCAGCTCCTTGCTCCTAACAGTGGA
GGCCAGACTTAGGCACAGCACAATGCCCACCACCACCAGTGTGCCGCACA
AGGCCGTGGCGGTAGGGTATGTGTCTGAAAATGAGCGTGGAGATTGGGCT
CGCACGGCTGACGCAGATGGAAGACTTAAGGCAGCGGCAGAAGAAGATGC
AGGCAGCTGAGTTGTTGTATTCTGATAAGAGTCAGAGGTAACTCCCGTTG
CGGTGCTGTTAACGGTGGAGGGCAGTGTAGTCTGAGCAGTACTCGTTGCT
GCCGCGCGCCACCAGACATAATAGCTGACAGACTAACAGACTGTTCCT
TTCCATGGGTCTTTTCTGCAGTCACCGTCGTCGACACGTGTGATCAGATA
TCCCACCATGTCTGTGAGAGGCCACGCTGTGAGAAGAAGAAGGGCTAGCA
CCAGAAGCCACGCCCCTAGCGCCCACAGAGCCGATAGCCCTGTGGAGGAT
GAGCCTGAGGGCGGAGGAGGGGGCCTGATGGGCTACCTGAGGGCCGTGTT
TAACGTGGACGACGATAGCGAAGTGGAAGCCGCCGGAGAGATGGCCTCTG
AGGAGCCCCCTCCTAGAAGGAGAAGAGAGGCCAGAGGCCACCCCGGCTCT
AGGAGAGCCTCTGAGGCCAGAGCCGCCGCCCCACCTAGAAGAGCCAGCTT
CCCTAGACCTAGAAGCGTGACCGCCAGAAGCCAGTCTGTGCGCGGCAGGA
GGGATAGCGCTATCACCAGAGCCCCTAGAGGCGGCTACCTGGGCCCTATG
GACCCTCGCGACGTGCTGGGCAGAGTGGGCGGCTCTAGGGTGGTGCCTAG
CCCCCTGTTCCTGGATGAGCTGAGCTACGAGGAGGACGACTACCCTGCCG
CCGTGGCCCACGACGACGGAGCCGGAGCCAGACCCCCTGCCACCGTGGAG
ATCCTGGCCGGCAGAGTGAGCGGACCTGAGCTGCAAGCCGCCTTCCCCCT
GGATCGGCTGACCCCTCGGGTGGCCGCCTGGGATGAGTCTGTGAGGAGCG
CCCTGGCCCTGGGCCACCCTGCCGGCTTCTACCCCTGCCCTGATTCCGCC
TTCGGCCTGAGCAGAGTGGGAGTGATGCACTTCGCCAGCCCTGCCGACCC
TAAAGTGTTCTTCCGGCAAACACTGCAGCAGGGCGAGGCCCTCGCATGGT
ACATCACCGGCGACGCCATCCTGGATCTGACCGATAGACGGGCCAAGACC
AGCCCTAGCAGAGCTATGGGCTTTCTGGTGGACGCTATTGTGAGAGTGGC
TATTAACGGCTGGGTGTGCGGCACCAGACTGCACACCGAGGGCAGAGGCT
CTGAGCTGGATGATAGAGCCGCCGAGCTGAGGAGACAGTTCGCCAGCCTG
ACCGCCCTGAGACCTGTGGGCGCCGCTGCCGTGCCCCTGCTGAGCGCCGG
AGGAGCCGCCCCTCCCCACCCTGGCCCTGACGCCGCCGTGTTTCGGTCTA
GCCTGGGCAGCCTGCTGTACTGGCCCGGAGTGAGAGCCCTGCTGGGCAGG
GACTGTAGAGTGGCTGCCAGATACGCCGGCAGGATGACCTACATCGCCAC
CGGCGCCCTGCTGGCCAGATTTAACCCTGGCGCCGTGAAATGCGTGCTGC
CTAGAGAAGCCGCCTTCGCCGGAAGAGTGCTGGACGTCCTGGCCGTGCTG
GCTGAGCAGACCGTGCAGTGGCTGAGCGTGGTTGTGGGCGCCAGGCTGCA
CCCTCACAGCGCCCACCCTGCCTTCGCCGACGTGGAGCAGGAGGCCCTGT
TTAGAGCCCTGCCTCTGGGCAGCCCTGGCGTGGTGGCCGCCGAGCACGAA

FIGURE 14 (cont'd)

```
GCCCTGGGCGACACCGCTGCCAGGAGACTGCTCGCCACAAGCGGCCTGAA
CGCCGTGCTGGGAGCCGCCGTGTACGCCCTGCACACCGCCCTGGCCACCG
TGACCCTGAAATACGCCCTGGCCTGCGGCGACGCCCGCAGACGCCGCGAC
GACGCCGCTGCAGCCAGAGCCGTCCTGGCCACCGGCCTGATCCTGCAGAG
GCTGCTGGGCCTGGCCGACACCGTGGTGGCCTGCGTGGCCCTGGCCGCCT
TTGACGGCGGCAGCACCGCCCCTGAAGTGGGCACCTACACCCCTCTGAGA
TACGCCTGCGTGCTGAGAGCCACCCAGCCTCTGTACGCCAGAACCACCCC
TGCCAAGTTCTGGGCCGATGTGAGGGCCGCCGCCGAACACGTGGACCTGA
GACCCGCCTCTAGCGCCCCAAGGGCCCCTGTGAGCGGCACCGCCGACCCC
GCCTTCCTGCTGGAGGATCTGGCCGCTTTCCCTCCCGCCCCTCTGAATAG
CGAGAGCGTGCTGGGGCCTAGAGTGAGAGTGGTGGATATTATGGCCCAGT
TTAGAAAGCTGCTGATGGGCGACGAGGAAACAGCCGCCCTGAGGGCCCAC
GTGTCTGGCAGAAGAGCCACAGGCCTGGGCGGACCTCCTAGACCTCCTAG
GTGAT
```

| | |
|---|---|
| Molecule: | VR2145, 7080 bps DNA Circular |
| Description: | AvrII HSV.Tag removed from VR2138 (HSV2 UL46 in VR1012) |
| Details: | UL46, 9 to 2171, Draw as Gene<br>HSV-2 UL46<br>Translation product  721 aas<br>Mol Wt  77580.0, Isoelectric Pt (pI) 8.47 |

(SEQ ID NO.: 7)
Translation: MQRRARGASSLRLARCLTPANLIRGANAGVPERRIFAGCLLPTPEGLLSA
AVGVLRQRADDLQPAFLTGADRSVRLAARHHNTVPESLIVDGLASDPHYD
YIRHYASAAKQALGEVELSGGQLSRAILAQYWKYLQTVVPSGLDIPDDPA
GDCDPSLHVLLRPTLLPKLLVRAPFKSGAAAAKYAAAVAGLRDAAHRLQQ
YMFFMRPADPSRPSTDTALRLSELLAYVSVLYHWASWMLWTADKYVCRRL
GPADRRFVALSGSLEAPAETFARHLDRGPSGTTGSMQCMALRAAVSDVLG
HLTRLAHLWETGKRSGGTYGIVDAIVSTVEVLSIVHHHAQYIINATLTGY
VVWASDSLNNEYLRAAVDSQERFCRTAAPLFPTMTAPSWARMELSIKSWF
GAALAPDLLRSGTPSPHYESILRLAASGPPGGRGAVGGSCRDKIQRTRRD
NAPPPLPRARPHSTPAAPRRFRRHREDLPEPPHVDAADRGPEPCAGRPAT
YYTHMAGAPPRLPPRNPAPPEQRPAAAARPLAAQREAAGVYDAVRTWGPD
AEAEPDQMENTYLLPDDDAAMPAGVGLGATPAADTTAAAWPAKSHAPRAP
SEDADSIYESVSEDGGRVYEEIPWVRVYENICLRRQDAGGAAPPGDAPDS
PYIEAENPLYDWGGSALFSPPGATRAPDPGLSLSPMPARPRTNALANDGP
TNVAALSALLTKLKRGRHQSH (SEQ ID NO. 8)
ATCCCACCATGCAGCGGAGAGCCAGAGGCGCCTCTAGCCTGAGACTGGCC
CGGTGCCTGACCCCCGCCAATCTGATTAGAGGCGCCAACGCCGGCGTGCC
TGAGAGAAGAATCTTCGCCGGCTGCCTGCTGCCTACCCCTGAGGGCCTGC
TGAGCGCCGCTGTGGGCGTGCTGAGACAGAGGGCCGATGACCTGCAGCCC
GCCTTCCTGACCGGCGCCGATAGATCTGTGAGGCTGGCCGCCAGACACCA
CAACACCGTGCCTGAGTCCCTGATCGTGGACGGCCTGGCCTCTGACCCCC
ACTACGACTACATTAGGCACTACGCCAGCGCCGCCAAGCAGGCCCTGGGC
GAAGTGGAGCTGAGCGGCGGACAGCTGAGCAGAGCCATCCTGGCCCAGTA
CTGGAAGTACCTGCAGACCGTGGTGCCTAGCGGCCTGGACATCCCTGATG
ATCCTGCCGGCGACTGTGACCCTAGCCTGCACGTGCTGCTGAGACCCACA
CTGCTGCCTAAGCTGCTTGTGAGGGCCCCCTTTAAGAGCGGCGCTGCCGC
CGCCAAATACGCCGCCGCCGTGGCCGGCCTGAGGGACGCCGCCCACAGAC
TGCAGCAGTATATGTTCTTTATGAGACCCGCCGACCCTAGCAGACCTAGC
ACCGACACCGCCCTGAGACTGAGCGAGCTGCTGGCCTATGTGAGCGTGCT
GTACCACTGGGCCAGCTGGATGCTGTGGACCGCCGATAAATACGTGTGTA
GGCGGCTGGGCCCTGCCGATAGAAGATTCGTGGCCCTGAGCGGCAGCCTG
GAGGCCCCTGCCGAGACCTTTGCCCGGCACCTGGATAGAGGCCCTAGCGG
CACCACCGGCTCTATGCAGTGTATGGCCCTGAGAGCCGCCGTGTCTGACG
TGCTGGGCCACCTGACCAGACTGGCCCACCTGTGGGAGACCGGCAAGAGA
AGCGGCGGCACCTACGGCATCGTGGACGCCATTGTGAGCACCGTGGAAGT
GCTGAGCATCGTGCACCACCACGCCCAGTACATCATTAACGCCACCCTGA
CCGGCTACGTTGTGTGGGCCTCTGATAGCCTGAATAATGAGTACCTGAGG
GCTGCCGTCGATAGCCAGGAGCGGTTCTGTAGAACAGCCGCCCCTCTGTT
CCCCACCATGACCGCCCCTTCCTGGGCCAGAATGGAACTGAGCATTAAGA FIGURE 15 (cont'd)

```
GCTGGTTCGGAGCCGCCCTGGCCCCTGACCTGCTGAGAAGCGGCACCCCT
AGCCCTCACTACGAGAGCATCCTGCGCCTGGCTGCCAGCGGCCCTCCTGG
CGGCAGAGGAGCTGTGGGCGGCAGCTGTAGGGATAAGATCCAGCGGACCC
GGAGAGATAACGCCCCTCCCCCCCTGCCTCGGGCCAGACCCCACAGCACC
CCTGCTGCCCCTCGGCGGTTTAGACGGCACAGAGAGGACCTGCCTGAGCC
TCCCCACGTGGACGCCGCCGATAGGGGCCCTGAGCCCTGCGCCGGCAGAC
CCGCCACCTACTACACCCACATGGCCGGAGCCCCCCTCGGCTGCCCCCT
CGGAACCCTGCCCCTCCTGAGCAGAGACCTGCCGCCGCTGCCCGGCCTCT
GGCCGCCCAGAGAGAAGCCGCCGGAGTGTATGACGCTGTGAGAACCTGGG
GCCCTGACGCCGAGGCCGAGCCTGATCAGATGGAGAACACCTACCTGCTG
CCTGACGACGACGCCGCCATGCCTGCCGGAGTGGGCCTGGGCGCCACCCC
AGCCGCCGATACCACAGCCGCCGCCTGGCCCGCCAAGAGCCACGCCCCTA
GAGCCCCTAGCGAGGACGCCGATAGCATCTACGAAAGCGTGTCTGAGGAC
GGCGGCAGAGTGTATGAGGAGATCCCCTGGGTGCGGGTGTACGAAAACAT
CTGCCTGAGGAGACAGGACGCCGGAGGAGCCGCCCCACCCGGCGACGCCC
CTGATAGCCCTTACATTGAGGCCGAGAACCCCCTGTACGACTGGGGCGGC
AGCGCCCTGTTTAGCCCCCCTGGCGCCACCAGAGCCCCTGACCCCGGCCT
GAGCCTGAGCCCCATGCCCGCCAGACCTAGAACCAACGCCCTGGCCAATG
ACGGCCCCACCAACGTGGCCGCCCTGAGCGCCCTGCTGACCAAGCTGAAG
AGGGGCAGACACCAGAGCCACCCTAGGTAATCTAGACCAGGCCCTGGATC
CAGATCTGCTGTGCCTTCTAGTTGCCAGCCATCTGTTGTTTGCCCCTCCC
CCGTGCCTTCCTTGACCCTGGAAGGTGCCACTCCCACTGTCCTTTCCTAA
TAAAATGAGGAAATTGCATCGCATTGTCTGAGTAGGTGTCATTCTATTCT
GGGGGGTGGGGTGGGGCAGGACAGCAAGGGGGAGGATTGGGAAGACAATA
GCAGGCATGCTGGGGATGCGGTGGGCTCTATGGGTACCCAGGTGCTGAAG
AATTGACCCGGTTCCTCCTGGGCCAGAAAGAAGCAGGCACATCCCCTTCT
CTGTGACACACCCTGTCCACGCCCCTGGTTCTTAGTTCCAGCCCCACTCA
TAGGACACTCATAGCTCAGGAGGGCTCCGCCTTCAATCCCACCCGCTAAA
GTACTTGGAGCGGTCTCTCCCTCCCTCATCAGCCCACCAAACCAAACCTA
GCCTCCAAGAGTGGGAAGAAATTAAAGCAAGATAGGCTATTAAGTGCAGA
GGGAGAGAAAATGCCTCCAACATGTGAGGAAGTAATGAGAGAAATCATAG
AATTTCTTCCGCTTCCTCGCTCACTGACTCGCTGCGCTCGGTCGTTCGGC
TGCGGCGAGCGGTATCAGCTCACTCAAAGGCGGTAATACGGTTATCCACA
GAATCAGGGGATAACGCAGGAAAGAACATGTGAGCAAAAGGCCAGCAAAA
GGCCAGGAACCGTAAAAAGGCCGCGTTGCTGGCGTTTTTCCATAGGCTCC
GCCCCCCTGACGAGCATCACAAAAATCGACGCTCAAGTCAGAGGTGGCGA
AACCCGACAGGACTATAAAGATACCAGGCGTTTCCCCCTGGAAGCTCCCT
CGTGCGCTCTCCTGTTCCGACCCTGCCGCTTACCGGATACCTGTCCGCCT
TTCTCCCTTCGGGAAGCGTGGCGCTTTCTCATAGCTCACGCTGTAGGTAT
CTCAGTTCGGTGTAGGTCGTTCGCTCCAAGCTGGGCTGTGTGCACGAACC
CCCCGTTCAGCCCGACCGCTGCGCCTTATCCGGTAACTATCGTCTTGAGT
CCAACCCGGTAAGACACGACTTATCGCCACTGGCAGCAGCCACTGGTAAC
AGGATTAGCAGAGCGAGGTATGTAGGCGGTGCTACAGAGTTCTTGAAGTG
GTGGCCTAACTACGGCTACACTAGAAGAACAGTATTTGGTATCTGCGCTC
TGCTGAAGCCAGTTACCTTCGGAAAAAGAGTTGGTAGCTCTTGATCCGGC
AAACAAACCACCGCTGGTAGCGGTGGTTTTTTTGTTTGCAAGCAGCAGAT
TACGCGCAGAAAAAAGGATCTCAAGAAGATCCTTTGATCTTTTCTACGG
GGTCTGACGCTCAGTGGAACGAAAACTCACGTTAAGGGATTTTGGTCATG
AGATTATCAAAAGGATCTTCACCTAGATCCTTTTAAATTAAAAATGAAG
TTTTAAATCAATCTAAAGTATATATGAGTAAACTTGGTCTGACAGTTACC
AATGCTTAATCAGTGAGGCACCTATCTCAGCGATCTGTCTATTTCGTTCA
TCCATAGTTGCCTGACTCGGGGGGGGGGCGCTGAGGTCTGCCTCGTGA
AGAAGGTGTTGCTGACTCATACCAGGCCTGAATCGCCCCATCATCCAGCC
AGAAAGTGAGGGAGCCACGGTTGATGAGAGCTTTGTTGTAGGTGGACCAG
```

FIGURE 15 (cont'd)

```
TTGGTGATTTTGAACTTTTGCTTTGCCACGGAACGGTCTGCGTTGTCGGG
AAGATGCGTGATCTGATCCTTCAACTCAGCAAAAGTTCGATTTATTCAAC
AAAGCCGCCGTCCCGTCAAGTCAGCGTAATGCTCTGCCAGTGTTACAACC
AATTAACCAATTCTGATTAGAAAAACTCATCGAGCATCAAATGAAACTGC
AATTTATTCATATCAGGATTATCAATACCATATTTTTGAAAAAGCCGTTT
CTGTAATGAAGGAGAAAACTCACCGAGGCAGTTCCATAGGATGGCAAGAT
CCTGGTATCGGTCTGCGATTCCGACTCGTCCAACATCAATACAACCTATT
AATTTCCCCTCGTCAAAAATAAGGTTATCAAGTGAGAAATCACCATGAGT
GACGACTGAATCCGGTGAGAATGGCAAAAGCTTATGCATTTCTTTCCAGA
CTTGTTCAACAGGCCAGCCATTACGCTCGTCATCAAAATCACTCGCATCA
ACCAAACCGTTATTCATTCGTGATTGCGCCTGAGCGAGACGAAATACGCG
ATCGCTGTTAAAAGGACAATTACAAACAGGAATCGAATGCAACCGGCGCA
GGAACACTGCCAGCGCATCAACAATATTTTCACCTGAATCAGGATATTCT
TCTAATACCTGGAATGCTGTTTTCCCGGGGATCGCAGTGGTGAGTAACCA
TGCATCATCAGGAGTACGGATAAAATGCTTGATGGTCGGAAGAGGCATAA
ATTCCGTCAGCCAGTTTAGTCTGACCATCTCATCTGTAACATCATTGGCA
ACGCTACCTTTGCCATGTTTCAGAAACAACTCTGGCGCATCGGGCTTCCC
ATACAATCGATAGATTGTCGCACCTGATTGCCCGACATTATCGCGAGCCC
ATTTATACCCATATAAATCAGCATCCATGTTGGAATTTAATCGCGGCCTC
GAGCAAGACGTTTCCCGTTGAATATGGCTCATAACACCCCTTGTATTACT
GTTTATGTAAGCAGACAGTTTTATTGTTCATGATGATATATTTTTATCTT
GTGCAATGTAACATCAGAGATTTTGAGACACAACGTGGCTTTCCCCCCCC
CCCCATTATTGAAGCATTTATCAGGGTTATTGTCTCATGAGCGGATACAT
ATTTGAATGTATTTAGAAAAATAAACAAATAGGGGTTCCGCGCACATTTC
CCCGAAAAGTGCCACCTGACGTCTAAGAAACCATTATTATCATGACATTA
ACCTATAAAATAGGCGTATCACGAGGCCCTTTCGTCTCGCGCGTTTCGG
TGATGACGGTGAAAACCTCTGACACATGCAGCTCCCGGAGACGGTCACAG
CTTGTCTGTAAGCGGATGCCGGGAGCAGACAAGCCCGTCAGGGCGCGTCA
GCGGGTGTTGGCGGGTGTCGGGGCTGGCTTAACTATGCGGCATCAGAGCA
GATTGTACTGAGAGTGCACCATATGCGGTGTGAAATACCGCACAGATGCG
TAAGGAGAAAATACCGCATCAGATTGGCTATTGGCCATTGCATACGTTGT
ATCCATATCATAATATGTACATTTATATTGGCTCATGTCCAACATTACCG
CCATGTTGACATTGATTATTGACTAGTTATTAATAGTAATCAATTACGGG
GTCATTAGTTCATAGCCCATATATGGAGTTCCGCGTTACATAACTTACGG
TAAATGGCCCGCCTGGCTGACCGCCCAACGACCCCCGCCCATTGACGTCA
ATAATGACGTATGTTCCCATAGTAACGCCAATAGGGACTTTCCATTGACG
TCAATGGGTGGAGTATTTACGGTAAACTGCCCACTTGGCAGTACATCAAG
TGTATCATATGCCAAGTACGCCCCCTATTGACGTCAATGACGGTAAATGG
CCCGCCTGGCATTATGCCCAGTACATGACCTTATGGGACTTTCCTACTTG
GCAGTACATCTACGTATTAGTCATCGCTATTACCATGGTGATGCGGTTTT
GGCAGTACATCAATGGGCGTGGATAGCGGTTTGACTCACGGGGATTTCCA
AGTCTCCACCCCATTGACGTCAATGGGAGTTTGTTTTGGCACCAAAATCA
ACGGGACTTTCCAAAATGTCGTAACAACTCCGCCCCATTGACGCAAATGG
GCGGTAGGCGTGTACGGTGGGAGGTCTATATAAGCAGAGCTCGTTTAGTG
AACCGTCAGATCGCCTGGAGACGCCATCCACGCTGTTTTGACCTCCATAG
AAGACACCGGGACCGATCCAGCCTCCGCGGCCGGGAACGGTGCATTGGAA
CGCGGATTCCCCGTGCCAAGAGTGACGTAAGTACCGCCTATAGACTCTAT
AGGCACACCCCTTTGGCTCTTATGCATGCTATACTGTTTTTGGCTTGGGG
CCTATACACCCCGCTTCCTTATGCTATAGGTGATGGTATAGCTTAGCCT
ATAGGTGTGGGTTATTGACCATTATTGACCACTCCCTATTGGTGACGAT
ACTTTCCATTACTAATCCATAACATGGCTCTTTGCCACAACTATCTCTAT
TGGCTATATGCCAATACTCTGTCCTTCAGAGACTGACACGGACTCTGTAT
TTTTACAGGATGGGGTCCCATTTATTATTTACAAATTCACATATACAACA
ACGCCGTCCCCCGTGCCCGCAGTTTTTATTAAACATAGCGTGGGATCTCC
```

FIGURE 15 (cont'd)

```
ACGCGAATCTCGGGTACGTGTTCCGGACATGGGCTCTTCTCCGGTAGCGG
CGGAGCTTCCACATCCGAGCCCTGGTCCCATGCCTCCAGCGGCTCATGGT
CGCTCGGCAGCTCCTTGCTCCTAACAGTGGAGGCCAGACTTAGGCACAGC
ACAATGCCCACCACCACCAGTGTGCCGCACAAGGCCGTGGCGGTAGGGTA
TGTGTCTGAAAATGAGCGTGGAGATTGGGCTCGCACGGCTGACGCAGATG
GAAGACTTAAGGCAGCGGCAGAAGAAGATGCAGGCAGCTGAGTTGTTGTA
TTCTGATAAGAGTCAGAGGTAACTCCCGTTGCGGTGCTGTTAACGGTGGA
GGGCAGTGTAGTCTGAGCAGTACTCGTTGCTGCCGCGCGCCACCAGAC
ATAATAGCTGACAGACTAACAGACTGTTCCTTTCCATGGGTCTTTTCTGC
AGTCACCGTCGTCGACACGTGTGATCAGAT
```

FIGURE 16

(SEQ ID NO. 9) gD2

ATGGGCAGACTGACTAGCGGAGTGGGCACAGCCGCCCTGCTCGTGGTGGC
TGTGGGCCTGAGAGTGGTGTGTGCTAAGTACGCCCTGGCTGACCCTAGCC
TGAAGATGGCTGATCCTAATAGGTTTAGGGGCAAGAACCTGCCCGTGCTG
GACCAGCTGACTGACCCCCCTGGCGTGAAGAGAGTGTACCACATCCAGCC
TAGCCTGGAGGACCCCTTCCAGCCCCCTAGCATCCCTATCACCGTGTACT
ACGCCGTGCTGGAGAGAGCCTGTAGAAGCGTGCTGCTGCACGCCCCTAGT
GAGGCCCCTCAGATTGTGAGAGGCGCTAGTGACGAGGCTAGGAAGCACAC
CTATAACCTGACCATCGCCTGGTATAGGATGGGCGATAACTGCGCCATCC
CCATCACAGTGATGGAGTACACTGAGTGCCCCTATAATAAGAGCCTGGGC
GTGTGTCCCATTAGGACCCAGCCTAGGTGGAGCTACTACGATAGCTTTAG
CGCCGTGAGTGAGGATAACCTGGGCTTCCTGATGCACGCCCCAGCCTTTG
AGACCGCCGGCACCTACCTGAGACTGGTGAAGATTAACGACTGGACTGAG
ATCACCCAGTTCATCCTGGAGCATAGGGCTAGGGCTAGCTGTAAATACGC
CCTGCCCCTGAGAATCCCCCCTGCCGCCTGCCTGACTAGTAAGGCCTACC
AGCAAGGCGTGACCGTGGATAGCATCGGCATGCTGCCTAGATTCATCCCT
GAGAACCAGAGAACCGTGGCCCTGTATAGCCTGAAAATCGCCGGCTGGCA
CGGCCCTAAGCCTCCTTACACTAGCACCCTGCTGCCCCCTGAGCTGAGTG
ATACCACTAACGCCACCCAGCCTGAGCTGGTGCCTGAGGACCCTGAGGAT
AGCGCTCTGCTGGAAGATCCTGCCGGCACCGTGAGTAGCCAGATCCCCCC
TAACTGGCACATCCCTAGCATTCAGGACGTGGCCCCCCACCACGCCCCTG
CCGCTCCTAGTAACCCTGGCTGA

FIGURE 17

(SEQ ID NO. 10) UL49

ATGACCTCTAGGCGGAGCGTGAAGAGCTGCCCTAGAGAGGCCCCTAGAGG
CACCCACGAGGAGCTGTACTACGGCCCTGTGTCCCCTGCCGACCCTGAGA
GCCCTAGAGATGACTTTAGACGGGGAGCCGGCCCTATGAGAGCCAGACCT
AGAGGCGAAGTGAGATTCCTGCACTACGACGAGGCCGGCTACGCCCTGTA
TCGGGATAGCAGCTCTGACGACGACGAGTCTAGGGATACCGCCAGGCCTA
GAAGAAGCGCCAGCGTGGCCGGCAGCCACGGCCCTGGCCCTGCCAGAGCC
CCCCCTCCTCCTGGCGGCCCTGTGGGAGCCGGCGGAAGAAGCCACGCCCC
TCCCGCCCGGACCCCTAAGATGACCAGAGGCGCCCCTAAGGCCAGCGCCA
CCCCCGCCACCGATCCCGCCAGAGGCAGGAGACCCGCCCAGGCCGATAGC
GCCGTGCTGCTGGACGCCCCTGCCCCCACCGCCTCCGGCAGAACCAAGAC
CCCTGCCCAGGGCCTGGCCAAGAAGCTGCACTTTAGCACCGCCCCTCCTT
CCCCCACCGCCCCCTGGACCCCTAGAGTGGCCGGCTTTAATAAGCGCGTG
TTCTGTGCCGCTGTGGGCAGACTGGCCGCCACCCACGCCAGGCTGGCCGC
CGTGCAGCTGTGGGATATGAGCAGACCCCACACCGACGAGGACCTGAACG
AGCTGCTGGACCTGACCACAATTAGAGTGACCGTGTGTGAGGGCAAGAAC
CTGCTGCAGAGGGCCAACGAGCTGGTGAACCCTGACGCCGCCCAGGACGT
GGACGCCACCGCCGCCGCCAGGGGCAGACCTGCCGGCAGAGCCGCCGCCA
CAGCCAGGGCCCCTGCCAGAAGCGCCTCTAGGCCAAGACGGCCCCTGGAG

FIGURE 18

(SEQ ID NO. 11) UL47

ATGTCTGTGAGAGGCCACGCTGTGAGAAGAAGAAGGGCTAGCACCAGAAG
CCACGCCCCTAGCGCCCACAGAGCCGATAGCCCTGTGGAGGATGAGCCTG
AGGGCGGAGGAGGGGGCCTGATGGGCTACCTGAGGGCCGTGTTTAACGTG
GACGACGATAGCGAAGTGGAAGCCGCCGGAGAGATGGCCTCTGAGGAGCC
CCCTCCTAGAAGGAGAAGAGAGGCCAGAGGCCACCCCGGCTCTAGGAGAG
CCTCTGAGGCCAGAGCCGCCGCCCCACCTAGAAGAGCCAGCTTCCCTAGA
CCTAGAAGCGTGACCGCCAGAAGCCAGTCTGTGCGCGGCAGGAGGGATAG
CGCTATCACCAGAGCCCCTAGAGGCGGCTACCTGGGCCCTATGGACCCTC
GCGACGTGCTGGGCAGAGTGGGCGGCTCTAGGGTGGTGCCTAGCCCCCTG
TTCCTGGATGAGCTGAGCTACGAGGAGGACGACTACCCTGCCGCCGTGGC
CCACGACGACGGAGCCGGAGCCAGACCCCTGCCACCGTGGAGATCCTGG
CCGGCAGAGTGAGCGGACCTGAGCTGCAAGCCGCCTTCCCCCTGGATCGG
CTGACCCCTCGGGTGGCCGCCTGGGATGAGTCTGTGAGGAGCGCCCTGGC
CCTGGGCCACCCTGCCGGCTTCTACCCCTGCCCTGATTCCGCCTTCGGCC
TGAGCAGAGTGGGAGTGATGCACTTCGCCAGCCCTGCCGACCCTAAAGTG
TTCTTCCGGCAAACACTGCAGCAGGGCGAGGCCCTCGCATGGTACATCAC
CGGCGACGCCATCCTGGATCTGACCGATAGACGGGCCAAGACCAGCCCTA
GCAGAGCTATGGGCTTTCTGGTGGACGCTATTGTGAGAGTGGCTATTAAC
GGCTGGGTGTGCGGCACCAGACTGCACACCGAGGGCAGAGGCTCTGAGCT
GGATGATAGAGCCGCCGAGCTGAGGAGACAGTTCGCCAGCCTGACCGCCC
TGAGACCTGTGGGCGCCGCTGCCGTGCCCCTGCTGAGCGCCGGAGGAGCC
GCCCCTCCCCACCCTGGCCCTGACGCCGCCGTGTTTCGGTCTAGCCTGGG
CAGCCTGCTGTACTGGCCCGGAGTGAGAGCCCTGCTGGGCAGGGACTGTA
GAGTGGCTGCCAGATACGCCGGCAGGATGACCTACATCGCCACCGGCGCC
CTGCTGGCCAGATTTAACCCTGGCGCCGTGAAATGCGTGCTGCCTAGAGA
AGCCGCCTTCGCCGGAAGAGTGCTGGACGTCCTGGCCGTGCTGGCTGAGC
AGACCGTGCAGTGGCTGAGCGTGGTTGTGGGCGCCAGGCTGCACCCTCAC
AGCGCCCACCCTGCCTTCGCCGACGTGGAGCAGGAGGCCCTGTTTAGAGC
CCTGCCTCTGGGCAGCCCTGGCGTGGTGGCCGCCGAGCACGAAGCCCTGG
GCGACACCGCTGCCAGGAGACTGCTCGCCACAAGCGGCCTGAACGCCGTG
CTGGGAGCCGCCGTGTACGCCCTGCACACCGCCCTGGCCACCGTGACCCT
GAAATACGCCCTGGCCTGCGGCGACGCCCGCAGACGCCGCGACGACGCCG
CTGCAGCCAGAGCCGTCCTGGCCACCGGCCTGATCCTGCAGAGGCTGCTG
GGCCTGGCCGACACCGTGGTGGCCTGCGTGGCCCTGGCCGCCTTTGACGG
CGGCAGCACCGCCCCTGAAGTGGGCACCTACACCCCTCTGAGATACGCCT
GCGTGCTGAGAGCCACCCAGCCTCTGTACGCCAGAACCACCCCTGCCAAG
TTCTGGGCCGATGTGAGGGCCGCCGCCGAACACGTGGACCTGAGACCCGC
CTCTAGCGCCCCAAGGGCCCCTGTGAGCGGCACCGCCGACCCCGCCTTCC
TGCTGGAGGATCTGGCCGCTTTCCCTCCCGCCCCTCTGAATAGCGAGAGC
GTGCTGGGGCCTAGAGTGAGAGTGGTGGATATTATGGCCCAGTTTAGAAA
GCTGCTGATGGGCGACGAGGAAACAGCCGCCCTGAGGGCCCACGTGTCTG
GCAGAAGAGCCACAGGCCTGGGCGGACCTCCTAGACCT

FIGURE 19

(SEQ ID NO. 12) UL46

```
ATGCAGCGGAGAGCCAGAGGCGCCTCTAGCCTGAGACTGGCCCGGTGCCT
GACCCCCGCCAATCTGATTAGAGGCGCCAACGCCGGCGTGCCTGAGAGAA
GAATCTTCGCCGGCTGCCTGCTGCCTACCCCTGAGGGCCTGCTGAGCGCC
GCTGTGGGCGTGCTGAGACAGAGGGCCGATGACCTGCAGCCCGCCTTCCT
GACCGGCGCCGATAGATCTGTGAGGCTGGCCGCCAGACACCACAACACCG
TGCCTGAGTCCCTGATCGTGGACGGCCTGGCCTCTGACCCCCACTACGAC
TACATTAGGCACTACGCCAGCGCCGCCAAGCAGGCCCTGGGCGAAGTGGA
GCTGAGCGGCGGACAGCTGAGCAGAGCCATCCTGGCCCAGTACTGGAAGT
ACCTGCAGACCGTGGTGCCTAGCGGCCTGGACATCCCTGATGATCCTGCC
GGCGACTGTGACCCTAGCCTGCACGTGCTGCTGAGACCCACACTGCTGCC
TAAGCTGCTTGTGAGGGCCCCCTTTAAGAGCGGCGCTGCCGCCGCCAAAT
ACGCCGCCGCCGTGGCCGGCCTGAGGGACGCCGCCCACAGACTGCAGCAG
TATATGTTCTTTATGAGACCCGCCGACCCTAGCAGACCTAGCACCGACAC
CGCCCTGAGACTGAGCGAGCTGCTGGCCTATGTGAGCGTGCTGTACCACT
GGGCCAGCTGGATGCTGTGGACCGCCGATAAATACGTGTGTAGGCGGCTG
GGCCCTGCCGATAGAAGATTCGTGGCCCTGAGCGGCAGCCTGGAGGCCCC
TGCCGAGACCTTTGCCCGGCACCTGGATAGAGGCCCTAGCGGCACCACCG
GCTCTATGCAGTGTATGGCCCTGAGAGCCGCCGTGTCTGACGTGCTGGGC
CACCTGACCAGACTGGCCCACCTGTGGGAGACCGGCAAGAGAAGCGGCGG
CACCTACGGCATCGTGGACGCCATTGTGAGCACCGTGGAAGTGCTGAGCA
TCGTGCACCACCACGCCCAGTACATCATTAACGCCACCCTGACCGGCTAC
GTTGTGTGGGCCTCTGATAGCCTGAATAATGAGTACCTGAGGGCTGCCGT
CGATAGCCAGGAGCGGTTCTGTAGAACAGCCGCCCCTCTGTTCCCCACCA
TGACCGCCCCTTCCTGGGCCAGAATGGAACTGAGCATTAAGAGCTGGTTC
GGAGCCGCCCTGGCCCCTGACCTGCTGAGAAGCGGCACCCCTAGCCCTCA
CTACGAGAGCATCCTGCGCCTGGCTGCCAGCGGCCCTCCTGGCGGCAGAG
GAGCTGTGGGCGGCAGCTGTAGGGATAAGATCCAGCGGACCCGGAGAGAT
AACGCCCCTCCCCCCCTGCCTCGGGCCAGACCCCACAGCACCCCTGCTGC
CCCTCGGCGGTTTAGACGGCACAGAGAGGACCTGCCTGAGCCTCCCCACG
TGGACGCCGCCGATAGGGGCCCTGAGCCCTGCGCCGGCAGACCCGCCACC
TACTACACCCACATGGCCGGAGCCCCCCCTCGGCTGCCCCCTCGGAACCC
TGCCCCTCCTGAGCAGAGACCTGCCGCCGCTGCCCGGCCTCTGGCCGCCC
AGAGAGAAGCCGCCGGAGTGTATGACGCTGTGAGAACCTGGGGCCCTGAC
GCCGAGGCCGAGCCTGATCAGATGGAGAACACCTACCTGCTGCCTGACGA
CGACGCCGCCATGCCTGCCGGAGTGGGCCTGGGCGCCACCCCAGCCGCCG
ATACCACAGCCGCCGCCTGGCCCGCCAAGAGCCACGCCCCTAGAGCCCCT
AGCGAGGACGCCGATAGCATCTACGAAAGCGTGTCTGAGGACGGCGGCAG
AGTGTATGAGGAGATCCCCTGGGTGCGGGTGTACGAAAACATCTGCCTGA
GGAGACAGGACGCCGGAGGAGCCGCCCCACCCGGCGACGCCCCTGATAGC
CCTTACATTGAGGCCGAGAACCCCCTGTACGACTGGGGCGGCAGCGCCCT
GTTTAGCCCCCCTGGCGCCACCAGAGCCCCTGACCCCGGCCTGAGCCTGA
GCCCCATGCCCGCCAGACCTAGAACCAACGCCCTGGCCAATGACGGCCCC
ACCAACGTGGCCGCCCTGAGCGCCCTGCTGACCAAGCTGAAGAGGGGCAG
ACACCAGAGCCAC
```

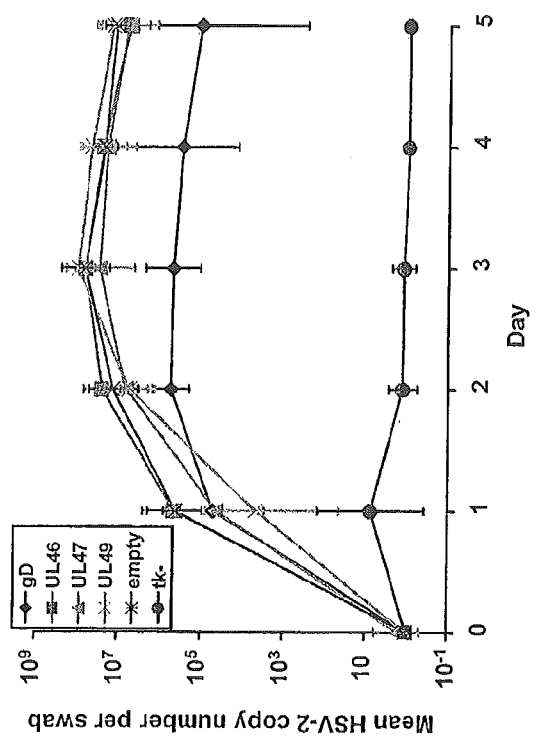
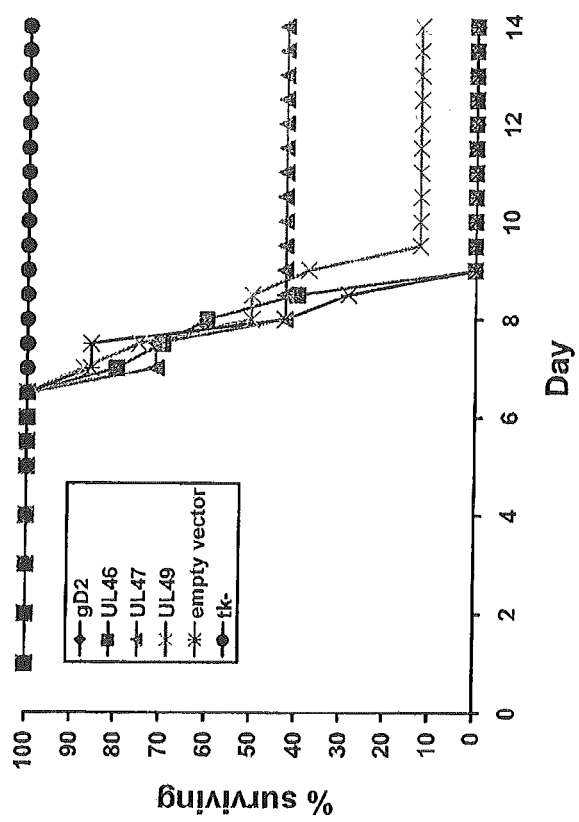
FIGURE 24A
FIGURE 24B
COMPOSITIONS AND METHODS FOR VACCINATING AGAINST HSV-2

CROSS REFERENCE TO RELATED APPLICATIONS

This application is a continuation application of U.S. application Ser. No. 13/585,668, filed Aug. 14, 2012, now pending, which is a divisional application of U.S. application Ser. No. 12/604,694, filed Oct. 23, 2009, now issued as U.S. Pat. No. 8,263,087, issued Sep. 11, 2012, which is a divisional application of U.S. application Ser. No. 11/781,153, filed Jul. 20, 2007, now issued as U.S. Pat. No. 7,628,993, issued Dec. 8, 2009; which claims the benefit under 35 USC §119(e) to U.S. Application Ser. No. 60/807,911, filed Jul. 20, 2006. The disclosure of each of the prior applications is considered part of and is incorporated by reference in the disclosure of this application.

GRANT INFORMATION

This invention was made with government support under Grant No. 1 R41 AI065015-01 awarded by National Institutes of Health, National Institute of Allergy and Infectious Diseases and Grant No. AI50132 awarded by National Institutes of Health. The government has certain rights in the invention.

BACKGROUND OF THE INVENTION

1. Field of the Invention

The present invention relates to prophylactic and therapeutic compositions and methods for inducing an immune response to herpes simplex virus type 2 (HSV-2). More particularly, the invention pertains to prophylactic and therapeutic compositions and methods for inducing an immune response in a vertebrate by introducing and expressing a DNA vaccine encoding at least one of the HSV-2 proteins such as: gD, VP11/12, VP13/14 and/or VP22.

2. Background Information

Vaccination with immunogenic proteins has eliminated or reduced the incidence of many diseases; however there are major difficulties in using proteins associated with certain pathogens and disease states as immunogens. Many protein antigens are not intrinsically immunogenic. More often, they are not effective as vaccines because of the manner in which the immune system operates.

The immune system of vertebrates consists of several interacting components. The best characterized and most important parts are the humoral and cellular (cytolytic) branches. Humoral immunity involves antibodies, proteins which are secreted into the body fluids and which directly recognize an antigen. The cellular system, in contrast, relies on special cells which recognize and kill other cells which are producing foreign antigens. This basic functional division reflects two different strategies of immune defense. Humoral immunity is mainly directed at antigens which are exogenous to the animal whereas the cellular system responds to antigens which are actively synthesized within the animal.

Antibody molecules, the effectors of humoral immunity, are secreted by special B lymphoid cells, B cells, in response to antigen. Antibodies can bind to and inactivate antigen directly (neutralizing antibodies) or activate other cells of the immune system to destroy the antigen.

Cellular immune recognition is mediated by a special class of lymphoid cells, the cytotoxic T cells. These cells do not recognize whole antigens but instead they respond to degraded peptide fragments thereof which appear on the surface of the target cell bound to proteins called class I major histocompatibility complex (MHC) molecules. Essentially all nucleated cells have class I molecules. It is believed that proteins produced within the cell are continually degraded to peptides as part of normal cellular metabolism. These fragments are bound to the MHC molecules and are transported to the cell surface. Thus the cellular immune system is constantly monitoring the spectra of proteins produced in all cells in the body and is poised to eliminate any cells producing foreign antigens.

Vaccination is the process of preparing an animal to respond to an antigen. Vaccination is more complex than immune recognition and involves not only B cells and cytotoxic T cells, but other types of lymphoid cells as well. During vaccination, cells which recognize the antigen (B cells or cytotoxic T cells) are clonally expanded. In addition, the population of ancillary cells (helper T cells) specific for the antigen also increase. Vaccination also involves specialized antigen presenting cells which can process the antigen and display it in a form which can stimulate one of the two pathways.

Vaccination has changed little since the time of Louis Pasteur. A foreign antigen is introduced into an animal where it activates specific B cells by binding to surface immunoglobulins. It is also taken up by antigen processing cells, wherein it is degraded, and appears in fragments on the surface of these cells bound to Class II MHC molecules. Peptides bound to class II molecules are capable of stimulating the helper class of T cells. Both helper T cells and activated B cells are required to produce active humoral immunization. Cellular immunity is thought to be stimulated by a similar but less understood mechanism.

Thus two different and distinct pathways of antigen processing produce exogenous antigens bound to class II MHC molecules where they can stimulate T helper cells, as well as endogenous proteins degraded and bound to class I MHC molecules and recognized by the cytotoxic class of T cells.

There is little or no difference in the distribution of MHC molecules. Essentially all nucleated cells express class I molecules whereas class II MHC proteins are restricted to some few types of lymphoid cells.

Normal vaccination schemes will produce a humoral immune response. They may also provide cytotoxic immunity. The humoral system protects a vaccinated individual from subsequent challenge from a pathogen and can prevent the spread of an intracellular infection if the pathogen goes through an extracellular phase during its life cycle; however, it can do relatively little to eliminate intracellular pathogens. Cytotoxic immunity complements the humoral system by eliminating the infected cells. Thus effective vaccination should activate both types of immunity.

A cytotoxic T cell response is necessary to remove intracellular pathogens, such as viruses, as well as malignant cells. It has proven difficult to present an exogenously administered antigen in adequate concentrations in conjunction with Class I molecules to assure an adequate response. This has severely hindered the development of vaccines against tumor-specific antigens (e.g., on breast or colon cancer cells), and against weakly immunogenic viral proteins (e.g., HIV, Herpes, non-A, non-B hepatitis, CMV and EBV).

It would be desirable to provide a cellular immune response alone in immunizing against agents, such as viruses, for which antibodies have been shown to enhance infectivity. It would also be useful to provide such a response against both chronic and latent viral infections and against malignant cells.

The use of synthetic peptide vaccines does not necessarily solve these problems because either the peptides do not readily associate with histocompatibility molecules, have a short serum half-life, are rapidly proteolyzed, or do not specifically localize to antigen-presenting monocytes and macrophages. At best, all exogenously administered antigens must compete with the universe of self-proteins for binding to antigen-presenting macrophages.

Major efforts have been mounted to elicit immune responses to poorly immunogenic viral proteins from the herpes viruses, non-A, non-B hepatitis, HIV, and the like. These pathogens are difficult and hazardous to propagate in vitro. Genital herpes is a highly prevalent sexually transmitted disease worldwide, and is considered to be a major health burden. The causative agent is usually herpes simplex virus type 2 (HSV-2). Cellular immune responses to HSV-2 are believed to be important for both the prevention of disease and the control of recurrent disease. The HSV-2 tegument proteins VP11/12, VP13/14, VP22, and gD are respectively known as, or encoded by genes, UL46, UL47, UL49, and US6. These proteins contain human CD8+ T-cell epitopes restricted by HLA A*0101, A*0201 (x2), and B*0702, respectively.

As mentioned above, synthetic peptide vaccines corresponding to viral-encoded proteins have been made, but have severe pitfalls. Attempts have also been made to use vaccinia virus vectors to express proteins from other viruses. However, the results have been disappointing, since (a) recombinant vaccinia viruses may be rapidly eliminated from the circulation in already immune individuals, and (b) the administration of complex viral antigens may induce a phenomenon known as "antigenic competition," in which weakly immunogenic portions of the virus fail to elicit an immune response.

Another major problem with protein or peptide vaccines is anaphylactic reaction which can occur when injections of antigen are repeated in efforts to produce a potent immune response. In this phenomenon, IgE antibodies formed in response to the antigen cause severe and sometimes fatal allergic reactions.

Accordingly, there is a need for a method for invoking a safe and effective immune response to a protein or polypeptide associated with herpes simplex virus type 2 (HSV-2). Moreover, there is a great need for a method that will associate these antigens with Class I histocompatibility antigens on the cell surface to elicit a cytotoxic T cell response, avoid anaphylaxis and proteolysis of the material in the serum, and facilitate localization of the material to monocytes and macrophages.

SUMMARY OF THE INVENTION

The present invention provides for DNA vaccines, some of which comprise the HSV-2 tegument genes UL46, UL47 and UL49 and another alternative comprises the HSV-2 gD gene all of which were individually cloned into expression plasmids (VR1012) and used to immunize a vertebrate. Each animal received three 100 µg doses of formulated DNA vaccine by intramuscular (IM) injection. Formulations based on VAXFECTIN adjuvant (an adjuvant composition comprising GAP-DMORIE and DPyPE) and poloxamer were evaluated for their ability to boost the immune responses to the HSV DNA vaccines. Plasmid DNA formulated with PBS was used as a control. Each tegument protein DNA vaccine induced strong humoral responses. Regardless of vaccine formulation, UL49 and UL47 elicited stronger cellular responses than did UL46. Poloxamer significantly boosted the cellular immune responses to the UL47 DNA vaccine, relative to the other vaccine formulations. VAXFECTIN adjuvant boosted by about two-fold the antibody responses to the UL46 and UL49 DNA vaccines.

The present invention provides a method for immunizing a vertebrate against herpes simplex virus, comprising obtaining a formulated polynucleotide, that is, a positively charged liposome containing an expressible polynucleotide coding for an immunogenic peptide, and introducing the formulated polynucleotide into a vertebrate, whereby the liposome is incorporated into a monocyte, a macrophage, or another cell, where an immunogenic translation product of the polynucleotide is formed, and the product is processed and presented by the cell in the context of the major histocompatibility complex, thereby eliciting an immune response against the immunogen. Again, the polynucleotide is DNA, although mRNA may also be used.

In another embodiment, there is provided a method for delivering a pharmaceutical or immunogenic polypeptide to the interior of a cell of a vertebrate in vivo comprising introducing an unformulated polynucleotide, that is, a preparation comprising a pharmaceutically acceptable injectable carrier and a polynucleotide operatively coding for the herpes simplex virus polypeptide, into the interstitial space of a tissue comprising the cell, whereby the polynucleotide is taken up into the interior of the cell and has an immunogenic or pharmacological effect on the vertebrate. Also provided is a method for introducing a polynucleotide into muscle cells in vivo, comprising providing a composition comprising a polynucleotide in a pharmaceutically acceptable carrier, and contacting the composition with muscle tissue of a vertebrate in vivo, whereby the polynucleotide is introduced into muscle cells of the tissue. In this embodiment, the carrier preferably is isotonic, hypotonic, or weakly hypertonic, and has a relatively low ionic strength, such as provided by a sucrose solution.

One particularly attractive aspect of the invention is a method for obtaining long term administration of a herpes simplex polypeptide to a vertebrate, comprising introducing an unformulated or formulated DNA sequence operatively coding for the polypeptide interstitially into tissue of the vertebrate, whereby cells of the tissue produce the polypeptide for at least one month or at least 3 months, more preferably at least 6 months. In this embodiment of the invention, the cells producing the polypeptide are nonproliferating cells, such as muscle cells.

Another method according to the invention is a method for obtaining transitory expression of a herpes simplex polypeptide in a vertebrate, comprising introducing unformulated or formulated mRNA sequence operatively coding for the polypeptide interstitially into tissue of the vertebrate, whereby cells of the tissue produce the polypeptide for less than about 20 days, usually less than about 10 days, and often less than 3 or 5 days. For many of the methods of the invention, administration into solid tissue is preferred.

One important aspect of the present invention is a method for treatment of genital herpes, comprising introducing a therapeutic amount of a composition comprising at least one polynucleotide operatively coding for gD, VP11/12, VP13/14 and/or VP22 in a pharmaceutically acceptable injectable carrier in vivo into muscle tissue of an animal suffering from genital herpes, whereby the polynucleotide is taken up into the cells and gD, VP11/12, VP13/14 and/or VP22 is produced in vivo. Preferably, the polynucleotide is a formulated polynucleotide and the composition is introduced interstitially into the muscle tissue; however, an unformulated polynucleotide is also contemplated.

The present invention also includes pharmaceutical products for all of the uses contemplated in the methods described herein. For example, there is a pharmaceutical product, comprising unformulated or formulated polynucleotide, operatively coding for a herpes simplex polypeptide, in physiologically acceptable administrate form, in a container.

In another embodiment, the invention provides a pharmaceutical product, comprising unformulated or formulated polynucleotide, operatively coding for a herpes simplex peptide, in solution in a physiologically acceptable injectable carrier and suitable for introduction interstitially into a tissue to cause cells of the tissue to express the polypeptide, and a container enclosing the solution. The peptide may be immunogenic and administration of the solution to a human may serve to vaccinate the human, or an animal. Similarly, the peptide may be therapeutic and administration of the solution to a vertebrate in need of therapy relating to the polypeptide will have a therapeutic effect.

Also provided by the present invention is a pharmaceutical product, comprising unformulated or formulated antisense polynucleotide, in solution in a physiologically acceptable injectable carrier and suitable for introduction interstitially into a tissue to cause cells of the tissue to take up the polynucleotide and provide a therapeutic effect, and a container enclosing the solution.

One particularly important aspect of the invention relates to a pharmaceutical product for treatment of genital herpes, comprising a sterile, pharmaceutically acceptable carrier, a pharmaceutically effective amount of a unformulated or formulated polynucleotide operatively coding for at least one gD, VP11/12, VP13/14 and/or VP22 protein in the carrier, and a container enclosing the carrier and the polynucleotide in sterile fashion. Preferably, the polynucleotide is DNA.

From yet another perspective, the invention includes a pharmaceutical product for use in supplying a herpes simplex polypeptide to a vertebrate, comprising a pharmaceutically effective amount of a unformulated or formulated polynucleotide operatively coding for either gD, VP11/12, VP13/14, VP22 or a combination thereof, a container enclosing the carrier and the polynucleotide in a sterile fashion, and means associated with the container for permitting transfer of the polynucleotide from the container to the interstitial space of a tissue, whereby cells of the tissue can take up and express the polynucleotide. The means for permitting such transfer can include a conventional septum that can be penetrated, e.g., by a needle. Alternatively, when the container is a syringe, the means may be considered to comprise the plunger of the syringe or a needle attached to the syringe. Containers used in the present invention will usually have at least 1, preferably at least 5 or 10, and more preferably at least 50 or 100 micrograms of polynucleotide, to provide one or more unit dosages. For many applications, the container will have at least 500 micrograms or 1 milligram, and often will contain at least 50 or 100 milligrams of polynucleotide.

Another aspect of the invention provides a pharmaceutical product for use in immunizing a vertebrate, comprising a pharmaceutically effective amount of an unformulated or formulated polynucleotide operatively coding for either gD, VP11/12, VP13/14, VP22 or a combination thereof, a sealed container enclosing the polynucleotide in a sterile fashion, and means associated with the container for permitting transfer of the polynucleotide from the container to the interstitial space of a tissue, whereby cells of the tissue can take up and express the polynucleotide.

Still another aspect of the present invention is the use of unformulated or formulated polynucleotide operatively coding for a physiologically active form of either gD, VP11/12, VP13/14, VP22 or a combination thereof, in the preparation of a pharmaceutical for introduction interstitially into tissue to cause cells comprising the tissue to produce the either gD, VP11/12, VP13/14, VP22 or a combination thereof for treatment of genital herpes.

The tissue into which the polynucleotide is introduced can be a persistent, non-dividing cell. The polynucleotide may be either a DNA or RNA sequence. When the polynucleotide is DNA, it can also be a DNA sequence which is itself non-replicating, but is inserted into a plasmid, and the plasmid further comprises a replicator. The DNA may be a sequence engineered so as not to integrate into the host cell genome. The polynucleotide sequences may code for a herpes simplex virus polypeptide which is either contained within the cells or secreted therefrom, or may comprise a sequence which directs the secretion of the peptide.

The DNA sequence may also include a promoter sequence. In one preferred embodiment, the DNA sequence includes a cell-specific promoter that permits substantial transcription of the DNA only in predetermined cells. The DNA may also code for a polymerase for transcribing the DNA, and may comprise recognition sites for the polymerase and the injectable preparation may include an initial quantity of the polymerase.

In many instances, it is preferred that the polynucleotide is translated for a limited period of time so that the polypeptide delivery is transitory. The polypeptide may advantageously be a therapeutic polypeptide, and may comprise an enzyme, a hormone, a lymphokine, a receptor, particularly a cell surface receptor, a regulatory protein, such as a growth factor or other regulatory agent, or any other protein or peptide that one desires to deliver to a cell in a living vertebrate and for which corresponding DNA or mRNA can be obtained.

In preferred embodiments, the polynucleotide is introduced into muscle tissue; in other embodiments the polynucleotide is incorporated into tissues of skin, brain, lung, liver, spleen or blood. The preparation is injected into the vertebrate by a variety of routes, which may be intradermally, subdermally, intrathecally, or intravenously, or it may be placed within cavities of the body. In a preferred embodiment, the polynucleotide is injected intramuscularly. In still other embodiments, the preparation comprising the polynucleotide is impressed into the skin. Transdermal administration is also contemplated, as is inhalation.

In one preferred embodiment, the polynucleotide is DNA coding for both a polypeptide and a polymerase for transcribing the DNA, and the DNA includes recognition sites for the polymerase and the injectable preparation further includes a means for providing an initial quantity of the polymerase in the cell. The initial quantity of polymerase may be physically present together with the DNA. Alternatively, it may be provided by including mRNA coding therefore, which mRNA is translated by the cell. In this embodiment of the invention, the DNA is preferably a plasmid. Preferably, the polymerase is phage T7 polymerase and the recognition site is a T7 origin of replication sequence.

In accordance with another aspect of the present invention, there is provided a method for immunizing a vertebrate, comprising the steps of obtaining a preparation comprising an expressible polynucleotide coding for an immunogenic translation product (that is, either gD, VP11/12, VP13/14, VP22 or a combination thereof), and introducing the preparation into a vertebrate wherein the translation product of the polynucleotide is formed by a cell of the vertebrate, which elicits an immune response against the herpes simplex virus immunogen. In one embodiment of the method, the injectable preparation comprises a pharmaceutically acceptable carrier containing an expressible polynucleotide coding for an immunogenic peptide, and on the introduction of the preparation into the vertebrate, the polynucleotide is incorporated into a cell of the vertebrate wherein an immunogenic translation product of the polynucleotide is formed, which elicits an immune response against the immunogen.

In an alternative embodiment, the preparation comprises one or more cells obtained from the vertebrate and transfected in vitro with the polynucleotide (that is, either, UL46, UL47, UL49, or US6 or a combination thereof), whereby the polynucleotide is incorporated into said cells, where an immunogenic translation product of the polynucleotide is formed, and whereby on the introduction of the preparation into the vertebrate, an immune response against the immunogen is elicited. In any of the embodiments of the invention, the immunogenic product may be secreted by the cells, or it may be presented by a cell of the vertebrate in the context of the major histocompatibility antigens, thereby eliciting an immune response against the immunogen. The method may be practiced using non-dividing, differentiated cells from the vertebrates, which cells may be lymphocytes, obtained from a blood sample; alternatively, it may be practiced using partially differentiated skin fibroblasts which are capable of dividing. In a preferred embodiment, the method is practiced by incorporating the polynucleotide coding for an immunogenic translation product into muscle tissue.

The method may be used to selectively elicit a humoral immune response, a cellular immune response, or a mixture of these. In embodiments wherein the cell expresses major histocompatibility complex of Class I, and the immunogenic peptide is presented in the context of the Class I complex, the immune response is cellular and comprises the production of cytotoxic T-cells.

In one such embodiment, the immunogenic peptide is associated with the HSV-2 virus and is presented in the context of Class I antigens, and stimulates cytotoxic T-cells which are capable of destroying cells infected with the virus. A cytotoxic T-cell response may also be produced according the method where the polynucleotide codes for either a truncated gD, VP11/12, VP13/14, VP22 or a combination thereof antigen lacking humoral epitopes.

In another embodiment, there is provided a method of immunizing a vertebrate, comprising obtaining a positively charged liposome containing an expressible polynucleotide coding for either gD, VP11/12, VP13/14, VP22 or a combination thereof, and introducing the liposome into a vertebrate, whereby the liposome is incorporated into a monocyte, a macrophage, or another cell, where an immunogenic translation product of the polynucleotide is formed, and the product is processed and presented by the cell in the context of the major histocompatibility complex, thereby eliciting an immune response against the immunogen. Again, the polynucleotide is preferably DNA, although mRNA may also be used. And as before, the method may be practiced without the liposome, utilizing just the polynucleotide in an injectable carrier.

The present invention is directed to enhancing the immune response of a vertebrate or mammal in need of protection against herpes simplex virus infection by administering in vivo, into a tissue of the vertebrate, at least one polynucleotide, wherein the polynucleotide comprises one or more nucleic acid fragments, where the one or more nucleic acid fragments are optionally fragments of codon-optimized coding regions operably encoding one or more herpes simplex virus polypeptides, or fragments, variants, or derivatives thereof. The present invention is further directed to enhancing the immune response of a vertebrate in need of protection against herpes simplex virus infection by administering, in vivo, into a tissue of the vertebrate, a polynucleotide described above plus at least one isolated herpes simplex virus polypeptide or a fragment, a variant, or derivative thereof. The isolated herpes simplex virus polypeptide can be, for example, a purified subunit, a recombinant protein, a viral vector expressing an isolated herpes simplex virus polypeptide, or can be an inactivated or attentuated herpes simplex virus, such as those present in conventional herpes simplex virus vaccines. According to either method, the polynucleotide is incorporated into the cells of the vertebrate in vivo, and an immunologically effective amount of an immunogenic epitope of the encoded herpes simplex virus polypeptide, or a fragment, variant, or derivative thereof, is produced in vivo. When utilized, an isolated herpes simplex virus polypeptide or a fragment, variant, or derivative thereof is also administered in an immunologically effective amount According to the present invention, the polynucleotide can be administered either prior to, at the same time (simultaneously), or subsequent to the administration of the isolated herpes simplex virus polypeptide. The herpes simplex virus polypeptide or fragment, variant, or derivative thereof encoded by the polynucleotide comprises at least one immunogenic epitope capable of eliciting an immune response to herpes simplex virus in a vertebrate. In addition, an isolated herpes simplex virus polypeptide or fragment, variant, or derivative thereof, when used, comprises at least one immunogenic epitope capable of eliciting an immune response in a vertebrate. The herpes simplex virus polypeptide or fragment, variant, or derivative thereof encoded by the polynucleotide can, but need not, be the same protein or fragment, variant, or derivative thereof as the isolated herpes simplex virus polypeptide which can be administered according to the method.

The polynucleotide of the invention can comprise a nucleic acid fragment, where the nucleic acid fragment is a fragment of a codon-optimized coding region operably encoding any herpes simplex virus polypeptide or fragment, variant, or derivative thereof, including, but not limited to, gD, VP11/12, VP13/14 and/or VP22 proteins or fragments, variants or derivatives thereof. A polynucleotide of the invention can also encode a derivative fusion protein, wherein two or more nucleic acid fragments, at least one of which encodes a herpes simplex virus polypeptide or fragment, variant, or derivative thereof, are joined in frame to encode a single polypeptide, such as, but not limited to, gD, VP11/12, VP13/14 and/or VP22. Additionally, a polynucleotide of the invention can further comprise a heterologous nucleic acid or nucleic acid fragment. Such heterologous nucleic acid or nucleic acid fragment may encode a heterologous polypeptide fused in frame with the polynucleotide encoding the herpes simplex virus polypeptide, e.g., a hepatitis B core protein or a secretory signal peptide. Preferably, the polynucleotide encodes a herpes simplex virus polypeptide or fragment, variant, or derivative thereof comprising at least one immunogenic epitope of herpes simplex virus, wherein the epitope elicits a B-cell (antibody) response, a T-cell (e.g., CTL) response, or both.

Similarly, the isolated herpes simplex virus polypeptide or fragment, variant, or derivative thereof to be delivered (either a recombinant protein, a purified subunit, or viral vector expressing an isolated herpes simplex virus polypeptide, or in the form of an inactivated herpes simplex virus vaccine) can be any isolated herpes simplex virus polypeptide or fragment, variant, or derivative thereof, including but not limited to the gD, VP11/12, VP13/14 and/or VP22 proteins or fragments, variants or derivatives thereof. In certain embodiments, a derivative protein can be a fusion protein. In other embodiments, the isolated herpes simplex virus polypeptide or fragment, variant, or derivative thereof can be fused to a heterologous protein, e.g., a secretory signal peptide or the hepatitis B virus core protein.

Nucleic acids and fragments thereof of the present invention can be altered from their native state in one or more of the following ways. First, a nucleic acid or fragment thereof which encodes a herpes simplex virus polypeptide or fragment, variant, or derivative thereof can be part or all of a codon-optimized coding region, optimized according to codon usage in the animal in which the vaccine is to be delivered. In addition, a nucleic acid or fragment thereof which encodes a herpes simplex virus polypeptide can be a fragment which encodes only a portion of a full-length polypeptide, and/or can be mutated so as to, for example, remove from the encoded polypeptide non-desired protein motifs present in the encoded polypeptide or virulence factors associated with the encoded polypeptide. For example, the nucleic acid sequence could be mutated so as not to encode a membrane anchoring region that would prevent release of the polypeptide from the cell. Upon delivery, the polynucleotide of the invention is incorporated into the cells of the vertebrate in vivo, and a prophylactically or therapeutically effective amount of an immunologic epitope of a herpes simplex virus is produced in vivo.

The invention further provides immunogenic compositions comprising at least one polynucleotide, wherein the polynucleotide comprises one or more nucleic acid fragments, where each nucleic acid fragment is a fragment of a codon-optimized coding region encoding a herpes simplex virus polypeptide or a fragment, a variant, or a derivative thereof; and immunogenic compositions comprising a polynucleotide as described above and at least one isolated herpes simplex virus polypeptide or a fragment, a variant, or derivative thereof. Such compositions can further comprise, for example, carriers; excipients, transfection facilitating agents, and/or adjuvants as described herein.

The immunogenic compositions comprising a polynucleotide and an isolated herpes simplex virus polypeptide or fragment, variant, or derivative thereof as described above can be provided so that the polynucleotide and protein formulation are administered separately, for example, when the polynucleotide portion of the composition is administered prior (or subsequent) to the isolated herpes simplex virus polypeptide portion of the composition. Alternatively, immunogenic compositions comprising the polynucleotide and the isolated herpes simplex virus polypeptide or fragment, variant, or derivative thereof can be provided as a single formulation, comprising both the polynucleotide and the protein, for example, when the polynucleotide and the protein are administered simultaneously. In another alternative, the polynucleotide portion of the composition and the isolated herpes simplex virus polypeptide portion of the composition can be provided simultaneously, but in separate formulations.

Compositions comprising at least one polynucleotide comprising one or more nucleic acid fragments, where each nucleic acid fragment is optionally a fragment of a codon-optimized coding region operably encoding a herpes simplex virus polypeptide or fragment, variant, or derivative thereof together with and one or more isolated herpes simplex virus polypeptides or fragments, variants or derivatives thereof (as either a recombinant protein, a purified subunit, a viral vector expressing the protein, or in the form of an inactivated or attenuated herpes simplex virus vaccine) will be referred to herein as "combinatorial polynucleotide (e.g., DNA) vaccine compositions" or "single formulation heterologous prime-boost vaccine compositions."

The compositions of the invention can be univalent, bivalent, trivalent or multivalent. A univalent composition will comprise only one polynucleotide comprising a nucleic acid fragment, where the nucleic acid fragment is optionally a fragment of a codon-optimized coding region encoding a herpes simplex virus polypeptide or a fragment, variant, or derivative thereof, and optionally the same herpes simplex virus polypeptide or a fragment, variant, or derivative thereof in isolated form. In a single formulation heterologous prime-boost vaccine composition, a univalent composition can include a polynucleotide comprising a nucleic acid fragment, where the nucleic acid fragment is optionally a fragment of a codon-optimized coding region encoding a herpes simplex virus polypeptide or a fragment, variant, or derivative thereof and an isolated polypeptide having the same antigenic region as the polynucleotide. A bivalent composition will comprise, either in polynucleotide or protein form, two different herpes simplex virus polypeptides or fragments, variants, or derivatives thereof, each capable of eliciting an immune response. The polynucleotide(s) of the composition can encode two herpes simplex virus polypeptides or alternatively, the polynucleotide can encode only one herpes simplex virus polypeptide and the second herpes simplex virus polypeptide would be provided by an isolated herpes simplex virus polypeptide of the invention as in, for example, a single formulation heterologous prime-boost vaccine composition. In the case where both herpes simplex virus polypeptides of a bivalent composition are delivered in polynucleotide form, the nucleic acid fragments operably encoding those herpes simplex virus polypeptides need not be on the same polynucleotide, but can be on two different polynucleotides. A trivalent or further multivalent composition will comprise three herpes simplex virus polypeptides or fragments, variants or derivatives thereof, either in isolated form or encoded by one or more polynucleotides of the invention.

The present invention further provides plasmids and other polynucleotide constructs for delivery of nucleic acid fragments of the invention to a vertebrate, e.g., a human, which provide expression of herpes simplex virus polypeptides, or fragments, variants, or derivatives thereof. The present invention further provides carriers, excipients, transfection-facilitating agents, immunogenicity-enhancing agents, e.g., adjuvants, or other agent or agents to enhance the transfection, expression or efficacy of the administered gene and its gene product.

In one embodiment, a multivalent composition comprises a single polynucleotide, e.g., plasmid, comprising one or more nucleic acid regions operably encoding herpes simplex virus polypeptides or fragments, variants, or derivatives thereof. Reducing the number of polynucleotides, e.g., plasmids in the compositions of the invention can have significant impacts on the manufacture and release of product, thereby reducing the costs associated with manufacturing the compositions. There are a number of approaches to include more than one expressed antigen coding sequence on a single plasmid. These include, for example, the use of Internal Ribosome Entry Site (IRES) sequences, dual promoters/expression cassettes, and fusion proteins.

The invention also provides methods for enhancing the immune response of a vertebrate to herpes simplex virus infection by administering to the tissues of a vertebrate one or more polynucleotides each comprising one or more nucleic acid fragments, where each nucleic acid fragment is optionally a fragment of a codon-optimized coding region encoding a herpes simplex virus polypeptide or fragment, variant, or derivative thereof; and optionally administering to the tissues of the vertebrate one or more isolated herpes simplex virus polypeptides, or fragments, variants, or derivatives thereof. The isolated herpes simplex virus polypeptide can be administered prior to, at the same time (simultaneously), or subsequent to administration of the polynucleotides encoding herpes simplex virus polypeptides.

In addition, the invention provides consensus amino acid sequences for herpes simplex virus polypeptides, or fragments, variants or derivatives thereof, including, but not limited to, the gD, VP11/12, VP13/14 and/or VP22 proteins or fragments, variants or derivatives thereof. Polynucleotides which encode the consensus polypeptides or fragments, variants or derivatives thereof, are also embodied in this invention. Such polynucleotides can be obtained by known methods, for example by backtranslation of the amino acid sequence and PCR synthesis of the corresponding polynucleotide as described below.

BRIEF DESCRIPTION OF THE DRAWINGS

The accompanying drawings, which are incorporated in and form a part of the specifications, illustrate the preferred embodiments of the present invention, and together with the description serve to explain the principles of the invention.

FIG. 22C is same mouse, DMSO control. FIG. 22B is naive mouse splenocytes stimulated with UL47 CD8 epitope peptide pool.

FIGS. 24A through 24C establish that tegument vaccines are beneficial in an HSV-2 intravaginal challenge model. Groups of 10 mice were challenged with $50 \times LD_{50}$ of HSV-2 strain 186 and observed for 14 days. FIG. 24A: mortality. FIG. 24B: mean intravaginal HSV-2 DNA copy numbers. FIG. 24C: Clinical scores in surviving animals.

DETAILED DESCRIPTION OF THE INVENTION

Figure 1:
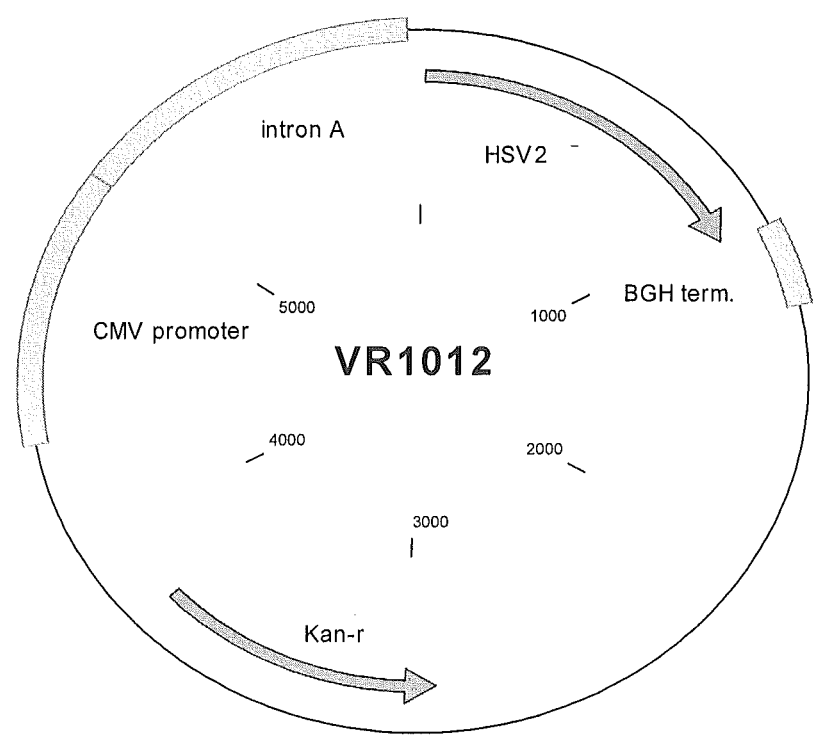
FIG. 1 is a schematic representation of the VR1012 DNA vaccine backbone or plasmid.
Figure 2B:
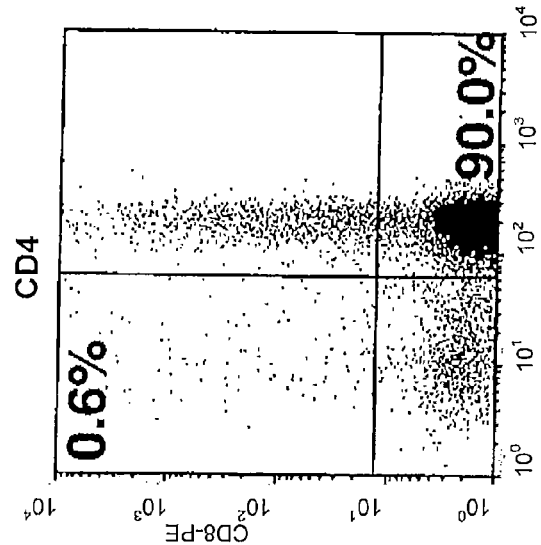
FIGS. 2A through 2C demonstrate sample data for CD4 and CD8 enrichment by negative selection. Fractions were stained with labeled monoclonal antibody (mAb) and analyzed by flow cytometry.
Figure 2C:
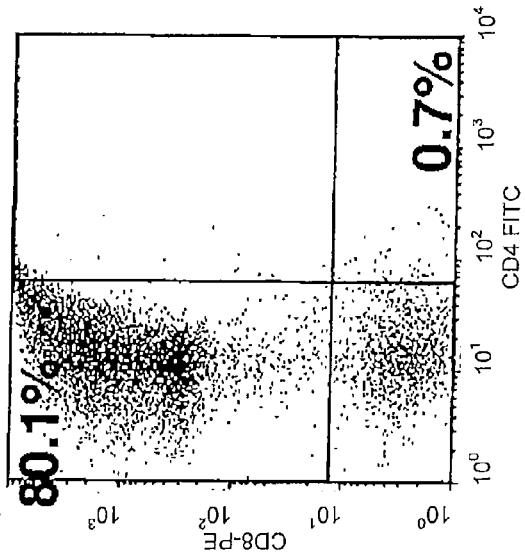
Figure 2A:
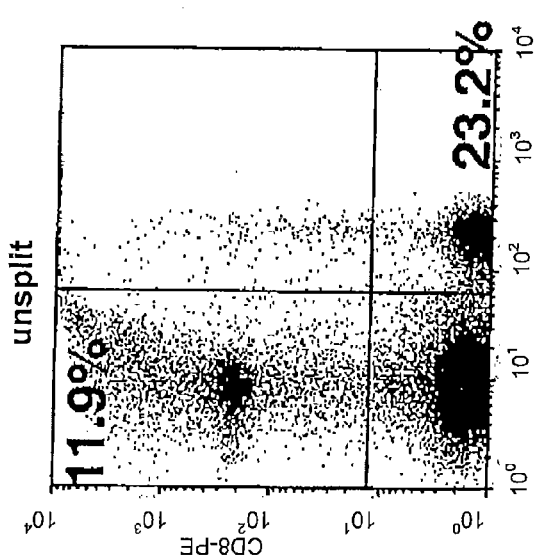
Figure 3B:
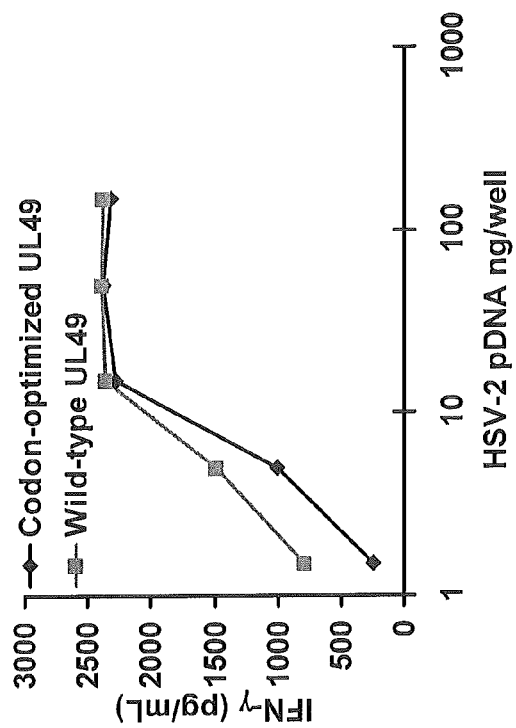
FIGS. 3A through 3C illustrate comparison of codon-optimized and wild-type plasmids encoding full-length HSV-2 genes for activation of cloned CD8+ T-cells specific for HSV-2 epitopes. Cos-7 cells were transfected with either ("codon optimized") vaccines, or wild-type (strain HG52) plasmids, and 50 ng/well from 2-3 immunized mice and tested by IFN-γ ELISPOT with 13-amino acid and shorter peptides. Peptides were titrated in 10-fold dilutions from 10 μM to $10^{-6}$ μM. In general, responder cells reacting to CD8+ epitopes showed higher avidity than cells reacting to CD4+ epitopes. In some cases, strong ELISPOT responses were at $10^{-12}$ M. The amino acid positions are designated for each peptide.
Figure 3A:
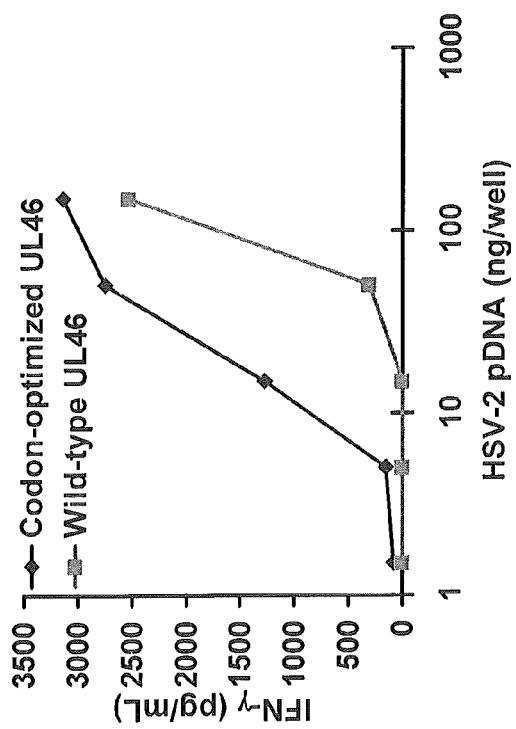
Figure 3C:
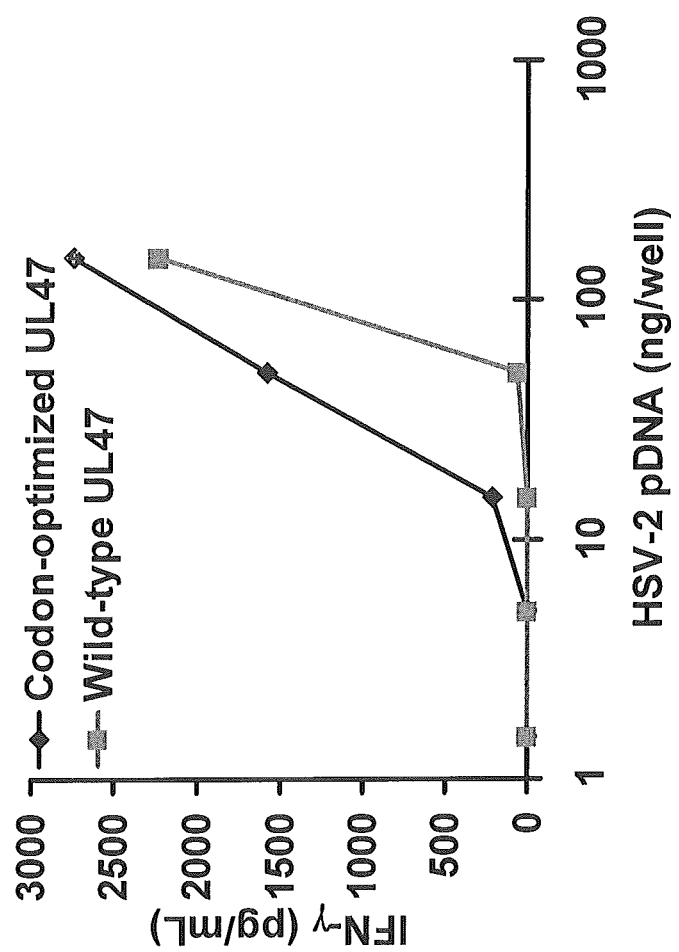

The practice of the present invention requires obtaining a formulated or unformulated polynucleotide operatively coding for a polypeptide for incorporation into vertebrate cells. A polynucleotide operatively codes for a polypeptide when it has all the genetic information necessary for expression by a target cell, such as promoters and the like. These polynucleotides can be administered to the vertebrate by any method that delivers injectable materials to cells of the vertebrate, such as by injection into the interstitial space of tissues such as muscles or skin, introduction into the circulation or into body cavities or by inhalation or insufflation. A formulated polynucleotide is injected or otherwise delivered to a vertebrate with a pharmaceutically acceptable lipid or liposome, for example, when the polynucleotide is to be associated with a liposome, it requires a material for forming liposomes, preferably cationic or positively charged liposomes, and requires that liposomal preparations be made from these materials. With the liposomal material in hand, the polynucleotide may advantageously be used to transfect cells in vitro for use as immunizing agents, or to administer polynucleotides into bodily sites where liposomes may be taken up by phagocytic cells.

Alternatively an unformulated polynucleotide is injected or otherwise delivered to the animal with a pharmaceutically acceptable liquid carrier. For all applications, the liquid carrier is aqueous or partly aqueous, comprising sterile, pyrogen-free water. The pH of the preparation is suitably adjusted and buffered.

Polynucleotide Materials

The formulated or unformulated polynucleotide materials used according to the methods of the invention comprise DNA and RNA sequences or DNA and RNA sequences coding for either gD, VP11/12, VP13/14, VP22 or a combination thereof. (See U.S. Pat. Nos. 6,413,518; 6,855,317; and 7,037,509; and U.S. Patent Publication US2006/0216304). These polynucleotide sequences are unformulated in the sense that they are free from any delivery vehicle that can act to facilitate entry into the cell, for example, the polynucleotide sequences are free of viral sequences, particularly any viral particles which may carry genetic information. Alternatively, these polynucleotide sequences are formulated with a material which promotes transfection, such as liposomal formulations, charged lipids such as, but not limited to, LIPOFECTIN reagent (cationic lipid N-[1-(2,3-dioleyloxy)propyl]-n,n,n-trimethylammonium chloride (DOTMA) and dioleoyl phophotidylethanolamine (DOPE)), or VAXFECTIN adjuvant disclosed in U.S. Pat. No. 7,105,574.

The DNA sequences used in these methods can be those sequences which do not integrate into the genome of the host cell. These may be non-replicating DNA sequences, or specific replicating sequences genetically engineered to lack the genome-integration ability.

The polynucleotide sequences of the invention are DNA or RNA sequences of either HSV-2 proteins gD, VP11/12, VP13/14, VP22 or a combination thereof. The polynucleotides of the invention also can code for therapeutic polypeptides. A polypeptide is understood to be any translation product of a polynucleotide regardless of size, and whether glycosylated or not. Therapeutic polypeptides include as a primary example, those polypeptides that can compensate for defective or deficient species in an animal, or those that act through toxic effects to limit or remove harmful cells from the body. Polynucleotide sequences of the invention preferably code for either gD, VP11/12, VP13/14, VP22 or a combination thereof, and these sequences may be used in association with other polynucleotide sequences coding for regulatory proteins that control the expression of these polypeptides. The regulatory protein can act by binding to genomic DNA so as to regulate its transcription; alternatively, it can act by binding to messenger RNA to increase or decrease its stability or translation efficiency.

Where the polynucleotide is DNA, promoters suitable for use in various vertebrate systems are well known. For example, for use in murine systems, suitable strong promoters include RSV LTR, MPSV LTR, SV40 IEP, and metallothionein promoter. In humans, on the other hand, promoters such as CMV IEP may advantageously be used. All forms of DNA, whether replicating or non-replicating, which do not become integrated into the genome, and which are expressible, are within the methods contemplated by the invention.

With the availability of automated nucleic acid synthesis equipment, both DNA and RNA can be synthesized directly when the nucleotide sequence is known or by a combination of PCR cloning and fermentation. Moreover, when the sequence of the desired polypeptide is known, a suitable coding sequence for the polynucleotide can be inferred.

When the polynucleotide is mRNA, it can be readily prepared from the corresponding DNA in vitro. For example, conventional techniques utilize phage RNA polymerases SP6, T3, or T7 to prepare mRNA from DNA templates in the presence of the individual ribonucleoside triphosphates. An appropriate phage promoter, such as a T7 origin of replication site is placed in the template DNA immediately upstream of the gene to be transcribed. Systems utilizing T7 in this manner are well known, and are described in the literature, e.g., in Current Protocols in Molecular Biology, §3.8 (vol. 1 1988).

DNA and mRNA Vaccines

According to the methods of the invention, both expressible DNA and mRNA can be delivered to cells to form therein a polypeptide translation product. If the nucleic acids contain the proper control sequences, they will direct the synthesis of relatively large amounts of either gD, VP11/12, VP13/14, VP22 or a combination thereof. When the DNA and mRNA delivered to the cells code either gD, VP11/12, VP13/14, VP22 or a combination thereof, the methods can be applied to achieve improved and more effective immunity. Since the immune systems of all vertebrates operate similarly, the applications described can be implemented in all vertebrate systems, comprising mammalian and avian species, as well as fish.

The methods of the invention may be applied by direct injection of the polynucleotide into cells of the animal in vivo, or by in vitro transfection of some of the animal cells which are then re-introduced into the animal body.

The polynucleotides may be delivered to various cells of the animal body, including muscle, skin, brain, lung, liver, spleen, or to the cells of the blood. Delivery of the polynucleotides directly in vivo is preferably to the cells of muscle or skin. The polynucleotides may be injected into muscle or skin using an injection syringe. They may also be delivered into muscle or skin using a vaccine gun.

It has recently been shown that cationic lipids can be used to facilitate the transfection of cells in certain applications, particularly in vitro transfection. Cationic lipid based transfection technology is preferred over other methods; it is more efficient and convenient than calcium phosphate, DEAE dextran or electroporation methods, and retrovirus mediated transfection, as discussed previously, can lead to integration events in the host cell genome that result in oncogene activation or other undesirable consequences. The knowledge that cationic lipid technology works with messenger RNA is a further advantage to this approach, because RNA is turned over rapidly by intracellular nucleases and is not integrated into the host genome. A transfection system that results in high levels of reversible expression is preferred to alternative methodology requiring selection and expansion of stably transformed clones because many of the desired primary target cells do not rapidly divide in culture.

The ability to transfect cells at high efficiency with cationic liposomes provides an alternative method for immunization. The gene for an antigen is introduced into cells which have been removed from an animal. The transfected cells, now expressing the antigen, are reinjected into the animal where the immune system can respond to the (now) endogenous antigen. The process can possibly be enhanced by coinjection of either an adjuvant or lymphokines to further stimulate the lymphoid cells.

Vaccination with nucleic acids containing either gD, VP11/12, VP13/14, VP22 or a combination thereof provides a way to specifically target the cellular immune response. Cells expressing at least one gD, VP11/12, VP13/14, and/or VP22 proteins which are secreted will enter the normal antigen processing pathways and produce both a humoral and cytotoxic response. The response to proteins which are not secreted is more selective. Non-secreted proteins synthesized in cells expressing only class I MHC molecules are expected to produce only a cytotoxic vaccination. Expression of the same antigen in cells bearing both class I and class II molecules may produce a more vigorous response by stimulating both cytotoxic and helper T cells. Enhancement of the immune response may also be possible by injecting the gene for either gD, VP11/12, VP13/14, VP22 or a combination thereof along with a peptide fragment of the protein. The antigen is presented via class I MHC molecules to the cellular immune system while the peptide is presented via class II MHC molecules to stimulate helper T cells. In any case, this method provides a way to stimulate and modulate the immune response in a way which has not previously been possible.

Liposome-Forming Materials

Liposomes are unilamellar or multilamellar vesicles, having a membrane portion formed of lipophilic material and an interior aqueous portion. The aqueous portion is used in the present invention to contain the polynucleotide material to be delivered to the target cell. It is preferred that the liposome forming materials used herein have a cationic group, such as a quaternary ammonium group, and one or more lipophilic groups, such as saturated or unsaturated alkyl groups having from about 6 to about 30 carbon atoms. One group of suitable materials is described in European Patent Publication No. 0187702 and is incorporated herein by reference. These compounds may be prepared as detailed in the above-identified patent application; alternatively, at least one of these compounds, N-(2,3-di-(9-(Z)-octadecenyloxy))-prop-1-yl-N,N, N-trimethylammonium chloride (DOTMA), is commercially available from Bethesda Research Laboratories (BRL), Gaithersburg, Md. 20877, USA.

Moreover, many suitable liposome-forming cationic lipid compounds are described in the literature. See, e.g., L. Stamatatos, et al., *Biochemistry,* 27:3917-3925 (1988); H. Eibl, et al, *Biophysical Chemistry,* 10:261-271 (1979).

Liposome Preparation

Suitable liposomes for use in the present invention are commercially available. DOTMA liposomes, for example, are available under the trademark Lipofectin from Bethesda Research Labs, Gaithersburg, Md.

Alternatively, liposomes can be prepared from readily-available or freshly synthesized starting materials of the type previously described. Preparation of DOTMA liposomes is explained in the literature, see, e.g., p. Felgner, et al., *Proc. Nat'l Acad. Sci. USA,* 84:7413-7417. Similar methods can be used to prepare liposomes from other cationic lipid materials. Moreover, conventional liposome forming materials can be used to prepare liposomes having negative charge or neutral charge. Such materials include phosphatidylcholine, cholesterol, phosphatidyl-ethanolamine, and the like. These materials can also advantageously be mixed with the DOTAP or DOTMA starting materials in ratios from 0% to about 75%.

Conventional methods can be used to prepare other, non-cationic liposomes. These liposomes do not fuse with cell walls as readily as cationic liposomes. However, they are taken up by macrophages in vivo, and are thus particularly effective for delivery of polynucleotide to these cells. For example, commercially dioleoyl-phosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15° C. Alternatively, negatively charged vesicles can be prepared without sonication to produce multilamellar vesicles or by extrusion through nucleopore membranes to produce unilamellar vesicles of discrete size. Other methods are known and available to those of skill in the art.

Therapeutic Formulations Polynucleotide Salts

Administration of pharmaceutically acceptable salts of the polynucleotides described herein is included within the scope of the invention. Such salts may be prepared from pharmaceutically acceptable non-toxic bases including organic bases and inorganic bases. Salts derived from inorganic bases include sodium, potassium, lithium, ammonium, calcium, magnesium, and the like. Salts derived from pharmaceutically acceptable organic non-toxic bases include salts of primary, secondary, and tertiary amines, basic amino acids, and the like. For a helpful discussion of pharmaceutical salts, see S. M. Berge et al., Journal of Pharmaceutical Sciences 66:1-19 (1977).

Polynucleotides for injection, a preferred route of delivery, may be prepared in unit dosage form in ampules, or in multidose containers. The polynucleotides may be present in such forms as suspensions, solutions, or emulsions in oily or preferably aqueous vehicles. Alternatively, the polynucleotide salt may be in lyophilized form for reconstitution, at the time of delivery, with a suitable vehicle, such as sterile pyrogen-free water. Both liquid as well as lyophilized forms that are to be reconstituted will comprise agents, preferably buffers, in amounts necessary to suitably adjust the pH of the injected solution. For any parenteral use, particularly if the formulation is to be administered intravenously, the total concentration of solutes should be controlled to make the preparation isotonic, hypotonic, or weakly hypertonic. Nonionic materials, such as sugars, are preferred for adjusting tonicity, and sucrose is particularly preferred. Any of these forms may further comprise suitable formulatory agents, such as starch or sugar, glycerol or saline. The compositions per unit dosage, whether liquid or solid, may contain from 0.1% to 99% of polynucleotide material.

The units dosage ampules or multidose containers, in which the polynucleotides are packaged prior to use, may comprise an hermetically sealed container enclosing an amount of polynucleotide or solution containing a polynucleotide suitable for a pharmaceutically effective dose thereof, or multiples of an effective dose. The polynucleotide is packaged as a sterile formulation, and the hermetically sealed container is designed to preserve sterility of the formulation until use.

The container in which the polynucleotide is packaged is labeled, and the label bears a notice in the form prescribed by a governmental agency, for example the Food and Drug Administration, which notice is reflective of approval by the agency under Federal law, of the manufacture, use, or sale of the polynucleotide material therein for human administration.

Federal law requires that the use of pharmaceutical agents in the therapy of humans be approved by an agency of the Federal government. Responsibility for enforcement is the responsibility of the Food and Drug Administration, which issues appropriate regulations for securing such approval, detailed in 21 U.S.C. §§301-392. Regulation for biologic material, comprising products made from the tissues of animals is provided under 42 U.S.C. §262. Similar approval is required by most foreign countries. Regulations vary from country to country, but the individual procedures are well known to those in the art.

Dosage and Route of Administration

The dosage to be administered depends to a large extent on the condition and size of the subject being treated as well as the frequency of treatment and the route of administration. Regimens for continuing therapy, including dose and frequency may be guided by the initial response and clinical judgment. The parenteral route of injection into the interstitial space of tissues is preferred, although other parenteral routes, such as inhalation of an aerosol formulation, may be required in specific administration, as for example to the mucous membranes of the nose, throat, bronchial tissues or lungs.

In preferred protocols, a formulation comprising the naked polynucleotide in an aqueous carrier is injected into tissue in amounts of from 10 µl per site to about 1 ml per site. The concentration of polynucleotide in the formulation is from about 0.1 µg/ml to about 20 mg/ml.

The present invention is directed to compositions and methods for enhancing the immune response of a vertebrate in need of protection against herpes simplex virus infection by administering in vivo, into a tissue of a vertebrate, at least one polynucleotide comprising one or more nucleic acid fragments, where each nucleic acid fragment is optionally a fragment of a codon-optimized coding region operably encoding a herpes simplex virus polypeptide, or a fragment, variant, or derivative thereof in cells of the vertebrate in need of protection. The present invention is also directed to administering in vivo, into a tissue of the vertebrate the above described polynucleotide and at least one isolated herpes simplex virus polypeptide, or a fragment, variant, or derivative thereof. The isolated herpes simplex virus polypeptide or fragment, variant, or derivative thereof can be, for example, a recombinant protein, a purified subunit protein, a protein expressed and carried by a heterologous live or inactivated or attenuated viral vector expressing the protein, or can be an inactivated herpes simplex virus, such as those present in conventional, commercially available, inactivated herpes simplex virus vaccines. According to either method, the polynucleotide is incorporated into the cells of the vertebrate in vivo, and an immunologically effective amount of the herpes simplex protein, or fragment or variant encoded by the polynucleotide is produced in vivo. The isolated protein or fragment, variant, or derivative thereof is also administered in an immunologically effective amount. The polynucleotide can be administered to the vertebrate in need thereof either prior to, at the same time (simultaneously), or subsequent to the administration of the isolated herpes simplex virus polypeptide or fragment, variant, or derivative thereof.

Non-limiting examples of herpes simplex virus polypeptides within the scope of the invention include, but are not limited to, gD, VP11/12, VP13/14 and/or VP22 polypeptides, and fragments, derivatives, and variants thereof. Nucleotide and amino acid sequences of herpes simplex virus polypeptides from a wide variety of herpes simplex virus types and subtypes are known in the art.

The present invention also provides vaccine compositions and methods for delivery of herpes simplex virus coding sequences to a vertebrate with optimal expression and safety conferred through codon optimization and/or other manipulations. These vaccine compositions are prepared and administered in such a manner that the encoded gene products are optimally expressed in the vertebrate of interest. As a result, these compositions and methods are useful in stimulating an immune response against herpes simplex virus infection. Also included in the invention are expression systems, delivery systems, and codon-optimized herpes simplex virus coding regions.

In a specific embodiment, the invention provides combinatorial polynucleotide (e.g., DNA) vaccines which combine both a polynucleotide vaccine and polypeptide (e.g., either a recombinant protein, a purified subunit protein, a viral vector expressing an isolated herpes simplex virus polypeptide, or in the form of an inactivated or attenuated herpes simplex virus vaccine) vaccine in a single formulation. The single formulation comprises a herpes simplex virus polypeptide-encoding polynucleotide vaccine as described herein, and optionally, an effective amount of a desired isolated herpes simplex virus polypeptide or fragment, variant, or derivative thereof. The polypeptide may exist in any form, for example, a recombinant protein, a purified subunit protein, a viral vector expressing an isolated herpes simplex virus polypeptide, or in the form of an inactivated or attenuated herpes simplex virus vaccine. The herpes simplex virus polypeptide or fragment, variant, or derivative thereof encoded by the polynucleotide vaccine may be identical to the isolated herpes simplex virus polypeptide or fragment, variant, or derivative thereof. Alternatively, the herpes simplex virus polypeptide or fragment, variant, or derivative thereof encoded by the polynucleotide may be different from the isolated herpes simplex virus polypeptide or fragment, variant, or derivative thereof.

It is to be noted that the term "a" or "an" entity refers to one or more of that entity, for example, "a polynucleotide," is understood to represent one or more polynucleotides. As such, the terms "a" (or "an"), "one or more," and "at least one" can be used interchangeably herein.

The term "polynucleotide" is intended to encompass a singular nucleic acid or nucleic acid fragment as well as plural nucleic acids or nucleic acid fragments, and refers to an isolated molecule or construct, e.g., a virus genome (e.g., a non-infectious viral genome), messenger RNA (mRNA), plasmid DNA (pDNA), or derivatives of pDNA (e.g., minicircles as described in (Darquet, A-M et al., Gene Therapy 4:1341-1349 (1997)) comprising a polynucleotide. A polynucleotide may comprise a conventional phosphodiester bond or a non-conventional bond (e.g., an amide bond, such as found in peptide nucleic acids (PNA)).

The terms "nucleic acid" or "nucleic acid fragment" refer to any one or more nucleic acid segments, e.g., DNA or RNA fragments, present in a polynucleotide or construct. A nucleic acid or fragment thereof may be provided in linear (e.g., mRNA) or circular (e.g., plasmid) form as well as double-stranded or single-stranded forms. By "isolated" nucleic acid or polynucleotide is intended a nucleic acid molecule, DNA or RNA, which has been removed from its native environment. For example, a recombinant polynucleotide contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of the polynucleotides of the present invention. Isolated polynucleotides or nucleic acids according to the present invention further include such molecules produced synthetically.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, and the like, are not part of a coding region. Two or more nucleic acids or nucleic acid fragments of the present invention can be present in a single polynucleotide construct, e.g., on a single plasmid, or in separate polynucleotide constructs, e.g., on separate (different) plasmids. Furthermore, any nucleic acid or nucleic acid fragment may encode a single herpes simplex virus polypeptide or fragment, derivative, or variant thereof, e.g., or may encode more than one polypeptide, e.g., a nucleic acid may encode two or more polypeptides. In addition, a nucleic acid may include a regulatory element such as a promoter, ribosome binding site, or a transcription terminator, or may encode heterologous coding regions fused to the herpes simplex virus coding region, e.g., specialized elements or motifs, such as a secretory signal peptide or a heterologous functional domain.

The terms "fragment," "variant," "derivative" and "analog" when referring to herpes simplex virus polypeptides of the present invention include any polypeptides which retain at least some of the immunogenicity or antigenicity of the corresponding native polypeptide. Fragments of herpes simplex virus polypeptides of the present invention include proteolytic fragments, deletion fragments and in particular, fragments of herpes simplex virus polypeptides which exhibit increased secretion from the cell or higher immunogenicity or reduced pathogenicity when delivered to an animal. Polypeptide fragments further include any portion of the polypeptide which comprises an antigenic or immunogenic epitope of the native polypeptide, including linear as well as three-dimensional epitopes. Variants of herpes simplex virus polypeptides of the present invention include fragments as described above, and also polypeptides with altered amino acid sequences due to amino acid substitutions, deletions, or insertions. Variants may occur naturally, such as an allelic variant. By an "allelic variant" is intended alternate forms of a gene occupying a given locus on a chromosome or genome of an organism or virus. Genes II, Lewin, B., ed., John Wiley & Sons, New York (1985). For example, as used herein, variations in a given gene product. When referring to herpes simplex virus gD, VP11/12, VP13/14 and/or VP22 proteins, each such protein is a "variant," in that native herpes simplex virus strains are distinguished by the type of proteins encoded by the virus. However, within a single gD, VP11/12, VP13/14 and/or VP22 variant type, further naturally or non-naturally occurring variations such as amino acid deletions, insertions or substitutions may occur. Non-naturally occurring variants may be produced using art-known mutagenesis techniques. Variant polypeptides may comprise conservative or non-conservative amino acid substitutions, deletions or additions. Derivatives of herpes simplex virus polypeptides of the present invention, are polypeptides which have been altered so as to exhibit additional features not found on the native polypeptide. Examples include fusion proteins. An analog is another form of a herpes simplex virus polypeptide of the present invention. An example is a proprotein which can be activated by cleavage of the proprotein to produce an active mature polypeptide.

The terms "infectious polynucleotide" or "infectious nucleic acid" are intended to encompass isolated viral polynucleotides and/or nucleic acids which are solely sufficient to mediate the synthesis of complete infectious virus particles upon uptake by permissive cells. Thus, "infectious nucleic acids" do not require pre-synthesized copies of any of the polypeptides it encodes, e.g., viral replicases, in order to initiate its replication cycle in a permissive host cell.

The terms "non-infectious polynucleotide" or "non-infectious nucleic acid" as defined herein are polynucleotides or nucleic acids which cannot, without additional added materials, e.g., polypeptides, mediate the synthesis of complete infectious virus particles upon uptake by permissive cells. An infectious polynucleotide or nucleic acid is not made "non-infectious" simply because it is taken up by a non-permissive cell. For example, an infectious viral polynucleotide from a virus with limited host range is infectious if it is capable of mediating the synthesis of complete infectious virus particles when taken up by cells derived from a permissive host (i.e., a host permissive for the virus itself). The fact that uptake by cells derived from a non-permissive host does not result in the synthesis of complete infectious virus particles does not make the nucleic acid "non-infectious." In other words, the term is not qualified by the nature of the host cell, the tissue type, or the species taking up the polynucleotide or nucleic acid fragment.

In some cases, an isolated infectious polynucleotide or nucleic acid may produce fully-infectious virus particles in a host cell population which lacks receptors for the virus particles, i.e., is non-permissive for virus entry. Thus viruses produced will not infect surrounding cells. However, if the supernatant containing the virus particles is transferred to cells which are permissive for the virus, infection will take place.

The terms "replicating polynucleotide" or "replicating nucleic acid" are meant to encompass those polynucleotides and/or nucleic acids which, upon being taken up by a permissive host cell, are capable of producing multiple, e.g., one or more copies of the same polynucleotide or nucleic acid. Infectious polynucleotides and nucleic acids are a subset of replicating polynucleotides and nucleic acids; the terms are not synonymous. For example, a defective virus genome lacking the genes for virus coat proteins may replicate, e.g., produce multiple copies of itself, but is NOT infectious because it is incapable of mediating the synthesis of complete infectious virus particles unless the coat proteins, or another nucleic acid encoding the coat proteins, are exogenously provided.

In certain embodiments, the polynucleotide, nucleic acid, or nucleic acid fragment is DNA. In the case of DNA, a polynucleotide comprising a nucleic acid which encodes a polypeptide normally also comprises a promoter and/or other transcription or translation control elements operably associated with the polypeptide-encoding nucleic acid fragment. An operable association is when a nucleic acid fragment encoding a gene product, e.g., a polypeptide, is associated with one or more regulatory sequences in such a way as to place expression of the gene product under the influence or control of the regulatory sequence(s). Two DNA fragments (such as a polypeptide-encoding nucleic acid fragment and a promoter associated with the 5' end of the nucleic acid fragment) are "operably associated" if induction of promoter function results in the transcription of mRNA encoding the desired gene product and if the nature of the linkage between the two DNA fragments does not (1) result in the introduction of a frame-shift mutation, (2) interfere with the ability of the expression regulatory sequences to direct the expression of the gene product, or (3) interfere with the ability of the DNA template to be transcribed. Thus, a promoter region would be operably associated with a nucleic acid fragment encoding a polypeptide if the promoter was capable of effecting transcription of that nucleic acid fragment. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, elements from picornaviruses (particularly an internal ribosome entry site, or IRES, also referred to as a CITE sequence).

A DNA polynucleotide of the present invention may be a circular or linearized plasmid or vector, or other linear DNA which may also be non-infectious and nonintegrating (i.e., does not integrate into the genome of vertebrate cells). A linearized plasmid is a plasmid that was previously circular but has been linearized, for example, by digestion with a restriction endonuclease. Linear DNA may be advantageous in certain situations as discussed, e.g., in Chemg, J. Y., et al., J. Control. Release 60:343-53 (1999), and Chen, Z. Y., et al. Mol. Ther. 3:403-10 (2001). As used herein, the terms plasmid and vector can be used interchangeably.

Alternatively, DNA virus genomes may be used to administer DNA polynucleotides into vertebrate cells. In certain embodiments, a DNA virus genome of the present invention is nonreplicative, noninfectious, and/or nonintegrating. Suitable DNA virus genomes include without limitation, herpes simplex virus genomes, adenovirus genomes, adeno-associated virus genomes, and poxvirus genomes. References citing methods for the in vivo introduction of non-infectious virus genomes to vertebrate tissues are well known to those of ordinary skill in the art.

In other embodiments, a polynucleotide of the present invention is RNA, for example, in the form of messenger RNA (mRNA). Methods for introducing RNA sequences into vertebrate cells are described in U.S. Pat. No. 5,580,859.

Polynucleotides, nucleic acids, and nucleic acid fragments of the present invention may be associated with additional nucleic acids which encode secretory or signal peptides, which direct the secretion of a polypeptide encoded by a nucleic acid fragment or polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native leader sequence is used, or a functional derivative of that sequence that retains the ability to direct the secretion of the polypeptide that is operably associated with it. Alternatively, a heterologous mammalian leader sequence, or a functional derivative thereof, may be used. For example, the wild-type leader sequence may be substituted with the leader sequence of human tissue plasminogen activator (TPA) or mouse β-glucuronidase.

In accordance with one aspect of the present invention, there is provided a polynucleotide construct, for example, a plasmid, comprising a nucleic acid fragment, where the nucleic acid fragment is a fragment of a codon-optimized coding region operably encoding a herpes simplex virus-derived polypeptide, where the coding region is optimized for expression in vertebrate cells, of a desired vertebrate species, e.g., humans, to be delivered to a vertebrate to be treated or immunized. Suitable herpes simplex virus polypeptides, or fragments, variants, or derivatives thereof may be derived from, but are not limited to, the herpes simplex virus gD, VP11/12, VP13/14 and/or VP22 proteins. Additional herpes simplex virus-derived coding sequences, may also be included on the plasmid, or on a separate plasmid, and expressed, either using native herpes simplex virus codons or codons optimized for expression in the vertebrate to be treated or immunized. When such a plasmid encoding one or more optimized herpes simplex sequences is delivered, in vivo to a tissue of the vertebrate to be treated or immunized, one or more of the encoded gene products will be expressed, i.e., transcribed and translated. The level of expression of the gene product(s) will depend to a significant extent on the strength of the associated promoter and the presence and activation of an associated enhancer element, as well as the degree of optimization of the coding region.

As used herein, the term "plasmid" refers to a construct made up of genetic material (i.e., nucleic acids). Typically a plasmid contains an origin of replication which is functional in bacterial host cells, e.g., *Escherichia coli*, and selectable markers for detecting bacterial host cells comprising the plasmid. Plasmids of the present invention may include genetic elements as described herein arranged such that an inserted coding sequence can be transcribed and translated in eukaryotic cells. Also, the plasmid may include a sequence from a viral nucleic acid. However, such viral sequences normally are not sufficient to direct or allow the incorporation of the plasmid into a viral particle, and the plasmid is therefore a non-viral vector. In certain embodiments described herein, a plasmid is a closed circular DNA molecule.

The term "expression" refers to the biological production of a product encoded by a coding sequence. In most cases a DNA sequence, including the coding sequence, is transcribed to form a messenger-RNA (mRNA). The messenger-RNA is then translated to form a polypeptide product which has a relevant biological activity. Also, the process of expression may involve further processing steps to the RNA product of transcription, such as splicing to remove introns, and/or post-translational processing of a polypeptide product.

As used herein, the term "polypeptide" is intended to encompass a singular "polypeptide" as well as plural "polypeptides," and comprises any chain or chains of two or more amino acids. Thus, as used herein, terms including, but not limited to "peptide," "dipeptide," "tripeptide," "protein," "amino acid chain," or any other term used to refer to a chain or chains of two or more amino acids, are included in the definition of a "polypeptide," and the term "polypeptide" can be used instead of, or interchangeably with any of these terms. The term further includes polypeptides which have undergone post-translational modifications, for example, glycosylation, acetylation, phosphorylation, amidation, derivatization by known protecting/blocking groups, proteolytic cleavage, or modification by non-naturally occurring amino acids.

Also included as polypeptides of the present invention are fragments, derivatives, analogs, or variants of the foregoing polypeptides, and any combination thereof. Polypeptides, and fragments, derivatives, analogs, or variants thereof of the present invention can be antigenic and immunogenic polypeptides related to herpes simplex virus polypeptides, which are used to prevent or treat, i.e., cure, ameliorate, lessen the severity of, or prevent or reduce contagion of infectious disease caused by the herpes simplex virus.

As used herein, an "antigenic polypeptide" or an "immunogenic polypeptide" is a polypeptide which, when introduced into a vertebrate, reacts with the vertebrate's immune system molecules, i.e., is antigenic, and/or induces an immune response in the vertebrate, i.e., is immunogenic. It is quite likely that an immunogenic polypeptide will also be antigenic, but an antigenic polypeptide, because of its size or conformation, may not necessarily be immunogenic. Examples of antigenic and immunogenic polypeptides of the present invention include, but are not limited to, e.g., gD, VP11/12, VP13/14 and/or VP22 or fragments or variants thereof, or any of the foregoing polypeptides or fragments fused to a heterologous polypeptide, for example, a hepatitis B core antigen. Isolated antigenic and immunogenic polypeptides of the present invention in addition to those encoded by polynucleotides of the invention, may be provided as a recombinant protein, a purified subunit, a viral vector expressing the protein, or may be provided in the form of an inactivated herpes simplex virus vaccine, e.g., a live-attenuated virus vaccine, a heat-killed virus vaccine, etc.

Immunospecific binding excludes non-specific binding but does not exclude cross-reactivity with other antigens. Where all immunogenic epitopes are antigenic, antigenic epitopes need not be immunogenic.

By an "isolated" herpes simplex virus polypeptide or a fragment, variant, or derivative thereof is intended a herpes simplex virus polypeptide or protein that is not in its natural form. No particular level of purification is required. For example, an isolated herpes simplex virus polypeptide can be removed from its native or natural environment. Recombinantly produced herpes simplex virus polypeptides and proteins expressed in host cells are considered isolated for purposed of the invention, as are native or recombinant herpes simplex virus polypeptides which have been separated, fractionated, or partially or substantially purified by any suitable technique, including the separation of herpes simplex virus virions from eggs or culture cells in which they have been propagated. In addition, an isolated herpes simplex virus polypeptide or protein can be provided as a live or inactivated viral vector expressing an isolated herpes simplex virus polypeptide and can include those found in inactivated herpes simplex virus vaccine compositions. Thus, isolated herpes simplex virus polypeptides and proteins can be provided as, for example, recombinant herpes simplex virus polypeptides, a purified subunit of herpes simplex virus, a viral vector expressing an isolated herpes simplex virus polypeptide, or in the form of an inactivated or attenuated herpes simplex virus vaccine.

The term "epitopes," as used herein, refers to portions of a polypeptide having antigenic or immunogenic activity in a vertebrate, for example a human. An "immunogenic epitope," as used herein, is defined as a portion of a protein that elicits an immune response in an animal, as determined by any method known in the art. The term "antigenic epitope," as used herein, is defined as a portion of a protein to which an antibody or T-cell receptor can immunospecifically bind as determined by any method well known in the art.

The term "immunogenic carrier" as used herein refers to a first polypeptide or fragment, variant, or derivative thereof which enhances the immunogenicity of a second polypeptide or fragment, variant, or derivative thereof. Typically, an "immunogenic carrier" is fused to or conjugated to the desired polypeptide or fragment thereof. An example of an "immunogenic carrier" is a recombinant hepatitis B core antigen expressing, as a surface epitope, an immunogenic epitope of interest. See, e.g., European Patent No. EP 0385610 B1.

In the present invention, antigenic epitopes preferably contain a sequence of at least 4, at least 5, at least 6, at least 7, at least 8, at least 9, at least 10, at least 15, at least 20, at least 25, or between about 8 to about 30 amino acids contained within the amino acid sequence of a herpes simplex virus polypeptide of the invention, e.g., an gD, VP11/12, VP13/14 and/or VP22 polypeptide. Certain polypeptides comprising immunogenic or antigenic epitopes are at least 5, 10, 15, 20, 25, 30, 35, 40, 45, 50, 55, 60, 65, 70, 75, 80, 85, 90, 95, or 100 amino acid residues in length. Antigenic as well as immunogenic epitopes may be linear, i.e., be comprised of contiguous amino acids in a polypeptide, or may be three dimensional, i.e., where an epitope is comprised of non-contiguous amino acids which come together due to the secondary or tertiary structure of the polypeptide, thereby forming an epitope.

As to the selection of peptides or polypeptides bearing an antigenic epitope (e.g., that contain a region of a protein molecule to which an antibody or T cell receptor can bind), it is well known in that art that relatively short synthetic peptides that mimic part of a protein sequence are routinely capable of eliciting an antiserum that reacts with the partially mimicked protein. See, e.g., Sutcliffe, J. G., et al., Science 219:660-666 (1983).

Peptides capable of eliciting an immunogenic response are frequently represented in the primary sequence of a protein, can be characterized by a set of simple chemical rules, and are confined neither to immunodominant regions of intact proteins nor to the amino or carboxyl terminals. Peptides that are extremely hydrophobic and those of six or fewer residues generally are ineffective at inducing antibodies that bind to the mimicked protein; longer peptides, especially those containing proline residues, usually are effective. Sutcliffe et al., supra, at 661.

Codon Optimization

"Codon optimization" is defined as modifying a nucleic acid sequence for enhanced expression in the cells of the vertebrate of interest, e.g. human, by replacing at least one, more than one, or a significant number, of codons of the native sequence with codons that are more frequently or most frequently used in the genes of that vertebrate. Various species exhibit particular bias for certain codons of a particular amino acid.

In one aspect, the present invention relates to polynucleotides comprising nucleic acid fragments of codon-optimized coding regions which encode herpes simplex virus polypeptides, or fragments, variants, or derivatives thereof, with the codon usage adapted for optimized expression in the cells of a given vertebrate, e.g., humans. These polynucleotides are prepared by incorporating codons preferred for use in the genes of the vertebrate of interest into the DNA sequence. Also provided are polynucleotide expression constructs, vectors, and host cells comprising nucleic acid fragments of codon-optimized coding regions which encode herpes simplex virus polypeptides, and fragments, variants, or derivatives thereof, and various methods of using the polynucleotide expression constructs, vectors, host cells to treat or prevent herpes simplex disease in a vertebrate.

As used herein the term "codon-optimized coding region" means a nucleic acid coding region that has been adapted for expression in the cells of a given vertebrate by replacing at least one, or more than one, or a significant number, of codons with one or more codons that are more frequently used in the genes of that vertebrate.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation (stop or termination)). The "genetic code" which shows which codons encode which amino acids is reproduced herein as Table 1. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 1

The Standard Genetic Code

| | T(U) | C | A | G |
|---|---|---|---|---|
| T(U) | TTT Phe (F) | TCT Ser (S) | TAT Tyr (Y) | TGT Cys (C) |
| | TTC Phe | TCC Ser | TAC Tyr | TGC Cys |
| | TTA Leu (L) | TCA Ser | TAA Ter | TGA Ter |
| | TTG Leu | TCG Ser | TAG Ter | TGG Trp (W) |
| C | CTT Leu (L) | CCT Pro (P) | CAT His (H) | CGT Arg (R) |
| | CTC Leu | CCC Pro | CAC His | CGC Arg |
| | CTA Leu | CCA Pro | CAA Gln (Q) | CGA Arg |
| | CTG Leu | CCG Pro | CAG Gln | CGG Arg |
| A | ATT Ile (I) | ACT Thr (T) | AAT Asn (N) | AGT Ser (S) |
| | ATC Ile | ACC Thr | AAC Asn | AGC Ser |
| | ATA Ile | ACA Thr | AAA Lys (K) | AGA Arg (R) |
| | ATG Met (M) | ACG Thr | AAG Lys | AGG Arg |
| G | GTT Val (V) | GCT Ala (A) | GAT Asp (D) | GGT Gly (G) |
| | GTC Val | GCC Ala | GAC Asp | GGC Gly |
| | GTA Val | GCA Ala | GAA Glu (E) | GGA Gly |
| | GTG Val | GCG Ala | GAG Glu | GGG Gly |

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables are readily available. See Nakamura, Y., et al. "Codon usage tabulated from the international DNA sequence databases: status for the year 2000" Nucl. Acids Res. 28:292 (2000). As examples, the codon usage tables for human, mouse, domestic cat, and cow, calculated from GenBank Release 128.0 (15 Feb. 2002), are reproduced below as Tables 2-5. These Tables use mRNA nomenclature, and so instead of thymine (T) which is found in DNA, the Tables use uracil (U) which is found in RNA. The Tables have been adapted so that frequencies are calculated for each amino acid, rather than for all 64 codons.

TABLE 2

Codon Usage Table for Human Genes (*Homo sapiens*)

| Amino Acid | Codon | Number | Frequency |
|---|---|---|---|
| Phe | UUU | 326146 | 0.4525 |
| Phe | UUC | 394680 | 0.5475 |
| Total | | 720826 | |
| Leu | UUA | 139249 | 0.0728 |
| Leu | UUG | 242151 | 0.1266 |
| Leu | CUU | 246206 | 0.1287 |
| Leu | CUC | 374262 | 0.1956 |
| Leu | CUA | 133980 | 0.0700 |
| Leu | CUG | 777077 | 0.4062 |
| Total | | 1912925 | |
| Ile | AUU | 303721 | 0.3554 |
| Ile | AUC | 414483 | 0.4850 |
| Ile | AUA | 136399 | 0.1596 |
| Total | | 854603 | |
| Met | AUG | 1430946 | 1.0000 |
| Total | | 1430946 | |
| Val | GUU | 210423 | 0.1773 |
| Val | GUC | 282445 | 0.2380 |
| Val | GUA | 134991 | 0.1137 |
| Val | GUG | 559044 | 0.4710 |
| Total | | 1186903 | |
| Ser | UCU | 282407 | 0.1840 |
| Ser | UCC | 336349 | 0.2191 |
| Ser | UCA | 225963 | 0.1472 |
| Ser | UCG | 86761 | 0.0565 |
| Ser | AGU | 230047 | 0.1499 |
| Ser | AGC | 373362 | 0.2433 |
| Total | | 1534889 | |
| Pro | CCU | 333705 | 0.2834 |
| Pro | CCC | 386462 | 0.3281 |
| Pro | CCA | 322220 | 0.2736 |
| Pro | CCG | 135317 | 0.1149 |
| Total | | 1177704 | |
| Thr | ACU | 247913 | 0.2419 |
| Thr | ACC | 371420 | 0.3624 |
| Thr | ACA | 285655 | 0.2787 |
| Thr | ACG | 120022 | 0.1171 |
| Total | | 1025010 | |

TABLE 2-continued

Codon Usage Table for Human Genes (*Homo sapiens*)

| Amino Acid | Codon | Number | Frequency |
|---|---|---|---|
| Ala | GCU | 360146 | 0.2637 |
| Ala | GCC | 551452 | 0.4037 |
| Ala | GCA | 308034 | 0.2255 |
| Ala | GCG | 146233 | 0.1071 |
| Total | | 1365865 | |
| Tyr | UAU | 232240 | 0.4347 |
| Tyr | UAC | 301978 | 0.5653 |
| Total | | 534218 | |
| His | CAU | 201389 | 0.4113 |
| His | CAC | 288200 | 0.5887 |
| Total | | 489589 | |
| Gln | CAA | 227742 | 0.2541 |
| Gln | CAG | 668391 | 0.7459 |
| Total | | 896133 | |
| Asn | AAU | 322271 | 0.4614 |
| Asn | AAC | 376210 | 0.5386 |
| Total | | 698481 | |
| Lys | AAA | 462660 | 0.4212 |
| Lys | AAG | 635755 | 0.5788 |
| Total | | 1098415 | |
| Asp | GAU | 430744 | 0.4613 |
| Asp | GAC | 502940 | 0.5387 |
| Total | | 933684 | |
| Glu | GAA | 561277 | 0.4161 |
| Glu | GAG | 787712 | 0.5839 |
| Total | | 1348989 | |
| Cys | UGU | 190962 | 0.4468 |
| Cys | UGC | 236400 | 0.5532 |
| Total | | 427362 | |
| Trp | UGG | 248083 | 1.0000 |
| Total | | 248083 | |
| Arg | CGU | 90899 | 0.0830 |
| Arg | CGC | 210931 | 0.1927 |
| Arg | CGA | 122555 | 0.1120 |
| Arg | CGG | 228970 | 0.2092 |
| Arg | AGA | 221221 | 0.2021 |
| Arg | AGG | 220119 | 0.2011 |
| Total | | 1094695 | |
| Gly | GGU | 209450 | 0.1632 |
| Gly | GGC | 441320 | 0.3438 |
| Gly | GGA | 315726 | 0.2459 |
| Gly | GGG | 317263 | 0.2471 |
| Total | | 1283759 | |
| Stop | UAA | 13963 | |
| Stop | UAG | 10631 | |
| Stop | UGA | 24607 | |

TABLE 3

Codon Usage Table for Mouse Genes (*Mus musculus*)

| Amino Acid | Codon | Number | Frequency |
|---|---|---|---|
| Phe | UUU | 150467 | 0.4321 |
| Phe | UUC | 197795 | 0.5679 |
| Total | | 348262 | |
| Leu | UUA | 55635 | 0.0625 |
| Leu | UUG | 116210 | 0.1306 |
| Leu | CUU | 114699 | 0.1289 |
| Leu | CUC | 179248 | 0.2015 |

TABLE 3-continued

Codon Usage Table for Mouse Genes (*Mus musculus*)

| Amino Acid | Codon | Number | Frequency |
|---|---|---|---|
| Leu | CUA | 69237 | 0.0778 |
| Leu | CUG | 354743 | 0.3987 |
| Total | | 889772 | |
| Ile | AUU | 137513 | 0.3367 |
| Ile | AUC | 208533 | 0.5106 |
| Ile | AUA | 62349 | 0.1527 |
| Total | | 408395 | |
| Met | AUG | 1204546 | 1.0000 |
| Total | | 1204546 | |
| Val | GUU | 93754 | 0.1673 |
| Val | GUC | 140762 | 0.2513 |
| Val | GUA | 64417 | 0.1150 |
| Val | GUG | 261308 | 0.4664 |
| Total | | 560241 | |
| Ser | UCU | 139576 | 0.1936 |
| Ser | UCC | 160313 | 0.2224 |
| Ser | UCA | 100524 | 0.1394 |
| Ser | UCG | 38632 | 0.0536 |
| Ser | AGU | 108413 | 0.1504 |
| Ser | AGC | 173518 | 0.2407 |
| Total | | 720976 | |
| Pro | CCU | 162613 | 0.3036 |
| Pro | CCC | 164796 | 0.3077 |
| Pro | CCA | 151091 | 0.2821 |
| Pro | CCG | 57032 | 0.1065 |
| Total | | 535532 | |
| Thr | ACU | 119832 | 0.2472 |
| Thr | ACC | 172415 | 0.3556 |
| Thr | ACA | 140420 | 0.2896 |
| Thr | ACG | 52142 | 0.1076 |
| Total | | 484809 | |
| Ala | GCU | 178593 | 0.2905 |
| Ala | GCC | 236018 | 0.3839 |
| Ala | GCA | 139697 | 0.2272 |
| Ala | GCG | 60444 | 0.0983 |
| Total | | 614752 | |
| Tyr | UAU | 108556 | 0.4219 |
| Tyr | UAC | 148772 | 0.5781 |
| Total | | 257328 | |
| His | CAU | 88786 | 0.3973 |
| His | CAC | 134705 | 0.6027 |
| Total | | 223491 | |
| Gln | CAA | 101783 | 0.2520 |
| Gln | CAG | 302064 | 0.7480 |
| Total | | 403847 | |
| Asn | AAU | 138868 | 0.4254 |
| Asn | AAC | 187541 | 0.5746 |
| Total | | 326409 | |
| Lys | AAA | 188707 | 0.3839 |
| Lys | AAG | 302799 | 0.6161 |
| Total | | 491506 | |
| Asp | GAU | 189372 | 0.4414 |
| Asp | GAC | 239670 | 0.5586 |
| Total | | 429042 | |
| Glu | GAA | 235842 | 0.4015 |
| Glu | GAG | 351582 | 0.5985 |
| Total | | 587424 | |
| Cys | UGU | 97385 | 0.4716 |
| Cys | UGC | 109130 | 0.5284 |
| Total | | 206515 | |
| Trp | UGG | 112588 | 1.0000 |
| Total | | 112588 | |
| Arg | CGU | 41703 | 0.0863 |
| Arg | CGC | 86351 | 0.1787 |
| Arg | CGA | 58928 | 0.1220 |
| Arg | CGG | 92277 | 0.1910 |
| Arg | AGA | 101029 | 0.2091 |
| Arg | AGG | 102859 | 0.2129 |
| Total | | 483147 | |
| Gly | GGU | 103673 | 0.1750 |
| Gly | GGC | 198604 | 0.3352 |
| Gly | GGA | 151497 | 0.2557 |
| Gly | GGG | 138700 | 0.2341 |
| Total | | 592474 | |
| Stop | UAA | 5499 | |
| Stop | UAG | 4661 | |
| Stop | UGA | 10356 | |

TABLE 4

Codon Usage Table for Domestic Cat Genes (*Felis cattus*)

| Amino Acid | Codon | Number | Frequency of usage |
|---|---|---|---|
| Phe | UUU | 1204.00 | 0.4039 |
| Phe | UUC | 1777.00 | 0.5961 |
| Total | | 2981 | |
| Leu | UUA | 404.00 | 0.0570 |
| Leu | UUG | 857.00 | 0.1209 |
| Leu | CUU | 791.00 | 0.1116 |
| Leu | CUC | 1513.00 | 0.2135 |
| Leu | CUA | 488.00 | 0.0688 |
| Leu | CUG | 3035.00 | 0.4282 |
| Total | | 7088 | |
| Ile | AUU | 1018.00 | 0.2984 |
| Ile | AUC | 1835.00 | 0.5380 |
| Ile | AUA | 558.00 | 0.1636 |
| Total | | 3411 | |
| Met | AUG | 1553.00 | 0.0036 |
| Total | | 1553 | |
| Val | GUU | 696.00 | 0.1512 |
| Val | GUC | 1279.00 | 0.2779 |
| Val | GUA | 463.00 | 0.1006 |
| Val | GUG | 2164.00 | 0.4702 |
| Total | | 4602 | |
| Ser | UCU | 940.00 | 0.1875 |
| Ser | UCC | 1260.00 | 0.2513 |
| Ser | UCA | 608.00 | 0.1213 |
| Ser | UCG | 332.00 | 0.0662 |
| Ser | AGU | 672.00 | 0.1340 |
| Ser | AGC | 1202.00 | 0.2397 |
| Total | | 5014 | |
| Pro | CCU | 958.00 | 0.2626 |
| Pro | CCC | 1375.00 | 0.3769 |
| Pro | CCA | 850.00 | 0.2330 |
| Pro | CCG | 465.00 | 0.1275 |
| Total | | 3648 | |
| Thr | ACU | 822.00 | 0.2127 |
| Thr | ACC | 1574.00 | 0.4072 |
| Thr | ACA | 903.00 | 0.2336 |
| Thr | ACG | 566.00 | 0.1464 |
| Total | | 3865 | |

TABLE 4-continued

Codon Usage Table for Domestic Cat Genes (*Felis cattus*)

| Amino Acid | Codon | Number | Frequency of usage |
|---|---|---|---|
| Ala | GCU | 1129.00 | 0.2496 |
| Ala | GCC | 1951.00 | 0.4313 |
| Ala | GCA | 883.00 | 0.1952 |
| Ala | GCG | 561.00 | 0.1240 |
| Total |  | 4524 |  |
| Tyr | UAU | 837.00 | 0.3779 |
| Tyr | UAC | 1378.00 | 0.6221 |
| Total |  | 2215 |  |
| His | CAU | 594.00 | 0.3738 |
| His | CAC | 995.00 | 0.6262 |
| Total |  | 1589 |  |
| Gln | CAA | 747.00 | 0.2783 |
| Gln | CAG | 1937.00 | 0.7217 |
| Total |  | 2684 |  |
| Asn | AAU | 1109.00 | 0.3949 |
| Asn | AAC | 1699.00 | 0.6051 |
| Total |  | 2808 |  |
| Lys | AAA | 1445.00 | 0.4088 |
| Lys | AAG | 2090.00 | 0.5912 |
| Total |  | 3535 |  |
| Asp | GAU | 1255.00 | 0.4055 |
| Asp | GAC | 1840.00 | 0.5945 |
| Total |  | 3095 |  |
| Glu | GAA | 1637.00 | 0.4164 |
| Glu | GAG | 2294.00 | 0.5836 |
| Total |  | 3931 |  |
| Cys | UGU | 719.00 | 0.4425 |
| Cys | UGC | 906.00 | 0.5575 |
| Total |  | 1625 |  |
| Trp | UGG | 1073.00 | 1.0000 |
| Total |  | 1073 |  |
| Arg | CGU | 236.00 | 0.0700 |
| Arg | CGC | 629.00 | 0.1865 |
| Arg | CGA | 354.00 | 0.1050 |
| Arg | CGG | 662.00 | 0.1963 |
| Arg | AGA | 712.00 | 0.2112 |
| Arg | AGG | 779.00 | 0.2310 |
| Total |  | 3372 |  |
| Gly | GGU | 648.00 | 0.1498 |
| Gly | GGC | 1536.00 | 0.3551 |
| Gly | GGA | 1065.00 | 0.2462 |
| Gly | GGG | 1077.00 | 0.2490 |
| Total |  | 4326 |  |
| Stop | UAA | 55 |  |
| Stop | UAG | 36 |  |
| Stop | UGA | 110 |  |

TABLE 5

Codon Usage Table for Cow Genes (*Bos taunts*)

| Amino Acid | Codon | Number | Frequency of usage |
|---|---|---|---|
| Phe | UUU | 13002 | 0.4112 |
| Phe | UUC | 18614 | 0.5888 |
| Total |  | 31616 |  |
| Leu | UUA | 4467 | 0.0590 |
| Leu | UUG | 9024 | 0.1192 |
| Leu | CUU | 9069 | 0.1198 |
| Leu | CUC | 16003 | 0.2114 |
| Leu | CUA | 4608 | 0.0609 |
| Leu | CUG | 32536 | 0.4298 |
| Total |  | 75707 |  |
| Ile | AUU | 12474 | 0.3313 |
| Ile | AUC | 19800 | 0.5258 |
| Ile | AUA | 5381 | 0.1429 |
| Total |  | 37655 |  |
| Met | AUG | 17770 | 1.0000 |
| Total |  | 17770 |  |
| Val | GUU | 8212 | 0.1635 |
| Val | GUC | 12846 | 0.2558 |
| Val | GUA | 4932 | 0.0982 |
| Val | GUG | 24222 | 0.4824 |
| Total |  | 50212 |  |
| Ser | UCU | 10287 | 0.1804 |
| Ser | UCC | 13258 | 0.2325 |
| Ser | UCA | 7678 | 0.1347 |
| Ser | UCG | 3470 | 0.0609 |
| Ser | AGU | 8040 | 0.1410 |
| Ser | AGC | 14279 | 0.2505 |
| Total |  | 57012 |  |
| Pro | CCU | 11695 | 0.2684 |
| Pro | CCC | 15221 | 0.3493 |
| Pro | CCA | 11039 | 0.2533 |
| Pro | CCG | 5621 | 0.1290 |
| Total |  | 43576 |  |
| Thr | ACU | 9372 | 0.2203 |
| Thr | ACC | 16574 | 0.3895 |
| Thr | ACA | 10892 | 0.2560 |
| Thr | ACG | 5712 | 0.1342 |
| Total |  | 42550 |  |
| Ala | GCU | 13923 | 0.2592 |
| Ala | GCC | 23073 | 0.4295 |
| Ala | GCA | 10704 | 0.1992 |
| Ala | GCG | 6025 | 0.1121 |
| Total |  | 53725 |  |
| Tyr | UAU | 9441 | 0.3882 |
| Tyr | UAC | 14882 | 0.6118 |
| Total |  | 24323 |  |
| His | CAU | 6528 | 0.3649 |
| His | CAC | 11363 | 0.6351 |
| Total |  | 17891 |  |
| Gln | CAA | 8060 | 0.2430 |
| Gln | CAG | 25108 | 0.7570 |
| Total |  | 33168 |  |
| Asn | AAU | 12491 | 0.4088 |
| Asn | AAC | 18063 | 0.5912 |
| Total |  | 30554 |  |
| Lys | AAA | 17244 | 0.3897 |
| Lys | AAG | 27000 | 0.6103 |
| Total |  | 44244 |  |
| Asp | GAU | 16615 | 0.4239 |
| Asp | GAC | 22580 | 0.5761 |
| Total |  | 39195 |  |
| Glu | GAA | 21102 | 0.4007 |
| Glu | GAG | 31555 | 0.5993 |
| Total |  | 52657 |  |
| Cys | UGU | 7556 | 0.4200 |
| Cys | UGC | 10436 | 0.5800 |
| Total |  | 17992 |  |

TABLE 5-continued

Codon Usage Table for Cow Genes (*Bos taunts*)

| Amino Acid | Codon | Number | Frequency of usage |
|---|---|---|---|
| Trp | UGG | 10706 | 1.0000 |
| Total | | 10706 | |
| Arg | CGU | 3391 | 0.0824 |
| Arg | CGC | 7998 | 0.1943 |
| Arg | CGA | 4558 | 0.1108 |
| Arg | CGG | 8300 | 0.2017 |
| Arg | AGA | 8237 | 0.2001 |
| Arg | AGG | 8671 | 0.2107 |
| Total | | 41155 | |
| Gly | GGU | 8508 | 0.1616 |
| Gly | GGC | 18517 | 0.3518 |
| Gly | GGA | 12838 | 0.2439 |
| Gly | GGG | 12772 | 0.2427 |
| Total | | 52635 | |
| Stop | UAA | 555 | |
| Stop | UAG | 394 | |
| Stop | UGA | 392 | |

By utilizing these or similar tables, one of ordinary skill in the art can apply the frequencies to any given polypeptide sequence, and produce a nucleic acid fragment of a codon-optimized coding region which encodes the polypeptide, but which uses codons more optimal for a given species. Codon-optimized coding regions can be designed by various different methods.

In another method, termed "full-optimization," the actual frequencies of the codons are distributed randomly throughout the coding region. Thus, using this method for optimization, if a hypothetical polypeptide sequence had 100 leucine residues, referring to Table 2 for frequency of usage in humans, about 7, or 7% of the leucine codons would be UUA, about 13, or 13% of the leucine codons would be UUG, about 13, or 13% of the leucine codons would be CUU, about 20, or 20% of the leucine codons would be CUC, about 7, or 7% of the leucine codons would be CUA, and about 41, or 41% of the leucine codons would be CUG. These frequencies would be distributed randomly throughout the leucine codons in the coding region encoding the hypothetical polypeptide. As will be understood by those of ordinary skill in the art, the distribution of codons in the sequence can vary significantly using this method; however, the sequence always encodes the same polypeptide.

In using the "full-optimization" method, an entire polypeptide sequence may be codon-optimized as described above. With respect to various desired fragments, variants or derivatives of the complete polypeptide, the fragment variant, or derivative may first be designed, and is then codon-optimized individually. Alternatively, a full-length polypeptide sequence is codon-optimized for a given species resulting in a codon-optimized coding region encoding the entire polypeptide, and then nucleic acid fragments of the codon-optimized coding region, which encode fragments, variants, and derivatives of the polypeptide are made from the original codon-optimized coding region. As would be well understood by those of ordinary skill in the art, if codons have been randomly assigned to the full-length coding region based on their frequency of use in a given species, nucleic acid fragments encoding fragments, variants, and derivatives would not necessarily be fully codon-optimized for the given species. However, such sequences are still much closer to the codon usage of the desired species than the native codon usage. The advantage of this approach is that synthesizing codon-optimized nucleic acid fragments encoding each fragment, variant, and derivative of a given polypeptide, although routine, would be time consuming and would result in significant expense.

When using the "full-optimization" method, the term "about" is used precisely to account for fractional percentages of codon frequencies for a given amino acid. As used herein, "about" is defined as one amino acid more or one amino acid less than the value given. The whole number value of amino acids is rounded up if the fractional frequency of usage is 0.50 or greater, and is rounded down if the fractional frequency of use is 0.49 or less. Using again the example of the frequency of usage of leucine in human genes for a hypothetical polypeptide having 62 leucine residues, the fractional frequency of codon usage would be calculated by multiplying 62 by the frequencies for the various codons. Thus, 7.28 percent of 62 equals 4.51 UUA codons, or "about 5," i.e., 4, 5, or 6 UUA codons, 12.66 percent of 62 equals 7.85 UUG codons or "about 8," i.e., 7, 8, or 9 TUG codons, 12.87 percent of 62 equals 7.98 CUU codons, or "about 8," i.e., 7, 8, or 9 CTU codons, 19.56 percent of 62 equals 12.13 CUC codons or "about 12," i.e., 11, 12, or 13 CUC codons, 7.00 percent of 62 equals 4.34 CUA codons or "about 4," i.e., 3, 4, or 5 CUA codons, and 40.62 percent of 62 equals 25.19 CUG codons, or "about 25," i.e., 24, 25, or 26 CUG codons.

In a third method termed "minimal optimization," coding regions are only partially optimized. For example, the invention includes a nucleic acid fragment of a codon-optimized coding region encoding a polypeptide in which at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95% or 100% of the codon positions have been codon-optimized for a given species. That is, they contain a codon that is preferentially used in the genes of a desired species, e.g., a vertebrate species, e.g., humans, in place of a codon that is normally used in the native nucleic acid sequence. Codons that are rarely found in the genes of the vertebrate of interest are changed to codons more commonly utilized in the coding regions of the vertebrate of interest.

This minimal human codon optimization for highly variant codons has several advantages, which include but are not limited to the following examples. Since fewer changes are made to the nucleotide sequence of the gene of interest, fewer manipulations are required, which leads to reduced risk of introducing unwanted mutations and lower cost, as well as allowing the use of commercially available site-directed mutagenesis kits, and reducing the need for expensive oligonucleotide synthesis. Further, decreasing the number of changes in the nucleotide sequence decreases the potential of altering the secondary structure of the sequence, which can have a significant impact on gene expression in certain host cells. The introduction of undesirable restriction sites is also reduced, facilitating the subcloning of the genes of interest into the plasmid expression vector.

The present invention also provides isolated polynucleotides comprising coding regions of herpes simplex virus polypeptides, e.g., gD, VP11/12, VP13/14 and/or VP22 or fragments, variants, or derivatives thereof. The isolated polynucleotides can also be codon-optimized.

A human codon-optimized coding region can be designed by any of the methods discussed herein. For "uniform" optimization, each amino acid is assigned the most frequent codon used in the human genome for that amino acid.

As described above, the term "about" means that the number of amino acids encoded by a certain codon may be one more or one less than the number given. It would be understood by those of ordinary skill in the art that the total number of any amino acid in the polypeptide sequence must remain constant, therefore, if there is one "more" of one codon encoding a give amino acid, there would have to be one "less" of another codon encoding that same amino acid.

In another form of minimal optimization, a Codon Usage Table (CUT) for the specific herpes simplex virus sequence in question is generated and compared to CUT for human genomic DNA. Amino acids are identified for which there is a difference of at least 10 percentage points in codon usage between human and herpes simplex virus DNA (either more or less). Then the wild type herpes simplex virus codon is modified to conform to predominant human codon for each such amino acid. Furthermore, the remainder of codons for that amino acid are also modified such that they conform to the predominant human codon for each such amino acid.

Compositions and Methods

In certain embodiments, the present invention is directed to compositions and methods of enhancing the immune response of a vertebrate in need of protection against herpes simplex virus infection by administering in vivo, into a tissue of a vertebrate, one or more polynucleotides comprising at least one codon-optimized coding region encoding a herpes simplex virus polypeptide, or a fragment, variant, or derivative thereof. In addition, the present invention is directed to compositions and methods of enhancing the immune response of a vertebrate in need of protection against herpes simplex virus infection by administering to the vertebrate a composition comprising one or more polynucleotides as described herein, and at least one isolated herpes simplex virus polypeptide, or a fragment, variant, or derivative thereof. The polynucleotide may be administered either prior to, at the same time (simultaneously), or subsequent to the administration of the isolated polypeptide.

The coding regions encoding herpes simplex virus polypeptides or fragments, variants, or derivatives thereof may be codon optimized for a particular vertebrate. Codon optimization is carried out by the methods described herein, for example, in certain embodiments codon-optimized coding regions encoding polypeptides of herpes simplex virus, or nucleic acid fragments of such coding regions encoding fragments, variants, or derivatives thereof are optimized according to the codon usage of the particular vertebrate. The polynucleotides of the invention are incorporated into the cells of the vertebrate in vivo, and an immunologically effective amount of a herpes simplex virus polypeptide or a fragment, variant, or derivative thereof is produced in vivo. The coding regions encoding a herpes simplex virus polypeptide or a fragment, variant, or derivative thereof may be codon optimized for mammals, e.g., humans, apes, monkeys (e.g., owl, squirrel, cebus, rhesus, African green, patas, cynomolgus, and cercopithecus), orangutans, baboons, gibbons, and chimpanzees, dogs, wolves, cats, lions, and tigers, horses, donkeys, zebras, cows, pigs, sheep, deer, giraffes, bears, rabbits, mice, ferrets, seals, whales; birds, e.g., ducks, geese, terns, shearwaters, gulls, turkeys, chickens, quail, pheasants, geese, starlings and budgerigars, or other vertebrates.

In one embodiment, the present invention relates to codon-optimized coding regions encoding polypeptides of herpes simplex virus, or nucleic acid fragments of such coding regions fragments, variants, or derivatives thereof which have been optimized according to human codon usage. For example, human codon-optimized coding regions encoding polypeptides of herpes simplex virus, or fragments, variants, or derivatives thereof are prepared by substituting one or more codons preferred for use in human genes for the codons naturally used in the DNA sequence encoding the herpes simplex virus polypeptide or a fragment, variant, or derivative thereof. Also provided are polynucleotides, vectors, and other expression constructs comprising codon-optimized coding regions encoding polypeptides of herpes simplex virus, or nucleic acid fragments of such coding regions encoding fragments, variants, or derivatives thereof, pharmaceutical compositions comprising polynucleotides, vectors, and other expression constructs comprising codon-optimized coding regions encoding polypeptides of herpes simplex virus, or nucleic acid fragments of such coding regions encoding fragments, variants, or derivatives thereof, and various methods of using such polynucleotides, vectors and other expression constructs. Coding regions encoding herpes simplex virus polypeptides can be uniformly optimized, fully optimized, minimally optimized, codon-optimized by region and/or not codon-optimized, as described herein.

The present invention is further directed towards polynucleotides comprising codon-optimized coding regions encoding polypeptides of herpes simplex virus antigens, for example, gD, VP11/12, VP13/14 and/or VP22 optionally in conjunction with other antigens. The invention is also directed to polynucleotides comprising codon-optimized nucleic acid fragments encoding fragments, variants and derivatives of these polypeptides.

In certain embodiments, the present invention provides an isolated polynucleotide comprising a nucleic acid fragment, where the nucleic acid fragment is a fragment of a codon-optimized coding region encoding a polypeptide at least 60%, 65%, 70%, 75%, 80%, 85%, 86%, 87%, 88%, 89%, 90%, 91%, 92%, 93%, 94%, 95%, 96%, 97%, 98%, or 99% identical to a herpes simplex virus polypeptide, e.g., gD, VP11/12, VP13/14 and/or VP22 and where the nucleic acid fragment is a variant of a codon-optimized coding region encoding a herpes simplex virus polypeptide, e.g., gD, VP11/12, VP13/14 and/or VP22. The human codon-optimized coding region can be optimized for any vertebrate species and by any of the methods described herein.

Isolated Herpes Simplex Virus Polypeptides

The present invention is further drawn to compositions which include at least one polynucleotide comprising one or more nucleic acid fragments, where each nucleic acid fragment is optionally a fragment of a codon-optimized coding region operably encoding a herpes simplex virus polypeptide or fragment, variant, or derivative thereof; together with one or more isolated herpes simplex virus component or isolated polypeptide. The herpes simplex virus component may be inactivated virus, attenuated virus, a viral vector expressing an isolated herpes simplex virus polypeptide, or a herpes simplex virus protein, fragment, variant or derivative thereof.

The isolated herpes simplex virus polypeptides of the invention may be in any form, and are generated using techniques well known in the art. Examples include isolated herpes simplex virus proteins produced recombinantly, isolated herpes simplex virus proteins directly purified from their natural milieu, recombinant (non-herpes simplex virus) virus vectors expressing an isolated herpes simplex virus protein, or proteins delivered in the form of an inactivated herpes simplex virus vaccine, such as conventional vaccines.

In the instant invention, the combination of conventional antigen vaccine compositions with the codon-optimized nucleic acid compositions provides for therapeutically beneficial effects at dose sparing concentrations. For example, immunological responses sufficient for a therapeutically beneficial effect in patients predetermined for an approved commercial product, such as for the conventional product described above, can be attained by using less of the approved commercial product when supplemented or enhanced with the appropriate amount of codon-optimized nucleic acid.

Thus, dose sparing is contemplated by administration of conventional herpes simplex virus vaccines administered in combination with the codon-optimized nucleic acids of the invention In particular, the dose of conventional vaccine may be reduced by at least 5%, at least 10%, at least 20%, at least 30%, at least 40%, at least 50%, at least 60% or at least 70% when administered in combination with the codon-optimized nucleic acid compositions of the invention.

Similarly, a desirable level of an immunological response afforded by a DNA based pharmaceutical alone may be attained with less DNA by including an aliquot of a conventional vaccine. Further, using a combination of conventional and DNA based pharmaceuticals may allow both materials to be used in lesser amounts while still affording the desired level of immune response arising from administration of either component alone in higher amounts (e.g. one may use less of either immunological product when they are used in combination). This may be manifest not only by using lower amounts of materials being delivered at any time, but also to reducing the number of administrations points in a vaccination regime (e.g. 2 versus 3 or 4 injections), and/or to reducing the kinetics of the immunological response (e.g. desired response levels are attained in 3 weeks instead of 6 after immunization).

In particular, the dose of DNA based pharmaceuticals, may be reduced by at least 5%, at least 10%, at least 20%, at least 30%, at least 40%, at least 50%, at least 60% or at least 70% when administered in combination with conventional herpes simplex virus vaccines.

Determining the precise amounts of DNA based pharmaceutical and conventional antigen is based on a number of factors as described above, and is readily determined by one of ordinary skill in the art.

In addition to dose sparing, the claimed combinatorial compositions provide for a broadening of the immune response and/or enhanced beneficial immune responses. Such broadened or enhanced immune responses are achieved by: adding DNA to enhance cellular responses to a conventional vaccine; adding a conventional vaccine to a DNA pharmaceutical to enhance humoral response; using a combination that induces additional epitopes (both humoral and/or cellular) to be recognized and/or more desirably responded to (epitope broadening); employing a DNA-conventional vaccine combination designed for a particular desired spectrum of immunological responses; obtaining a desirable spectrum by using higher amounts of either component. The broadened immune response is measurable by one of ordinary skill in the art by standard immunological assay specific for the desirable response spectrum.

Both broadening and dose sparing can be obtained simultaneously.

The isolated herpes simplex virus polypeptide or fragment, variant, or derivative thereof to be delivered (either a recombinant protein, a purified subunit, or viral vector expressing an isolated herpes simplex virus polypeptide, or in the form of an inactivated herpes simplex virus vaccine) can be any isolated herpes simplex virus polypeptide or fragment, variant, or derivative thereof, including but not limited to the gD, VP11/12, VP13/14 and/or VP22 proteins or fragments, variants or derivatives thereof. It should be noted that any isolated herpes simplex virus polypeptide or fragment, variant, or derivative thereof described herein can be combined in a composition with any polynucleotide comprising a nucleic acid fragment, where the nucleic acid fragment is optionally a fragment of a codon-optimized coding region operably encoding a herpes simplex virus polypeptide or fragment, variant, or derivative thereof. The proteins can be different, the same, or can be combined in any combination of one or more isolated herpes simplex virus proteins and one or more polynucleotides.

In certain embodiments, the isolated herpes simplex virus polypeptides, or fragments, derivatives or variants thereof can be fused to or conjugated to a second isolated herpes simplex virus polypeptide, or fragment, derivative or variant thereof, or can be fused to other heterologous proteins, including for example, hepatitis B proteins including, but not limited to the hepatitis B core antigen (HBcAg), or those derived from diphtheria or tetanus. The second isolated herpes simplex virus polypeptide or other heterologous protein can act as a "carrier" that potentiates the immunogenicity of the herpes simplex virus polypeptide or a fragment, variant, or derivative thereof to which it is attached. Hepatitis B virus proteins and fragments and variants thereof useful as carriers within the scope of the invention are disclosed in U.S. Pat. Nos. 6,231,864 and 5,143,726. Polynucleotides comprising coding regions encoding said fused or conjugated proteins are also within the scope of the invention.

The use of recombinant particles comprising hepatitis B core antigen ("HBcAg") and heterologous protein sequences as potent immunogenic moieties is well documented. For example, addition of heterologous sequences to the amino terminus of a recombinant HBcAg results in the spontaneous assembly of particulate structures which express the heterologous epitope on their surface, and which are highly immunogenic when inoculated into experimental animals. See Clarke et al., Nature 330:381-384 (1987). Heterologous epitopes can also be inserted into HBcAg particles by replacing approximately 40 amino acids of the carboxy terminus of the protein with the heterologous sequences. These recombinant HBcAg proteins also spontaneously form immunogenic particles. See Stahl and Murray, Proc. Natl. Acad. Sci. USA, 86:6283-6287 (1989). Additionally, chimeric HBcAg particles may be constructed where the heterologous epitope is inserted in or replaces all or part of the sequence of amino acid residues in a more central region of the HBcAg protein, in an immunodominant loop, thereby allowing the heterologous epitope to be displayed on the surface of the resulting particles. See EP Patent No. 0421635 B1 and Galibert, F., et al., Nature 281:646-650 (1979); see also U.S. Pat. Nos. 4,818,527, 4,882,145 and 5,143,726.

Chimaeric HBcAg particles comprising isolated herpes simplex virus proteins or variants, fragments or derivatives thereof are prepared by recombinant techniques well known to those of ordinary skill in the art. A polynucleotide, e.g., a plasmid, which carries the coding region for the HBcAg operably associated with a promoter is constructed. Convenient restrictions sites are engineered into the coding region encoding the N-terminal, central, and/or C-terminal portions of the HBcAg, such that heterologous sequences may be inserted. A construct which expresses a HBcAg/herpes simplex virus fusion protein is prepared by inserting a DNA sequence encoding a herpes simplex virus protein or variant, fragment or derivative thereof, in frame, into a desired restriction site in the coding region of the HBcAg. The resulting construct is then inserted into a suitable host cell, e.g., *E. coli*, under conditions where the chimeric HBcAg will be expressed. The chimaeric HBcAg self-assembles into particles when expressed, and can then be isolated, e.g., by ultracentrifugation. The particles formed resemble the natural 27 nm HBcAg particles isolated from a hepatitis B virus, except that an isolated herpes simplex virus protein or fragment, variant, or derivative thereof is contained in the particle, preferably exposed on the outer particle surface.

The herpes simplex virus protein or fragment, variant, or derivative thereof expressed in a chimaeric HBcAg particle may be of any size which allows suitable particles of the chimeric HBcAg to self-assemble. As discussed above, even small antigenic epitopes may be immunogenic when expressed in the context of an immunogenic carrier, e.g., a HBcAg. Thus, HBcAg particles of the invention may comprise at least 4, at least 5, at least 6, at least 7, at least 8, at least 9, at least 10, at least 15, at least 20, at least 25, or between about 15 to about 30 amino acids of a herpes simplex virus protein fragment of interest inserted therein. HBcAg particles of the invention may further comprise immunogenic or antigenic epitopes of at least 5, 10, 15, 20, 25, 30, 35, 40, 45, 50, 55, 60, 65, 70, 75, 80, 85, 90, 95, or 100 amino acid residues of a herpes simplex virus protein fragment of interest inserted therein.

The immunodominant loop region of HBcAg was mapped to about amino acid residues 75 to 83, to about amino acids 75 to 85 or to about amino acids 130 to 140. See Colucci et al., J. Immunol. 141:4376-4380 (1988), and Salfeld et al. J. Virol. 63:798 (1989). A chimeric HBcAg is still often able to form core particles when foreign epitopes are cloned into the immunodominant loop. Thus, for example, amino acids of the herpes simplex virus protein fragment may be inserted into the sequence of HBcAg amino acids at various positions, for example, at the N-terminus, from about amino acid 75 to about amino acid 85, from about amino acid 75 to about amino acid 83, from about amino acid 130 to about amino acid 140, or at the C-terminus. Where amino acids of the herpes simplex virus protein fragment replace all or part of the native core protein sequence, the inserted herpes simplex virus sequence is generally not shorter, but may be longer, than the HBcAg sequence it replaces.

Alternatively, if particle formation is not desired, full-length herpes simplex virus coding sequences can be fused to the coding region for the HBcAg. The HBcAg sequences can be fused either at the N- or C-terminus of any of the Herpes simplex antigens described herein. Fusions could include flexible protein linkers. These fusion constructs could be codon optimized by any of the methods described.

The chimeric HBcAg can be used in the present invention in conjunction with a polynucleotide comprising a nucleic acid fragment, where each nucleic acid fragment is optionally a fragment of a codon-optimized coding region operably encoding a herpes simplex virus polypeptide, or a fragment, variant, or derivative thereof, as a herpes simplex vaccine for a vertebrate.

Methods and Administration

The present invention also provides methods for delivering a herpes simplex virus polypeptide or a fragment, variant, or derivative thereof to a human, which comprise administering to a human one or more of the compositions described herein; such that upon administration of compositions such as those described herein, a herpes simplex virus polypeptide or a fragment, variant, or derivative thereof is expressed in human cells, in an amount sufficient to generate an immune response to the herpes simplex virus or administering the herpes simplex virus polypeptide or a fragment, variant, or derivative thereof itself to the human in an amount sufficient to generate an immune response.

The present invention further provides methods for delivering a herpes simplex virus polypeptide or a fragment, variant, or derivative thereof to a human, which comprise administering to a vertebrate one or more of the compositions described herein; such that upon administration of compositions such as those described herein, an immune response is generated in the vertebrate.

The term "vertebrate" is intended to encompass a singular "vertebrate" as well as plural "vertebrates" and comprises mammals and birds, as well as fish, reptiles, and amphibians.

The term "mammal" is intended to encompass a singular "mammal" and plural "mammals," and includes, but is not limited to humans; primates such as apes, monkeys (e.g., owl, squirrel, cebus, rhesus, African green, patas, cynomolgus, and cercopithecus), orangutans, baboons, gibbons, and chimpanzees; canids such as dogs and wolves; felids such as cats, lions, and tigers; equines such as horses, donkeys, and zebras, food animals such as cows, pigs, and sheep; ungulates such as deer and giraffes; ursids such as bears; and others such as rabbits, mice, ferrets, seals, whales. In particular, the mammal can be a human subject, a food animal or a companion animal.

The term "bird" is intended to encompass a singular "bird" and plural "birds," and includes, but is not limited to, feral water birds such as ducks, geese, terns, shearwaters, and gulls; as well as domestic avian species such as turkeys, chickens, quail, pheasants, geese, and ducks. The term "bird" also encompasses passerine birds such as starlings and budgerigars.

The present invention further provides a method for generating, enhancing or modulating an immune response to a herpes simplex virus comprising administering to a vertebrate one or more of the compositions described herein. In this method, the compositions may include one or more isolated polynucleotides comprising at least one nucleic acid fragment where the nucleic acid fragment is optionally a fragment of a codon-optimized coding region encoding a herpes simplex virus polypeptide, or a fragment, variant, or derivative thereof. In another embodiment, the compositions may include both a polynucleotide as described above, and also an isolated herpes simplex virus polypeptide, or a fragment, variant, or derivative thereof, wherein the protein is provided as a recombinant protein, in particular, a fusion protein, a purified subunit, viral vector expressing the protein, or in the form of an inactivated herpes simplex virus vaccine. Thus, the latter compositions include both a polynucleotide encoding a herpes simplex virus polypeptide or a fragment, variant, or derivative thereof and an isolated herpes simplex virus polypeptide or a fragment, variant, or derivative thereof. The herpes simplex virus polypeptide or a fragment, variant, or derivative thereof encoded by the polynucleotide of the compositions need not be the same as the isolated herpes simplex virus polypeptide or a fragment, variant, or derivative thereof of the compositions. Compositions to be used according to this method may be univalent, bivalent, trivalent or multivalent.

The polynucleotides of the compositions may comprise a fragment of a human (or other vertebrate) codon-optimized coding region encoding a protein of the herpes simplex virus, or a fragment, variant, or derivative thereof. The polynucleotides are incorporated into the cells of the vertebrate in vivo, and an antigenic amount of the herpes simplex virus polypeptide, or fragment, variant, or derivative thereof, is produced in vivo. Upon administration of the composition according to this method, the herpes simplex virus polypeptide or a fragment, variant, or derivative thereof is expressed in the vertebrate in an amount sufficient to elicit an immune response. Such an immune response might be used, for example, to generate antibodies to the herpes simplex virus for use in diagnostic assays or as laboratory reagents, or as therapeutic or preventative vaccines as described herein.

The present invention further provides a method for generating, enhancing, or modulating a protective and/or therapeutic immune response to herpes simplex virus in a vertebrate, comprising administering to a vertebrate in need of therapeutic and/or preventative immunity one or more of the compositions described herein. In this method, the compositions include one or more polynucleotides comprising at least one nucleic acid fragment, where the nucleic acid fragment is optionally a fragment of a codon-optimized coding region encoding a herpes simplex virus polypeptide, or a fragment, variant, or derivative thereof. In a further embodiment, the composition used in this method includes both an isolated polynucleotide comprising at least one nucleic acid fragment, where the nucleic acid fragment is optionally a fragment of a codon-optimized coding region encoding a herpes simplex virus polypeptide, or a fragment, variant, or derivative thereof; and at least one isolated herpes simplex virus polypeptide, or a fragment, variant, or derivative thereof. Thus, the latter composition includes both an isolated polynucleotide encoding a herpes simplex virus polypeptide or a fragment, variant, or derivative thereof and an isolated herpes simplex virus polypeptide or a fragment, variant, or derivative thereof, for example, a recombinant protein, a purified subunit, viral vector expressing the protein, or an inactivated virus vaccine. Upon administration of the composition according to this method, the herpes simplex virus polypeptide or a fragment, variant, or derivative thereof is expressed in the human in a therapeutically or prophylactically effective amount.

As used herein, an "immune response" refers to the ability of a vertebrate to elicit an immune reaction to a composition delivered to that vertebrate. Examples of immune responses include an antibody response or a cellular, e.g., cytotoxic T-cell, response. One or more compositions of the present invention may be used to prevent herpes simplex infection in vertebrates, e.g., as a prophylactic vaccine, to establish or enhance immunity to herpes simplex virus in a healthy individual prior to exposure to herpes simplex or contraction of herpes simplex disease, thus preventing the disease or reducing the severity of disease symptoms.

As mentioned above, compositions of the present invention can be used both to prevent herpes simplex virus infection, and also to therapeutically treat herpes simplex virus infection. In individuals already exposed to herpes simplex, or already suffering from herpes simplex disease, the present invention is used to further stimulate the immune system of the vertebrate, thus reducing or eliminating the symptoms associated with that disease or disorder. As defined herein, "treatment" refers to the use of one or more compositions of the present invention to prevent, cure, retard, or reduce the severity of herpes simplex disease symptoms in a vertebrate, and/or result in no worsening of herpes simplex disease over a specified period of time in a vertebrate which has already been exposed to herpes simplex virus and is thus in need of therapy. The term "prevention" refers to the use of one or more compositions of the present invention to generate immunity in a vertebrate which has not yet been exposed to a particular strain of herpes simplex virus, thereby preventing or reducing disease symptoms if the vertebrate is later exposed to the particular strain of herpes simplex virus. The methods of the present invention therefore may be referred to as therapeutic vaccination or preventative or prophylactic vaccination. It is not required that any composition of the present invention provide total immunity to herpes simplex or totally cure or eliminate all herpes simplex disease symptoms. As used herein, a "vertebrate in need of therapeutic and/or preventative immunity" refers to an individual for whom it is desirable to treat, i.e., to prevent, cure, retard, or reduce the severity of herpes simplex disease symptoms, and/or result in no worsening of herpes simplex disease over a specified period of time.

One or more compositions of the present invention are utilized in a "prime boost" regimen. An example of a "prime boost" regimen may be found in Yang, Z. et al. J. Virol. 77:799-803 (2002). In these embodiments, one or more polynucleotide vaccine compositions of the present invention are delivered to a vertebrate, thereby priming the immune response of the vertebrate to a herpes simplex virus, and then a second immunogenic composition is utilized as a boost vaccination. One or more compositions of the present invention are used to prime immunity, and then a second immunogenic composition, e.g., a recombinant viral vaccine or vaccines, a different polynucleotide vaccine, or one or more purified subunit isolated herpes simplex virus polypeptides or fragments, variants or derivatives thereof is used to boost the anti-herpes simplex virus immune response.

In one embodiment, a priming composition and a boosting composition are combined in a single composition or single formulation. For example, a single composition may comprise an isolated herpes simplex virus polypeptide or a fragment, variant, or derivative thereof as the priming component and a polynucleotide encoding a herpes simplex protein as the boosting component. In this embodiment, the compositions may be contained in a single vial where the priming component and boosting component are mixed together. In general, because the peak levels of expression of protein from the polynucleotide does not occur until later (e.g. 7-10 days) after administration, the polynucleotide component may provide a boost to the isolated protein component. Compositions comprising both a priming component and a boosting component are referred to herein as "combinatorial vaccine compositions" or "single formulation heterologous prime-boost vaccine compositions." In addition, the priming composition may be administered before the boosting composition, or even after the boosting composition, if the boosting composition is expected to take longer to act.

In another embodiment, the priming composition may be administered simultaneously with the boosting composition, but in separate formulations where the priming component and the boosting component are separated.

The terms "priming" or "primary" and "boost" or "boosting" as used herein may refer to the initial and subsequent immunizations, respectively, i.e., in accordance with the definitions these terms normally have in immunology. However, in certain embodiments, e.g., where the priming component and boosting component are in a single formulation, initial and subsequent immunizations may not be necessary as both the "prime" and the "boost" compositions are administered simultaneously.

In certain embodiments, one or more compositions of the present invention are delivered to a vertebrate by methods described herein, thereby achieving an effective therapeutic and/or an effective preventative immune response. More specifically, the compositions of the present invention may be administered to any tissue of a vertebrate, including, but not limited to, muscle, skin, brain tissue, lung tissue, liver tissue, spleen tissue, bone marrow tissue, thymus tissue, heart tissue, e.g., myocardium, endocardium, and pericardium, lymph tissue, blood tissue, bone tissue, pancreas tissue, kidney tissue, gall bladder tissue, stomach tissue, intestinal tissue, testicular tissue, ovarian tissue, uterine tissue, vaginal tissue, rectal tissue, nervous system tissue, eye tissue, glandular tissue, tongue tissue, and connective tissue, e.g., cartilage.

Furthermore, the compositions of the present invention may be administered to any internal cavity of a vertebrate, including, but not limited to, the lungs, the mouth, the nasal cavity, the stomach, the peritoneal cavity, the intestine, any heart chamber, veins, arteries, capillaries, lymphatic cavities, the uterine cavity, the vaginal cavity, the rectal cavity, joint cavities, ventricles in brain, spinal canal in spinal cord, the ocular cavities, the lumen of a duct of a salivary gland or a liver. When the compositions of the present invention is administered to the lumen of a duct of a salivary gland or liver, the desired polypeptide is expressed in the salivary gland and the liver such that the polypeptide is delivered into the blood stream of the vertebrate from each of the salivary gland or the liver. Certain modes for administration to secretory organs of a gastrointestinal system using the salivary gland, liver and pancreas to release a desired polypeptide into the bloodstream is disclosed in U.S. Pat. Nos. 5,837,693 and 6,004,944.

In certain embodiments, the compositions are administered to muscle, either skeletal muscle or cardiac muscle, or to lung tissue. Specific, but non-limiting modes for administration to lung tissue are disclosed in Wheeler, C. J., et al., Proc. Natl. Acad. Sci. USA 93:11454-11459 (1996), which is incorporated herein by reference in its entirety.

According to the disclosed methods, compositions of the present invention can be administered by intramuscular (i.m.), interdermal (i.d.), subcutaneous (s.c), or intrapulmonary routes. Other suitable routes of administration include, but are not limited to intratracheal, transdermal, intraocular, intranasal, inhalation, intracavity, intravenous (i.v.), intraductal (e.g., into the pancreas) and intraparenchymal (i.e., into any tissue) administration. Transdermal delivery includes, but not limited to intradermal (e.g., into the dermis or epidermis), transdermal (e.g., percutaneous) and transmucosal administration (i.e., into or through skin or mucosal tissue). Intracavity administration includes, but not limited to administration into oral, vaginal, rectal, nasal, peritoneal, or intestinal cavities as well as, intrathecal (i.e., into spinal canal), intraventricular (i.e., into the brain ventricles or the heart ventricles), intraatrial (i.e., into the heart atrium) and sub arachnoid (i.e., into the sub arachnoid spaces of the brain) administration.

For oral indications, the present invention may be administered in the form of tongue strips wherein the composition is embedded or applied to the strip. The user places the strip on the tongue and the strip melts or dissolves in the mouth thereby releasing the composition.

Any mode of administration can be used so long as the mode results in the expression of the desired peptide or protein, in the desired tissue, in an amount sufficient to generate an immune response to herpes simplex virus and/or to generate a prophylactically or therapeutically effective immune response to herpes simplex virus in a human in need of such response. Administration means of the present invention include needle injection, catheter infusion, biolistic injectors, particle accelerators (e.g., "gene guns" or pneumatic "needleless" injectors) Med-E-Jet (Vahlsing, H., et al., J. Immunol. Methods 171:11-22 (1994)), Pigjet (Schrijver, R., et al., Vaccine 15: 1908-1916 (1997)), Biojector (Davis, H., et al., Vaccine 12: 1503-1509 (1994); Gramzinski, R., et al., Mol. Med. 4: 109-118 (1998)), AdvantaJet (Linmayer, I., et al., Diabetes Care 9:294-297 (1986)), Medi-jector (Martins, J., and Roedl, E. J. Occup. Med. 21:821-824 (1979)), U.S. Pat. No. 5,399,163; U.S. Pat. No. 5,383,851; gelfoam sponge depots, other commercially available depot materials (e.g., hydrogels), osmotic pumps (e.g., Alza minipumps), oral or suppositorial solid (tablet or pill) pharmaceutical formulations, topical skin creams, and decanting, use of polynucleotide coated suture (Qin, Y., et al., Life Sciences 65:2193-2203 (1999)) or topical applications during surgery. Certain modes of administration are intramuscular or intradermal needle-based injection and pulmonary application via catheter infusion. Energy-assisted plasmid delivery (EAPD) methods may also be employed to administer the compositions of the invention. One such method involves the application of brief electrical pulses to injected tissues, a procedure commonly known as electroporation. See generally Mir, L. M. et al., Proc. Natl. Acad. Sci. USA 96:4262-7 (1999); Hartikka, J. et al., Mol. Ther. 4:407-15 (2001); Mathiesen, I., Gene Ther. 6:508-14 (1999); Rizzuto G. et al., Hum. Gen. Ther. 11:1891-900 (2000).

Determining an effective amount of one or more compositions of the present invention depends upon a number of factors including, for example, the antigen being expressed or administered directly, e.g., gD, VP11/12, VP13/14 and/or VP22, or fragments, variants, or derivatives thereof, the age and weight of the subject, the precise condition requiring treatment and its severity, and the route of administration. Based on the above factors, determining the precise amount, number of doses, and timing of doses are within the ordinary skill in the art and will be readily determined by the attending physician or veterinarian.

Compositions of the present invention may include various salts, excipients, delivery vehicles and/or auxiliary agents as are disclosed, e.g., in U.S. patent application Publication No. 2002/0019358, published Feb. 14, 2002.

Furthermore, compositions of the present invention may include one or more transfection facilitating compounds that facilitate delivery of polynucleotides to the interior of a cell, and/or to a desired location within a cell. As used herein, the terms "transfection facilitating compound," "transfection facilitating agent," and "transfection facilitating material" are synonymous, and may be used interchangeably. It should be noted that certain transfection facilitating compounds may also be "adjuvants" as described infra, i.e., in addition to facilitating delivery of polynucleotides to the interior of a cell, the compound acts to alter or increase the immune response to the antigen encoded by that polynucleotide. Examples of the transfection facilitating compounds include, but are not limited to, inorganic materials such as calcium phosphate, alum (aluminum sulfate), and gold particles (e.g., "powder" type delivery vehicles); peptides that are, for example, canonic, intercell targeting (for selective delivery to certain cell types), intracell targeting (for nuclear localization or endosomal escape), and ampipathic (helix forming or pore forming); proteins that are, for example, basic (e.g., positively charged) such as histories, targeting (e.g., asialoprotein), viral (e.g., Sendai virus coat protein), and pore-forming; lipids that are, for example, cationic (e.g., DMRIE, DOSPA, DC-Chol), basic (e.g., steryl amine), neutral (e.g., cholesterol), anionic (e.g., phosphatidyl serine), and zwitterionic (e.g., DOPE, DOPC); and polymers such as dendrimers, star-polymers, "homogenous" poly-amino acids (e.g., poly-lysine, poly-arginine), "heterogeneous" poly-amino acids (e.g., mixtures of lysine & glycine), co-polymers, polyvinylpyrrolidinone (PVP), poloxamers (e.g. CRL 1005) and polyethylene glycol (PEG). A transfection facilitating material can be used alone or in combination with one or more other transfection facilitating materials. Two or more transfection facilitating materials can be combined by chemical bonding (e.g., covalent and ionic such as in lipidated polylysine, PEGylated polylysine) (Toncheva, et al., Biochim. Biophys. Acta 1380(3): 354-368 (1988)), mechanical mixing (e.g., tree moving materials in liquid or solid phase such as "polylysine+cationic lipids") (Gao and Huang, Biochemistry 35:1027-1036 (1996); Trubetskoy, et al., Biochem. Biophys. Acta 1131:311-313 (1992)), and aggregation (e.g., co-precipitation, gel forming such as in cationic lipids+poly-lactide, and polylysine+gelatin).

One category of transfection facilitating materials is cationic lipids. Examples of cationic lipids are 5-carboxyspermylglycine dioctadecylamide (DOGS) and dipalmitoyl-phophatidylethanolamine-5-carboxyspermylamide (DPPES). Cationic cholesterol derivatives are also useful, including {3β-[N—N',N'-dimethylamino)ethane]-carbomoyl}-cholesterol (DC-Chol). Dimethyldioctdecyl-ammonium bromide (DDAB), N-(3-aminopropyl)-N,N-(bis-(2-tetradecyloxyethyl))-N-methyl-ammonium bromide (PA-DEMO), N-(3-aminopropyl)-N,N-(bis-(2-dodecyloxyethyl))-N-methyl-ammonium bromide (PA-DELO), N,N,N-tris-(2-dodecyloxy)ethyl-N-(3-amino) propyl-ammonium bromide (PA-TELO), and N1-(3-aminopropyl)((2-dodecyloxy)ethyl)-N2-(2-dodecyloxy) ethyl-1-piperazinaminium bromide (GA-LOE-BP) can also be employed in the present invention.

Non-diether cationic lipids, such as DL-1,2-doleoyl-3-dimethylaminopropyl-β-hydroxyethylammonium (DORI diester), 1-O-oleyl-2-oleoyl-3-dimethylaminopropyl-p-hydroxyethylammonium (DORI ester/ether), and their salts promote in vivo gene delivery. In some embodiments, cationic lipids comprise groups attached via a heteroatom attached to the quaternary ammonium moiety in the head group. A glycyl spacer can connect the linker to the hydroxyl group.

Specific, but non-limiting cationic lipids for use in certain embodiments of the present invention include DMRIE ((±)-N-(2-hydroxyethyl)-N,N-dimethyl-2,3-bis(tetradecyloxy)-1-propanaminium bromide), GAP-DMORIE ((±)-N-(3-aminopropyl)-N,N-dimethyl-2,3-bis(syn-9-tetradecenyloxy)-1-propanaminium bromide), and GAP-DMRIE((±)-N-(3-aminopropyl)-N,N-dimethyl-2,3-(bis-dodecyloxy)-1-propaniminium bromide).

Other specific but non-limiting cationic surfactants for use in certain embodiments of the present invention include Bn-DHRIE, DhxRIE, DhxRIE-OAc, DhxRIE-OBz and Pr-DOctRIE-OAc. These lipids are disclosed in copending U.S. patent application Ser. No. 10/725,015. In another aspect of the present invention, the cationic surfactant is Pr-DOctRIE-OAc.

Other cationic lipids include (±)-N,N-dimethyl-N-[2-(sperminecarboxamido)ethyl]-2,3-bis(dioleyloxy)-1-propaniminium pentahydrochloride (DOSPA), (±)-N-(2-aminoethyl)-N,N-dimethyl-2,3-bis(tetradecyloxy)-1-propaniminium bromide (β-aminoethyl-DMRIE or βAE-DMRIE) (Wheeler, et al., Biochim. Biophys. Acta 1280:1-11 (1996), and (±)-N-(3-aminopropyl)-N,N-dimethyl-2,3-bis (dodecyloxy)-1-propaniminium bromide (GAP-DLRIE) (Wheeler, et al., Proc. Natl. Acad. Sci. USA 93:11454-11459 (1996)), which have been developed from DMRIE.

Other examples of DMRIE-derived cationic lipids that are useful for the present invention are (±)-N-(3-aminopropyl)-N,N-dimethyl-2,3-(bis-decyloxy)-1-propanaminium bromide (GAP-DDRIE), (±)-N-(3-aminopropyl)-N,N-dimethyl-2,3-(bis-tetradecyloxy)-1-propanaminium bromide (GAP-DMRIE), (±)-N—((N"-methyl)-N'-ureyl)propyl-N,N-dimethyl-2,3-bis(tetradecyloxy-)-1-propanaminium bromide (GMU-DMRIE), (±)-N-(2-hydroxyethyl)-N,N-dimethyl-2,3-bis(dodecyloxy)-1-propanaminium bromide (DLRIE), and (±)-N-(2-hydroxyethyl)-N,N-dimethyl-2,3-bis-([Z]-9-octadecenyloxy)propyl-1-propaniminium bromide (HP-DORIE).

In the embodiments where the immunogenic composition comprises a cationic lipid, the cationic lipid may be mixed with one or more co-lipids. For purposes of definition, the term "co-lipid" refers to any hydrophobic material which may be combined with the cationic lipid component and includes amphipathic lipids, such as phospholipids, and neutral lipids, such as cholesterol. Cationic lipids and co-lipids may be mixed or combined in a number of ways to produce a variety of non-covalently bonded macroscopic structures, including, for example, liposomes, multilamellar vesicles, unilamellar vesicles, micelles, and simple films. One non-limiting class of co-lipids are the zwitterionic phospholipids, which include the phosphatidylethanolamines and the phosphatidylcholines. Examples of phosphatidylethanolamines, include DOPE, DMPE and DPyPE. In certain embodiments, the co-lipid is DPyPE which comprises two phytanoyl substituents incorporated into the diacylphosphatidylethanolamine skeleton and the cationic lipid is GAP-DMORIE, (resulting in VAXFECTIN adjuvant). In other embodiments, the co-lipid is DOPE, the CAS name is 1,2-diolyeoyl-sn-glycero-3-phosphoethanolamine.

When a composition of the present invention comprises a cationic lipid and co-lipid, the cationic lipid:co-lipid molar ratio may be from about 9:1 to about 1:9, from about 4:1 to about 1:4, from about 2:1 to about 1:2, or about 1:1.

In order to maximize homogeneity, the cationic lipid and co-lipid components may be dissolved in a solvent such as chloroform, followed by evaporation of the cationic lipid/co-lipid solution under vacuum to dryness as a film on the inner surface of a glass vessel (e.g., a Rotovap round-bottomed flask). Upon suspension in an aqueous solvent, the amphipathic lipid component molecules self-assemble into homogenous lipid vesicles. These lipid vesicles may subsequently be processed to have a selected mean diameter of uniform size prior to complexing with, for example, a codon-optimized polynucleotide of the present invention, according to methods known to those skilled in the art. For example, the sonication of a lipid solution is described in Felgner et al., Proc. Natl. Acad. Sci. USA 8:, 7413-7417 (1987) and in U.S. Pat. No. 5,264,618.

In those embodiments where the composition includes a cationic lipid, polynucleotides of the present invention are complexed with lipids by mixing, for example, a plasmid in aqueous solution and a solution of cationic lipid:co-lipid as prepared herein are mixed. The concentration of each of the constituent solutions can be adjusted prior to mixing such that the desired final plasmid/cationic lipid:co-lipid ratio and the desired plasmid final concentration will be obtained upon mixing the two solutions. The cationic lipid:co-lipid mixtures are suitably prepared by hydrating a thin film of the mixed lipid materials in an appropriate volume of aqueous solvent by vortex mixing at ambient temperatures for about 1 minute. The thin films are prepared by admixing chloroform solutions of the individual components to afford a desired molar solute ratio followed by aliquoting the desired volume of the solutions into a suitable container. The solvent is removed by evaporation, first with a stream of dry, inert gas (e.g. argon) followed by high vacuum treatment.

Other hydrophobic and amphiphilic additives, such as, for example, sterols, fatty acids, gangliosides, glycolipids, lipopeptides, liposaccharides, neobees, niosomes, prostaglandins and sphingolipids, may also be included in compositions of the present invention. In such compositions, these additives may be included in an amount between about 0.1 mol % and about 99.9 mol % (relative to total lipid), about 1-50 mol %, or about 2-25 mol %.

Additional embodiments of the present invention are drawn to compositions comprising an auxiliary agent which is administered before, after, or concurrently with the polynucleotide. As used herein, an "auxiliary agent" is a substance included in a composition for its ability to enhance, relative to a composition which is identical except for the inclusion of the auxiliary agent, the entry of polynucleotides into vertebrate cells in vivo, and/or the in vivo expression of polypeptides encoded by such polynucleotides. Certain auxiliary agents may, in addition to enhancing entry of polynucleotides into cells, enhance an immune response to an immunogen encoded by the polynucleotide. Auxiliary agents of the present invention include nonionic, anionic, canonic, or zwitterionic surfactants or detergents, with nonionic surfactants or detergents being preferred, chelators, DNase inhibitors, poloxamers, agents that aggregate or condense nucleic acids, emulsifying or solubilizing agents, wetting agents, gel-forming agents, and buffers.

Auxiliary agents for use in compositions of the present invention include, but are not limited to non-ionic detergents and surfactants IGEPAL CA 6300 octylphenyl-polyethylene glycol, NONIDET NP-40 nonylphenoxypolyethoxyethanol, NONIDET P-40 octylphenoxypolyethoxyethanol, TWEEN-20 polysorbate 20, TWEEN-80 polysorbate 80, PLURONIC F68 poloxamer (ave. MW: 8400; approx. MW of hydrophobe, 1800; approx. wt. % of hydrophile, 80%), PLURONIC F77 poloxamer (ave. MW: 6600; approx. MW of hydrophobe, 2100; approx. wt. % of hydrophile, 70%), PLURONIC P65 poloxamer (ave. MW: 3400; approx. MW of hydrophobe, 1800; approx. wt. % of hydrophile, 50%), TRITON X-100 4-(1,1,3,3-tetramethylbutyl)phenyl-polyethylene glycol, and TRITON X-114 (1,1,3,3-tetramethylbutyl) phenyl-polyethylene glycol; the anionic detergent sodium dodecyl sulfate (SDS); the sugar stachyose; the condensing agent DMSO; and the chelator/DNAse inhibitor EDTA, CRL 1005 (12 kpa, 5% POE), and BAK (Benzalkonium chloride 50% solution, available from Ruger Chemical Co. Inc.). In certain specific embodiments, the auxiliary agent is DMSO, NONIDET P-40 octylphenoxypolyethoxyethanol, PLURONIC F68 poloxamer (ave. MW: 8400; approx. MW of hydrophobe, 1800; approx. wt. % of hydrophile, 80%), PLURONIC F77 poloxamer (ave. MW: 6600; approx. MW of hydrophobe, 2100; approx. wt. % of hydrophile, 70%), PLURONIC P65 (ave. MW: 3400; approx. MW of hydrophobe, 1800; approx. wt. % of hydrophile, 50%), Pluronic PLURONIC L64 poloxamer (ave. MW: 2900; approx. MW of hydrophobe, 1800; approx. wt. % of hydrophile, 40%), and PLURONIC F108 poloxamer (ave. MW: 14600; approx. MW of hydrophobe, 3000; approx. wt. % of hydrophile, 80%). See, e.g., U.S. patent application Publication No. 2002/0019358, published Feb. 14, 2002.

Certain compositions of the present invention can further include one or more adjuvants before, after, or concurrently with the polynucleotide. The term "adjuvant" refers to any material having the ability to (1) alter or increase the immune response to a particular antigen or (2) increase or aid an effect of a pharmacological agent. It should be noted, with respect to polynucleotide vaccines, that an "adjuvant," can be a transfection facilitating material. Similarly, certain "transfection facilitating materials" described supra, may also be an "adjuvant." An adjuvant maybe used with a composition comprising a polynucleotide of the present invention. In a prime-boost regimen, as described herein, an adjuvant may be used with either the priming immunization, the booster immunization, or both. Suitable adjuvants include, but are not limited to, cytokines and growth factors; bacterial components (e.g., endotoxins, in particular superantigens, exotoxins and cell wall components); aluminum-based salts; calcium-based salts; silica; polynucleotides; toxoids; serum proteins, viruses and virally-derived materials, poisons, venoms, imidazoquiniline compounds, poloxamers, and cationic lipids.

A great variety of materials have been shown to have adjuvant activity through a variety of mechanisms. Any compound which may increase the expression, antigenicity or immunogenicity of the polypeptide is a potential adjuvant. The present invention provides an assay to screen for improved immune responses to potential adjuvants. Potential adjuvants which may be screened for their ability to enhance the immune response according to the present invention include, but are not limited to: inert carriers, such as alum, bentonite, latex, and acrylic particles; PLURONIC block polymers, such as TITERMAX (block copolymer CRL-8941, squalene (a metabolizable oil) and a microparticulate silica stabilizer); depot formers, such as Freunds adjuvant, surface active materials, such as saponin, lysolecithin, retinal, Quil A, liposomes, and PLURONIC polymer formulations; macrophage stimulators, such as bacterial lipopolysaccharide; alternate pathway complement activators, such as insulin, zymosan, endotoxin, and levamisole; and non-ionic surfactants, such as poloxamers, poly(oxyethylene)-poly (oxypropylene) tri-block copolymers. Also included as adjuvants are transfection-facilitating materials, such as those described above.

Poloxamers which may be screened for their ability to enhance the immune response according to the present invention include, but are not limited to, commercially available poloxamers such as PLURONIC surfactants, which are block copolymers of propylene oxide and ethylene oxide in which the propylene oxide block is sandwiched between two ethylene oxide blocks. Examples of PLURONIC surfactants include PLURONIC L121 poloxamer (ave. MW: 4400; approx. MW of hydrophobe, 3600; approx. wt % of hydrophile, 10%), PLURONIC L101 poloxamer (ave. MW: 3800; approx. MW of hydrophobe, 3000; approx. wt. % of hydrophile, 10%), PLURONIC L81 poloxamer (ave. MW: 2750; approx. MW of hydrophobe, 2400; approx. wt. % of hydrophile, 10%), PLURONIC L61 poloxamer (ave. MW: 2000; approx. MW of hydrophobe, 1800; approx. wt. % of hydrophile, 10%), PLURONIC L31 poloxamer (ave. MW: 1100; approx. MW of hydrophobe, 900; approx. wt. % of hydrophile, 10%), PLURONIC L122 poloxamer (ave. MW: 5000; approx. MW of hydrophobe, 3600; approx. wt. % of hydrophile, 20%), PLURONIC L92 poloxamer (ave. MW: 3650; approx. MW of hydrophobe, 2700; approx. wt. % of hydrophile, 20%), PLURONIC L72 poloxamer (ave. MW: 2750; approx. MW of hydrophobe, 2100; approx. wt. % of hydrophile, 20%), PLURONIC L62 poloxamer (ave. MW: 2500; approx. MW of hydrophobe, 1800; approx. wt. % of hydrophile, 20%), PLURONIC L42 poloxamer (ave. MW: 1630; approx. MW of hydrophobe, 1200; approx. wt. % of hydrophile, 20%), PLURONIC L63 poloxamer (ave. MW: 2650; approx. MW of hydrophobe, 1800; approx. wt. % of hydrophile, 30%), PLURONIC L43 poloxamer (ave. MW: 1850; approx. MW of hydrophobe, 1200; approx. wt. % of hydrophile, 30%), PLURONIC L64 poloxamer (ave. MW: 2900; approx. MW of hydrophobe, 1800; approx. wt. % of hydrophile, 40%), PLURONIC L44 poloxamer (ave. MW: 2200; approx. MW of hydrophobe, 1200; approx. wt. % of hydrophile, 40%), PLURONIC L35 poloxamer (ave. MW: 1900; approx. MW of hydrophobe, 900; approx. wt. % of hydrophile, 50%), PLURONIC P123 poloxamer (ave. MW: 5750; approx. MW of hydrophobe, 3600; approx. wt. % of hydrophile, 30%), PLURONIC P103 poloxamer (ave. MW: 4950; approx. MW of hydrophobe, 3000; approx. wt. % of hydrophile, 30%), PLURONIC P104 poloxamer (ave. MW: 5900; approx. MW of hydrophobe, 3000; approx. wt. % of hydrophile, 40%), PLURONIC P84 poloxamer (ave. MW: 4200; approx. MW of hydrophobe, 2400; approx. wt. % of hydrophile, 40%), PLURONIC P105 poloxamer (ave. MW: 6500; approx. MW of hydrophobe, 3000; approx. wt. % of hydrophile, 50%), PLURONIC P85 poloxamer (ave. MW: 4600; approx. MW of hydrophobe, 2400; approx. wt. % of hydrophile, 50%), PLURONIC P75 poloxamer (ave. MW: 4150; approx. MW of hydrophobe, 2100; approx. wt. % of hydrophile, 50%), PLURONIC P65 poloxamer (ave. MW: 3400; approx. MW of hydrophobe, 1800; approx. wt. % of hydrophile, 50%), PLURONIC F127 poloxamer (ave. MW: 12600; approx. MW of hydrophobe, 3600; approx. wt. % of hydrophile, 70%), PLURONIC F98 poloxamer (ave. MW: 13000; approx. MW of hydrophobe, 2700; approx. wt. % of hydrophile, 80%), PLURONIC F87 poloxamer (ave. MW: 7700; approx. MW of hydrophobe, 2400; approx. wt. % of hydrophile, 70%), PLURONIC F77 poloxamer (ave. MW: 6600; approx. MW of hydrophobe, 2100; approx. wt. % of hydrophile, 70%), PLURONIC F108 poloxamer (ave. MW: 14600; approx. MW of hydrophobe, 3000; approx. wt. % of hydrophile, 80%), PLURONIC F98 poloxamer (ave. MW: 13000; approx. MW of hydrophobe, 2700; approx. wt. % of hydrophile, 80%), PLURONIC F88 poloxamer (ave. MW: 11400; approx. MW of hydrophobe, 2400; approx. wt. % of hydrophile, 80%), PLURONIC F68 poloxamer (ave. MW: 8400; approx. MW of hydrophobe, 1800; approx. wt. % of hydrophile, 80%), PLURONIC F38 poloxamer (ave. MW: 4700; approx. MW of hydrophobe, 900; approx. wt. % of hydrophile, 80%).

Reverse poloxamers which may be screened for their ability to enhance the immune response according to the present invention include, but are not limited to PLURONIC R 31R1 reverse poloxamer (ave. MW: 3250; approx. MW of hydrophobe, 3100; approx. wt. % of hydrophile, 10%), PLURONIC R25R1 reverse poloxamer (ave. MW: 2700; approx. MW of hydrophobe, 2500; approx. wt. % of hydrophile, 10%), PLURONIC R 17R1 reverse poloxamer (ave. MW: 1900; approx. MW of hydrophobe, 1700; approx. wt. % of hydrophile, 10%), PLURONIC R 31R2 reverse poloxamer (ave. MW: 3300; approx. MW of hydrophobe, 3100; approx. wt. % of hydrophile, 20%), PLURONIC R 25R2 reverse poloxamer (ave. MW: 3100; approx. MW of hydrophobe, 2500; approx. wt. % of hydrophile, 20%), PLURONIC R 17R2 reverse poloxamer (ave. MW: 2150; approx. MW of hydrophobe, 1700; approx. wt. % of hydrophile, 20%), PLURONIC R 12R3 reverse poloxamer (ave. MW: 1800; approx. MW of hydrophobe, 1200; approx. wt. % of hydrophile, 30%), PLURONIC R 31R4 reverse poloxamer (ave. MW: 4150; approx. MW of hydrophobe, 3100; approx. wt. % of hydrophile, 40%), PLURONIC R 25R4 reverse poloxamer (ave. MW: 3600; approx. MW of hydrophobe, 2500; approx. wt. % of hydrophile, 40%), PLURONIC R 22R4 reverse poloxamer (ave. MW: 3350; approx. MW of hydrophobe, 2200; approx. wt. % of hydrophile, 40%), PLURONIC R17R4 reverse poloxamer (ave. MW: 3650; approx. MW of hydrophobe, 1700; approx. wt. % of hydrophile, 40%), PLURONIC R 25R5 reverse poloxamer (ave. MW: 4320; approx. MW of hydrophobe, 2500; approx. wt. % of hydrophile, 50%), PLURONIC R10R5 reverse poloxamer (ave. MW: 1950; approx. MW of hydrophobe, 1000; approx. wt. % of hydrophile, 50%), PLURONIC R 25R8 reverse poloxamer (ave. MW: 8550; approx. MW of hydrophobe, 2500; approx. wt. % of hydrophile, 80%), PLURONIC R 17R8 reverse poloxamer (ave. MW: 7000; approx. MW of hydrophobe, 1700; approx. wt. % of hydrophile, 80%), and PLURONIC R 10R8 reverse poloxamer (ave. MW: 4550; approx. MW of hydrophobe, 1000; approx. wt. % of hydrophile, 80%).

Other commercially available poloxamers which may be screened for their ability to enhance the immune response according to the present invention include compounds that are block copolymer of polyethylene and polypropylene glycol such as SYNPERONIC L121 (ave. MW: 4400), SYNPERONIC L122 (ave. MW: 5000), SYNPERONIC P104 (ave. MW: 5850), SYNPERONIC P105 (ave. MW: 6500), SYNPERONIC P123 (ave. MW: 5750), SYNPERONIC P85 (ave. MW: 4600) and SYNPERONIC P94 (ave. MW: 4600), in which L indicates that the surfactants are liquids, P that they are pastes, the first digit is a measure of the molecular weight of the polypropylene portion of the surfactant and the last digit of the number, multiplied by 10, gives the percent ethylene oxide content of the surfactant; and compounds that are nonylphenyl polyethylene glycol such as SYNPERONIC NP10 (nonylphenol ethoxylated surfactant—10% solution), SYNPERONIC NP30 (condensate of 1 mole of nonylphenol with 30 moles of ethylene oxide) and SYNPERONIC NP5 (condensate of 1 mole of nonylphenol with 5.5 moles of naphthalene oxide).

Other poloxamers which may be screened for their ability to enhance the immune response according to the present invention include: (a) a polyether block copolymer comprising an A-type segment and a B-type segment, wherein the A-type segment comprises a linear polymeric segment of relatively hydrophilic character, the repeating units of which contribute an average Hansch-Leo fragmental constant of about −0.4 or less and have molecular weight contributions between about 30 and about 500, wherein the B-type segment comprises a linear polymeric segment of relatively hydrophobic character, the repeating units of which contribute an average Hansch-Leo fragmental constant of about −0.4 or more and have molecular weight contributions between about 30 and about 500, wherein at least about 80% of the linkages joining the repeating units for each of the polymeric segments comprise an ether linkage; (b) a block copolymer having a polyether segment and a polycation segment, wherein the polyether segment comprises at least an A-type block, and the polycation segment comprises a plurality of cationic repeating units; and (c) a polyether-polycation copolymer comprising a polymer, a polyether segment and a polycationic segment comprising a plurality of cationic repeating units of formula —NH—$R^0$, wherein $R^0$ is a straight chain aliphatic group of 2 to 6 carbon atoms, which may be substituted, wherein said polyether segments comprise at least one of an A-type of B-type segment. See U.S. Pat. No. 5,656,611. Other poloxamers of interest include CRL1005 (12 kDa, 5% POE), CRL8300 (11 kDa, 5% POE), CRL2690 (12 kDa, 10% POE), CRL4505 (15 kDa, 5% POE) and CRL1415 (9 kDa, 10% POE).

Other auxiliary agents which may be screened for their ability to enhance the immune response according to the present invention include, but are not limited to, Acacia (gum arabic); the poloxyethylene ether R—O—$(C_2H_4O)_x$—H (BRIJ), e.g., polyethylene glycol dodecyl ether (BRIJ 35, x=23), polyethylene glycol dodecyl ether (BRIJ 30, x=4), polyethylene glycol hexadecyl ether (BRIJ 52 x=2), polyethylene glycol hexadecyl ether (BRIJ 56, x=10), polyethylene glycol hexadecyl ether (BRIJ 58P, x=20), polyethylene glycol octadecyl ether (BRIJ 72, x=2), polyethylene glycol octadecyl ether (BRIJ 76, x=10), polyethylene glycol octadecyl ether (BRIJ® 78P, x=20), polyethylene glycol oleyl ether (BRIJ 92V, x=2), and polyoxyl 10 oleyl ether (BRIJ 97, x=10); poly-D-glucosamine (chitosan); chlorbutanol; cholesterol; diethanolamine; digitonin; dimethylsulfoxide (DMSO), ethylenediamine tetraacetic acid (EDTA); glyceryl monosterate; lanolin alcohols; mono- and di-glycerides; monoethanolamine; nonylphenol polyoxyethylene ether (NP-40); octylphenoxypolyethoxyethanol (NONIDET NP-40 from Amresco); ethyl phenol poly (ethylene glycol ether)$^n$, n=11 (NONIDET P40 from Roche); octyl phenol ethylene oxide condensate with about 9 ethylene oxide units (NONIDET P40); IGEPAL CA 630 ((octyl phenoxy) polyethoxyethanol; structurally same as NONIDET NP-40); oleic acid; oleyl alcohol; polyethylene glycol 8000; polyoxyl 20 cetostearyl ether; polyoxyl 35 castor oil; polyoxyl 40 hydrogenated castor oil; polyoxyl 40 stearate; polyoxyethylene sorbitan monolaurate (polysorbate 20, or TWEEN-20; polyoxyethylene sorbitan monooleate (polysorbate 80, or TWEEN-80); propylene glycol diacetate; propylene glycol monstearate; protamine sulfate; proteolytic enzymes; sodium dodecyl sulfate (SDS); sodium monolaurate; sodium stearate; sorbitan derivatives (SPAN), e.g., sorbitan monopalmitate (SPAN 40), sorbitan monostearate (SPAN 60), sorbitan tristearate (SPAN 65), sorbitan monooleate (SPAN 80), and sorbitan trioleate (SPAN 85); 2,6,10,15,19,23-hexamethyl-2,6,10,14,18,22-tetracosa-hexaene (squalene); stachyose; stearic acid; sucrose; surfactin (lipopeptide antibiotic from *Bacillus subtilis*); dodecylpoly(ethyleneglycolether)9 (THESIT) MW 582.9; octyl phenol ethylene oxide condensate with about 9-10 ethylene oxide units (TRITON X-100); octyl phenol ethylene oxide condensate with about 7-8 ethylene oxide units (TRITON X-114); tris(2-hydroxyethyl) amine (trolamine); and emulsifying wax.

In certain adjuvant compositions, the adjuvant is a cytokine. A composition of the present invention can comprise one or more cytokines, chemokines, or compounds that induce the production of cytokines and chemokines, or a polynucleotide encoding one or more cytokines, chemokines, or compounds that induce the production of cytokines and chemokines. Examples include, but are not limited to, granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interleukin 15 (IL-15), interleukin 18 (IL-18), interferon alpha (IFN$\alpha$), interferon beta (IFN$\beta$), interferon gamma (IFN$\gamma$), interferon omega (IFN$\Omega$), interferon tau (IFN$\tau$), interferon gamma inducing factor I (IGIF), transforming growth factor beta (TGF-$\beta$), RANTES (regulated upon activation, normal T-cell expressed and presumably secreted), macrophage inflammatory proteins (e.g., MIP-1 alpha and M3P-1 beta), *Leishmania* elongation initiating factor (LEIF), and Flt-3 ligand.

In certain compositions of the present invention, the polynucleotide construct may be complexed with an adjuvant composition comprising ($\pm$)-N-(3-aminopropyl)-N,N-dimethyl-2,3-bis(syn-9-tetradeceneyloxy)-1-propanaminium bromide (GAP-DMORIE). The composition may also comprise one or more co-lipids, e.g., 1,2-dioleoyl-sn-glycero-3-phosphoethanolamine (DOPE), 1,2-diphytanoyl-sn-glycero-3-phosphoethanolamine (DPyPE), and/or 1,2-dimyristoyl-glycer-3-phosphoethanolamine (DMPE). An adjuvant composition comprising GAP-DMORIE and DPyPE at a 1:1 molar ratio is referred to herein as VAXFECTIN adjuvant. See, e.g., PCT Publication No. WO 00/57917.

In other embodiments, the polynucleotide itself may function as an adjuvant as is the case when the polynucleotides of the invention are derived, in whole or in part, from bacterial DNA. Bacterial DNA containing motifs of unmethylated CpG-dinucleotides (CpG-DNA) triggers innate immune cells in vertebrates through a pattern recognition receptor (including toll receptors such as TLR 9) and thus possesses potent immunostimulatory effects on macrophages, dendritic cells and B-lymphocytes. See, e.g., Wagner, H., Curr. Opin. Microbiol. 5:62-69 (2002); Jung, J. et al., J. Immunol. 169: 2368-73 (2002); see also Klinman, D. M. et al., Proc. Natl Acad. Sci. U.S.A. 93:2879-83 (1996). Methods of using unmethylated CpG-dinucleotides as adjuvants are described in, for example, U.S. Pat. Nos. 6,207,646, 6,406,705 and 6,429,199.

The ability of an adjuvant to increase the immune response to an antigen is typically manifested by a significant increase in immune-mediated protection. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant may also alter an immune response, for example, by changing a primarily humoral or Th$_2$ response into a primarily cellular, or Th$_1$ response.

Nucleic acid molecules and/or polynucleotides of the present invention, e.g., plasmid DNA, mRNA, linear DNA or oligonucleotides, may be solubilized in any of various buffers. Suitable buffers include, for example, phosphate buffered saline (PBS), normal saline, Tris buffer, and sodium phosphate (e.g., 150 mM sodium phosphate). Insoluble polynucleotides may be solubilized in a weak acid or weak base, and then diluted to the desired volume with a buffer. The pH of the buffer may be adjusted as appropriate. In addition, a pharmaceutically acceptable additive can be used to provide an appropriate osmolarity. Such additives are within the purview of one skilled in the art. For aqueous compositions used in vivo, sterile pyrogen-free water can be used. Such formulations will contain an effective amount of a polynucleotide together with a suitable amount of an aqueous solution in order to prepare pharmaceutically acceptable compositions suitable for administration to a human.

Compositions of the present invention can be formulated according to known methods. Suitable preparation methods are described, for example, in Remington's Pharmaceutical Sciences, 16th Edition, A. Osol, ed., Mack Publishing Co., Easton, Pa. (1980), and Remington's Pharmaceutical Sciences, 19th Edition, A. R. Gennaro, ed., Mack Publishing Co., Easton, Pa. (1995). Although the composition may be administered as an aqueous solution, it can also be formulated as an emulsion, gel, solution, suspension, lyophilized form, or any other form known in the art. In addition, the composition may contain pharmaceutically acceptable additives including, for example, diluents, binders, stabilizers, and preservatives.

The following examples are included for purposes of illustration only and are not intended to limit the scope of the present invention, which is defined by the appended claims.

EXAMPLES

Materials and Methods

The following materials and methods apply generally to all the examples disclosed herein. Specific materials and methods are disclosed in each example, as necessary.

The practice of the present invention will employ, unless otherwise indicated, conventional techniques of cell biology, cell culture, molecular biology (including PCR), vaccinology, microbiology, recombinant DNA, and immunology, which are within the skill of the art. Such techniques are explained fully in the literature. See, for example, Molecular Cloning A Laboratory Manual, 2nd Ed., Sambrook et al., ed., Cold Spring Harbor Laboratory Press: (1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); and in Ausubel et al., Current Protocols in Molecular Biology, John Wiley and Sons, Baltimore, Md. (1989).

Gene Construction

Constructs of the present invention are constructed based on the sequence information provided herein or in the art utilizing standard molecular biology techniques, including, but not limited to, the following. First, a series complementary oligonucleotide pairs of 80-90 nucleotides each in length and spanning the length of the construct are synthesized by standard methods. These oligonucleotide pairs are synthesized such that upon annealing, they form double stranded fragments of 80-90 base pairs, containing cohesive ends. The single-stranded ends of each pair of oligonucleotides are designed to anneal with a single-stranded end of an adjacent oligonucleotide duplex. Several adjacent oligonucleotide pairs prepared in this manner are allowed to anneal, and approximately five to six adjacent oligonucleotide duplex fragments are then allowed to anneal together via the cohesive single stranded ends. This series of annealed oligonucleotide duplex fragments is then ligated together and cloned into a suitable plasmid, such as the TOPO® vector available from Invitrogen Corporation, Carlsbad, Calif. The construct is then sequenced by standard methods. Constructs prepared in this manner, comprising 5 to 6 adjacent 80 to 90 base pair fragments ligated together, i.e., fragments of about 500 base pairs, are prepared, such that the entire desired sequence of the construct is represented in a series of plasmid constructs. The inserts of these plasmids are then cut with appropriate restriction enzymes and ligated together to form the final construct. The final construct is then cloned into a standard bacterial cloning vector, and sequenced. The oligonucleotides and primers referred to herein can easily be designed by a person of skill in the art based on the sequence information provided herein and in the art, and such can be synthesized by any of a number of commercial nucleotide providers, for example Retrogen, San Diego, Calif., and GENEART, Regensburg, Germany.

Plasmid Vectors

Constructs of the present invention can be inserted, for example, into eukaryotic expression vectors VR1012 or VR10551. These vectors are built on a modified pUC18 background (see Yanisch-Perron, C., et al. Gene 33:103-119 (1985)), and contain a kanamycin resistance gene, the human cytomegalovirus immediate early promoter/enhancer and intron A, and the bovine growth hormone transcription termination signal, and a polylinker for inserting foreign genes. See Hartikka, J., et al., Hum. Gene Ther. 7:1205-1217 (1996). However, other standard commercially available eukaryotic expression vectors may be used in the present invention, including, but not limited to: plasmids pcDNA3, pHCMV/Zeo, pCR3.1, pEF1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.).

An optimized backbone plasmid, termed VR10551, has minor changes from the VR1012 backbone described above. The VR10551 vector is derived from and similar to VR1012 in that it uses the human cytomegalovirus immediate early (hCMV-IE) gene enhancer/promoter and 5' untranslated region (UTR), including the hCMV-IE Intron A. The changes from the VR1012 to the VR10551 include some modifications to the multiple cloning site, and a modified rabbit 13 globin 3' untranslated region/polyadenylation signal sequence/transcriptional terminator has been substituted for the same functional domain derived from the bovine growth hormone gene.

Plasmid DNA Purification

Plasmid DNA may be transformed into competent cells of an appropriate *Escherichia coli* strain (including but not limited to the DH5α strain) and highly purified covalently closed circular plasmid DNA was isolated by a modified lysis procedure (Horn, N. A., et al., Hum. Gene Ther. 6:565-573 (1995)) followed by standard double CsCl-ethidium bromide gradient ultracentrifugation (Sambrook, J., et al., Molecular Cloning: A Laboratory Manual, 2nd Ed., Cold Spring Harbor Laboratory Press, Plainview, N.Y. (1989)). Alternatively, plasmid DNAs are purified using Giga columns from Qiagen (Valencia, Calif.) according to the kit instructions. All plasmid preparations were free of detectable chromosomal DNA, RNA and protein impurities based on gel analysis and the bicinchoninic protein assay (Pierce Chem. Co., Rockford Ill.). Endotoxin levels were measured using *Limulus Amebocyte* Lysate assay (LAL, Associates of Cape Cod, Falmouth, Mass.) and were less than 0.6 Endotoxin Units/mg of plasmid DNA. The spectrophotometric $A_{260}/A_{280}$ ratios of the DNA solutions were typically above 1.8. Plasmids were ethanol precipitated and resuspended in an appropriate solution, e.g., 150 mM sodium phosphate (for other appropriate excipients and auxiliary agents, see U.S. patent application Publication 2002/0019358, published Feb. 14, 2002). DNA was stored at −20° C. until use. DNA was diluted by mixing it with 300 mM salt solutions and by adding appropriate amount of USP water to obtain 1 mg/ml plasmid DNA in the desired salt at the desired molar concentration.

Plasmid Expression in Mammalian Cell Lines

The expression plasmids are analyzed in vitro by transfecting the plasmids into a well characterized mouse melanoma cell line (VM-92, also known as UM-449). See, e.g., Wheeler, C. J., Sukhu, L., Yang, G., Tsai, Y., Bustamente, C. Felgner, P. Norman, J & Manthorpe, M. "Converting an Alcohol to an Amine in a Cationic Lipid Dramatically Alters the Co-lipid Requirement, Cellular Transfection Activity and the Ultrastructure of DNA-Cytofectin Complexes," Biochim. Biophys. Acta. 1280:1-11 (1996). Other well-characterized human cell lines can also be used, e.g. MRC-5 cells, American Type Culture Collection (ATCC) Accession No. CCL-171 or human rhabdomyosarcoma cell line RD (ATCC CCL-136). The transfection is performed using cationic lipid-based transfection procedures well known to those of skill in the art. Other transfection procedures are well known in the art and may be used, for example electroporation and calcium chloride-mediated transfection (Graham F. L. and A. J. van der Eb Virology 52:456-67 (1973)). Following transfection, cell lysates and culture supernatants of transfected cells are evaluated to compare relative levels of expression of herpes simplex virus antigen proteins. The samples are assayed by western blots and ELISAs, using commercially available polyclonal and/or monoclonal antibodies (available, e.g., from Research Diagnostics Inc., Flanders N. J.), so as to compare both the quality and the quantity of expressed antigen.

In addition to plasmids encoding single herpes simplex virus proteins, single plasmids which contain two or more herpes simplex virus coding regions are constructed according to standard methods. For example, a polycistronic construct, where two or more herpes simplex virus coding regions are transcribed as a single transcript in eukaryotic cells may be constructed by separating the various coding regions with IRES sequences. Alternatively, two or more coding regions may be inserted into a single plasmid, each with their own promoter sequence.

Codon Optimization Algorithm

The following is an outline of the algorithm used to derive human codon-optimized sequences of herpes simplex antigens.

Back Translation

Starting with the amino acid sequence, one can either (a) manually backtranslate using the human codon usage table from the Codon Usage Database website,

*Homo sapiens* [gbpri]: 55194 CDS's (24298072 codons)
Fields: [triplet] [frequency: per thousand] ([number])

TABLE 6

| | | | | | | | |
|---|---|---|---|---|---|---|---|
| UUU | 17.1(415589) | UCU | 14.7(357770) | UAU | 12.1(294182) | UGU | 10.0(243198) |
| UUC | 20.6(500964) | UCC | 17.6(427664) | UAC | 15.5(377811) | UGC | 12.2(297010) |
| UUA | 7.5(182466) | UCA | 12.0(291788) | UAA | 0.7(17545) | UGA | 1.5(36163) |
| UUG | 12.6(306793) | UCG | 4.4(107809) | UAG | 0.6(13416) | UGG | 12.7(309683) |
| CUU | 13.0(315804) | CCU | 17.3(419521) | CAU | 10.5(255135) | CGU | 4.6(112673) |
| CUC | 19.8(480790) | CCC | 20.1(489224) | CAC | 15.0(364828) | CGC | 10.7(259950) |
| CUA | 7.8(189383) | CCA | 16.7(405320) | CAA | 12.0(292745) | CGA | 6.3(152905) |
| CUG | 39.8(967277) | CCG | 6.9(168542) | CAG | 34.1(827754) | CGG | 11.6(281493) |
| AUU | 16.1(390571) | ACU | 13.0(315736) | AAU | 16.7(404867) | AGU | 11.9(289294) |
| AUC | 21.6(525478) | ACC | 19.4(471273) | AAC | 19.5(473208) | AGC | 19.3(467869) |
| AUA | 7.7(186138) | ACA | 15.1(366753) | AAA | 24.1(585243) | AGA | 11.5(278843) |
| AUG | 22.2(538917) | ACG | 6.1(148277) | AAG | 32.2(781752) | AGG | 11.4(277693) |
| GUU | 11.0(266493) | GCU | 18.6(451517) | GAU | 21.9(533009) | GGU | 10.8(261467) |
| GUC | 14.6(354537) | GCC | 28.4(690382) | GAC | 25.6(621290) | GGC | 22.5(547729) |
| GUA | 7.2(174572) | GCA | 16.1(390964) | GAA | 29.0(703852) | GGA | 16.4(397574) |
| GUG | 28.4(690428) | GCG | 7.5(181803) | GAG | 39.9(970417) | GGG | 16.3(396931) |

* Coding GC 52.45% 1st letter GC 56.04% 2nd letter GC 42.37% 3rd letter GC 58.93% (Table as of Nov. 6, 2003)

Or (b) log on to the Entelechon website and use the backtranslation tool, as follows:

(1) Under Protein tab, paste amino acid sequence;

(2) Under download codon usage tab, highlight *homo sapiens* and then download CUT.

TABLE 7

| | | | |
|---|---|---|---|
| UUU 17.1(415589) | UCU 14.7(357770) | UAU 12.1(294182) | UGU 10.0(243198) |
| UUC 20.6(500964) | UCC 17.6(427664) | UAC 15.5(377811) | UGC 12.2(297010) |
| UUA 7.5(182466) | UCA 12.0(291788) | UAA 0.7(17545) | UGA 1.5(36163) |
| UUG 12.6(306793) | UCG 4.4(107809) | UAG 0.6(13416) | UGG 12.7(309683) |
| CUU 13.0(315804) | CCU 17.3(419521) | CAU 10.5(255135) | CGU 4.6(112673) |
| CUC 19.8(480790) | CCC 20.1(489224) | CAC 15.0(364828) | CGC 10.7(259950) |
| CUA 7.8(189383) | CCA 16.7(405320) | CAA 12.0(292745) | CGA 6.3(152905) |
| CUG 39.8(967277) | CCG 6.9(168542) | CAG 34.1(827754) | CGG 11.6(281493) |
| AUU 16.1(390571) | ACU 13.0(315736) | AAU 16.7(404867) | AGU 11.9(289294) |
| AUC 21.6(525478) | ACC 19.4(471273) | AAC 19.5(473208) | AGC 19.3(467869) |
| AUA 7.7(186138) | ACA 15.1(366753) | AAA 24.1(585243) | AGA 11.5(278843) |
| AUG 22.2(538917) | ACG 6.1(148277) | AAG 32.2(781752) | AGG 11.4(277693) |
| GUU 11.0(266493) | GCU 18.6(451517) | GAU 21.9(533009) | GGU 10.8(261467) |
| GUC 14.6(354537) | GCC 28.4(690382) | GAC 25.6(621290) | GGC 22.5(547729) |
| GUA 7.2(174572) | GCA 16.1(390964) | GAA 29.0(703852) | GGA 16.4(397574) |
| GUG 28.4(690428) | GCG 7.5(181803) | GAG 39.9(970417) | GGG 16.3(396931) |

(Table as of Nov. 6, 2003)
  (3) Hit Apply button.
  (4) Under Optimize TAB, open General TAB.
  (5) Check use only most frequent codon box.
  (6) Hit Apply button.
  (7) Under Optimize TAB, open Motif TAB.
  (8) Load desired cloning restriction sites into bad motifs; load any undesirable sequences, such as Pribnow Box sequences (TATAA), Chi sequences (GCTGGCGG), and restriction sites into bad motifs.
  (9) Under Output TAB, click on Start box. Output will include sequence, motif search results (under Report TAB), and codon usage report.

The program did not always use the most frequent codon for amino acids such as cysteine proline, and arginine. To change this, go back to the Edit CUT TAB and manually drag the rainbow colored bar to 100% for the desired codon. Then re-do start under the Output TAB.

The use of CGG for arginine can lead to very high GC content, so AGA can be used for arginine as an alternative. The difference in codon usage is 11.6 per thousand for CGG vs. 11.5 per thousand for AGA.

Splice Donor and Acceptor Site Search
  (1) Log on to Berkeley *Drosophila* Genome Project Website.
  (2) Check boxes for Human or other and both splice sites.
  (3) Select minimum scores for 5' and 3' splice sites between 0 and 1.
  Used the default setting at 0.4 where:
  Default minimum score is 0.4, where:

|  | % splice sites recognized | % false positives |
|---|---|---|
| Human 5' Splice sites | 93.2% | 5.2% |
| Human 3' Splice sites | 83.8% | 3.1% |

(4) Paste in sequence.
  (5) Submit.
  (6) Based on predicted donors or acceptors, change the individual codons until the sites are no longer predicted.
  Add in 5' and 3' Sequences.

On the 5' end of the gene sequence, the restriction enzyme site and Kozak sequence (gccacc) was added before ATG. On 3' end of the sequence, tca was added following the stop codon (tga on opposite strand) and then a restriction enzyme site. The GC content and Open Reading Frames were then checked in SEC Central.

Preparation of Vaccine Formulations

Plasmid constructs comprising codon-optimized and non-codon-optimized coding regions encoding gD, VP11/12, VP13/14 and/or VP22; or alternatively coding regions (either codon-optimized or non-codon optimized) encoding various herpes simplex virus proteins or fragments, variants or derivatives either alone or as fusions with a carrier protein, e.g., HBcAg, as well as various controls, e.g., empty vector, are formulated with the poloxamer CRL 1005 and BAK (Benzalkonium chloride 50% solution, available from Ruger Chemical Co. Inc.) by the following methods. Specific final concentrations of each component of the formulae are described in the following methods, but for any of these methods, the concentrations of each component maybe varied by basic stoichiometric calculations known by those of ordinary skill in the art to make a final solution having the desired concentrations.

For example, the concentration of CRL 1005 is adjusted depending on, for example, transfection efficiency, expression efficiency, or immunogenicity, to achieve a final concentration of between about 1 mg/ml to about 75 mg/ml, for example, about 1 mg/ml, about 2 mg/ml, about 3 mg/ml, about 4 mg/ml, about 5 mg/ml, about 6.5 mg/ml, about 7 mg/ml, about 7.5 mg/ml, about 8 mg/ml, about 9 mg/ml, about 10 mg/ml, about 15 mg/ml, about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, about 70 mg/ml, or about 75 mg/ml of CRL 1005.

Similarly the concentration of DNA is adjusted depending on many factors, including the amount of a formulation to be delivered, the age and weight of the subject, the delivery method and route and the immunogenicity of the antigen being delivered. In general, formulations of the present invention are adjusted to have a final concentration from about 1 ng/ml to about 30 mg/ml of plasmid (or other polynucleotide). For example, a formulation of the present invention may have a final concentration of about 1 ng/ml, about 5 ng/ml, about 10 ng/ml, about 50 ng/ml, about 100 ng/ml, about 500 ng/ml, about 1 µg/ml, about 5 µg/ml, about 10 µg/ml, about 50 µg/ml, about 200 µg/ml, about 400 µg/ml, about 600 µg/ml, about 800 µg/ml, about 1 mg/ml, about 2 mg/ml, about 2.5, about 3 mg/ml, about 3.5, about 4 mg/ml, about 4.5, about 5 mg/ml, about 5.5 mg/ml, about 6 mg/ml, about 7 mg/ml, about 8 mg/ml, about 9 mg/ml, about 10 mg/ml, about 20 mg/ml, or about 30 mg mg/ml of a plasmid.

Certain formulations of the present invention include a cocktail of plasmids of the present invention, e.g., comprising coding regions encoding herpes simplex virus proteins gD, VP11/12, VP13/14 and/or VP22 and optionally, plasmids encoding immunity enhancing proteins, e.g., cytokines. Various plasmids desired in a cocktail are combined together in PBS or other diluent prior to the addition to the other ingredients. Furthermore, plasmids may be present in a cocktail at equal proportions, or the ratios may be adjusted based on, for example, relative expression levels of the antigens or the relative immunogenicity of the encoded antigens. Thus, various plasmids in the cocktail may be present in equal proportion, or up to twice or three times as much of one plasmid may be included relative to other plasmids in the cocktail.

Additionally, the concentration of BAK may be adjusted depending on, for example, a desired particle size and improved stability. Indeed, in certain embodiments, formulations of the present invention include CRL 1005 and DNA, but are free of BAK. In general BAK-containing formulations of the present invention are adjusted to have a final concentration of BAK from about 0.05 mM to about 0.5 mM. For example, a formulation of the present invention may have a final BAK concentration of about 0.05 mM, 0.1 mM, 0.2 mM, 0.3 mM, 0.4 mM or 0.5 mM.

The total volume of the formulations produced by the methods below may be scaled up or down, by choosing apparatus of proportional size. Finally, in carrying out any of the methods described below, the three components of the formulation, BAK, CRL 1005, and plasmid DNA, may be added in any order. In each of these methods described below the term "cloud point" refers to the point in a temperature shift, or other titration, at which a clear solution becomes cloudy, i.e., when a component dissolved in a solution begins to precipitate out of solution.

Thermal Cycling of a Pre-Mixed Formulation

This example describes the preparation of a formulation comprising 0.3 mM BAK, 7.5 mg/ml CRL 1005, and 5 mg/ml of DNA in a total volume of 3.6 ml. The ingredients are combined together at a temperature below the cloud point and then the formulation is thermally cycled to room temperature (above the cloud point) several times.

A 1.28 mM solution of BAK is prepared in PBS, 846 µl of the solution is placed into a 15 ml round bottom flask fitted with a magnetic stirring bar, and the solution is stirred with moderate speed, in an ice bath on top of a stirrer/hotplate (hotplate off) for 10 minutes. CRL 1005 (27 µl) is then added using a 100 µl positive displacement pipette and the solution is stirred for a further 60 minutes on ice. Plasmids comprising codon-optimized coding regions, and optionally, additional plasmids comprising codon-optimized or non-codin-optimized coding regions encoding, e.g., additional herpes simplex virus proteins, and or other proteins, e.g., cytokines, are mixed together at desired proportions in PBS to achieve 6.4 mg/ml total DNA. This plasmid cocktail is added drop wise, slowly, to the stirring solution over 1 min using a 5 ml pipette. The solution at this point (on ice) is clear since it is below the cloud point of the poloxamer and is further stirred on ice for 15 min. The ice bath is then removed, and the solution is stirred at ambient temperature for 15 minutes to produce a cloudy solution as the poloxamer passes through the cloud point.

The flask is then placed back into the ice bath and stirred for a further 15 minutes to produce a clear solution as the mixture is cooled below the poloxamer cloud point. The ice bath is again removed and the solution stirred at ambient temperature for a further 15 minutes. Stirring for 15 minutes above and below the cloud point (total of 30 minutes), is defined as one thermal cycle. The mixture is cycled six more times. The resulting formulation may be used immediately, or may be placed in a glass vial, cooled below the cloud point, and frozen at −80° C. for use at a later time.

Animal Immunizations

The immunogenicity of the various herpes simplex virus expression products encoded by the codon-optimized polynucleotides described herein are initially evaluated based on each plasmid's ability to mount an immune response in vivo. Plasmids are tested individually and in combinations by injecting single constructs as well as multiple constructs. Immunizations are initially carried out in animals, such as mice, rabbits, goats, sheep, non-human primates, or other suitable animal, by intramuscular (IM) or intradermal (ID) injections. Serum is collected from immunized animals, and the antigen specific antibody response is quantified by ELISA assay using purified immobilized antigen proteins in a protein—immunized subject antibody—anti-species antibody type assay, according to standard protocols. The tests of immunogenicity further include measuring antibody titer, neutralizing antibody titer, T-cell proliferation, T-cell secretion of cytokines, cytolytic T cell responses, and by direct enumeration of antigen specific CD4+ and CD8+ T-cells. Correlation to protective levels of the immune responses in humans are made according to methods well known by those of ordinary skill in the art.

DNA Formulations

Plasmid DNA is formulated with a poloxamer. Alternatively, plasmid DNA is prepared and dissolved at a concentration of about 0.1 mg/ml to about 10 mg/ml, preferably about 1 mg/ml, in PBS with or without transfection-facilitating cationic lipids, e.g., DMRIE/DOPE at a 4:1 DNA:lipid mass ratio. Alternative DNA formulations include 150 mM sodium phosphate instead of PBS, adjuvants, e.g., VAXFECTIN adjuvant at a 4:1 DNA: VAXFECTIN adjuvant mass ratio, mono-phosphoryl lipid A (detoxified endotoxin) from S. Minnesota (MPL) and trehalosedicorynomycolateAF (TDM), in 2% oil (squalene)-TWEEN-80 polysorbate 80-water (MPL+TDM, available from Sigma/Aldrich, St. Louis, Mo., (catalog #M6536)), a solubilized mono-phosphoryl lipid A formulation (AF, available from Corixa), or (±)-N-(3-Acetoxypropyl)-N,N-dimethyl-2,3-bis(octyloxy)-1-propanaminium chloride (compound #VC1240) (see Shriver, J. W. et al., Nature 415:331-335 (2002), and P.C.T. Publication No. WO 02/00844 A2.

Animal Immunizations

Plasmid constructs comprising codon-optimized and non-codon-optimized coding regions encoding gD, VP11/12, VP13/14 and/or VP22; or alternatively coding regions (either codon-optimized or non-codon optimized) encoding various herpes simplex virus proteins or fragments, variants or derivatives either alone or as fusions with a carrier protein, e.g., HBcAg, as well as various controls, e.g., empty vector, are injected into BALB/c mice as single plasmids or as cocktails of two or more plasmids, as either DNA in PBS or formulated with the poloxamer-based delivery system: 2 mg/ml DNA, 3 mg/ml CRL 1005, and 0.1 mM BAK. Groups of 10 mice are immunized three times, at biweekly intervals, and serum is obtained to determine antibody titers to each of the antigens. Groups are also included in which mice are immunized with a trivalent preparation, containing each of the three plasmid constructs in equal mass.

The immunization schedule is as follows:

Day 3 Pre-bleed

Day 0 Plasmid injections, intramuscular, bilateral in rectus femoris, 5-50 μg/leg Day 21 Plasmid injections, intramuscular, bilateral in rectus femoris, 5-50 μg/leg Day 49 Plasmid injections, intramuscular, bilateral in rectus femoris, 5-50 μg/leg Day 59 Serum collection Serum antibody titers are determined by ELIS A with recombinant proteins, peptides or transfection supernatants and lysates from transfected VM-92 cells live, inactivated, or lysed virus.

Immunization of Mice with Vaccine Formulations Using a VAXFECTIN Adjuvant

VAXFECTIN adjuvant (a 1:1 molar ratio of the cationic lipid VC1052 and the neutral co-lipid DPyPE) is a synthetic cationic lipid formulation which enhances antibody titers against when administered with DNA intramuscularly to mice.

VAXFECTIN adjuvant mixtures are prepared by mixing chloroform solutions of VC1052 cationic lipid with chloroform solutions of DpyPE neutral co-lipid. Dried films are prepared in 2 ml sterile glass vials by evaporating the chloroform under a stream of nitrogen, and placing the vials under vacuum overnight to remove solvent traces. Each vial contains 1.5 μmole each of VC1052 and DPyPE. Liposomes are prepared by adding sterile water followed by vortexing. The resulting liposome solution is mixed with DNA at a phosphate mole:cationic lipid mole ratio of 4:1.

Plasmid constructs comprising codon-optimized and non-codon-optimized coding regions encoding gD, VP 11/12, VP13/14 and/or VP22; or alternatively coding regions (either codon-optimized or non-codon optimized) encoding various herpes simplex virus proteins or fragments, variants or derivatives either alone or as fusions with a carrier protein, e.g., HBcAg, as well as various controls, e.g., empty vector, are mixed together at desired proportions in PBS to achieve a final concentration of 1.0 mg/ml. The plasmid cocktail, as well as the controls, are formulated with VAXFECTIN adjuvant. Groups of 5 BALB/c female mice are injected bilaterally in the rectus femoris muscle with 50 μl of DNA solution (100 μl total/mouse), on days 1 and 21 and 49 with each formulation. Mice are bled for serum on days 0 (prebleed), 20 (bleed 1), and 41 (bleed 2), and 62 (bleed 3), and up to 40 weeks post-injection. Antibody titers to the various herpes simplex virus proteins encoded by the plasmid DNAs are measured by ELISA.

Cytolytic T-cell responses are measured as described in Hartikka et al. "Vaxfectin Enhances the Humoral Response to Plasmid DNA-encoded Antigens," Vaccine 19:1911-1923 (2001). Standard ELISPOT technology is used for the CD4+ and CD8+ T-cell assays.

Production of Antisera in Animals

Plasmid constructs comprising codon-optimized and non-codon-optimized coding regions encoding gD, VP11/12, VP13/14 and/or VP22; or alternatively coding regions (either codon-optimized or non-codon optimized) encoding various herpes simplex virus proteins or fragments, variants or derivatives either alone or as fusions with a carrier protein, e.g., HBcAg, as well as various controls, e.g., empty vector, are prepared according to the immunization scheme described above and injected into a suitable animal for generating polyclonal antibodies. Serum is collected and the antibody titered as above.

Monoclonal antibodies are also produced using hybridoma technology (Kohler, et al., Nature 256:495 (1975); Kohler, et al., Eur. J. Immunol. 6:511 (1976); Kohler, et al., Eur. J. Immunol. 6:292 (1976); Hammerling, et al., in Monoclonal Antibodies and T-Cell Hybridomas, Elsevier, N.Y., (1981), pp. 563-681. In general, such procedures involve immunizing an animal (preferably a mouse) as described above. The splenocytes of such mice are extracted and fused with a suitable myeloma cell line. Any suitable myeloma cell line may be employed in accordance with the present invention; however, it is preferable to employ the parent myeloma cell line (SP2O), available from the American Type Culture Collection, Rockville, Md. After fusion, the resulting hybridoma cells are selectively maintained in HAT medium, and then cloned by limiting dilution as described by Wands et al., Gastroenterology 80:225-232 (1981), incorporated herein by reference in its entirety. The hybridoma cells obtained through such a selection are then assayed to identify clones which secrete antibodies capable of binding the various herpes simplex virus proteins.

Alternatively, additional antibodies capable of binding to herpes simplex virus proteins described herein may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, various herpes simplex virus-specific antibodies are used to immunize an animal, preferably a mouse. The splenocytes of such an animal are then used to produce hybridoma cells, and the hybridoma cells are screened to identify clones which produce an antibody whose ability to bind to the herpes simplex virus protein-specific antibody can be blocked by the cognate herpes simplex virus protein. Such antibodies comprise anti-idiotypic antibodies to the herpes simplex virus protein-specific antibody and can be used to immunize an animal to induce formation of further herpes simplex virus-specific antibodies.

It will be appreciated that Fab and F(ab')2 and other fragments of the antibodies of the present invention maybe used. Such fragments are typically produced by proteolytic cleavage, using enzymes such as papain (to produce Fab fragments) or pepsin (to produce F(ab')2 fragments). Alternatively, gD, VP11/12, VP13/14 and/or VP22 binding fragments can be produced through the application of recombinant DNA technology or through synthetic chemistry.

It may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, Science 229:1202 (1985); Oi, et al., BioTechniques 4:214 (1986); Cabilly, et al., U.S. Pat. No. 4,816,567; Taniguchi, et al., EP 171496; Morrison, et al., EP 173494; Neuberger, et al., WO 8601533; Robinson, et al, WO 8702671; Boulianne, et al., Nature 312:643 (1984); Neuberger, et al., Nature 314:268 (1985).

These antibodies are used, for example, in diagnostic assays, as a research reagent, to screen animals for identification of the vaccine's effectiveness, or to further immunize animals to generate herpes simplex virus-specific anti-idiotypic antibodies. Non-limiting examples of uses for anti-herpes simplex virus antibodies include use in Western blots, ELISA (competitive, sandwich, and direct), immunofluorescence, immunoelectron microscopy, radioimmunoassay, immunoprecipitation, agglutination assays, immunodiffusion, immunoelectrophoresis, and epitope mapping (Weir, D. Ed. Handbook of Experimental Immunology, 4th ed. Vols. I and II, Blackwell Scientific Publications (1986)).

Mucosal Vaccination and Electrically Assisted Plasmid Delivery Mucosal DNA Vaccination Plasmid constructs comprising codon-optimized and non-codon-optimized coding regions encoding gD, VP11/12, VP13/14 and/or VP22; or alternatively coding regions (either codon-optimized or non-codon optimized) encoding various herpes simplex virus proteins or fragments, variants or derivatives either alone or as fusions with a carrier protein, e.g., HBcAg, as well as various controls, e.g., empty vector, (100 μg/50 μl total DNA) are delivered to BALB/c mice at 0, 2 and 4 weeks via i.m., intranasal (i.n.), intravenous (i.v.), intravaginal (i.vag.), intrarectal (i.r.) or oral routes. The DNA is delivered unformulated or formulated with the cationic lipids DMRIE/DOPE (DD) or GAP-DLRIE/DOPE (GD). As endpoints, serum IgG titers against the various herpes simplex virus antigens are measured by ELISA and splenic T-cell responses are measured by antigen-specific production of IFN-gamma and IL-4 in ELISPOT assays. Standard chromium release assays are used to measure specific cytotoxic T lymphocyte (CTL) activity against the various herpes simplex virus antigens. Tetramer assays are used to detect and quantify antigen specific T-cells, with quantification being confirmed and phenotypic characterization accomplished by intracellular cytokine staining. In addition, IgG and IgA responses against the various herpes simplex virus antigens are analyzed by ELISA of vaginal washes.

Electrically-Assisted Plasmid Delivery

In vivo gene delivery may be enhanced through the application of brief electrical pulses to injected tissues, a procedure referred to herein as electrically-assisted plasmid delivery (EAPD). See, e.g., Aihara, H. & Miyazaki, J. Nat. Biotechnol. 16:867-70 (1998); Mir, L. M. et al., Proc. Natl. Acad. Sci. USA 96:4262-67 (1999); Hartikka, J. et al., Mol. Ther. 4:407-15 (2001); and Mir, L. M. et al.; Rizzuto, G. et al., Hum Gene Ther 11:1891-900 (2000); Widera, G. et al, J. of Immuno. 164:4635-4640 (2000). The use of electrical pulses for cell electropermeabilization has been used to introduce foreign DNA into prokaryotic and eukaryotic cells in vitro. Cell permeabilization can also be achieved locally, in vivo, using electrodes and optimal electrical parameters that are compatible with cell survival.

The electroporation procedure can be performed with various electroporation devices. These devices include external plate type electrodes or invasive needle/rod electrodes and can possess two electrodes or multiple electrodes placed in an array. Distances between the plate or needle electrodes can vary depending upon the number of electrodes, size of target area and treatment subject.

The TriGrid needle array is a three electrode array comprising three elongate electrodes in the approximate shape of a geometric triangle. Needle arrays may include single, double, three, four, five, six or more needles arranged in various array formations. The electrodes are connected through conductive cables to a high voltage switching device that is connected to a power supply.

The electrode array is placed into the muscle tissue, around the site of nucleic acid injection, to a depth of approximately 3 mm to 3 cm. The depth of insertion varies depending upon the target tissue and size of patient receiving electroporation. After injection of foreign nucleic acid, such as plasmid DNA, and a period of time sufficient for distribution of the nucleic acid, square wave electrical pulses are applied to the tissue. The amplitude of each pulse ranges from about 100 volts to about 1500 volts, e.g., about 100 volts, about 200 volts, about 300 volts, about 400 volts, about 500 volts, about 600 volts, about 700 volts, about 800 volts, about 900 volts, about 1000 volts, about 1100 volts, about 1200 volts, about 1300 volts, about 1400 volts, or about 1500 volts or about 1-1.5 kV/cm, based on the spacing between electrodes. Each pulse has a duration of about 1 µs to about 1000 µs, e.g., about 1 µs, about 10 µs, about 50 µs, about 100 µs, about 200 µs, about 300 µs, about 400 µs, about 500 µs, about 600 µs, about 700 µs, about 800 µs, about 900 µs, or about 1000 µs, and a pulse frequency on the order of about 1-10 Hz. The polarity of the pulses may be reversed during the electroporation procedure by switching the connectors to the pulse generator. Pulses are repeated multiple times. The electroporation parameters (e.g. voltage amplitude, duration of pulse, number of pulses, depth of electrode insertion and frequency) will vary based on target tissue type, number of electrodes used and distance of electrode spacing, as would be understood by one of ordinary skill in the art.

Immediately after completion of the pulse regimen, subjects receiving electroporation can be optionally treated with membrane stabilizing agents to prolong cell membrane permeability as a result of the electroporation. Examples of membrane stabilizing agents include, but are not limited to, steroids (e.g. dexamethasone, methylprednisone and progesterone), angiotensin II and vitamin E. A single dose of dexamethasone, approximately 0.1 mg per kilogram of body weight, should be sufficient to achieve a beneficial affect.

EAPD techniques such as electroporation can also be used for plasmids contained in liposome formulations. The liposome-plasmid suspension is administered to the animal or patient and the site of injection is treated with a safe but effective electrical field generated, for example, by a TriGrid needle array. The electroporation may aid in plasmid delivery to the cell by destabilizing the liposome bilayer so that membrane fusion between the liposome and the target cellular structure occurs. Electroporation may also aid in plasmid delivery to the cell by triggering the release of the plasmid, in high concentrations, from the liposome at the surface of the target cell so that the plasmid is driven across the cell membrane by a concentration gradient via the pores created in the cell membrane as a result of the electroporation.

To test the effect of electroporation on therapeutic protein expression in non-human primates, male or female rhesus monkeys are given either 2 or 6 i.m. injections of plasmid constructs comprising codon-optimized and non-codon-optimized coding regions encoding gD, VP11/12, VP13/14 and/or VP22; or alternatively coding regions (either codon-optimized or non-codon optimized) encoding various herpes simplex virus proteins or fragments, variants or derivatives either alone or as fusions with a carrier protein, e.g., HBcAg, as well as various controls, e.g., empty vector, (0.1 to 10 mg DNA total per animal). Target muscle groups include, but are not limited to, bilateral rectus fermoris, cranial tibialis, biceps, gastrocenemius or deltoid muscles. The target area is shaved and a needle array, comprising between 4 and 10 electrodes, spaced between 0.5-1.5 cm apart, is implanted into the target muscle. Once injections are complete, a sequence of brief electrical pulses are applied to the electrodes implanted in the target muscle using an Ichor TGP-2 pulse generator. The pulses have an amplitude of approximately 120-200V. The pulse sequence is completed within one second. During this time, the target muscle may make brief contractions or twitches. The injection and electroporation may be repeated.

Sera are collected from vaccinated monkeys at various time points. As endpoints, serum IgG titers against the various herpes simplex virus antigens are measured by ELISA and PBMC T-cell proliferative responses are measured by antigen-specific production of IFN-gamma and IL-4 in ELISPOT assays or by tetramer assays to detect and quantify antigen specific T-cells, with quantification being confirmed and phenotypic characterization accomplished by intracellular cytokine staining. Standard chromium release assays are used to measure specific cytotoxic T lymphocyte (CTL) activity against the various TV antigens.

Vaccine Construction and Evaluation

UL46, 47, and 49 open reading frames (ORFs) from seven to eight HSV-2 strains isolated from primary genital infections were PCR-amplified and sequenced. The consensus was used for vaccine design.

Plasmids were constructed by cloning synthetic, full-length, codon-optimized UL46, UL47, or UL49 DNA into backbone plasmid VR1012.

Codon-optimized UL46, 47, and 49 constructs were compared with full length wild-type UL46, 47 and 49 by co-transfecting Cos-7 cells with the different individual constructs plus full-length cDNA encoding HLA A*0201, A*0101, or B*0702. $CD8^+$ T-cell clones known to react to UL46, UL47, or UL49 epitopes were incubated with the transfected cells, with an ELISA for IFN-γ secretion employed as readout.

DNA vaccines were formulated with PBS, with VAXFECTIN adjuvant at 1 μg DNA/1.09 μg VAXFECTIN adjuvant, or with poloxamer, such as, but not limited to, CRL1005, at 1 μg DNA/1.5 μg poloxamer in PBS.

Animals and Immunization Regimen

Female, 4-8 week old BALB/c mice (10 per group) were immunized with 50 μg DNA in 50 μL by IM injection in bilateral quadriceps (100 μg/immunization) on Days 0, 14, and 28.

Sera were collected from each animal Days—1 (pre-bleed), 13, 27, and 42. Splenocytes were isolated at terminal sacrifice Day 42.

EUSA Evaluation of Antibody Response

Antigens for ELISA were derived from recombinant full-length tegument proteins made by transiently transfecting VM92 cells with the vaccine constructs and collecting supernatants.

Sera were serially diluted in TBS with 0.1% BSA and 0.05% TWEEN-20 polysorbate 20. Standard reagents measured antigen-specific IgG by absorbance at $OD_{450}$ nm. A positive (Day 42) serum pool for each antigen was run on every ELISA plate. An exponential curve was generated from values in the mid portion of dilution vs. $OD_{450}$ (corrected for background absorbance). Antibody titers for each animal at a time point were calculated as the mean titer determined from the individual dilutions (calculated from the standard curve). If the $OD_{450}$ for all dilutions of experimental sera were very low, the titer was assigned as 1:1.

Evaluation of Cellular Response by ELISPOT Assay

IFN-γ secretion by T-cells was assessed by ELISPOT assay with standard reagents. Plates were read by computer.

Splenocytes ($0.5$-$1\times10^6$ cells/well in duplicate wells) from individual animals were stimulated using peptide pools (18-24 13-mer peptides overlapping by 9 amino acids, at 0.42-0.56 μg/ml each), or positive (Con A) or negative (media) controls. Pooled responder splenocytes were also tested with single 13-mer peptides at 10 μg/ml.

Peptides found to produce responses were further evaluated using shorter (9-11 aa) peptides, dose-response curves, and/or $CD4^+$ or $CD8^+$ responders (negative selection, Miltenyi, >80% pure) back-mixed with naive splenocyte APC. Plates with too-numerous-to-count spots were arbitrarily assigned 103 spots.

Discussion

HSV-2 UL46, UL47, and UL49 DNA vaccines are immunogenic in BALB/c (H-2d) mice.

H-2d CD8+ epitopes were found with all vaccines, and $CD4^+$ epitopes were found for UL46 and UL49.

$CD8^+$ splenocytes respond to peptides at concentrations from $10^{-3}$ to $10^{-6}$ μM; $CD4^+$ splenocytes require peptide concentrations of $10^{-1}$ μM or higher.

Cellular responses in BALB/c mice are greatest for UL47, followed by UL49 and UL46, when expressed as SFU/$10^6$ splenocytes.

Relative antibody titers are UL49>UL47>UL46.

The poloxamer-based formulation boosted humoral immunity on Day 42 for all three tegument DNA vaccines by 3-5-fold compared to no adjuvant. Formulations based on Vaxfectin™ boosted antibody responses to UL46 and UL49 DNA about 2-fold by Day 42 relative to no adjuvant.

Poloxamer significantly boosted cellular responses to UL47 DNA vaccine (p=0.03), but not to UL46 or UL49 DNA vaccines. VAXFECTIN adjuvant had no statistically significant adjuvant effect on any tested vaccine (p>0.05).

Cellular immunity to three HSV-2 tegument proteins was detectable after DNA vaccination. Responses to both UL47 and UL49 were particularly strong. Due to difficulties with peptide synthesis, 19% of the UL46 peptides were missing in the assay, as compared to 1 or 2 peptides missing for assays involving UL47 and UL49. Nonetheless, multiple $CD4^+$ and $CD8^+$ epitopes have been identified that should assist animal pathogenesis studies in BALB/c mice.

The adjuvant effects of poloxamer and VAXFECTIN adjuvant based formulations were moderate and inconsistent between antigens. Adjuvant effect may be more apparent with a lower dose of antigen, or when used in higher species.

Identify the HSV-2 Genes of Interest.

HSV-2 encodes ~85 proteins (Roizman, B., Knipe, D. M., Whitley, R. J., *Herpes simplex viruses, in Fields Virology*, D. M. Knipe, Howley, P. M., Editor. 2007, Lippincott, Williams, and Wilkins: Philadelphia, p. 2501-2602). The pDNA approach is limited to one or a few ORFs. Criteria for choosing ORFs include quick recognition of infected cells, immunodominance (within-person and within-population), antiviral effector functions, and localization to lesions.

Tegument proteins UL46, UL47, UL49, and UL7 are CD8+ antigens (Koelle, D. M., et al., *CD8 CTL from genital herpes simplex lesions: recognition of viral tegument and immediate early proteins and lysis of infected cutaneous cells*. Journal of Immunology, 2001. 166: p. 4049-4058). $CD8^+$ T-cells specific for UL47 and UL49 are abundant enough to be detected by "direct" PBMC staining with HLA-peptide tetramers (Koelle, D. M., et al., *Expression of cutaneous lymphocyte-associated antigen by CD8+ T-cells specific for a skin-tropic virus*. Journal of Clinical Investigation, 2002. 110: p. 537-548). $CD8^+$ cells specific for glycoprotein, capsid, or immediate early proteins are less abundant, and have never been detected in "direct" PBMC staining (Koelle, unpublished). Studies of up to 95 independently derived HSV-2-specific CD8+ clones per subject showed that responses to tegument proteins were immunodominant (Koelle, D. M., Liu Z., McClurkan C. L., Cevallos R. C., Vieira J., Hosken N. A., Meseda C. A., Snow D. C., Wald A., Corey L., *Immunodominance among herpes simplex virus-specific CD8 T-cells expressing a tissue-specific homing receptor*. Proc Natl Acad Sci USA, 2003. 100: p. 12899-12904).

We then measured human $CD8^+$ responses to 48 HSV-2 ORFs (57% of the total) by making 5,230 synthetic peptides covering these ORFs. $CD8^+$ T-cells from peripheral blood were probed by IFN-γ ELISPOT as the readout (Hosken, N., McGowan P., Meier A., Koelle D. M., Sleath P., Wegener F., Elliott M., Grabstein L., Posavad C., Corey L., *Diversity of the CD8+ T cell response to herpes simpolex virus type 2 proteins among persons with genital herpes*. Journal of Virology, 2006. 80: p. 5509-5515). Among 24 HSV-2-infected subjects, 50% recognized the tegument proteins UL46 and UL47. Responses to UL49 were slightly lower (~40%).

A trial of a HSV-2 therapeutic vaccine comprised of an HLA A*0201-restricted epitope in envelope glycoprotein B and an adjuvant is being conducted. At baseline (n=42 persons), the population prevalence of responses to an HLA A*0201 epitope in gB is 45% compared to 68% for an A*0201 epitope in the tegument protein UL47 (p=0.012, Fisher's exact test).

One advantage of tegument-specific $CD8^+$ T-cells, over cells specific for immediate early, capsid, or envelope proteins, is that tegument-specific $CD8^+$ T-cells can kill target cells immediately after they are infected. This is due to recognition of virion input protein, as proven in CTL assays with the transcriptional blocker actinomycin D, or target cells sensitized with UV-treated virus (Koelle, D. M., et al., *CD8 CTL from genital herpes simplex lesions: recognition of viral tegument and immediate early proteins and lysis of infected cutaneous cells*. Journal of Immunology, 2001. 166: p. 4049-4058).

Recognition of Processed Tegument Input Protein Bypasses the Immune Evasion by HSV TAP Inhibitor Protein ICP47.

In addition, tetramer in situ stain of human skin biopsies in healing/post-healing phases of genital HSV-2 lesions, show that tetramer-specific CD8+ T-cells localize adjacent to HSV-2-infected cells during recurrences, and monitor the region of peripheral nerve endings at the dermal-epidermal junction after healing (Zhu, J., Koelle, D. M., Cao, J., Vezquez, J., Huang, M X., Hladik, F., Wald, A., Corey, L., *Peripheral virus-specific CD8+ T cells contiguous to sensory nerve endings limit HSV-2 reactivation in human genital skin*. Journal of Experimental Medicine, 2007. epub Feb. 26, 2007: p. epub Feb. 26, 2007).

Taken together, within-population and within-subject dominance, high absolute numerical levels, localization to lesional and post-healing skin, antiviral effector functions, and immediate recognition of infected cells all argue that HSV-2 tegument proteins are rational targets for CD8+-directed therapeutic approach to decreasing HSV-2 lesions, symptoms, and shedding.

Determine the Amino Acid Sequence for Candidate Vaccine Tegument HSV-2 Genes.

We sequenced tegument proteins UL46, UL47, and UL49 in circulating North American HSV-2 strains. We isolated HSV-2 from persons with documented primary genital herpes (Ashley, R. A., et al., *Comparison of Western blot (immunoblot) and glycoprotein G-specific immunoblot for detecting antibodies to herpes simplex types* 1 *and* 2 *in human sera*. Journal of Clinical Microbiology, 1988. 26: p. 662-667), passaged them minimally in vitro, PCR-amplified tegument genes with an accurate polymerase, and sequenced them bidirectionally (Martin, E., Koelle D M, Byrd B, Huang M L, Vieira J, Corey L, Wald A, *Sequence-based methods for identifying epidemiologically linked herpes simplex virus type* 2 *strains*. J Clin Microbiol, 2006. 44(7): p. 2541-6). We identified many loci at which all the wild-type strains shared the same coding difference from HG52 (Dolan, A., et al., *The genome sequence of herpes simplex virus type* 2. Journal of Virology, 1998. 72: p. 2010-2021). At other loci, there were polymorphic amino acids that differed between wild-type strains. For these, we picked the prevalent alleles for our vaccine composition. (Table 8)

DNA polymerase, but mutations do occur during acyclovir therapy (Czartoski, T., et al., *Fulminant, acyclovir-resistant, herpes simplex virus type* 2 *hepatitis in an immunocompetent woman*. J Clin Microbiol, 2006. 44(4): p. 1584-6). We sequenced more than 100 additional wild-type HSV-2 strains, focusing on known $CD8^+$ epitopes regions in UL46, UL47, and UL49. We found no coding polymorphisms in or near CD8+ epitopes (Koelle, D. M., et al., *CD8 CTL from genital herpes simplex lesions: recognition of viral tegument and immediate early proteins and lysis of infected cutaneous cells*. Journal of Immunology, 2001. 166: p. 4049-4058; Koelle, D. M., Liu Z., McClurkan C. L., Cevallos R. C., Vieira J., Hosken N. A., Meseda C. A., Snow D. C., Wald A., Corey L., *Immunodominance among herpes simplex virus-specific CD*8 *T-cells expressing a tissue-specific homing receptor*. Proc Natl Acad Sci USA, 2003. 100: p. 12899-12904) in UL46 or UL47, or in or near $CD4^+$ epitopes (Koelle, D. M., et al., *Recognition of herpes simplex virus type* 2 *tegument proteins by CD*4 *T cells infiltrating human genital herpes lesions*. Journal of Virology, 1998. 72: p. 7476-7483; Posavad, C M., et al., *T cell immunity to herpes simplex virus in seronegative persons: silent infection or acquired immunity*. Journal of Immunology, 2003. 170: p. 4380-4388; Koelle, D. M., et al., *Tegument-specific, virus-reactive CD*4 *T-cells localize to the cornea in herpes simplex virus interstitial keratitis in humans*. Journal of Virology, 2000. 74: p. 10930-10938) in any protein.

TABLE 8

Selected coding polymorphisms in eight wild-type HSV-2 isolates. Amino acid (AA) numbers per HG52 nomenclature (Dolan, A., et al., *The genome sequence of herpes simplex virus type 2*. Journal of Virology, 1998. 72: p. 2010-2021). Table entries list HG52 AA followed by wild-type. Vaccine sequences VR2145, VR2144, and VR2143 are also shown.

UL46 amino acid

| strain | 78 | 110 | 364 | 425 | 436 | 471 | 474 | 587 | 594 | 613 | 634 | 637 | 638 | 644 | 672 | 673 |
|---|---|---|---|---|---|---|---|---|---|---|---|---|---|---|---|---|
| 346 | | | TR | | | CF | | delA | EK | | PL | RQ | LD | LP | RP | RG |
| 2589 | AS | | TR | | | CF | HP | | | | PL | RQ | LD | LP | RP | RG |
| 2899 | | KN | TR | | | CF | | delA | EK | GS | PL | RQ | LD | LP | RP | RG |
| 7124 | | | TR | | | CF | | delA | | GS | PL | RQ | LD | LP | RP | RG |
| 7566 | | KN | TR | | | CF | | delA | EK | GS | PL | RQ | LD | LP | RP | RG |
| 10875 | | KN | TR | | | CF | | delA | EK | GS | PL | RQ | LD | LP | RP | RG |
| 11449 | | | TR | AV | VG | CF | | delA | EK | GS | PL | RQ | LD | LP | RP | RG |
| 16293 | | KN | TR | | | CF | | delA | EK | GS | PL | RQ | LD | LP | RP | RG |
| VR2145 | A | K | R | A | V | F | H | delA | K | S | L | Q | D | P | P | G |

UL47 amino acid

| strain | 3 | 38 | 69 | 82 | 156 | 172 | 177 | 529 |
|---|---|---|---|---|---|---|---|---|
| 346 | VA | | PS | | | PA | SP | |
| 2589 | | | | | NS | PA | SP | RH |
| 2899 | | VG | | | NS | PA | SP | |
| 7566 | | VG | | | NS | PA | SP | |
| 10875 | | VG | | RQ | NS | PA | SP | |
| 11449 | | VG | | | NS | PA | SP | |
| 16293 | | VG | | | NS | PA | SP | |
| VR2144 | V | G | P | R | S | A | P | R |

UL49 amino acid

| strain | 73-74 | 76 | 87 | 94 | 134 |
|---|---|---|---|---|---|
| 346 | SE insert | | | SA | SP |
| 2589 | SE insert | DN | RH | | SP |
| 2899 | | | | | |
| 7566 | | | | | |
| 10875 | | | | | |
| 11449 | | | | | |
| 16293 | | | | | |
| VR2143 | no insert | D | R | S | S |

We were concerned that CD8+ T-cell epitopes might be under selective pressure to mutate and "escape" $CD8^+$ CTL, as proven for HIV (Nolan, D., I. James, and S. Mallal, *HIV/AIDS. HIV: experiencing the pressures of modern life*. Science, 2005. 307(5714): p. 1422-4). HSV-2 has an accurate In contrast, there is marked heterogeneity in the HLA B*0702-restricted CD8+ epitope in UL49 (AA 49-57). While 70% of isolates have the majority sequence RPRGEVREFL, 29% have the minority RPMREVRFL, and 1% have the rare RPRGKVRFL. Our immune studies (Koelle, D. M., Liu, C., Byrd, B., Sette, A., Sidney, J., Wald, A. *HSV-2 VP22 sequences from wild-type isolates that escape a dominant CD8 CTL response in linkage with a polymorphism at an adjacent casein kinase II substrate domain, in 30th International Herpesvirus Workshop,* 2005. Turku, Finland), in brief, show that while all 3 variants bind well to recombinant HLA B*0702 [$IC_{50}$<2 nM, assays as per (Southwood, S., et al., *Several common HLA-DR types share largely overlapping peptide binding repertoires.* J Immunol, 1998. 160(7): p. 3363-73)], CD8+ T-cells specific for the "majority" are not cross-reactive with "minority" or "rare" variants. Vaccination with the 70% consensus "majority" would miss 30% of circulating strains.

Optimize the Genes for Protein Expression and Stability, Synthesize them, and Clone them into a pDNA Backbone.

After establishing the AA sequences for the pDNA vaccines, we used proprietary codon optimization algorithms with the goals of high eukaryotic expression. The genes were synthesized by GeneArt. Versions of UL46, UL47, and UL49 were made with or without the $gD_1$ epitope tag QPELAPEDPED. Each was cloned into plasmid VR1012 (Hartikka, J., et al., *An improved plasmid DNA expression vector for direct injection into skeletal muscle*. Hum Gene Ther, 1996. 7(10): p. 1205-17). VR1012 encodes kanamycin resistance, and contains a promoter/enhancer and intron A of CMV immediate early gene 1, and a bovine growth hormone-based terminator. VR1012 was chosen because 1) it achieves high level expression in many cells, animal species, and tissues; 2) there has been no stability problems in in-house studies; 3) high plasmid yields are obtained in *E. coli*; and most importantly 4) VR1012-based products are in clinical trials. The inserts were sequence verified to an average redundancy of 4-fold.

VAXFECTIN adjuvant was used for intramuscular injection studies. VAXFECTIN adjuvant is an equimolar mixture of VC1052 ((±)-N-(3-aminopropyl)-N,N-dimethyl-2,3-bis (myristoleyloxy)-1-propanaminium bromide) and DPyPE (diphytanoylphosphatidyl-ethanolamine) (Hartikka, J., et al., *An improved plasmid DNA expression vector for direct injection into skeletal muscle*. Hum Gene Ther, 1996. 7(10): p. 1205-17). A lipid film was prepared by mixing chloroform solutions of VC1052 and DPyPE in glass vials, evaporating the chloroform, and vacuum packing. At the time of vaccination, the lipid film was reconstituted to 2.18 mg/mL with 1 mL of 0.9% saline. Vaccines were prepared at a final pDNA (phosphate): cationic lipid molar ratio of 4:1 by adding an equal volume of lipid to pDNA (2 mg/mL in 0.9% saline, 20 mM sodium phosphate). Reconstituted vaccine was held at room temperature and used within 60 minutes.

Initial experiments expressed the gD-tagged versions of UL46, UL47, and UL49 by transient transfection of VM92 cells (Kumar, S., et al., *A DNA vaccine encoding the 42 kDa C-terminus of merozoite surface protein 1 of Plasmodium falciparum induces antibody, interferon-gamma and cytotoxic T cell responses in rhesus monkeys: immuno-stimulatory effects of granulocyte macrophage-colony stimulating factor*. Immunol Lett, 2002. 81(1): p. 13-24). Immunoblots showed bands at the predicted MW (not shown). All subsequent experiments used the full-length tegument constructs without the epitope tag. We used human CD8+ CTL clones specific for UL46, UL47, and UL49 (Koelle, D. M., et al., *CD8 CTL from genital herpes simplex lesions: recognition of viral tegument and immediate early proteins and lysis of infected cutaneous cells*. Journal of Immunology, 2001. 166: p. 4049-4058; Koelle, D. M., Liu Z., McClurkan C. L., Cevallos R. C., Vieira J., Hosken N. A, Meseda C. A., Snow D. C., Wald A., Corey L., *Immunodominance among herpes simplex virus-specific CD8 T-cells expressing a tissue-specific homing receptor*. Proc Natl Acad Sci USA, 2003. 100: p. 12899-12904) to establish that the pDNA vaccines encoded proteins that are processed and presented to CD8+ T-cells. COS-7 cells were co-transfected with (1) candidate vaccine plasmid and (2) cDNA encoding a specific human HLA class I α-chain. The human HLA class I heavy chains form a functional heterodimer with non-human primate (COS-7 cell) $\beta_2$ microglobulin ($\beta_2$M). If the vaccine construct encodes a protein that can be processed to antigenic peptides, some HLA class I-$\beta_2$M heterodimers will translocate to the cell surface loaded with HSV-2 peptides. After two days, human $CD8^+$ T cell clones specific for relevant tegument proteins were added. T-cell activation was detected by IFN-γ ELISA of the supernatant (Koelle, D. M., et al., *CD8 CTL from genital herpes simplex lesions: recognition of viral tegument and immediate early proteins and lysis of infected cutaneous cells*. Journal of Immunology, 2001. 166: p. 4049-4058; Koelle, D. M., et al., *Expression of cutaneous lymphocyte-associated antigen by CD8+T-cells specific for a skin-tropic virus*. Journal of Clinical Investigation, 2002. 110: p. 537-548). Specific responses were detected (FIG. 3). T cell clones did not recognize COS-7 cells transfected with HLA class I cDNA alone, HSV-2 plasmid DNA alone, or HSV-2 DNA plus the "wrong" HLA (not shown).

The proteins encoded by the candidate vaccines were also recognized by human anti-HSV antibodies. To make vaccine-encoded protein, VM92 cells (Kumar, S., et al., *A DNA vaccine encoding the 42 kDa C-terminus of merozoite surf ace protein 1 of Plasmodium falciparum induces antibody, interferon-gamma and cytotoxic T cell responses in rhesus monkeys: immuno-stimulatory effects of granulocyte macrophage-colony stimulating factor*. Immunol Lett, 2002. 81(1): p. 13-24) were transfected with the vaccine plasmids, and supernatants collected. These were used as antigen (1:5 dilution) to coat ELISA plates. Pooled sera from HSV-2 seropositive individuals bound recombinant tegument proteins (FIG. 4), while pooled sera from HSV-2 seronegative individuals did not. These tests show that bona fide HSV-2-specific T-cells and antibodies recognize vaccine-encoded HSV-2 tegument proteins.

Measure Immune Responses to HSV-2 Tegument Plasmids Alone or in Combination in Mice.

We chose the female BALB/c mouse (H-$2^d$) so we could combine immunogenicity and protective efficacy tests. The only previously known HSV-2 CD8+ epitope in BALB/c mice is in protein ICP27 (Haynes, J., Arrington J, Dong L, Braun R P, Payne L G, *Potent protective cellular immune responses generated by a DNA vaccine encoding HSV-2 ICP27 and the E. coli heat labile enterotoxin*. Vaccine, 2006. 24(23): p. 5016-26). Several type-common regions of gD are CD4+ epitopes in these animals (BenMohamed, L., et al., *Identification of novel immunodominant CD4+ Th1-type T-cell peptide epitopes from herpes simplex virus glycoprotein D that confer protective immunity*. J Virol, 2003. 77(17): p. 9463-73). BALB/c mice are very susceptible to intravaginal infection with HSV-2 (Lopez, C., *Genetics of natural resistance to herpes virus infections in mice*. Nature, 1975. 258: p. 1352-1353).

Humoral response. We immunized mice with 100 μg pDNA on days 0, 14, and 28 as 50 IM per quadriceps. We compared VAXFECTIN adjuvant and a CRL 1005 poloxamer as shown in 6,844,001 as Example 1 (Selinsky, C, et al., *A DNA-based vaccine for the prevention of human cytomegalovirus-associated diseases.* Hum Vaccin, 2005.1(1): p. 16-23) as adjuvants versus PBS. As we have focused on VAXFECTIN adjuvant, and results (titers, speed to antibody, titers at each time point for antibody, and IFN-γ sfu/$10^6$ splenocytes for T-cells) were generally similar for the adjuvants and PBS at this high pDNA dose, only VAXFECTIN adjuvant data are shown.

Figure 4:
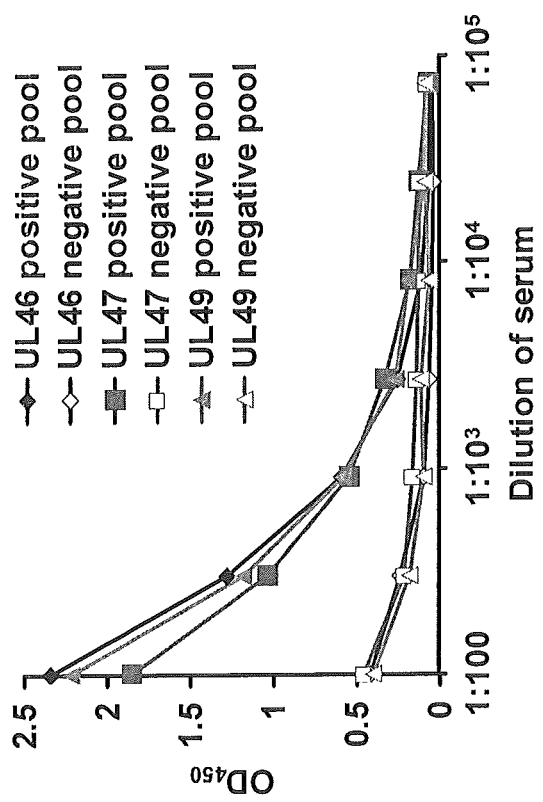
Figure 5A:
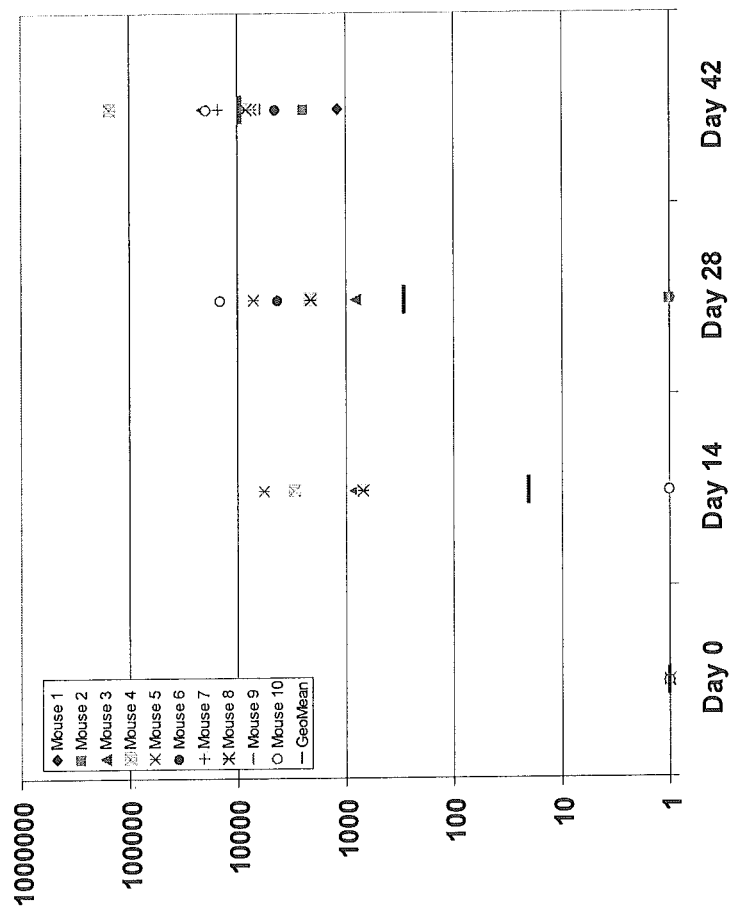
Figure 5B:
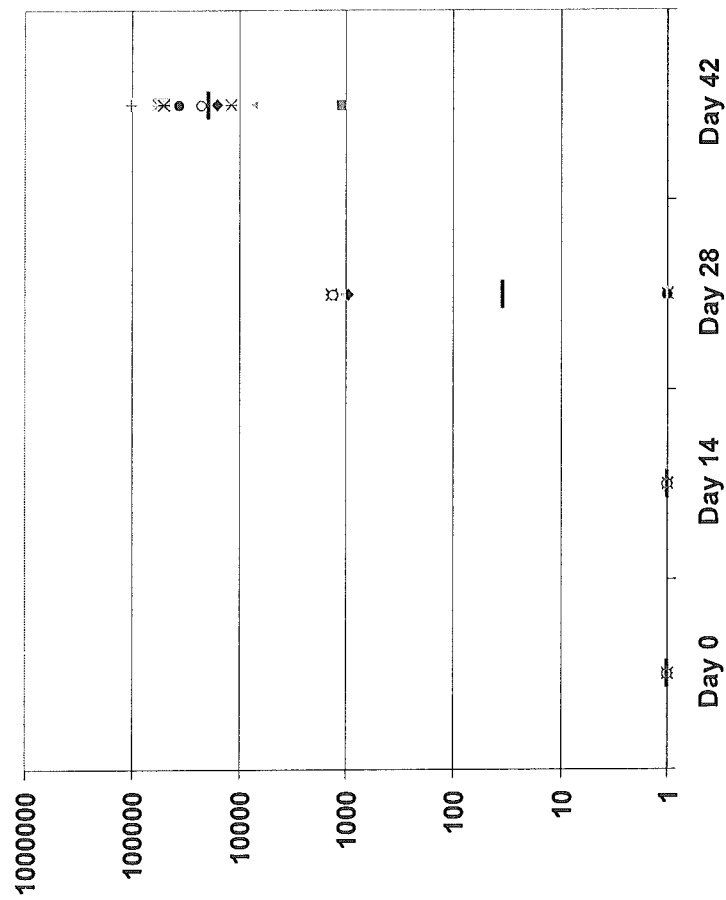
Figure 5C:
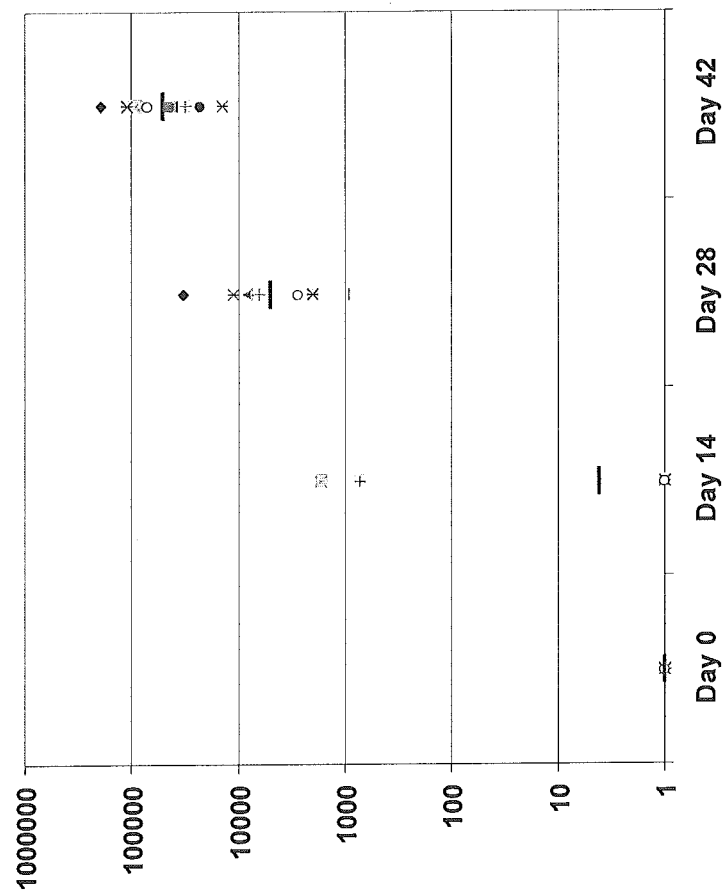
Figure 5D:
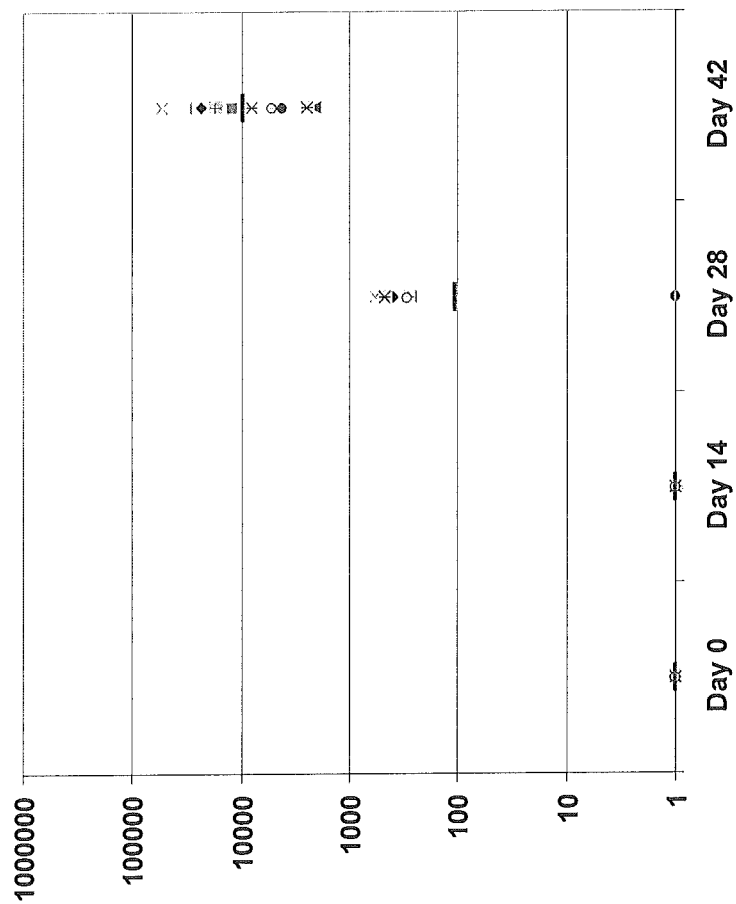
Figure 5E:
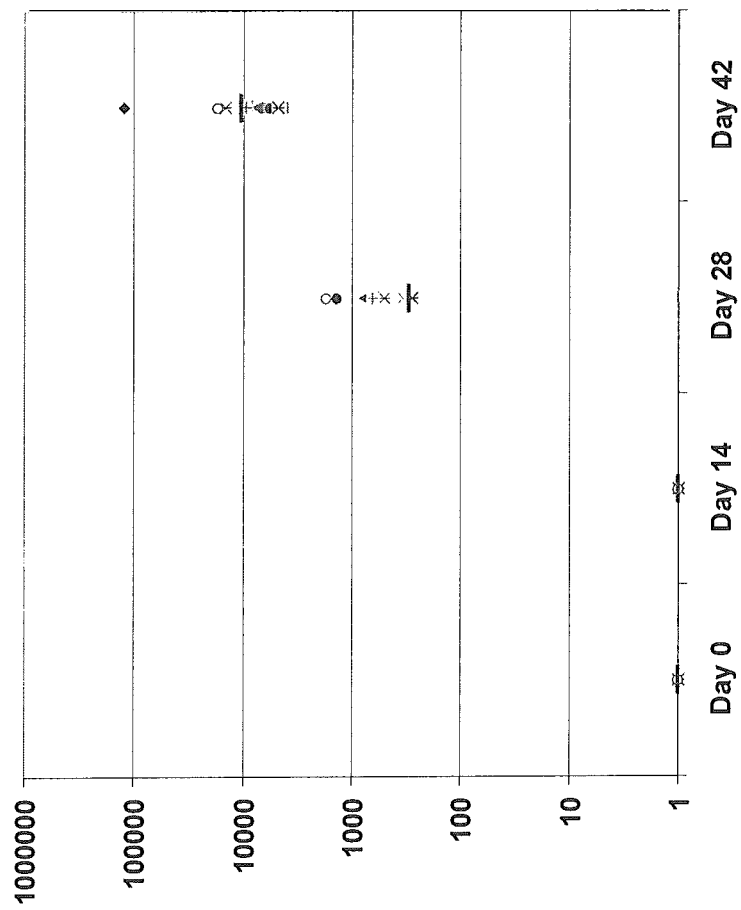
Figure 5F:
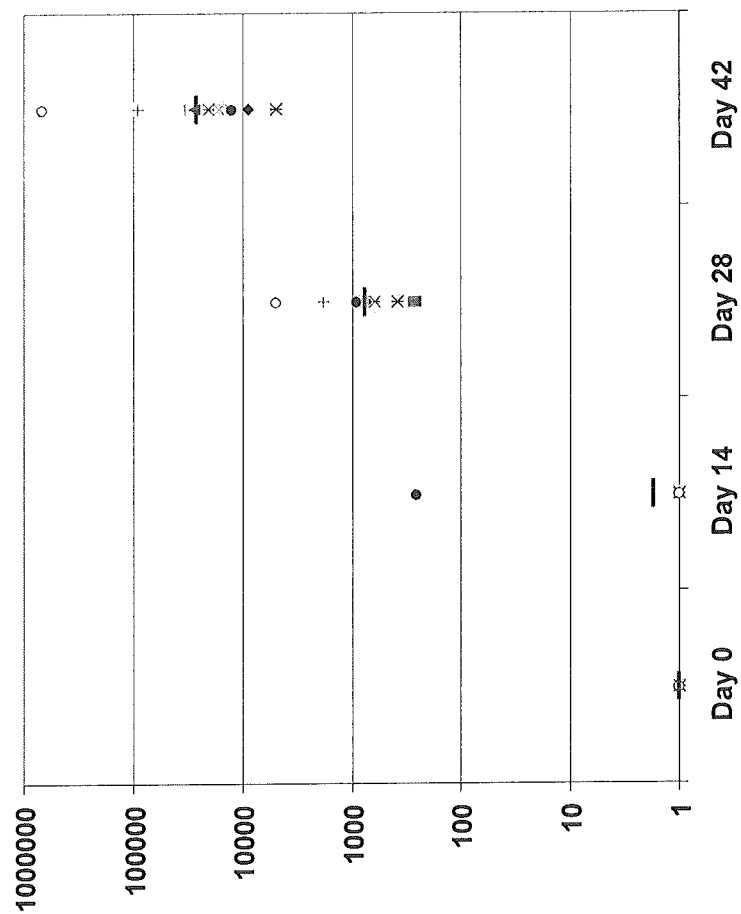
Figure 5G:
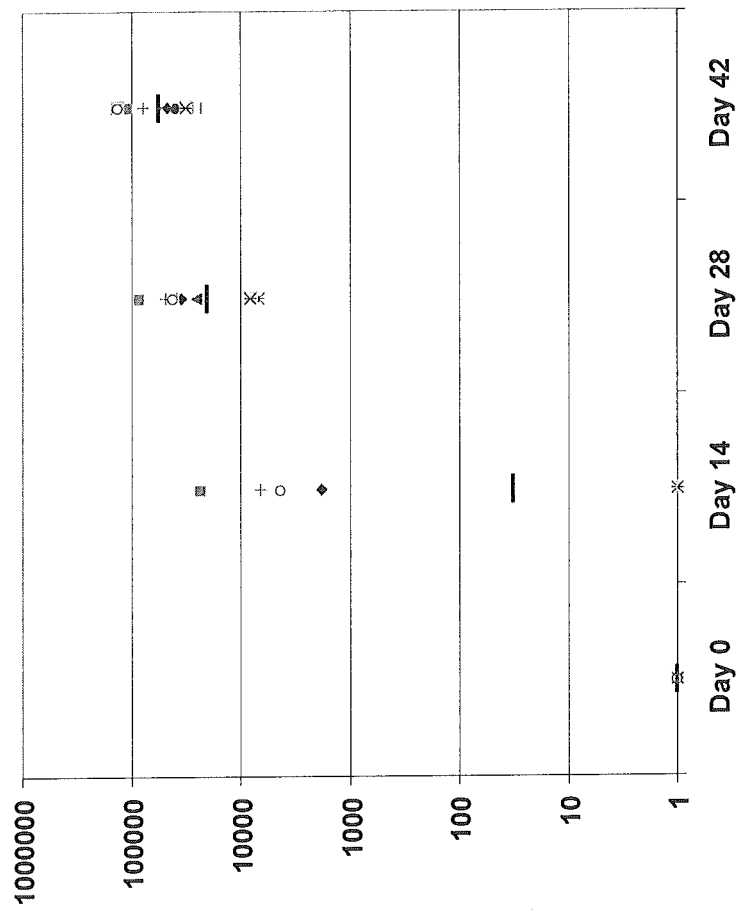
Figure 5H:
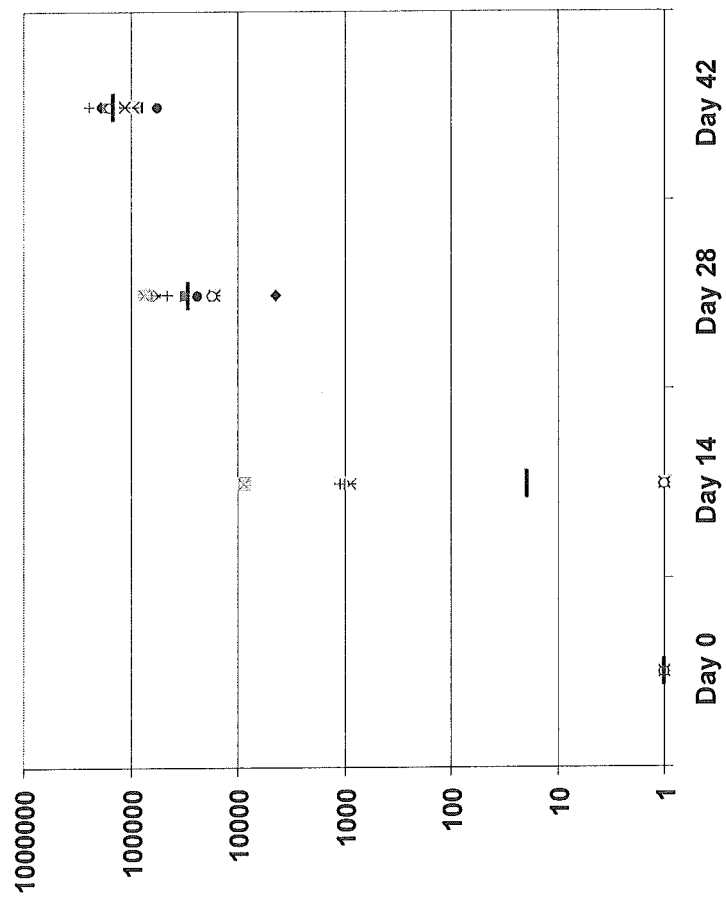
Figure 5I:
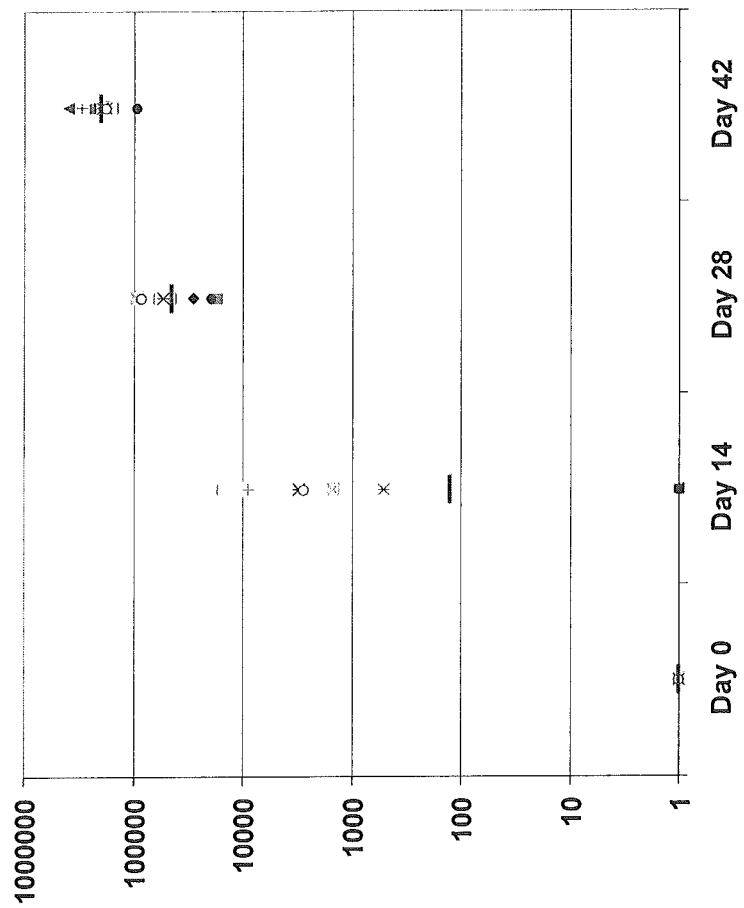
Figure 6A:
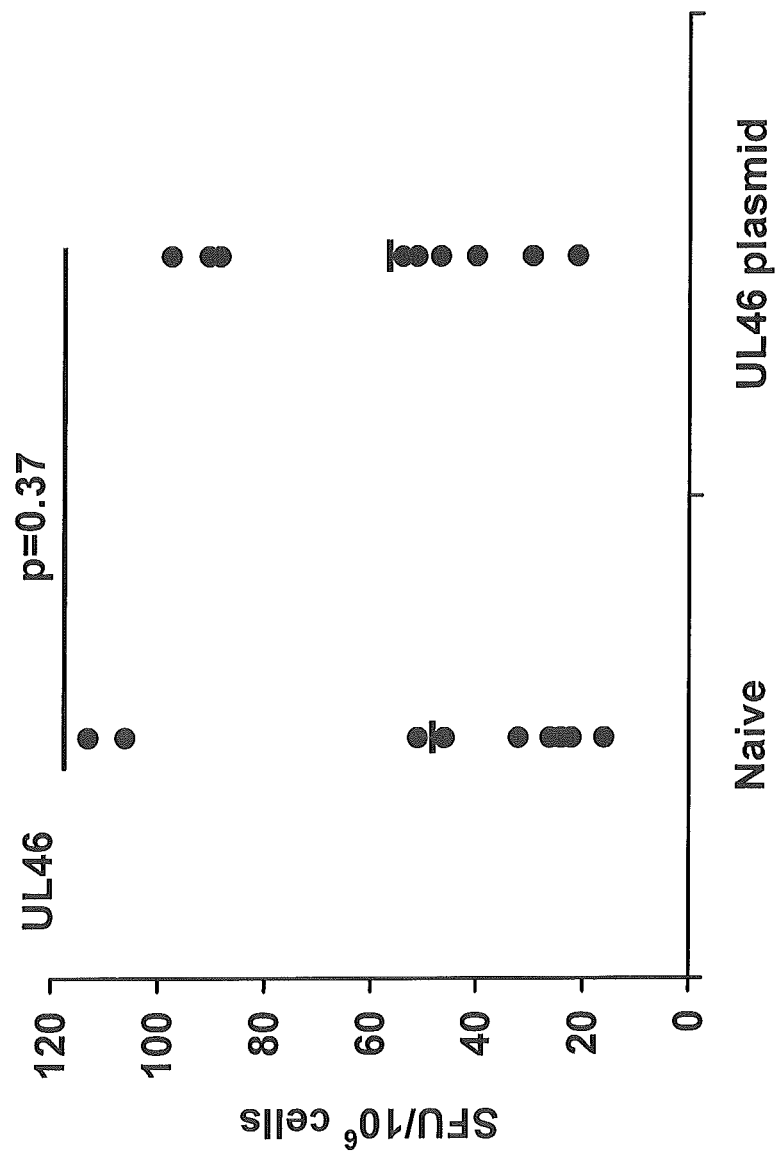
Figure 6B:
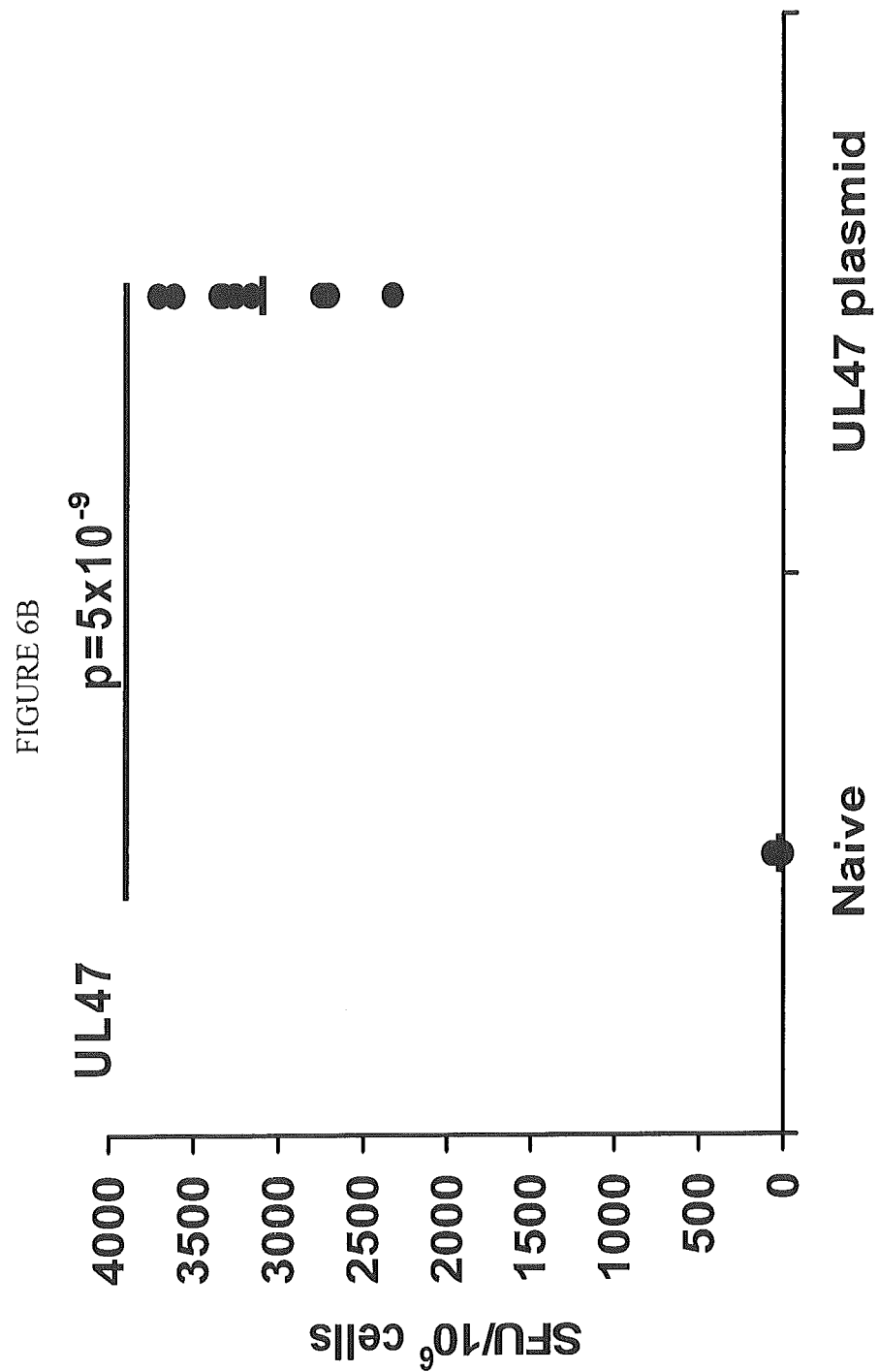
Figure 6C:
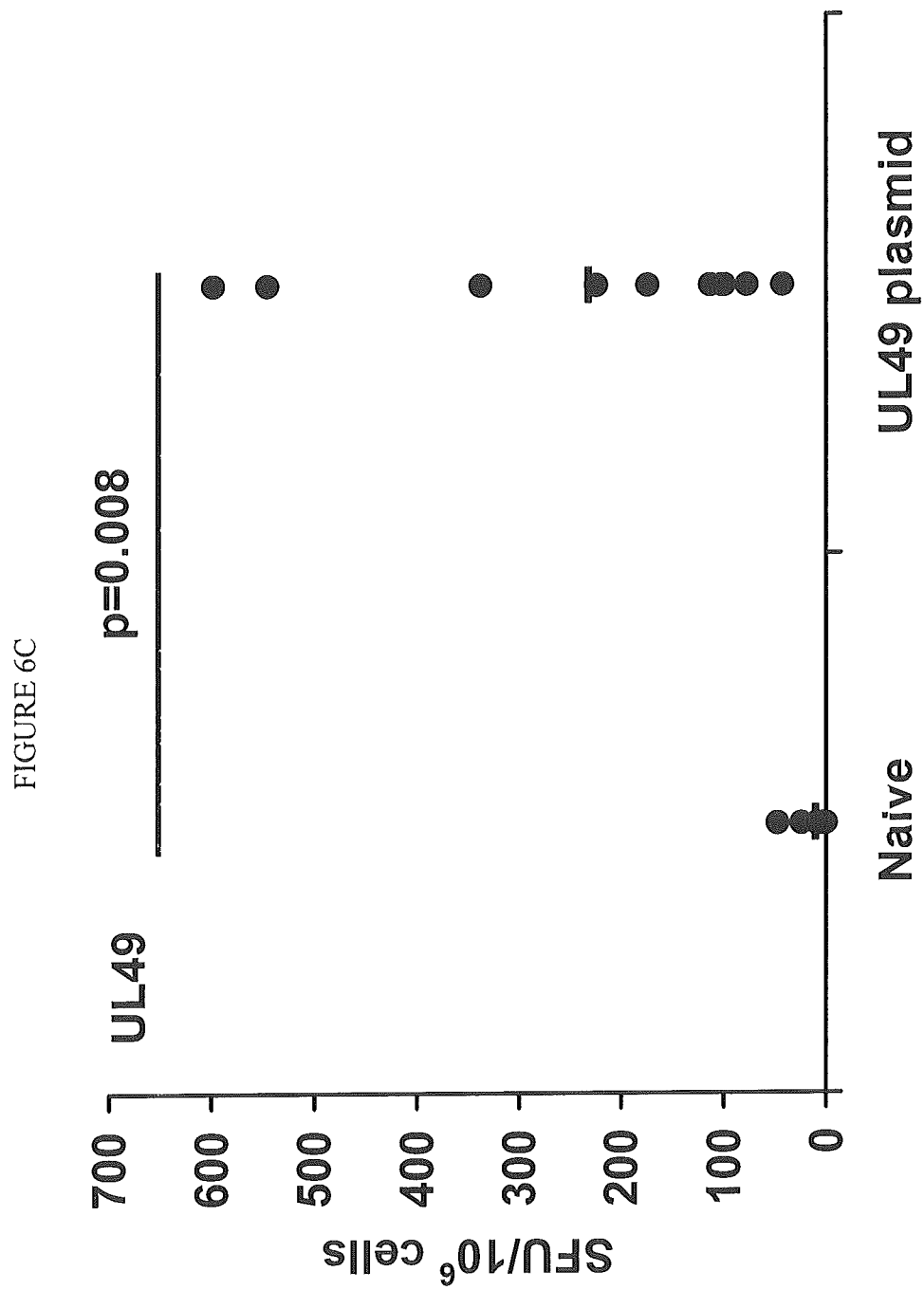
Figure 7:
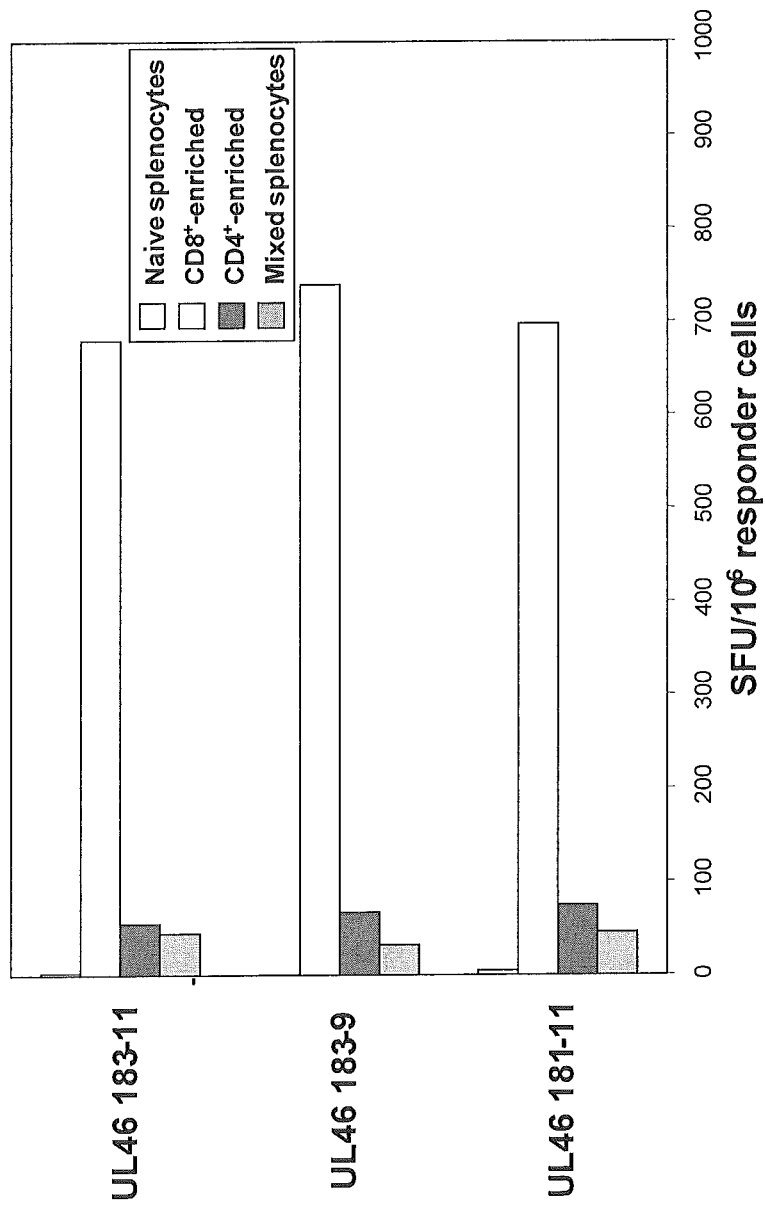
Figure 8:
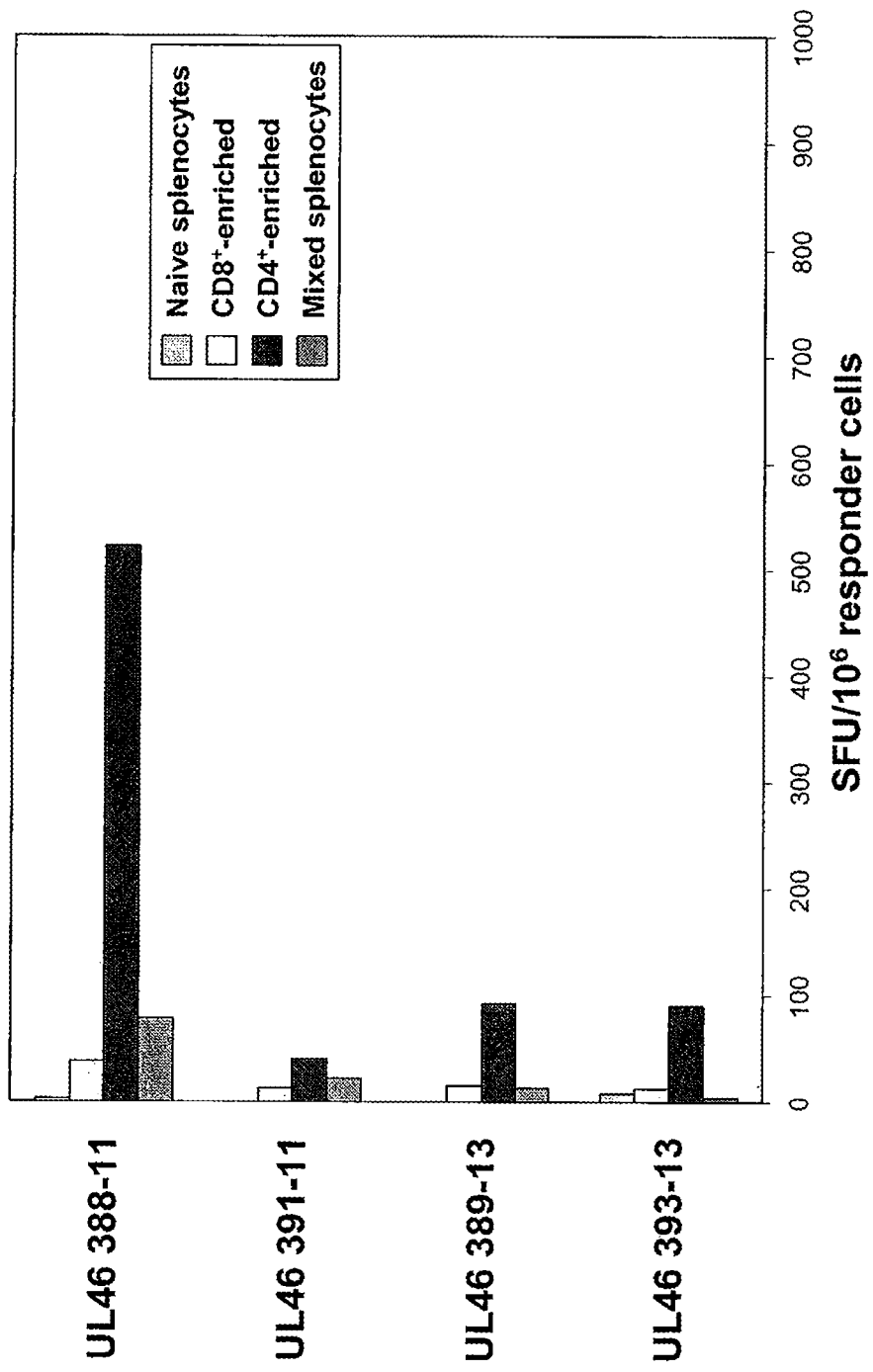
Figure 9:
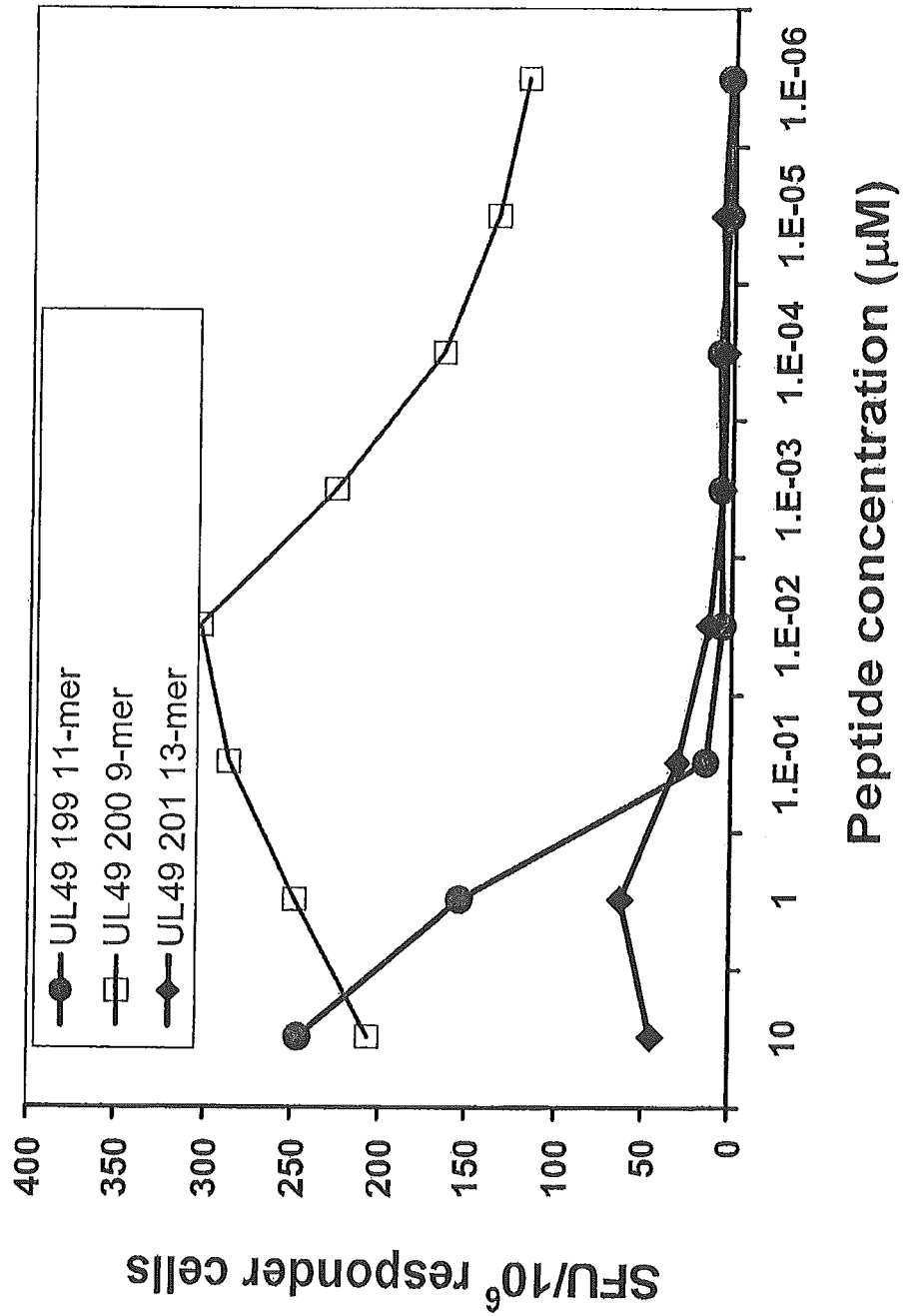
Figure 10:
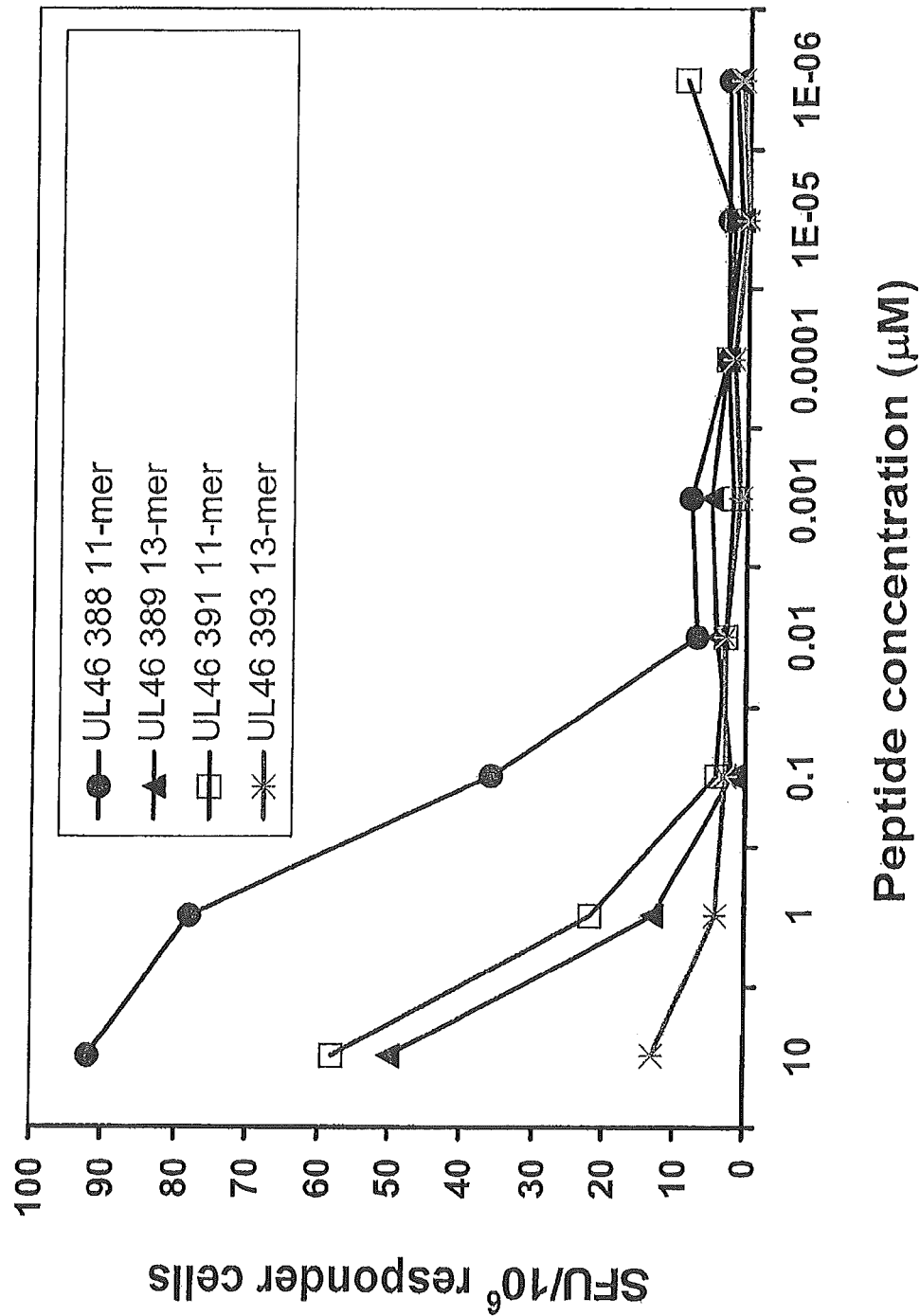
Figure 11:
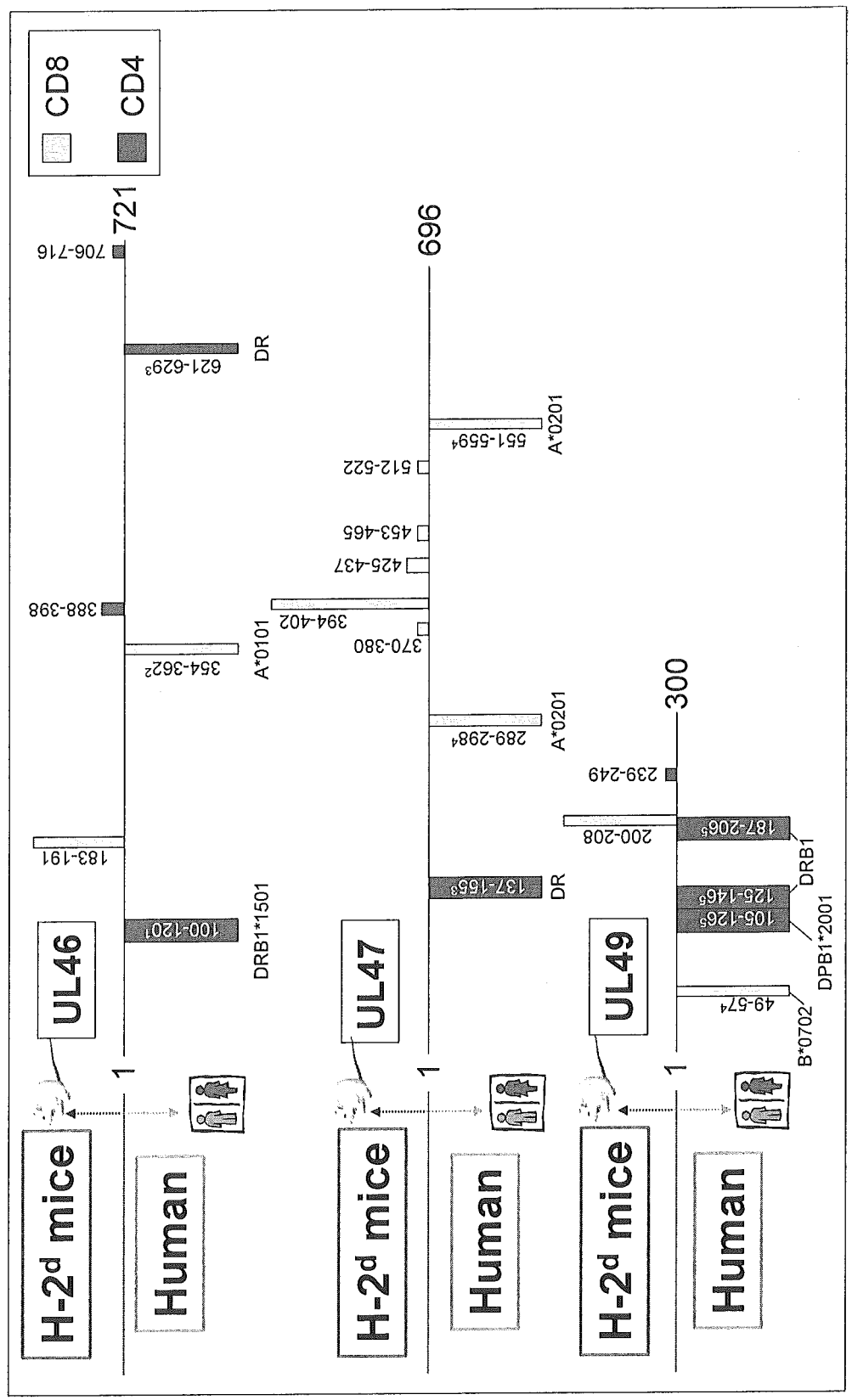
Figure 12:
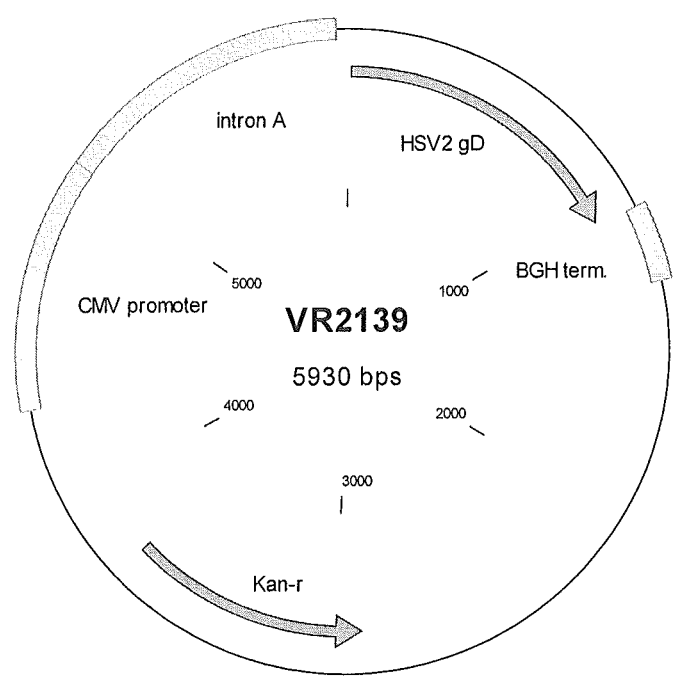
Figure 13:
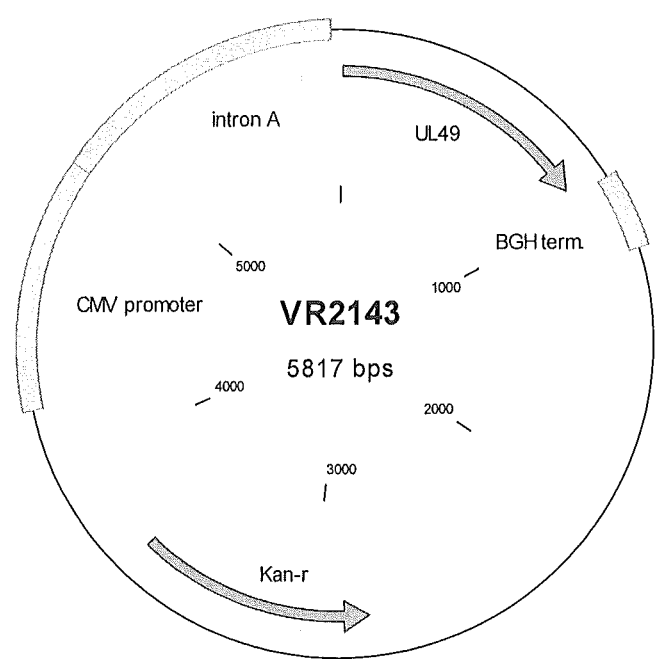
Figure 14:
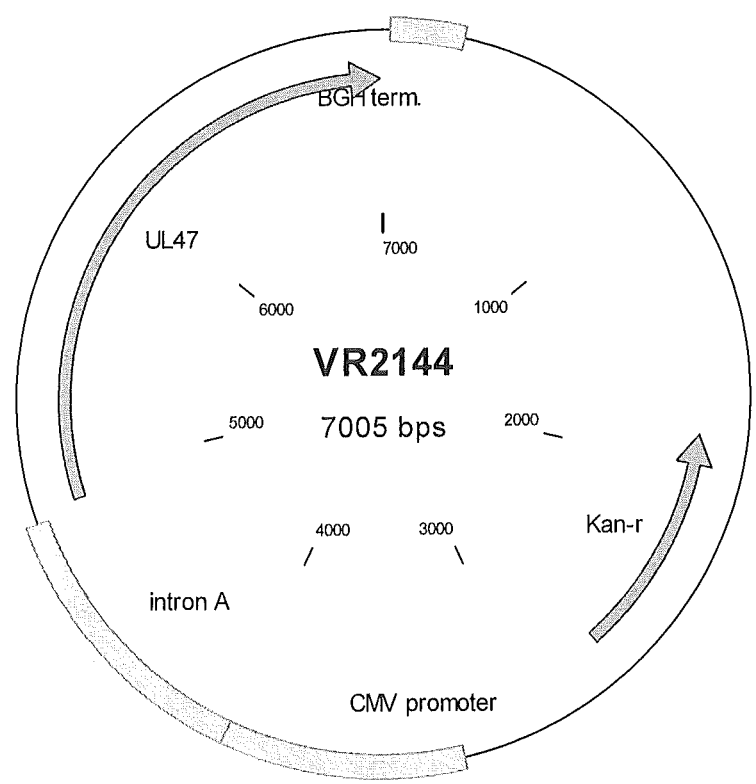
Figure 15:
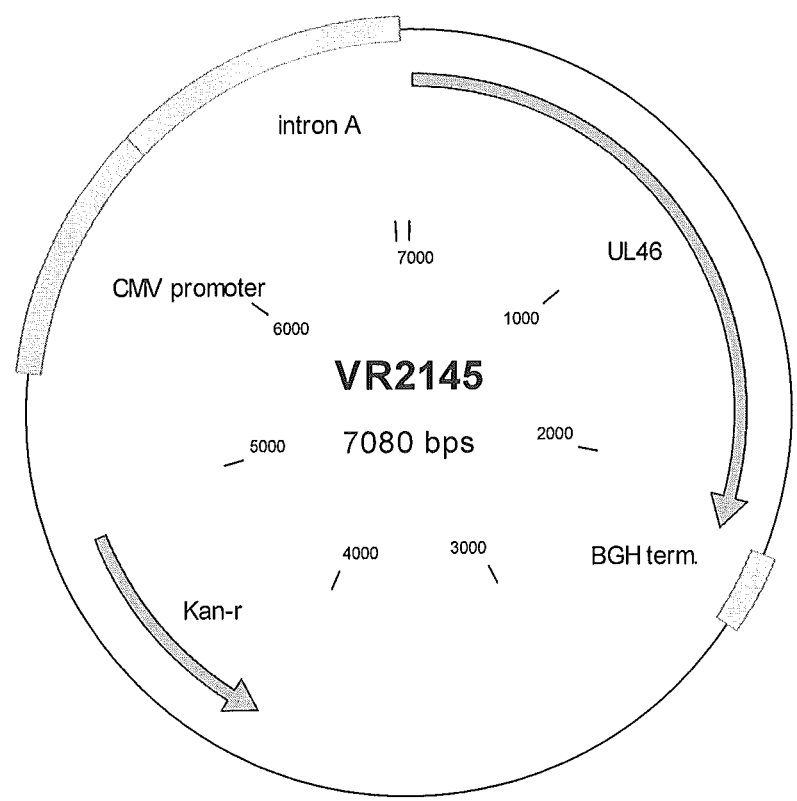
Figure 20A:
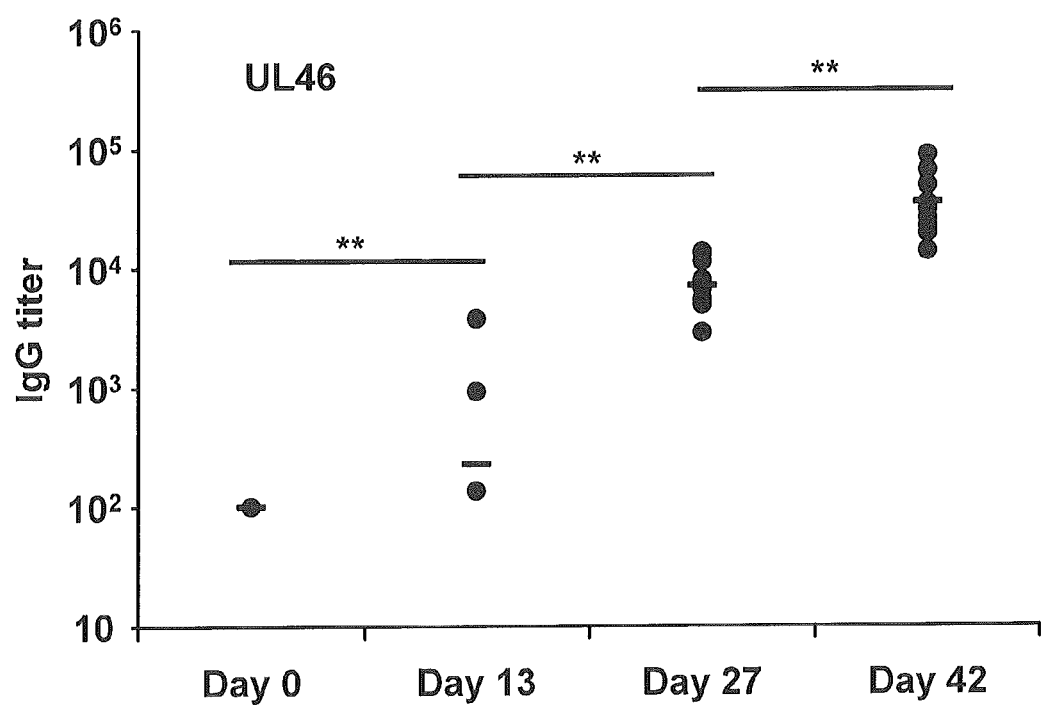
Figure 20B:
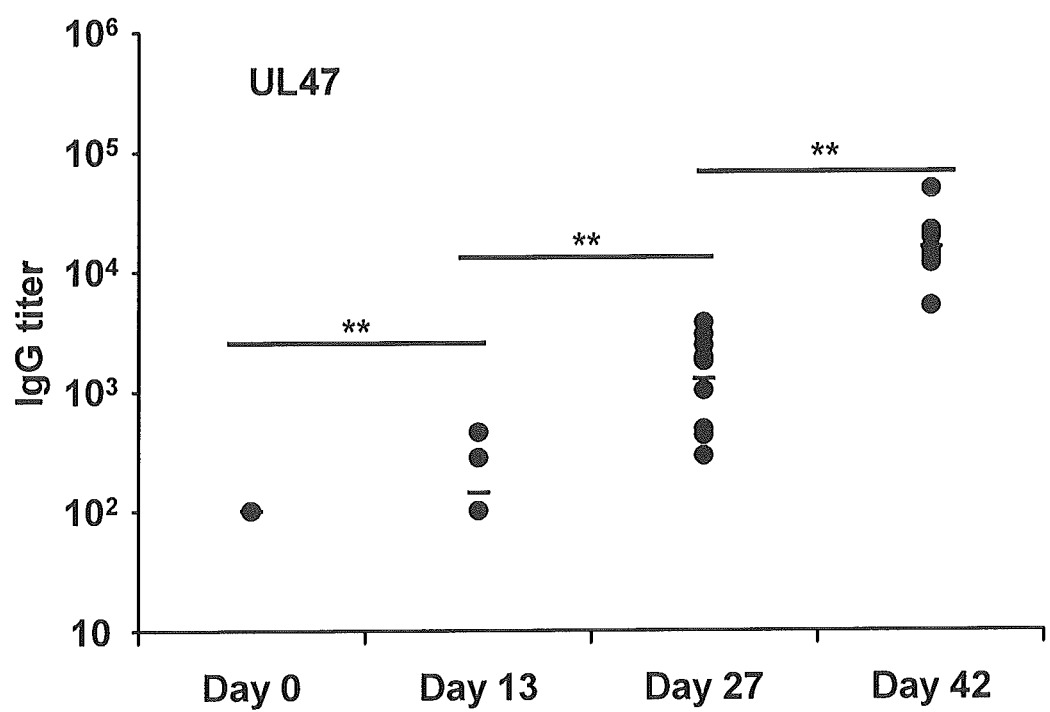
Figure 20C:
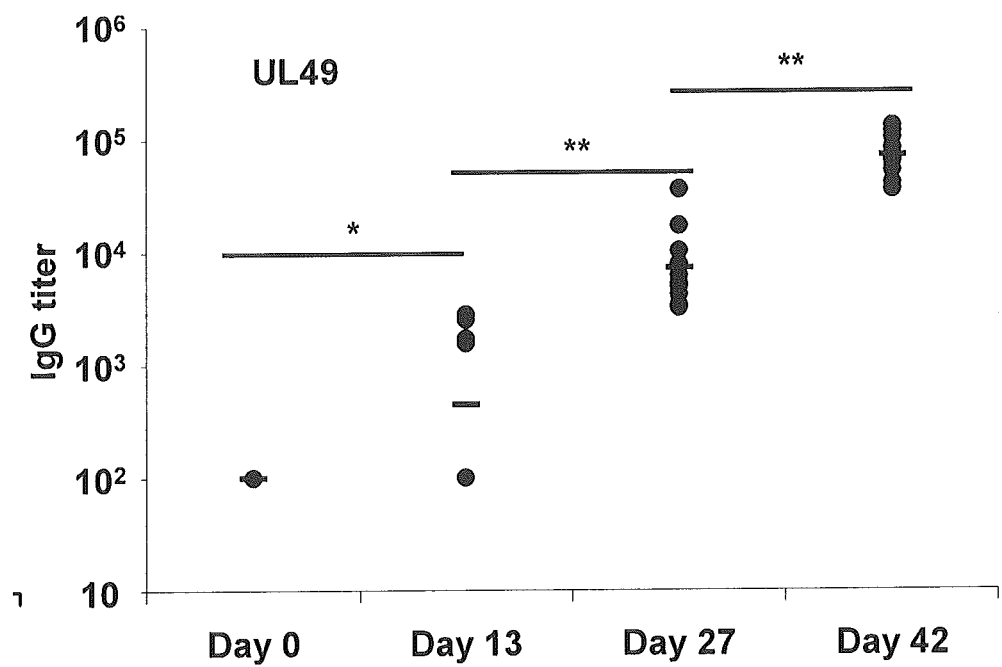
Figure 20D:
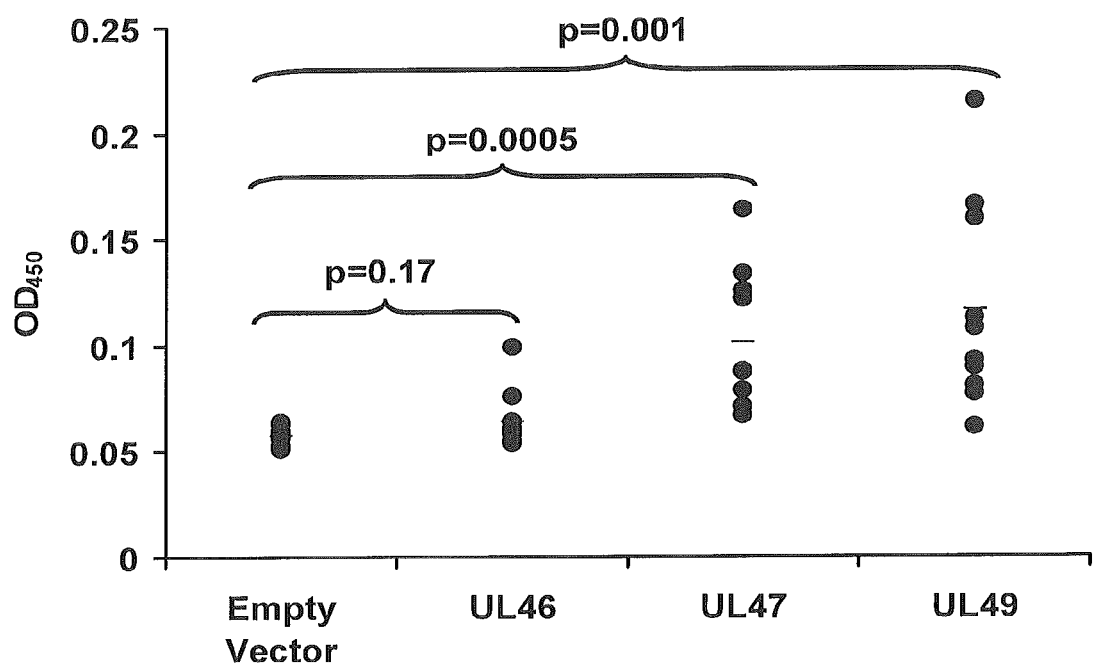
Figure 21A:
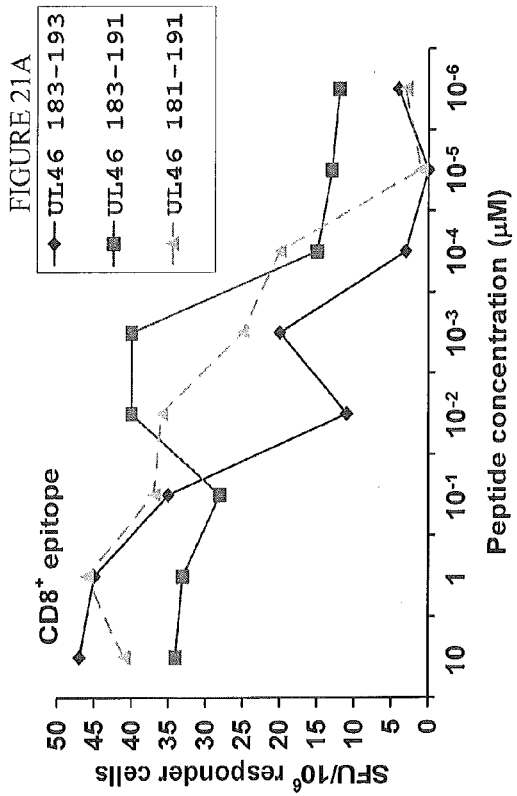
Figure 21B:
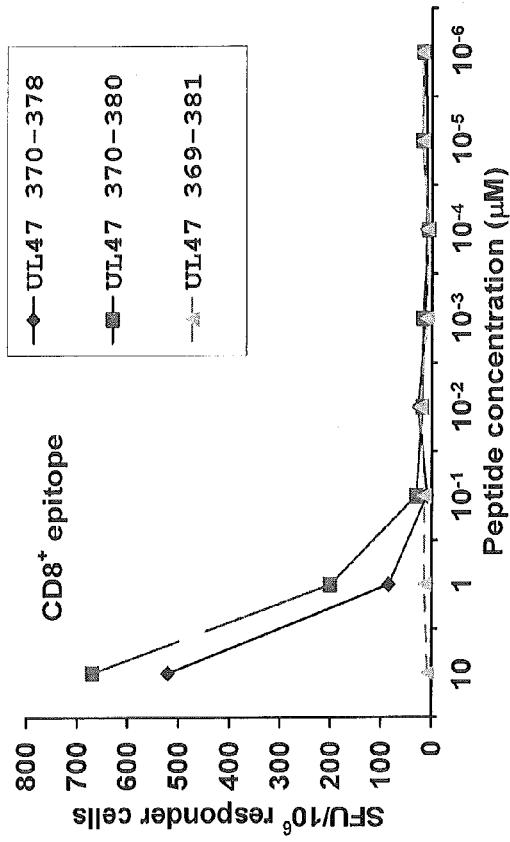
Figure 21C:
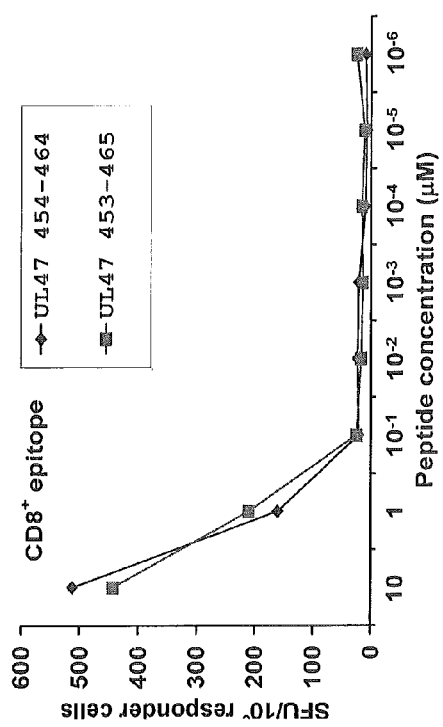
Figure 21D:
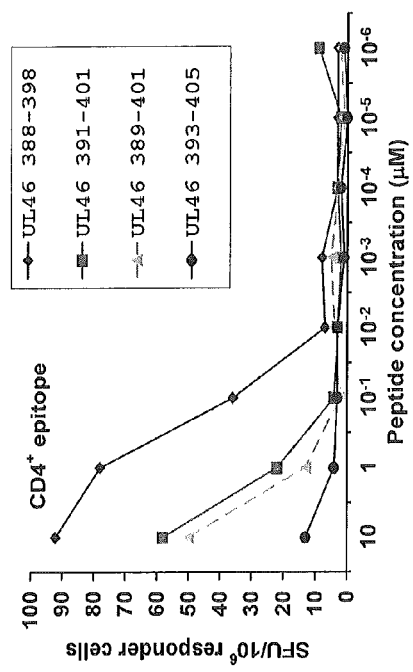
Figure 21E:
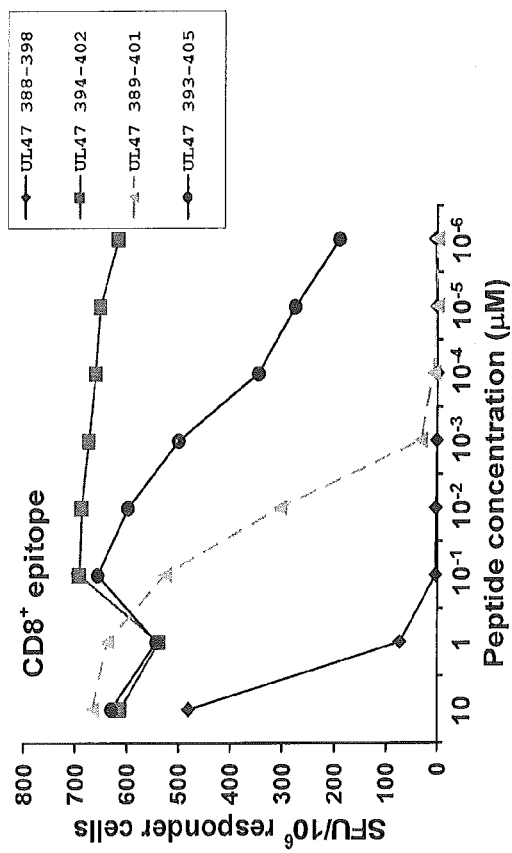
Figure 21F:
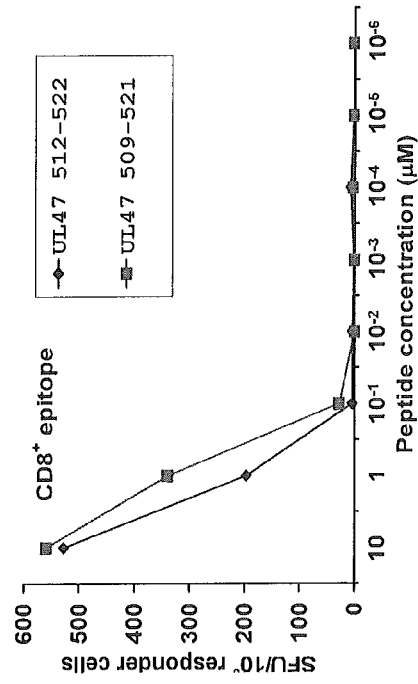
Figure 21G:
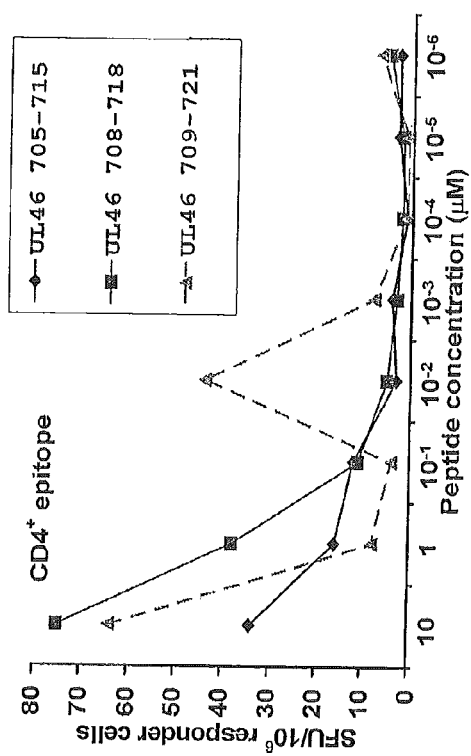
Figure 21H:
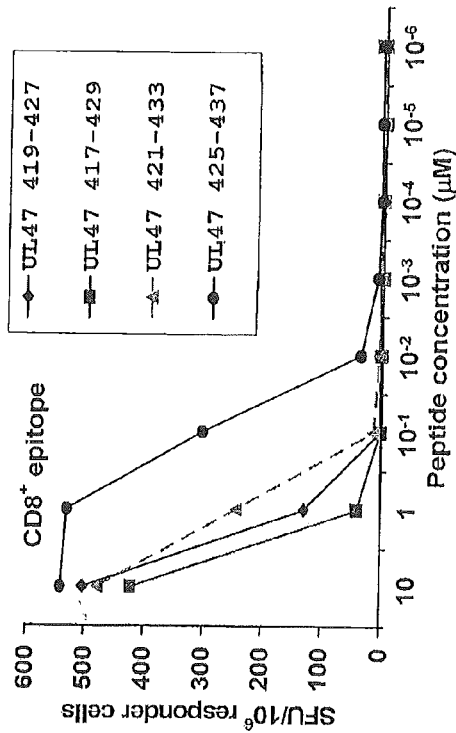
Figure 21I:
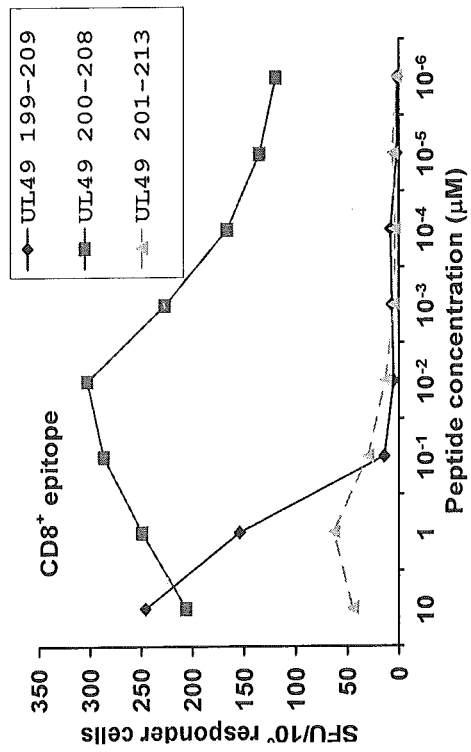
Figure 21J:
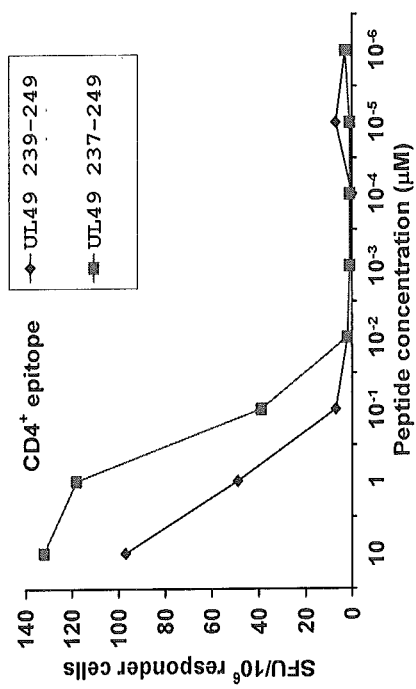
Figures 22A, 22B, 22C:
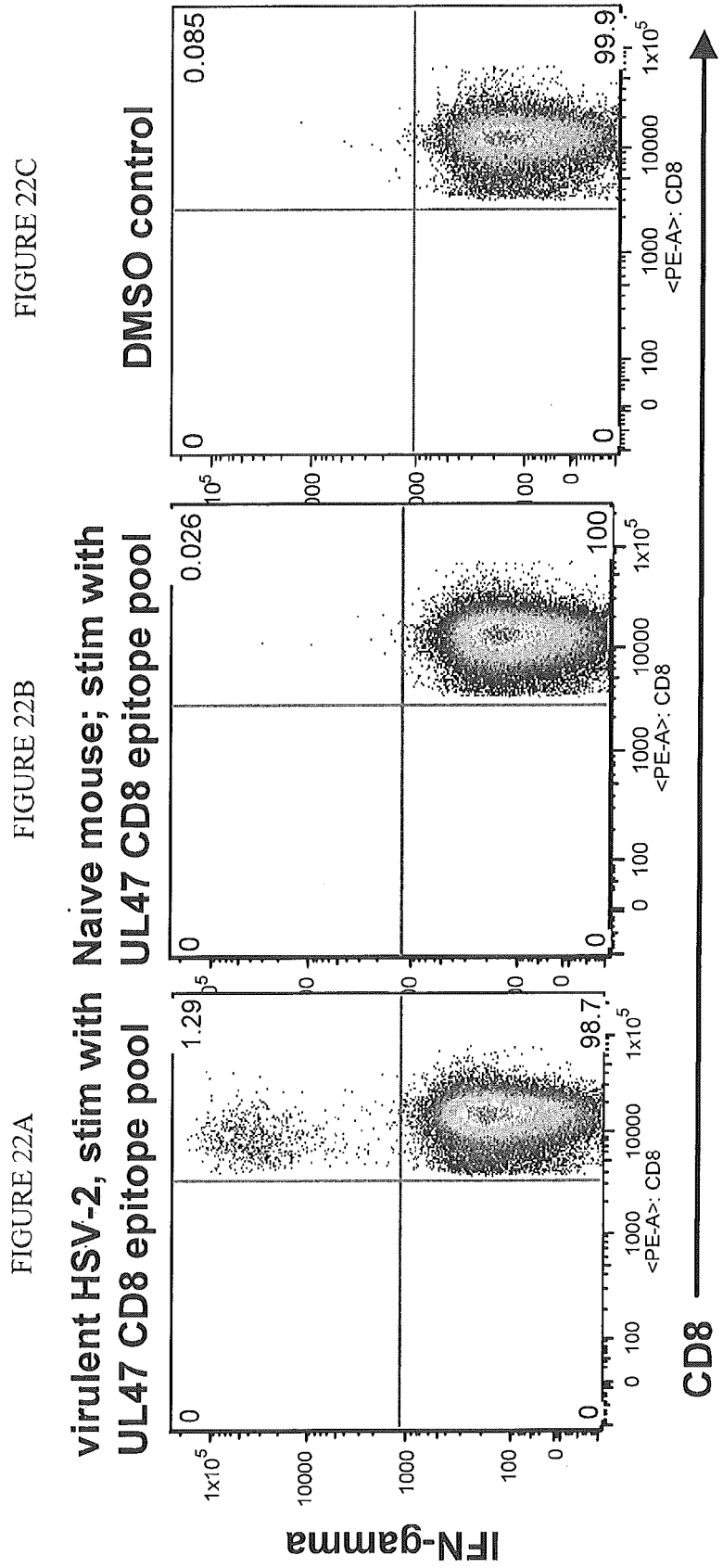
FIGS. 22A through 22C show the detection of tegument-specific CD8+ T-cells by intracellular cytokine cytometry. Splenocytes from a mouse vaccinated three times with UL47 pDNA and then surviving challenge with virulent HSV-2 were harvested 8 weeks later and stimulated with a pool of five optimal UL47 CD8 peptides at 1 μM each (FIG. 22A).
Figure 23:
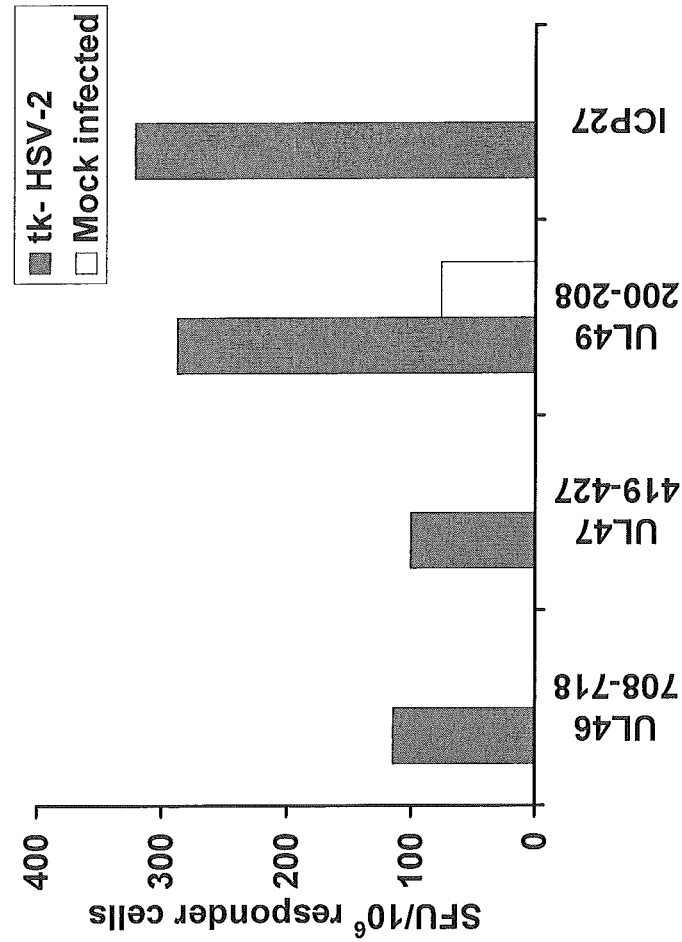
FIG. 23 provides that splenocytes from tk−-HSV-2-infected BALB/c mice recognize tegument protein epitopes. Mice were challenged with $4 \times 10^7$ pfu tk−-HSV-2 five days after Depo-provera. Cells at day 14 were testing in IFN-γ ELISPOT with CD8 peptide epitopes. A previously described ICP27 CD8+ epitope is the positive control (Haynes, J., Arlington J, Dong L, Braun R P, Payne L G, *Potent protective cellular immune responses generated by a DNA vaccine encoding HSV-2 ICP27 and the E. coli heat labile enterotoxin*. Vaccine, 2006. 24(23): p. 5016-26)
Figure 24C:
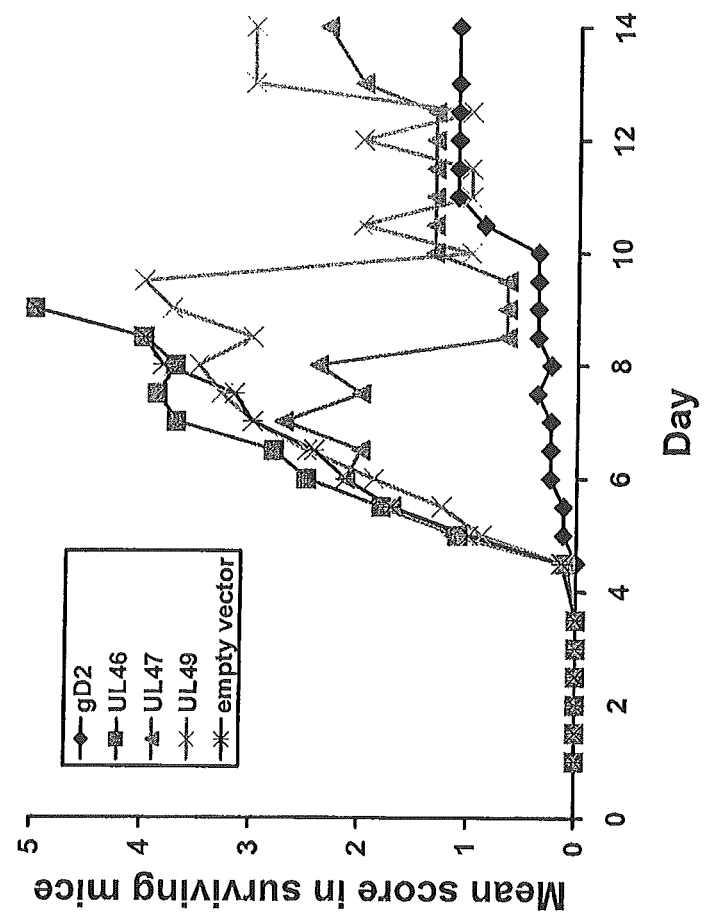
Figures 25A, 25B:
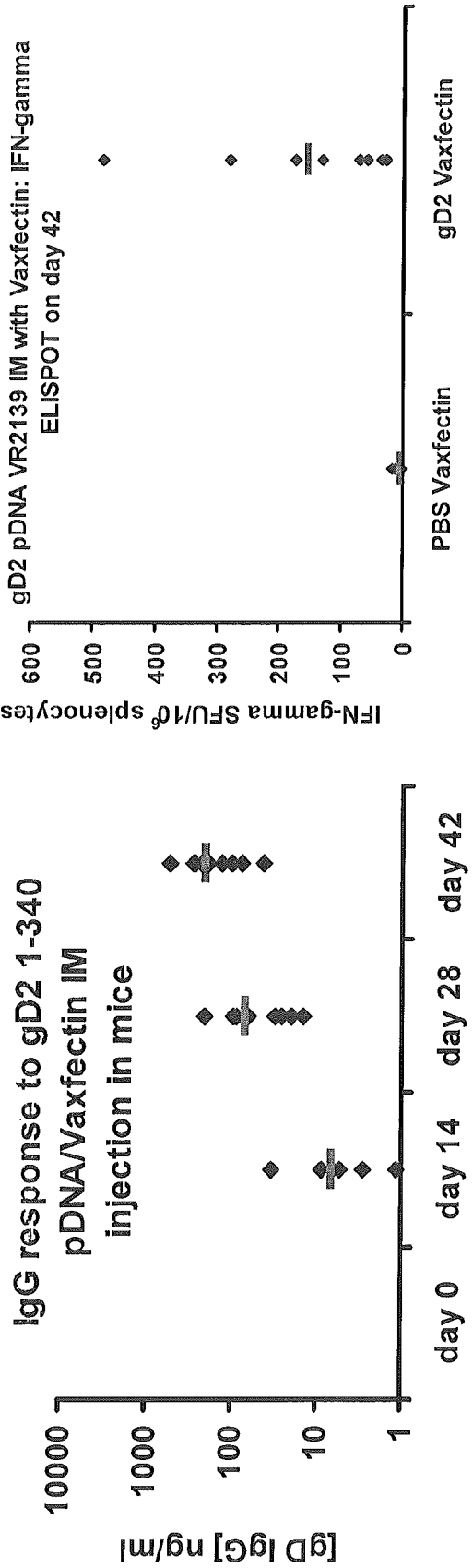
FIGS. 25A and 25B show the immune responses to pDNA vaccine VR2139 encoding $gD_2$ amino acid positions 1-340 administered IM to BALB/c mice with VAXFECTIN adjuvant. IgG titers by ELISA before each vaccine and at day 42 (FIG. 25A). Raw IFN-γ sfu/million splenocytes on day 42 (FIG. 25B) using pooled overlapping $gD_2$ peptides as antigen. Each dot is an individual mouse (n=9) and bars are mean.

Every mouse produced antibodies against the relevant protein by the second immunization (FIGS. 20A through 20I). Antibody titers were significantly higher from one measurement to the next (p<0.03, paired two-tailed t-test) for each vaccine and every time-point comparison. We also verified that vaccine-elicited antibodies bound to a whole HSV-2 lysate (FIG. 4). These data again show the plasmids encode bona fide HSV-2 proteins.

CD8+ and CD4+ Responses to Tegument DNA Vaccines in BALB/c Mice.

Overlapping peptides 13 AA long, offset by four AA, were synthesized to match the predicted vaccine sequences (Table 8). Initial assays used peptide pools (18-24 peptides/pool, concentration for each peptide 0.5 µg/mL). Splenocytes from individual mice (FIG. 6A through 6C), harvested two weeks after the third immunization, were assayed. The readout was IFN-γ ELISPOT (Haynes, J., Arrington J, Dong L, Braun R P, Payne L G, *Potent protective cellular immune responses generated by a DNA vaccine encoding HSV-2 ICP27 and the E. coli heat labile enterotoxin*. Vaccine, 2006. 24(23): p. 5016-26). Responses to pools were summed for each animal to give cumulative responses, expressed as spot forming units (sfu)/$10^6$ splenocytes. For UL47 and UL49, responses were higher than from naive mice ($p<0.01$, two-tailed t-test). For UL46, responses were not statistically different from naive ($p=0.37$), due to high responses in two naive mice. However, testing of single peptides from UL46 still disclosed antigenic peptides.

The individual peptides in positive pools were tested in follow-up ELISPOT, and in each case, single or neighboring overlapping peptides were positive. We used overlap regions (when present) and MHC-peptide epitope prediction algorithms (Bui, H. H., et al., *Automated generation and evaluation of specific MHC binding predictive tools: ARB matrix applications*. Immunogenetics, 2005; Parker, K. C., M. A. Bednarek, and J. E. Coligan, *Scheme for ranking potential HLA-A2 binding peptides based on independent binding of individual peptide side-chains. Journal of Immunology,* 1994. 152: p. 163-168; Rammensee, H., et al., *SYFPEITHI: database for MHC ligands and peptide motifs*. Immunogenetics, 1999. 50: p. 213-319) to pick shorter peptides for further tests. We used negative selection with magnetic bead-conjugated antibodies to enrich $CD4^+$ or $CD8^+$ splenocytes, and back-mixed these with naive congenic splenocytes as APC. In IFN-γ ELISPOT, potent $CD8^+$ epitopes were found for each vaccine protein. $CD4^+$ responses were detected in UL46 and UL49. $CD4^+$ responses were generally weaker than $CD8^+$ responses when quantified as sfu/$10^6$ splenocytes or $EC_{50}$ (the concentration giving 50% of the maximum response) (FIG. 21). Some $CD8^+$ epitopes were active at $10^{-12}$ M (FIG. 21). Such potent CD8+ epitopes typically bind tightly to relevant MCH class I molecules. The $IC_{50}$ for binding UL46 183-191 (KYAAAVAGL) to H-$2K^d$ was 9.91 nM (very tight binding) (Sette, A., et al., *A roadmap for the immunomics of category A-C pathogens*. Immunity, 2005. 22(2): p. 155-61). Overall, the tegument protein vaccines elicited high avidity, and often multi-epitope and combined ($CD4^+$ and $CD8^+$) T cell responses.

HSV-2-Infected Mice Generate T Cells Against Tegument Protein Epitopes.

T cells primed in vivo by HSV-2 infection would be boosted by vaccination. In this context, it was important to test if tegument-specific T cells were primed in vivo by HSV-2 infection, as well as by vaccine (above). We infected BALB/c mice with an attenuated HSV-2 strain 333 variant deficient in thymidine kinase (333tk−) (Milligan, G. N. and D. I. Bernstein, *Generation of humoral responses against herpes simplex virus type 2 in the murine female genital tract*. Virology, 1995. 206: p. 234-241). Mice were made susceptible to intravaginal infection by subcutaneous Depo-provera (progestin) 6 days before infection. Splenocytes from day 14 (FIGS. 22 and 23) mice showed T cell responses to CD8+ tegument epitopes previously discovered using pDNA vaccines (above). In both humans and mice, tegument proteins UL46, UL47, and UL49 are processed and presented via the MHC class I pathway during viral infection.

Tegument Vaccines Provide Partial Protection Against Lethal Intravaginal Challenge with HSV-2.

"$CD8^+$-only" vaccines can protect mice from lethal intracerebral or footpad HSV-1 challenge (Blaney, J. E., et al., *Immunization with a single major histocompatibility class I-restricted cytotoxic T-lymphocyte recognition epitope of herpes simplex virus type 2 confers protective immunity*. Journal of Virology, 1998. 72: p. 9567-9574; Orr, M. T., Orgun, N, N., Wilson, C. B., Way, S. S., *Cutting edge: recombinant listeria monocytogenes expressing a single immune-dominant peptide confers immunity to herpes simplex virus-1 infection*. Journal of Immunology, 2007. 178: p. In Press Apr. 15, 2007 edition), but have never been studied in the intravaginal HSV-2 model. We found that univalent tegument vaccines provided partial protection in the intravaginal model. We used the virulent HSV-2 strain 186 (Nishiyama, Y. and F. Rapp, *Latency in vitro using irradiated herpes simplex virus*. J Gen Virol, 1981. 52(Pt 1): p. 113-9) for lethal challenge. $3\times10^3$ pfu. The endpoints were measured twice a day, day 14 survival, and vaginal HSV-2 titers on day 1-5. All-dacron swabs were placed into 1 mL PCR buffer, extracted, and analyzed for HSV-2 DNA copy number by high-throughput real-time PCR as described (Ryncarz, A. J., et al., *Development of a high throughput quantitative assay for detecting HSV DNA in clinical samples. Journal of Clinical Microbiology,* 1999. 37: p. 1941-1947). Positive vaccine controls were intravaginal infection with $10^6$ pfu of attenuated HSV-2 333tk− (after Depo-provera), or three injections of a truncated $gD_2$ pDNA vaccine (please see below). Negative control was empty plasmid. pDNA vaccines were given as 3 doses on days 0, 14, and 28 at 100 μg/dose IM in PBS. Mice were challenged 14 days after vaccination with 50 times $LD_{50}$ ($50\times(3\times10^3)=1.5\times10^5$ pfu) after Depo-provera.

HSV-2 333tk− and $gD_2$ protected all animals (FIG. 24). UL47 pDNA provided 44% protection (4 of 9 animals), with possible slight protection for UL49. The UL47 and UL49 survivors were confirmed to have been infected by ELISA using whole HSV-2 lysate; they had much higher $OD_{450}$ values (data not shown) than could be explained by immunity to the immunizing construct alone (FIGS. 20A through 21). The tegument vaccines were non-sterilizing: HSV-2 replication occurred in the vagina after challenge (FIG. 24). The $gD_2$ vaccine (below) did lead to a measurable reduction in HSV-2 replication (FIG. 24). The clinical severity score was reduced after UL47, UL49, and $gD_2$ vaccination.

$gD_2$ Shows Minimal Sequence Variation and is an Effective Preventative Vaccine that Lowers HSV-2 Replication.

We sequenced six wild-type $gD_2$ genes. We found few changes from HG52: one had V169A and a second had V353A and L375P changes. No changes were detected in known gD$_2$ CD8+ or neutralizing epitopes (Koelle, D. M., Liu Z., McClurkan C. L., Cevallos R. C., Vieira J., Hosken N. A, Meseda C. A., Snow D. C., Wald A, Corey L., *Immunodominance among herpes simplex virus-specific CD8 T-cells expressing a tissue-specific homing receptor*. Proc Natl Acad Sci USA, 2003. 100: p. 12899-12904; Tigges, M. A., et al., *Human CD8+ herpes simplex virus-specific cytotoxic T lymphocyte clones recognize diverse virion protein antigens*. Journal of Virology, 1992. 66: p. 1622-1634; Spear, P. G., R. J. Eisenberg, and G. H. Cohen. *Three classes of surface receptors for alphaherpesvirus entry*. Virology, 2000. 275: p. 1-8.). Our candidate pDNA gD$_2$ vaccine, VR2139, encodes AA 1-340 of gD$_2$ using the HG52 sequence. AA 341-393 were omitted because they contain a leader and transmembrane domain. Humoral responses were detected by ELISA using commercially available $gD_1$ as coating antigen and a commercially available mAb against a type-common gD epitope as a calibrator (FIG. 25). Cellular responses were detected with overlapping 13-mer peptides exactly as described above for tegument proteins. After three vaccinations of 100 μg $gD_2$ pDNA vaccine on days 0, 14, and 28 with VAXFECTIN adjuvant, brisk humoral and total splenocyte IFN-γ ELISPOT responses were noted in most animals (FIG. 25). Survival, clinical severity and intravaginal HSV-2 DNA viral load benefits were described above.

SUMMARY $CD8^+$ T cell responses control HSV infection in mice and humans in the skin and ganglia. Tegument proteins are important targets of the CD8+ human immune response to HSV-2 (Koelle, D. M., et al., *CD8 CTL from genital herpes simplex lesions: recognition of viral tegument and immediate early proteins and lysis of infected cutaneous cells*. Journal of Immunology, 2001. 166: p. 4049-4058; Koelle, D. M., et al., *Recognition of herpes simplex virus type 2 tegument proteins by CD4 T cells infiltrating human genital herpes lesions*. Journal of Virology, 1998. 72: p. 7476-7483; Posavad, C. M., et al., *T cell immunity to herpes simplex virus in seronegative persons: silent infection or acquired immunity*. Journal of Immunology, 2003. 170: p. 4380-4388; Koelle, D. M., Liu Z., McClurkan C. L., Cevallos R. C., Vieira J., Hosken N. A, Meseda C. A., Snow D. C., Wald A., Corey L., *Immunodominance among herpes simplex virus-specific CD8 T-cells expressing a tissue-specific homing receptor*. Proc Natl Acad Sci USA, 2003. 100: p. 12899-12904; Koelle, D. M., et al., *Tegument-specific, virus-reactive CD4 T-cells localize to the cornea in herpes simplex virus interstitial keratitis in humans*. Journal of Virology, 2000. 74: p. 10930-10938; Verjans, G. M., et al., *Intraocular T cells of patients with herpes simplex (HSV)-induced acute retinal necrosis recognize HSV tegument proteins VP11/12 and VP13/14*. Journal of Infectious Diseases, 2000. 182: p. 923-927). DNA vaccines encoding HSV-2 tegument proteins were found to stimulate $CD8^+$, $CD4^+$, and antibody responses, and selected univalent vaccines were partially protective in an intravaginal challenge model.

Other Embodiments

The foregoing description is considered as illustrative only of the principles of the invention. Further, since numerous modifications and changes will readily occur to those skilled in the art, it is not desired to limit the invention to the exact construction and process as described above. Accordingly, all suitable modifications and equivalents may be resorted to falling within the scope of the invention as defined by the claims that follow. The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

All patent documents and references cited herein are incorporated by reference as if fully set forth.

What is claimed is:

1. An isolated polynucleotide comprising SEQ ID NO:11.
2. The polynucleotide of claim 1, further comprising a heterologous nucleic acid.
3. The polynucleotide of claim 2, wherein the heterologous nucleic acid encodes a heterologous polypeptide.
4. The polynucleotide of claim 1, which is operably associated with a promoter.
5. A vector comprising the polynucleotide of claim 1.
6. A DNA composition comprising the polynucleotide of claim 1 and an adjuvant.
7. The DNA composition of claim 6, wherein the adjuvant comprises (±)-N-(3-aminopropyl)-N,N-dimethyl-2,3-bis(syn-9-tetradecenyl oxy)-1-propanaminium bromide (GAP-DMORIE) and 1,2-diphytanoyl-sn-glycero-3-phosphoethanolamine (DPyPE).

* * * * *

```
                              SEQUENCE LISTING

<160> NUMBER OF SEQ ID NOS: 12

<210> SEQ ID NO 1
<211> LENGTH: 339
<212> TYPE: PRT
<213> ORGANISM: herpes simplex virus 2 gD

<400> SEQUENCE: 1

Met Gly Arg Leu Thr Ser Gly Val Gly Thr Ala Ala Leu Leu Val Val
1               5                   10                  15

Ala Val Gly Leu Arg Val Val Cys Ala Lys Tyr Ala Leu Ala Asp Pro
            20                  25                  30

Ser Leu Lys Met Ala Asp Pro Asn Arg Phe Arg Gly Lys Asn Leu Pro
        35                  40                  45

Val Leu Gln Leu Thr Asp Pro Pro Gly Val Lys Arg Val Tyr His Ile
    50                  55                  60

Gln Pro Ser Leu Glu Asp Pro Phe Gln Pro Pro Ser Ile Pro Ile Thr
65                  70                  75                  80

Val Tyr Tyr Ala Val Leu Glu Arg Ala Cys Arg Ser Val Leu Leu His
```

```
            85                  90                  95
Ala Pro Ser Glu Ala Pro Gln Ile Val Arg Gly Ala Ser Asp Glu Ala
            100                 105                 110

Arg Lys His Thr Tyr Asn Leu Thr Ile Ala Trp Tyr Arg Met Gly Asp
        115                 120                 125

Asn Cys Ala Ile Pro Ile Thr Val Met Glu Tyr Thr Glu Cys Pro Tyr
        130                 135                 140

Asn Lys Ser Leu Gly Val Cys Pro Ile Arg Thr Gln Pro Arg Trp Ser
145                 150                 155                 160

Tyr Tyr Asp Ser Phe Ser Ala Val Ser Glu Asp Asn Leu Gly Phe Leu
                165                 170                 175

Met His Ala Pro Ala Phe Glu Thr Ala Gly Thr Tyr Leu Arg Leu Val
            180                 185                 190

Lys Ile Asn Asp Trp Thr Glu Ile Thr Gln Phe Ile Leu Glu His Arg
        195                 200                 205

Ala Arg Ala Ser Cys Lys Tyr Ala Leu Pro Leu Arg Ile Pro Pro Ala
    210                 215                 220

Ala Cys Leu Thr Ser Lys Ala Tyr Gln Gln Gly Val Thr Val Asp Ser
225                 230                 235                 240

Ile Gly Met Leu Pro Arg Phe Ile Pro Glu Asn Gln Arg Thr Val Ala
                245                 250                 255

Leu Tyr Ser Leu Lys Ile Ala Gly Trp His Gly Pro Lys Pro Pro Tyr
            260                 265                 270

Thr Ser Thr Leu Leu Pro Pro Glu Leu Ser Asp Thr Thr Asn Ala Thr
        275                 280                 285

Gln Pro Glu Leu Val Pro Glu Asp Pro Glu Asp Ser Ala Leu Leu Glu
    290                 295                 300

Asp Pro Ala Gly Thr Val Ser Ser Gln Ile Pro Pro Asn Trp His Ile
305                 310                 315                 320

Pro Ser Ile Gln Asp Val Ala Pro His His Ala Pro Ala Ala Pro Ser
                325                 330                 335

Asn Pro Gly

<210> SEQ ID NO 2
<211> LENGTH: 4400
<212> TYPE: DNA
<213> ORGANISM: herpes simplex virus 2 gD

<400> SEQUENCE: 2
ggccgccgcc accatgggca gactgactag cggagtgggc acagccgccc tgctcgtggt     60
ggctgtgggc ctgagagtgg tgtgtgctaa gtacgccctg ctgaccccta gcctgaagat    120
ggctgatcct aataggttta ggggcaagaa cctgcccgtg ctggaccagc tgactgaccc    180
ccctggcgtg aagagagtgt accacatcca gcctagcctg aggacccctc cagccccc     240 tagcatccct atcaccgtgt actacgccgt gctggagaga gcctgtagaa gcgtgctgct    300
gcacgcccct agtgaggccc tcagattgt gagaggcgct agtgacgagg ctaggaagca    360
cacctataac ctgaccatcg cctggtatag gatgggcgat aactgcgcca tccccatcac    420
agtgatggag tacactgagt gccccctata taagagcctg gcgtgtgtc ccattaggac    480 ccagcctagg tggagctact acgatagctt tagcgccgtg agtgaggata acctgggctt    540
cctgatgcac gccccagcct ttgagaccgc cggcacctac ctgagactgg tgaagattaa    600
cgactggact gagatcaccc agttcatcct ggagcatagg gctagggcta gctgtaaata    660
```

```
cgccctgccc ctgagaatcc ccoctgccgc ctgcctgact agtaaggcct accagcaagg    720
cgtgaccgtg gatagcatcg gcatgctgcc tagattcatc cctgagaacc agagaaccgt    780
ggccctgtat agcctgaaaa tcgccggctg gcacggccct aagcctcctt acactagcac    840
cctgctgccc cctgagctga gtgataccac taacgccacc cagcctgagc tggtgcctga    900
ggaccctgag gatagcgctc tgctggaaga tcctgccggc accgtgagta gccagatccc    960
ccctaactgg cacatcccta gcattcagga cgtggccccc caccacgccc ctgccgctcc   1020
tagtaaccct ggctgatgag gatccagatc tgctgtgcct tctagttgcc agccatctgt   1080
tgtttgcccc tccccgtgc cttccttgac cctggaaggt gccactccca ctgtcctttc    1140
ctaataaaat gaggaaattg catcgcattg tctgagtagg tgtcattcta ttctgggggg    1200
tggggtgggg cagcacagca aggggggaga ttgggaagac aatagcaggc atgctgggga   1260
tgcggtgggc tctatgggta cccaggtgct gaagaattga cccggttcct cctgggccag   1320
aaagaagcag gcacatcccc ttctctgtga cacaccctgt ccacgcccct ggttcttagt   1380
tccagcccca ctcataggac actcatagct caggagggct ccgccttcaa tcccacccgc   1440
taaagtactt ggagcggtct ctccctccct catcagccca ccaaaccaaa cctagcctcc   1500
aagagtggga agaaattaaa gcaagatagg ctattaagtg cagagggaga gaaaatgcct   1560
ccaacatgtg aggaagtaat gagagaaatc atagaatttc ttccgcttcc tcgctcactg   1620
actcgctgcg ctcggtcgtt cggctgcggc gagcggtatc agctcactca aaggcggtaa   1680
tacggttatc cacagaatca ggggataacg caggaaagaa catgtgagca aaaggccagc   1740
aaaaggccag gaaccgtaaa aaggccgcgt tgctggcgtt tttccatagg ctccgccccc   1800
ctgacgagca tcacaaaaat cgacgctcaa gtcagaggtg gcgaaacccg acaggactat   1860
aaagatacca ggcgtttccc cctggaagct ccctcgtgcg ctctcctgtt ccgaccctgc   1920
cgcttaccgg atacctgtcc gcctttctcc cttcgggaag cgtggcgctt tctcaatgct   1980
cacgctgtag gtatctcagt tcggtgtagg tcgttcgctc caagctgggc tgtgtgcacg   2040
aaccccccgt tcagcccgac cgctgcgcct tatccggtaa ctatcgtctt gagtccaacc   2100
cggtaagaca cgacttatcg ccactggcag cagccactgg taacaggatt agcagagcga   2160
ggtatgtagg cggtgctaca gagttcttga agtggtggcc taactacggc tacactagaa   2220
ggacagtatt tggtatctgc gctctgctga agccagttac cttcggaaaa agagttggta   2280
gctcttgatc cggcaaacaa accaccgctg gtagcggtgg tttttttgtt tgcaagcagc   2340
agattacgcg cagaaaaaaa ggatctcaag aagatccttt gatcttttct acggggtctg   2400
acgctcagtg gaacgaaaac tcacgttaag ggattttggt catgagatta tcaaaaagga   2460
tcttcaccta gatccttta aattaaaaat gaagttttaa atcaatctaa agtatatatg   2520
agtaaacttg gtctgacagt taccaatgct taatcagtga ggcacctatc tcagcgatct   2580
gtctatttcg ttcatccata gttgcctgac tccggggggg ggggcgctg aggtctgcct   2640 cgtgaagaag gtgttgctga ctcataccag gcctgaatcg ccccatcatc cagccagaaa   2700
gtgagggagc cacggttgat gagagctttg ttgtaggtgg accagttggt gattttgaac   2760
ttttgctttg ccacgaacg gtctgcgttg tcggaagat gcgtgatctg atccttcaac    2820
tcagcaaaag ttcgatttat tcaacaaagc cgccgtcccg tcaagtcagc gtaatgctct   2880
gccagtgtta caaccaatta accaattctg attagaaaaa ctcatcgagc atcaaatgaa   2940
actgcaattt attcatatca ggattatcaa taccatattt ttgaaaaagc cgtttctgta   3000
atgaaggaga aaactcaccg aggcagttcc ataggatggc aagatcctgg tatcggtctg   3060
```

```
cgattccgac tcgtccaaca tcaatacaac ctattaattt ccctcgtca aaataaggt      3120 tatcaagtga gaaatcacca tgagtgacga ctgaatccgg tgagaatggc aaaagcttat    3180
gcatttcttt ccagacttgt tcaacaggcc agccattacg ctcgtcatca aaatcactcg    3240
catcaaccaa accgttattc attcgtgatt gcgcctgagc gagacgaaat acgcgatcgc    3300
tgttaaaagg acaattacaa acaggaatcg aatgcaaccg cgcaggaac actgccagcg     3360 catcaacaat attttcacct gaatcaggat attcttctaa tacctggaat gctgttttcc    3420
cggggatcgc agtggtgagt aaccatgcat catcaggagt acggataaaa tgcttgatgg    3480
tcggaagagg cataaattcc gtcagccagt ttagtctgac catctcatct gtaacatcat    3540
tggcaacgct accttgcca tgtttcagaa acaactctgg cgcatcgggc ttcccataca     3600
atcgatagat tgtcgcacct gattgcccga cattatcgcg agcccattta tacccatata    3660
aatcagcatc catgttggaa tttaatcgcg gcctcgagca agacgtttcc cgttgaatat    3720
ggctcataac ccccttgta ttactgttta tgtaagcaga cagttttatt gttcatgatg     3780
atatattttt atcttgtgca atgtaacatc agagattttg agacacaacg tggctttccc    3840
ccccccccca ttattgaagc atttatcagg gttattgtct catgagcgga tacatatttg    3900
aatgtattta gaaaaataaa caaataggg ttccgcgcac atttccccga aaagtgccac     3960
ctgacgtcta agaaaccatt attatcatga cattaaccta taaaaatagg cgtatcacga    4020
ggccctttcg tctcgcgcgt ttcggtgatg acggtgaaaa cctctgacac atgcagctcc    4080
cggagacggt cacagcttgt ctgtaagcgg atgccgggag cagacaagcc cgtcagggcg    4140
cgtcagcggg tgttggcggg tgtcggggct ggcttaacta tgcggcatca gagcagattg    4200
tactgagagt gcaccatatg cggtgtgaaa taccgcacag atgcgtaagg agaaaatacc    4260
gcatcagatt ggctattggc cattgcatac gttgtatcca tcataata tgtacattta     4320 tattggctca tgtccaacat taccgccatg ttgacattga ttattgacta gttattaata    4380
gtaatcaatt acgggtcat                                                 4400
```

<210> SEQ ID NO 3
<211> LENGTH: 300
<212> TYPE: PRT
<213> ORGANISM: herpes simplex virus 2   UL49

<400> SEQUENCE: 3

```
Met Thr Ser Arg Arg Ser Val Lys Ser Cys Pro Arg Glu Ala Pro Arg
1               5                   10                  15

Gly Thr His Glu Glu Leu Tyr Tyr Gly Pro Val Ser Pro Ala Asp Pro
            20                  25                  30

Glu Ser Pro Arg Asp Asp Phe Arg Arg Gly Ala Gly Pro Met Arg Ala
        35                  40                  45

Arg Pro Arg Gly Glu Val Arg Phe Leu His Tyr Asp Glu Ala Gly Tyr
    50                  55                  60

Ala Leu Tyr Arg Asp Ser Ser Ser Asp Asp Glu Ser Arg Asp Thr
65                  70                  75                  80

Ala Arg Pro Arg Arg Ser Ala Ser Val Ala Gly Ser His Gly Pro Gly
                85                  90                  95

Pro Ala Arg Ala Pro Pro Pro Gly Gly Pro Val Gly Ala Gly Gly
            100                 105                 110

Arg Ser His Ala Pro Pro Ala Arg Thr Pro Lys Met Thr Arg Gly Ala
        115                 120                 125
```

Pro Lys Ala Ser Ala Thr Pro Ala Thr Asp Pro Ala Arg Gly Arg Arg
    130                 135                 140

Pro Ala Gln Ala Asp Ser Ala Val Leu Leu Asp Ala Pro Ala Pro Thr
145                 150                 155                 160

Ala Ser Gly Arg Thr Lys Thr Pro Ala Gln Gly Leu Ala Lys Lys Leu
                165                 170                 175

His Phe Ser Thr Ala Pro Pro Ser Pro Thr Ala Pro Trp Thr Pro Arg
            180                 185                 190

Val Ala Gly Phe Asn Lys Arg Val Phe Cys Ala Ala Val Gly Arg Leu
        195                 200                 205

Ala Ala Thr His Ala Arg Leu Ala Ala Val Gln Leu Trp Asp Met Ser
    210                 215                 220

Arg Pro His Thr Asp Glu Asp Leu Asn Glu Leu Leu Asp Leu Thr Thr
225                 230                 235                 240

Ile Arg Val Thr Val Cys Glu Gly Lys Asn Leu Leu Gln Arg Ala Asn
                245                 250                 255

Glu Leu Val Asn Pro Asp Ala Ala Gln Asp Val Asp Ala Thr Ala Ala
            260                 265                 270

Ala Arg Gly Arg Pro Ala Gly Arg Ala Ala Thr Ala Arg Ala Pro
        275                 280                 285

Ala Arg Ser Ala Ser Arg Pro Arg Arg Pro Leu Glu
    290                 295                 300

<210> SEQ ID NO 4
<211> LENGTH: 5817
<212> TYPE: DNA
<213> ORGANISM: herpes simplex virus 2 UL49

<400> SEQUENCE: 4

```
atcccaccat gacctctagg cggagcgtga agagctgccc tagagaggcc cctagaggca      60
cccacgagga gctgtactac ggccctgtgt cccctgccga ccctgagagc ctagagatg     120
actttagacg gggagccggc ctatgagag ccagacctag aggcgaagtg agattcctgc     180
actacgacga ggccggctac gccctgtatc gggatagcag ctctgacgac gacgagtcta    240
gggataccgc caggcctaga agaagcgcca gcgtggccgg cagccacggc cctggccctg    300
ccagagcccc ccctcctcct ggcggccctg tgggagccgg cggaagaagc cacgcccctc    360
ccgcccggac ccctaagatg accagaggcg cccctaaggc cagcgccacc cccgccaccg    420
atcccgccag aggcaggaga cccgcccagg ccgatagcgc cgtgctgctg acgcccctg     480
cccccaccgc ctccggcaga accaagaccc ctgcccaggg cctggccaag aagctgcact    540
ttagcaccgc ccctccttcc cccaccgccc ctggaccccc tagagtggcc ggctttaata    600
agcgcgtgtt ctgtgccgct gtgggcagac tggccgccac ccacgccagg ctggccgccg    660
tgcagctgtg ggatatgagc agaccccaca ccgacgagga cctgaacgag ctgctggacc    720
tgaccacaat tagagtgacc gtgtgtgagg gcaagaacct gctgcagagg gccaacgagc    780
tggtgaaccc tgacgccgcc caggacgtgg acgccaccgc cgccgccagg gcagacctg    840
ccggcagagc cgccgccaca gccagggccc ctgccagaag cgcctctagg ccaagacggc    900
ccctggagcc taggtaatct agaccaggcc ctggatccag atctgctgtg ccttctagtt    960
gccagccatc tgttgtttgc ccctcccccg tgccttcctt gaccctggaa ggtgccactc   1020
ccactgtcct ttcctaataa aatgaggaaa ttgcatcgca ttgtctgagt aggtgtcatt   1080
ctattctggg gggtggggtg gggcaggaca gcaaggggga ggattgggaa gacaatagca   1140
```

```
ggcatgctgg ggatgcggtg ggctctatgg gtacccaggt gctgaagaat tgacccggtt    1200
cctcctgggc cagaaagaag caggcacatc cccttctctg tgacacaccc tgtccacgcc    1260
cctggttctt agttccagcc ccactcatag gacactcata gctcaggagg gctccgcctt    1320
caatcccacc cgctaaagta cttggagcgg tctctccctc cctcatcagc ccaccaaacc    1380
aaacctagcc tccaagagtg ggaagaaatt aaagcaagat aggctattaa gtgcagaggg    1440
agagaaaatg cctccaacat gtgaggaagt aatgagagaa atcatagaat ttcttccgct    1500
tcctcgctca ctgactcgct gcgctcggtc gttcggctgc ggcgagcggt atcagctcac    1560
tcaaaggcgg taatacggtt atccacagaa tcagggggata acgcaggaaa gaacatgtga    1620
gcaaaaggcc agcaaaaggc caggaaccgt aaaaaggccg cgttgctggc gtttttccat    1680
aggctccgcc cccctgacga gcatcacaaa aatcgacgct caagtcagag gtggcgaaac    1740
ccgacaggac tataaagata ccaggcgttt ccccctggaa gctccctcgt gcgctctcct    1800
gttccgaccc tgccgcttac cggatacctg tccgcctttc tcccttcggg aagcgtggcg    1860
ctttctcata gctcacgctg taggtatctc agttcggtgt aggtcgttcg ctccaagctg    1920
ggctgtgtgc acgaaccccc cgttcagccc gaccgctgcg ccttatccgg taactatcgt    1980
cttgagtcca acccggtaag acacgactta tcgccactgg cagcagccac tggtaacagg    2040
attagcagag cgaggtatgt aggcggtgct acagagttct tgaagtggtg gcctaactac    2100
ggctacacta gaagaacagt atttggtatc tgcgctctgc tgaagccagt taccttcgga    2160
aaaagagttg gtagctcttg atccggcaaa caaaccaccg ctggtagcgg tggttttttt    2220
gtttgcaagc agcagattac gcgcagaaaa aaaggatctc aagaagatcc tttgatcttt    2280
tctacggggt ctgacgctca gtggaacgaa aactcacgtt aagggatttt ggtcatgaga    2340
ttatcaaaaa ggatcttcac ctagatcctt ttaaattaaa aatgaagttt taaatcaatc    2400
taaagtatat atgagtaaac ttggtctgac agttaccaat gcttaatcag tgaggcacct    2460
atctcagcga tctgtctatt tcgttcatcc atagttgcct gactcggggg ggggggcgc    2520 tgaggtctgc ctcgtgaaga aggtgttgct gactcatacc aggcctgaat cgccccatca    2580
tccagccaga aagtgaggga gccacggttg atgagagctt tgttgtaggt ggaccagttg    2640
gtgattttga acttttgctt tgccacggaa cggtctgcgt tgtcgggaag atgcgtgatc    2700
tgatccttca actcagcaaa agttcgattt attcaacaaa gccgccgtcc cgtcaagtca    2760
gcgtaatgct ctgccagtgt tacaaccaat taaccaattc tgattagaaa aactcatcga    2820
gcatcaaatg aaactgcaat ttattcatat caggattatc aataccatat ttttgaaaaa    2880
gccgtttctg taatgaagga gaaaactcac cgaggcagtt ccataggatg caagatcct    2940 ggtatcggtc tgcgattccg actcgtccaa catcaataca acctattaat ttcccctcgt    3000
caaaaataag gttatcaagt gagaaatcac catgagtgac gactgaatcc ggtgagaatg    3060
gcaaaagctt atgcatttct ttccagactt gttcaacagg ccagccatta cgctcgtcat    3120
caaaatcact cgcatcaacc aaaccgttat tcattcgtga ttgcgcctga gcgagacgaa    3180
atacgcgatc gctgttaaaa ggacaattac aaacaggaat cgaatgcaac cggcgcagga    3240
acactgccag cgcatcaaca atattttcac ctgaatcagg atattcttct aatacctgga    3300
atgctgtttt cccggggatc gcagtggtga gtaaccatgc atcatcagga gtacggataa    3360
aatgcttgat ggtcggaaga ggcataaatt ccgtcagcca gtttagtctg accatctcat    3420
ctgtaacatc attggcaacg ctacctttgc catgtttcag aaacaactct ggcgcatcgg    3480
gcttcccata caatcgatag attgtcgcac ctgattgccc gacattatcg cgagcccatt    3540
```

```
tatacccata taaatcagca tccatgttgg aatttaatcg cggcctcgag caagacgttt    3600
cccgttgaat atggctcata acaccccttg tattactgtt tatgtaagca gacagtttta    3660
ttgttcatga tgatatattt ttatcttgtg caatgtaaca tcagagattt tgagacacaa    3720
cgtggctttc cccccccccc cattattgaa gcatttatca gggttattgt ctcatgagcg    3780
gatacatatt tgaatgtatt tagaaaaata acaaatagg ggttccgcgc acatttcccc     3840
gaaaagtgcc acctgacgtc taagaaacca ttattatcat gacattaacc tataaaaata    3900
ggcgtatcac gaggcccttt cgtctcgcgc gtttcggtga tgacggtgaa aacctctgac    3960
acatgcagct cccggagacg gtcacagctt gtctgtaagc ggatgccggg agcagacaag    4020
cccgtcaggg cgcgtcagcg ggtgttggcg ggtgtcgggg ctggcttaac tatgcggcat    4080
cagagcagat tgtactgaga gtgcaccata tgcggtgtga ataccgcac agatgcgtaa     4140
ggagaaaata ccgcatcaga ttggctattg gccattgcat acgttgtatc catatcataa    4200
tatgtacatt tatattggct catgtccaac attaccgcca tgttgacatt gattattgac    4260
tagttattaa tagtaatcaa ttacggggtc attagttcat agcccatata tggagttccg    4320
cgttacataa cttacggtaa atggcccgcc tggctgaccg cccaacgacc cccgcccatt    4380
gacgtcaata atgacgtatg ttcccatagt aacgccaata gggactttcc attgacgtca    4440
atgggtggag tatttacggt aaactgccca cttggcagta catcaagtgt atcatatgcc    4500
aagtacgccc cctattgacg tcaatgacgg taaatggccc gcctggcatt atgcccagta    4560
catgacctta tgggactttc ctacttggca gtacatctac gtattagtca tcgctattac    4620
catggtgatg cggttttggc agtacatcaa tgggcgtgga tagcggtttg actcacgggg    4680
atttccaagt ctccacccca ttgacgtcaa tgggagtttg ttttggcacc aaaatcaacg    4740
ggactttcca aaatgtcgta caactccgc cccattgacg caaatgggcg gtaggcgtgt     4800
acggtgggag gtctatataa gcagagctcg tttagtgaac cgtcagatcg cctggagacg    4860
ccatccacgc tgttttgacc tccatagaag acaccgggac cgatccagcc tccgcggccg    4920
ggaacggtgc attggaacgc ggattccccg tgccaagagt gacgtaagta ccgcctatag    4980
actctatagg cacaccccttt ggctcttat gcatgctata ctgttttgg cttggggcct    5040
atacaccccc gcttccttat gctataggtg atggtatagc ttagcctata ggtgtgggtt    5100
attgaccatt attgaccact cccctattgg tgacgatact ttccattact aatccataac    5160
atggctcttt gccacaacta tctctattgg ctatatgcca atactctgtc cttcagagac    5220
tgacacggac tctgtatttt tacaggatgg ggtcccattt attatttaca aattcacata    5280
tacaacaacg ccgtcccccg tgcccgcagt ttttattaaa catagcgtgg gatctccacg    5340
cgaatctcgg gtacgtgttc cggacatggg ctcttctccg gtagcggcgg agcttccaca    5400
tccgagccct ggtcccatgc ctccagcggc tcatggtcgc tcggcagctc cttgctccta    5460
acagtggagg ccagacttag gcacagcaca atgcccacca ccaccagtgt gccgcacaag    5520
gccgtggcgg tagggtatgt gtctgaaaat gagcgtggag attgggctcg cacggctgac    5580
gcagatggaa gacttaaggc agcggcagaa gaagatgcag gcagctgagt tgttgtattc    5640
tgataagagt cagaggtaac tcccgttgcg gtgctgttaa cggtggaggg cagtgtagtc    5700
tgagcagtac tcgttgctgc cgcgcgcgcc accagacata atagctgaca gactaacaga    5760
ctgttccttt ccatgggtct tttctgcagt caccgtcgtc gacacgtgtg atcagat      5817
```

<210> SEQ ID NO 5

<211> LENGTH: 696
<212> TYPE: PRT
<213> ORGANISM: herpes simplex virus 2  UL47

<400> SEQUENCE: 5

```
Met Ser Val Arg Gly His Ala Val Arg Arg Arg Ala Ser Thr Arg
1               5                   10                  15

Ser His Ala Pro Ser Ala His Arg Ala Asp Ser Pro Val Glu Asp Glu
                20                  25                  30

Pro Glu Gly Gly Gly Gly Leu Met Gly Tyr Leu Arg Ala Val Phe
                35                  40                  45

Asn Val Asp Asp Asp Ser Glu Val Glu Ala Ala Gly Glu Met Ala Ser
    50                  55                  60

Glu Glu Pro Pro Arg Arg Arg Glu Ala Arg Gly His Pro Gly
65                  70                  75                  80

Ser Arg Arg Ala Ser Glu Ala Arg Ala Ala Ala Pro Pro Arg Arg Ala
                85                  90                  95

Ser Phe Pro Arg Pro Arg Ser Val Thr Ala Arg Ser Gln Ser Val Arg
                100                 105                 110

Gly Arg Arg Asp Ser Ala Ile Thr Arg Ala Pro Arg Gly Gly Tyr Leu
                115                 120                 125

Gly Pro Met Asp Pro Arg Asp Val Leu Gly Arg Val Gly Gly Ser Arg
                130                 135                 140

Val Val Pro Ser Pro Leu Phe Leu Asp Glu Leu Ser Tyr Glu Glu Asp
145                 150                 155                 160

Asp Tyr Pro Ala Ala Val Ala His Asp Gly Ala Gly Ala Arg Pro
                165                 170                 175

Pro Ala Thr Val Glu Ile Leu Ala Gly Arg Val Ser Gly Pro Glu Leu
                180                 185                 190

Gln Ala Ala Phe Pro Leu Asp Arg Leu Thr Pro Arg Val Ala Ala Trp
                195                 200                 205

Asp Glu Ser Val Arg Ser Ala Leu Ala Leu Gly His Pro Ala Gly Phe
210                 215                 220

Tyr Pro Cys Pro Asp Ser Ala Phe Gly Leu Ser Arg Val Gly Val Met
225                 230                 235                 240

His Phe Ala Ser Pro Ala Asp Pro Lys Val Phe Arg Gln Thr Leu
                245                 250                 255

Gln Gln Gly Glu Ala Leu Ala Trp Tyr Ile Thr Gly Asp Ala Ile Leu
                260                 265                 270

Asp Leu Thr Asp Arg Arg Ala Lys Thr Ser Pro Ser Arg Ala Met Gly
                275                 280                 285

Phe Leu Val Asp Ala Ile Val Arg Val Ala Ile Asn Gly Trp Val Cys
290                 295                 300

Gly Thr Arg Leu His Thr Glu Gly Arg Gly Ser Glu Leu Asp Asp Arg
305                 310                 315                 320

Ala Ala Glu Leu Arg Arg Gln Phe Ala Ser Leu Thr Ala Leu Arg Pro
                325                 330                 335

Val Gly Ala Ala Ala Val Pro Leu Leu Ser Gly Gly Ala Ala Pro
                340                 345                 350

Pro His Pro Gly Pro Asp Ala Ala Val Phe Arg Ser Ser Leu Gly Ser
                355                 360                 365

Leu Leu Tyr Trp Pro Gly Val Arg Ala Leu Leu Gly Arg Asp Cys Arg
370                 375                 380

Val Ala Ala Arg Tyr Ala Gly Arg Met Thr Tyr Ile Ala Thr Gly Ala
```

Leu Leu Ala Arg Phe Asn Pro Gly Ala Val Lys Cys Val Leu Pro Arg
385                 390                 395                 400
                405                 410                 415

Glu Ala Ala Phe Ala Gly Arg Val Leu Asp Val Leu Ala Val Leu Ala
                420                 425                 430

Glu Gln Thr Val Gln Trp Leu Ser Val Val Gly Ala Arg Leu His
                435                 440                 445

Pro His Ser Ala His Pro Ala Phe Ala Asp Val Glu Gln Glu Ala Leu
        450                 455                 460

Phe Arg Ala Leu Pro Leu Gly Ser Pro Gly Val Val Ala Ala Glu His
465                 470                 475                 480

Glu Ala Leu Gly Asp Thr Ala Ala Arg Arg Leu Leu Ala Thr Ser Gly
                485                 490                 495

Leu Asn Ala Val Leu Gly Ala Ala Val Tyr Ala Leu His Thr Ala Leu
                500                 505                 510

Ala Thr Val Thr Leu Lys Tyr Ala Leu Ala Cys Gly Asp Ala Arg Arg
                515                 520                 525

Arg Arg Asp Asp Ala Ala Ala Arg Ala Val Leu Ala Thr Gly Leu
        530                 535                 540

Ile Leu Gln Arg Leu Leu Gly Leu Ala Asp Thr Val Val Ala Cys Val
545                 550                 555                 560

Ala Leu Ala Ala Phe Asp Gly Gly Ser Thr Ala Pro Glu Val Gly Thr
                565                 570                 575

Tyr Thr Pro Leu Arg Tyr Ala Cys Val Leu Arg Ala Thr Gln Pro Leu
                580                 585                 590

Tyr Ala Arg Thr Thr Pro Ala Lys Phe Trp Ala Asp Val Arg Ala Ala
                595                 600                 605

Ala Glu His Val Asp Leu Arg Pro Ala Ser Ser Ala Pro Arg Ala Pro
                610                 615                 620

Val Ser Gly Thr Ala Asp Pro Ala Phe Leu Leu Glu Asp Leu Ala Ala
625                 630                 635                 640

Phe Pro Pro Ala Pro Leu Asn Ser Glu Ser Val Leu Gly Pro Arg Val
                645                 650                 655

Arg Val Val Asp Ile Met Ala Gln Phe Arg Lys Leu Leu Met Gly Asp
                660                 665                 670

Glu Glu Thr Ala Ala Leu Arg Ala His Val Ser Gly Arg Arg Ala Thr
                675                 680                 685

Gly Leu Gly Gly Pro Pro Arg Pro
        690                 695

<210> SEQ ID NO 6
<211> LENGTH: 7005
<212> TYPE: DNA
<213> ORGANISM: herpes simplex virus 2  UL47

<400> SEQUENCE: 6
ctagaccagg ccctggatcc agatctgctg tgccttctag ttgccagcca tctgttgttt        60
gccccctccc cgtgccttcc ttgacccctgg aagtgccac tcccactgtc ctttcctaat       120
aaaatgagga aattgcatcg cattgtctga gtaggtgtca ttctattctg ggggtgggg        180 tggggcagga cagcaagggg gaggattggg aagacaatag caggcatgct ggggatgcgg       240
tgggctctat gggtacccag gtgctgaaga attgacccgg ttcctcctgg gccagaaaga       300
agcaggcaca tccccttctc tgtgacacac cctgtccacg ccctggttc ttagttccag       360

```
ccccactcat aggacactca tagctcagga gggctccgcc ttcaatccca cccgctaaag    420
tacttggagc ggtctctccc tccctcatca gcccaccaaa ccaaacctag cctccaagag    480
tgggaagaaa ttaaagcaag ataggctatt aagtgcagag ggagagaaaa tgcctccaac    540
atgtgaggaa gtaatgagag aaatcataga atttcttccg cttcctcgct cactgactcg    600
ctgcgctcgg tcgttcggct gcggcgagcg gtatcagctc actcaaaggc ggtaatacgg    660
ttatccacag aatcagggga taacgcagga agaacatgt gagcaaaagg ccagcaaaag    720
gccaggaacc gtaaaaaggc cgcgttgctg gcgttttttcc ataggctccg ccccctgac    780 gagcatcaca aaaatcgacg ctcaagtcag aggtggcgaa acccgacagg actataaaga    840
taccaggcgt ttccccctgg aagctccctc gtgcgctctc ctgttccgac cctgccgctt    900
accggatacc tgtccgcctt tctcccttcg ggaagcgtgg cgctttctca tagctcacgc    960
tgtaggtatc tcagttcggt gtaggtcgtt cgctccaagc tgggctgtgt gcacgaaccc   1020
cccgttcagc ccgaccgctg cgccttatcc ggtaactatc gtcttgagtc aacccggta   1080 agacacgact tatcgccact ggcagcagcc actggtaaca ggattagcag agcgaggtat   1140
gtaggcggtg ctacagagtt cttgaagtgg tggcctaact acggctacac tagaagaaca   1200
gtatttggta tctgcgctct gctgaagcca gttaccttcg gaaaaagagt ggtagctct   1260 tgatccggca acaaaccac cgctggtagc ggtggttttt ttgtttgcaa gcagcagatt   1320
acgcgcagaa aaaaggatc tcaagaagat cctttgatct tttctacggg gtctgacgct   1380
cagtggaacg aaaactcacg ttaagggatt ttggtcatga gattatcaaa aaggatcttc   1440
acctagatcc ttttaaatta aaaatgaagt tttaaatcaa tctaaagtat atatgagtaa   1500
acttggtctg acagttacca atgcttaatc agtgaggcac ctatctcagc gatctgtcta   1560
tttcgttcat ccatagttgc ctgactcggg ggggggggc gctgaggtct gcctcgtgaa   1620
gaaggtgttg ctgactcata ccaggcctga atcgccccat catccagcca gaaagtgagg   1680
gagccacggt tgatgagagc tttgttgtag gtggaccagt tggtgatttt gaacttttgc   1740
tttgccacgg aacggtctgc gttgtcggga agatgcgtga tctgatcctt caactcagca   1800
aaagttcgat ttattcaaca aagccgccgt cccgtcaagt cagcgtaatg ctctgccagt   1860
gttacaacca attaaccaat tctgattaga aaaactcatc gagcatcaaa tgaaactgca   1920
atttattcat atcaggatta tcaataccat attttttgaaa aagccgtttc tgtaatgaag   1980
gagaaaactc accgaggcag ttccatagga tggcaagatc ctggtatcgg tctgcgattc   2040
cgactcgtcc aacatcaata aacctatta atttcccctc gtcaaaaata aggttatcaa   2100
gtgagaaatc accatgagtg acgactgaat ccggtgagaa tggcaaaagc ttatgcattt   2160
ctttccagac ttgttcaaca ggccagccat tacgctcgtc atcaaaatca ctcgcatcaa   2220
ccaaaccgtt attcattcgt gattgcgcct gagcgagacg aaatacgcga tcgctgttaa   2280
aaggacaatt acaaacagga atcgaatgca accggcgcag gaacactgcc agcgcatcaa   2340
caatattttc acctgaatca ggatattctt ctaatacctg gaatgctgtt ttcccgggga   2400
tcgcagtggt gagtaaccat gcatcatcag gagtacggat aaaatgcttg atggtcggaa   2460
gaggcataaa ttccgtcagc cagtttagtc tgaccatctc atctgtaaca tcattggcaa   2520 cgctacctt gccatgtttc agaaacaact ctggcgcatc gggcttccca tacaatcgat   2580
agattgtcgc acctgattgc ccgacattat cgcgagccca tttatacca tataaatcag   2640 catccatgtt ggaatttaat cgcggcctcg agcaagacgt ttcccgttga atatggctca   2700 taacaccct tgtattactg tttatgtaag cagacagttt tattgttcat gatgatatat   2760
```

```
tttatcttg tgcaatgtaa catcagagat tttgagacac aacgtggctt tcccccccc    2820
cccattattg aagcatttat cagggttatt gtctcatgag cggatacata tttgaatgta    2880
tttagaaaaa taaacaaata ggggttccgc gcacatttcc ccgaaaagtg ccacctgacg    2940
tctaagaaac cattattatc atgacattaa cctataaaaa taggcgtatc acgaggccct    3000
ttcgtctcgc gcgtttcggt gatgacggtg aaaacctctg acacatgcag ctcccggaga    3060
cggtcacagc ttgtctgtaa gcggatgccg ggagcagaca gcccgtcag ggcgcgtcag     3120
cgggtgttgg cgggtgtcgg gctggctta actatgcggc atcagagcag attgtactga    3180
gagtgcacca tatgcggtgt gaaataccgc acagatgcgt aaggagaaaa taccgcatca    3240
gattggctat tggccattgc atacgttgta tccatatcat aatatgtaca tttatattgg    3300
ctcatgtcca acattaccgc catgttgaca ttgattattg actagttatt aatagtaatc    3360
aattacgggg tcattagttc atagcccata tatggagttc cgcgttacat aacttacggt    3420
aaatggcccg cctggctgac cgcccaacga ccccgccca ttgacgtcaa taatgacgta     3480
tgttcccata gtaacgccaa tagggacttt ccattgacgt caatgggtgg agtatttacg    3540
gtaaactgcc cacttggcag tacatcaagt gtatcatatg ccaagtacgc cccctattga    3600
cgtcaatgac ggtaaatggc ccgcctggca ttatgcccag tacatgacct tatgggactt    3660
tcctacttgg cagtacatct acgtattagt catcgctatt accatggtga tgcggttttg    3720
gcagtacatc aatgggcgtg atagcggtt tgactcacgg ggatttccaa gtctccaccc     3780
cattgacgtc aatgggagtt tgttttggca ccaaaatcaa cgggactttc caaaatgtcg    3840
taacaactcc gccccattga cgcaaatggg cggtaggcgt gtacggtggg aggtctatat    3900
aagcagagct cgtttagtga accgtcagat cgcctggaga cgccatccac gctgttttga    3960
cctccataga agacaccggg accgatccag cctccgcggc cgggaacggt gcattggaac    4020
gcggattccc cgtgccaaga gtgacgtaag taccgcctat agactctata ggcacacccc    4080
tttggctctt atgcatgcta tactgttttt ggcttgggc ctatacaccc ccgcttcctt     4140
atgctatagg tgatggtata gcttagccta taggtgtggg ttattgacca ttattgacca    4200
ctccctatt ggtgacgata cttcccatta ctaatccata acatggctct ttgccacaac     4260
tatctctatt ggctatatgc caatactctg tccttcagag actgacacgg actctgtatt    4320
tttacaggat ggggtcccat ttattattta caaattcaca tatacaacaa cgccgtcccc    4380
cgtgcccgca gttttattta aacatagcgt gggatctcca cgcgaatctc gggtacgtgt    4440
tccgacatg ggctcttctc cggtagcggc ggagcttcca catccgagcc ctggtcccat     4500
gcctccagcg gctcatggtc gctcggcagc tccttgctcc taacagtgga ggccagactt    4560
aggcacagca caatgcccac caccaccagt gtgccgcaca aggccgtggc ggtagggtat    4620
gtgtctgaaa atgagcgtgg agattgggct cgcacggctg acgcagatgg aagacttaag    4680
gcagcggcag aagaagatgc aggcagctga gttgttgtat tctgataaga gtcagaggta    4740
actcccgttg cggtgctgtt aacggtggag gcagtgtag tctgagcagt actcgttgct     4800
gccgcgcgcg ccaccagaca taatagctga cagactaaca gactgttcct ttccatgggt    4860
cttttctgca gtcaccgtcg tcgacacgtg tgatcagata tcccaccatg tctgtgagag    4920
gccacgctgt gagaagaaga agggctagca ccagaagcca cgcccctagc gcccacagag    4980
ccgatagccc tgtggaggat gagcctgagg cggaggagg gggcctgatg gctacctga     5040
gggccgtgtt taacgtggac gacgatagcg aagtggaagc cgccggagag atggcctctg    5100
```

| | | | | |
|---|---|---|---|---|
| aggagccccc | tcctagaagg | agaagagagg | ccagaggcca | ccccggctct aggagagcct | 5160 |
| ctgaggccag | agccgccgcc | ccacctagaa | gagccagctt | ccctagacct agaagcgtga | 5220 |
| ccgccagaag | ccagtctgtg | cgcggcagga | gggatagcgc | tatcaccaga gcccctagag | 5280 |
| gcggctacct | gggccctatg | gaccctcgcg | acgtgctggg | cagagtgggc ggctctaggg | 5340 |
| tggtgcctag | cccctgttc | ctggatgagc | tgagctacga | ggaggacgac taccctgccg | 5400 |
| ccgtggccca | cgacgacgga | gccggagcca | gaccccctgc | caccgtggag atcctggccg | 5460 |
| gcagagtgag | cggacctgag | ctgcaagccg | ccttccccct | ggatcggctg accctcgggg | 5520 |
| tggccgcctg | ggatgagtct | gtgaggagcg | ccctggccct | gggccaccct gccggcttct | 5580 |
| accctgccc | tgattccgcc | ttcggcctga | gcagagtggg | agtgatgcac ttcgccagcc | 5640 |
| ctgccgaccc | taaagtgttc | ttccggcaaa | cactgcagca | gggcgaggcc ctcgcatggt | 5700 |
| acatcaccgg | cgacgccatc | ctggatctga | ccgatagacg | ggccaagacc agccctagca | 5760 |
| gagctatggg | ctttctggtg | gacgctattg | tgagagtggc | tattaacggc tgggtgtgcg | 5820 |
| gcaccagact | gcacaccgag | ggcagaggct | ctgagctgga | tgatagagcc gccgagctga | 5880 |
| ggagacagtt | cgccagcctg | accgccctga | cctgtgggg | cgccgctgcc gtgcccctgc | 5940 |
| tgagcgccgg | aggagccgcc | cctccccacc | ctggccctga | cgccgccgtg tttcggtcta | 6000 |
| gcctgggcag | cctgctgtac | tggcccggag | tgagagccct | gctgggcagg gactgtagag | 6060 |
| tggctgccag | atacgccggc | aggatgacct | acatcgccac | cggcgccctg ctggccagat | 6120 |
| taaccctgg | cgccgtgaaa | tgcgtgctgc | ctagagaagc | cgccttcgcc ggaagagtgc | 6180 |
| tggacgtcct | ggccgtgctg | gctgagcaga | ccgtgcagtg | gctgagcgtg gttgtgggcg | 6240 |
| ccaggctgca | ccctcacagc | gcccaccctg | ccttcgccga | cgtggagcag gaggccctgt | 6300 |
| ttagagccct | gcctctgggc | agccctggcg | tggtggccgc | cgagcacgaa gccctgggcg | 6360 |
| acaccgctgc | caggagactg | ctcgccacaa | gcggcctgaa | cgccgtgctg ggagccgccg | 6420 |
| tgtacgccct | gcacaccgcc | ctggccaccg | tgacccctgaa | atacgccctg gcctgcggcg | 6480 |
| acgcccgcag | acgccgcgac | gacgccgctg | cagccagagc | cgtcctggcc accggcctga | 6540 |
| tcctgcagag | gctgctgggc | ctggccgaca | ccgtggtggc | ctgcgtggcc ctggccgcct | 6600 |
| ttgacggcgg | cagcaccgcc | cctgaagtgg | gcacctacac | ccctctgaga tacgcctgcg | 6660 |
| tgctgagagc | cacccagcct | ctgtacgcca | gaaccacccc | tgccaagttc tgggccgatg | 6720 |
| tgagggccgc | cgccgaacac | gtggacctga | acccgcctc | tagcgcccca agggcccctg | 6780 |
| tgagcggcac | cgccgacccc | gccttcctgc | tggaggatct | ggccgctttc cctcccgccc | 6840 |
| ctctgaatag | cgagagcgtg | ctggggccta | gagtgagagt | ggtggatatt atggcccagt | 6900 |
| ttagaaagct | gctgatgggc | gacgaggaaa | cagccgccct | gagggcccac gtgtctggca | 6960 |
| gaagagccac | aggcctgggc | ggacctccta | gacctcctag | gtgat | 7005 |

<210> SEQ ID NO 7
<211> LENGTH: 721
<212> TYPE: PRT
<213> ORGANISM: herpes simplex virus 2  UL46

<400> SEQUENCE: 7

Met Gln Arg Arg Ala Arg Gly Ala Ser Ser Leu Arg Leu Ala Arg Cys
1               5                   10                  15

Leu Thr Pro Ala Asn Leu Ile Arg Gly Ala Asn Ala Gly Val Pro Glu
            20                  25                  30

Arg Arg Ile Phe Ala Gly Cys Leu Leu Pro Thr Pro Glu Gly Leu Leu

-continued

```
                35                  40                  45
Ser Ala Ala Val Gly Val Leu Arg Gln Arg Ala Asp Asp Leu Gln Pro
 50                  55                  60
Ala Phe Leu Thr Gly Ala Asp Arg Ser Val Arg Leu Ala Ala Arg His
 65                  70                  75                  80
His Asn Thr Val Pro Glu Ser Leu Ile Val Asp Gly Leu Ala Ser Asp
                     85                  90                  95
Pro His Tyr Asp Tyr Ile Arg His Tyr Ala Ser Ala Ala Lys Gln Ala
                100                 105                 110
Leu Gly Glu Val Glu Leu Ser Gly Gln Leu Ser Arg Ala Ile Leu
                115                 120                 125
Ala Gln Tyr Trp Lys Tyr Leu Gln Thr Val Val Pro Ser Gly Leu Asp
    130                 135                 140
Ile Pro Asp Asp Pro Ala Gly Asp Cys Asp Pro Ser Leu His Val Leu
145                 150                 155                 160
Leu Arg Pro Thr Leu Leu Pro Lys Leu Leu Val Arg Ala Pro Phe Lys
                    165                 170                 175
Ser Gly Ala Ala Ala Ala Lys Tyr Ala Ala Val Ala Gly Leu Arg
                180                 185                 190
Asp Ala Ala His Arg Leu Gln Gln Tyr Met Phe Phe Met Arg Pro Ala
    195                 200                 205
Asp Pro Ser Arg Pro Ser Thr Asp Thr Ala Leu Arg Leu Ser Glu Leu
210                 215                 220
Leu Ala Tyr Val Ser Val Leu Tyr His Trp Ala Ser Trp Met Leu Trp
225                 230                 235                 240
Thr Ala Asp Lys Tyr Val Cys Arg Arg Leu Gly Pro Ala Asp Arg Arg
                    245                 250                 255
Phe Val Ala Leu Ser Gly Ser Leu Glu Ala Pro Ala Glu Thr Phe Ala
                260                 265                 270
Arg His Leu Asp Arg Gly Pro Ser Gly Thr Thr Gly Ser Met Gln Cys
    275                 280                 285
Met Ala Leu Arg Ala Ala Val Ser Asp Val Leu Gly His Leu Thr Arg
290                 295                 300
Leu Ala His Leu Trp Glu Thr Gly Lys Arg Ser Gly Gly Thr Tyr Gly
305                 310                 315                 320
Ile Val Asp Ala Ile Val Ser Thr Val Glu Val Leu Ser Ile Val His
                    325                 330                 335
His His Ala Gln Tyr Ile Ile Asn Ala Thr Leu Thr Gly Tyr Val Val
                340                 345                 350
Trp Ala Ser Asp Ser Leu Asn Asn Glu Tyr Leu Arg Ala Ala Val Asp
    355                 360                 365
Ser Gln Glu Arg Phe Cys Arg Thr Ala Ala Pro Leu Phe Pro Thr Met
370                 375                 380
Thr Ala Pro Ser Trp Ala Arg Met Glu Leu Ser Ile Lys Ser Trp Phe
385                 390                 395                 400
Gly Ala Ala Leu Ala Pro Asp Leu Leu Arg Ser Gly Thr Pro Ser Pro
                    405                 410                 415
His Tyr Glu Ser Ile Leu Arg Leu Ala Ala Ser Gly Pro Gly Gly
                420                 425                 430
Arg Gly Ala Val Gly Gly Ser Cys Arg Asp Lys Ile Gln Arg Thr Arg
    435                 440                 445
Arg Asp Asn Ala Pro Pro Pro Leu Pro Arg Ala Arg Pro His Ser Thr
450                 455                 460
```

Pro Ala Ala Pro Arg Arg Phe Arg Arg His Arg Glu Asp Leu Pro Glu
465                 470                 475                 480

Pro Pro His Val Asp Ala Ala Asp Arg Gly Pro Glu Pro Cys Ala Gly
            485                 490                 495

Arg Pro Ala Thr Tyr Tyr Thr His Met Ala Gly Ala Pro Pro Arg Leu
            500                 505                 510

Pro Pro Arg Asn Pro Ala Pro Pro Glu Gln Arg Pro Ala Ala Ala Ala
            515                 520                 525

Arg Pro Leu Ala Ala Gln Arg Glu Ala Ala Gly Val Tyr Asp Ala Val
            530                 535                 540

Arg Thr Trp Gly Pro Asp Ala Glu Ala Glu Pro Asp Gln Met Glu Asn
545                 550                 555                 560

Thr Tyr Leu Leu Pro Asp Asp Asp Ala Ala Met Pro Ala Gly Val Gly
            565                 570                 575

Leu Gly Ala Thr Pro Ala Ala Asp Thr Thr Ala Ala Ala Trp Pro Ala
            580                 585                 590

Lys Ser His Ala Pro Arg Ala Pro Ser Glu Asp Ala Asp Ser Ile Tyr
            595                 600                 605

Glu Ser Val Ser Glu Asp Gly Gly Arg Val Tyr Glu Glu Ile Pro Trp
610                 615                 620

Val Arg Val Tyr Glu Asn Ile Cys Leu Arg Arg Gln Asp Ala Gly Gly
625                 630                 635                 640

Ala Ala Pro Pro Gly Asp Ala Pro Asp Ser Pro Tyr Ile Glu Ala Glu
            645                 650                 655

Asn Pro Leu Tyr Asp Trp Gly Gly Ser Ala Leu Phe Ser Pro Pro Gly
            660                 665                 670

Ala Thr Arg Ala Pro Asp Pro Gly Leu Ser Leu Ser Pro Met Pro Ala
            675                 680                 685

Arg Pro Arg Thr Asn Ala Leu Ala Asn Asp Gly Pro Thr Asn Val Ala
            690                 695                 700

Ala Leu Ser Ala Leu Leu Thr Lys Leu Lys Arg Gly Arg His Gln Ser
705                 710                 715                 720

His

<210> SEQ ID NO 8
<211> LENGTH: 7080
<212> TYPE: DNA
<213> ORGANISM: herpes simplex virus 2  UL46

<400> SEQUENCE: 8
atcccaccat gcagcggaga gccagaggcg cctctagcct gagactggcc cggtgcctga        60
cccccgccaa tctgattaga ggcgccaacg ccggcgtgcc tgagagaaga atcttcgccg       120
gctgcctgct gcctaccect gagggcctgc tgagcgccgc tgtgggcgtg ctgagacaga       180
gggccgatga cctgcagccc gccttcctga ccggcgccga tagatctgtg aggctggccg       240
ccagacacca caacaccgtg cctgagtccc tgatcgtgga cggcctggcc tctgaccccc       300
actacgacta cattaggcac tacgccagcc ccgccaagca ggccctgggc gaagtggagc       360
tgagcggcgg acagctgagc agagccatcc tggcccagta ctggaagtac ctgcagaccg       420
tggtgcctag cggcctggac atccctgatg atcctgccgg cgactgtgac cctagcctgc       480
acgtgctgct gagacccaca ctgctgccta agctgcttgt gagggccccc tttaagagcg       540
gcgctgccgc cgccaaatac gccgccgccg tggccggcct gagggacgcc gcccacagac       600

-continued

```
tgcagcagta tatgttcttt atgagacccg ccgaccctag cagacctagc accgacaccg    660
ccctgagact gagcgagctg ctggcctatg tgagcgtgct gtaccactgg gccagctgga    720
tgctgtggac cgccgataaa tacgtgtgta ggcggctggg ccctgccgat agaagattcg    780
tggccctgag cggcagcctg gaggcccctg ccgagacctt gcccggcac ctggatagag     840
gccctagcgg caccaccggc tctatgcagt gtatggccct gagagccgcc gtgtctgacg    900
tgctgggcca cctgaccaga ctggcccacc tgtgggagac cggcaagaga agcggcggca    960
cctacggcat cgtggacgcc attgtgagca ccgtggaagt gctgagcatc gtgcaccacc   1020
acgcccagta catcattaac gccaccctga ccggctacgt tgtgtgggcc tctgatagcc   1080
tgaataatga gtacctgagg gctgccgtcg atagccagga gcggttctgt agaacagccg   1140
cccctctgtt ccccaccatg accgccccct cctgggccag aatggaactg agcattaaga   1200
gctggttcgg agccgccctg gccctgacc tgctgagaag cggcacccct agccctcact    1260
acgagagcat cctgcgcctg gctgccagcg ccctcctgg cggcagagga gctgtgggcg    1320
gcagctgtag ggataagatc cagcggaccc ggagagataa cgccctccc cccctgcctc    1380
gggccagacc ccacagcacc cctgctgccc ctcggcggtt tagacggcac agagaggacc   1440
tgcctgagcc tccccacgtg gacgccgcg ataggggccc tgagccctgc gccggcagac   1500
ccgccaccta ctacacccac atggccggag ccccccctcg gctgcccct cggaaccctg   1560
cccctcctga gcagagacct gccgccgctg cccggcctct ggccgccag agagaagccg    1620
ccggagtgta tgacgctgtg agaacctggg gccctgacgc cgaggccgag cctgatcaga   1680
tggagaacac ctacctgctg cctgacgacg acgccgccat gcctgccgga gtgggcctgg   1740
gcgccacccc agccgccgat accacagccg ccgcctggcc cgccaagagc cacgccccta   1800
gagcccctag cgaggacgcc gatagcatct acgaaagcgt gtctgaggac ggcggcagag   1860
tgtatgagga gatcccctgg gtgcgggtgt acgaaaacat ctgcctgagg agacaggacg   1920
ccggaggagc cgccccaccc ggcgacgccc ctgatagccc ttacattgag gccgagaacc   1980
ccctgtacga ctggggcggc agcgccctgt ttagcccccc tggcgccacc agagcccctg   2040
accccggcct gagcctgagc cccatgcccg ccagacctag aaccaacgcc ctggccaatg   2100
acggccccac caacgtggcc gccctgagcg ccctgctgac caagctgaag aggggcagac   2160
accagagcca ccctaggtaa tctagaccag gccctggatc cagatctgct gtgccttcta   2220
gttgccagcc atctgttgtt tgcccctccc ccgtgccttc cttgaccctg gaaggtgcca   2280
ctcccactgt cctttcctaa taaaatgagg aaattgcatc gcattgtctg agtaggtgtc   2340
attctattct ggggggtggg gtggggcagg acagcaaggg ggaggattgg gaagacaata   2400
gcaggcatgc tggggatgcg gtgggctcta tgggtaccca ggtgctgaag aattgacccg   2460
gttcctcctg ggccagaaag aagcaggcac atccccttct ctgtgacaca ccctgtccac   2520
gcccctggtt cttagttcca gccccactca taggacactc atagctcagg agggctccgc   2580
cttcaatccc acccgctaaa gtacttggag cggtctctcc ctccctcatc agcccaccaa   2640
accaaaccta gcctccaaga gtgggaagaa attaaagcaa gataggctat taagtgcaga   2700
gggagagaaa atgcctccaa catgtgagga agtaatgaga gaaatcatag aatttcttcc   2760
gcttcctcgc tcactgactc gctgcgctcg gtcgttcggc tgcggcgagc ggtatcagct   2820
cactcaaagg cggtaatacg gttatccaca gaatcagggg ataacgcagg aaagaacatg   2880
tgagcaaaag gccagcaaaa ggccaggaac cgtaaaaagg ccgcgttgct ggcgtttttc   2940
cataggctcc gcccccctga cgagcatcac aaaaatcgac gctcaagtca gaggtggcga   3000
```

```
aacccgacag gactataaag ataccaggcg tttcccctg gaagctccct cgtgcgctct    3060
cctgttccga ccctgccgct taccggatac ctgtccgcct ttctcccttc gggaagcgtg    3120
gcgctttctc atagctcacg ctgtaggtat ctcagttcgg tgtaggtcgt tcgctccaag    3180
ctgggctgtg tgcacgaacc ccccgttcag cccgaccgct gcgccttatc cggtaactat    3240
cgtcttgagt ccaacccggt aagacacgac ttatcgccac tggcagcagc cactggtaac    3300
aggattagca gagcgaggta tgtaggcggt gctacagagt tcttgaagtg gtggcctaac    3360
tacggctaca ctagaagaac agtatttggt atctgcgctc tgctgaagcc agttaccttc    3420
ggaaaaagag ttggtagctc ttgatccggc aaacaaacca ccgctggtag cggtggtttt    3480
tttgtttgca agcagcagat tacgcgcaga aaaaaggat ctcaagaaga tcctttgatc    3540
ttttctacgg ggtctgacgc tcagtggaac gaaaactcac gttaagggat tttggtcatg    3600
agattatcaa aaaggatctt cacctagatc cttttaaatt aaaaatgaag ttttaaatca    3660
atctaaagta tatatgagta aacttggtct gacagttacc aatgcttaat cagtgaggca    3720
cctatctcag cgatctgtct atttcgttca tccatagttg cctgactcgg gggggggggg    3780
cgctgaggtc tgcctcgtga agaaggtgtt gctgactcat accaggcctg aatcgcccca    3840
tcatccagcc agaaagtgag ggagccacgg ttgatgagag ctttgttgta ggtggaccag    3900
ttggtgattt tgaacttttg ctttgccacg gaacggtctg cgttgtcggg aagatgcgtg    3960
atctgatcct tcaactcagc aaaagttcga tttattcaac aaagccgccg tcccgtcaag    4020
tcagcgtaat gctctgccag tgttacaacc aattaaccaa ttctgattag aaaaactcat    4080
cgagcatcaa atgaaactgc aatttattca tatcaggatt atcaatacca tatttttgaa    4140
aaagccgttt ctgtaatgaa ggagaaaact caccgaggca gttccatagg atggcaagat    4200
cctggtatcg gtctgcgatt ccgactcgtc caacatcaat acaacctatt aatttcccct    4260
cgtcaaaaat aaggttatca agtgagaaat caccatgagt gacgactgaa tccggtgaga    4320
atggcaaaag cttatgcatt tctttccaga cttgttcaac aggccagcca ttacgctcgt    4380
catcaaaatc actcgcatca accaaaccgt tattcattcg tgattgcgcc tgagcgagac    4440
gaaatacgcg atcgctgtta aaaggacaat tacaaacagg aatcgaatgc aaccggcgca    4500
ggaacactgc cagcgcatca acaatatttt cacctgaatc aggatattct tctaatacct    4560
ggaatgctgt tttcccgggg atcgcagtgg tgagtaacca tgcatcatca ggagtacgga    4620
taaaatgctt gatggtcgga agaggcataa attccgtcag ccagtttagt ctgaccatct    4680
catctgtaac atcattggca acgctacctt tgccatgttt cagaaacaac tctggcgcat    4740
cgggcttccc atacaatcga tagattgtcg cacctgattg cccgacatta tcgcgagccc    4800
atttataccc atataaatca gcatccatgt tggaatttaa tcgcggcctc gagcaagacg    4860
tttcccgttg aatatggctc ataacacccc ttgtattact gtttatgtaa gcagacagtt    4920
ttattgttca tgatgatata ttttatctt gtgcaatgta acatcagaga ttttgagaca    4980
caacgtggct ttcccccccc ccccattatt gaagcattta tcagggttat tgtctcatga    5040
gcggatacat atttgaatgt atttagaaaa ataaacaaat agggggttccg cgcacatttc    5100 cccgaaaagt gccacctgac gtctaagaaa ccattattat catgacatta acctataaaa    5160
ataggcgtat cacgaggccc tttcgtctcg cgcgtttcgg tgatgacggt gaaaacctct    5220
gacacatgca gctcccggag acggtcacag cttgtctgta agcggatgcc gggagcagac    5280
aagcccgtca gggcgcgtca gcgggtgttg gcgggtgtcg gggctggctt aactatgcgg    5340
```

| | |
|---|---|
| catcagagca gattgtactg agagtgcacc atatgcggtg tgaaataccg cacagatgcg | 5400 |
| taaggagaaa ataccgcatc agattggcta ttggccattg catacgttgt atccatatca | 5460 |
| taatatgtac atttatattg gctcatgtcc aacattaccg ccatgttgac attgattatt | 5520 |
| gactagttat taatagtaat caattacggg gtcattagtt catagcccat atatggagtt | 5580 |
| ccgcgttaca taacttacgg taaatggccc gcctggctga ccgcccaacg accccgccc | 5640 |
| attgacgtca ataatgacgt atgttcccat agtaacgcca atagggactt tccattgacg | 5700 |
| tcaatgggtg gagtatttac ggtaaactgc ccacttggca gtacatcaag tgtatcatat | 5760 |
| gccaagtacg cccctattg acgtcaatga cggtaaatgg cccgcctggc attatgccca | 5820 |
| gtacatgacc ttatgggact ttcctacttg gcagtacatc tacgtattag tcatcgctat | 5880 |
| taccatggtg atgcggtttt ggcagtacat caatgggcgt ggatagcggt ttgactcacg | 5940 |
| gggatttcca agtctccacc ccattgacgt caatgggagt ttgttttggc accaaaatca | 6000 |
| acgggacttt ccaaaatgtc gtaacaactc cgccccattg acgcaaatgg gcggtaggcg | 6060 |
| tgtacggtgg gaggtctata taagcagagc tcgtttagtg aaccgtcaga tcgcctggag | 6120 |
| acgccatcca cgctgttttg acctccatag aagacaccgg gaccgatcca gcctccgcgg | 6180 |
| ccgggaacgg tgcattggaa cgcggattcc ccgtgccaag agtgacgtaa gtaccgccta | 6240 |
| tagactctat aggcacaccc ctttggctct tatgcatgct atactgtttt tggcttgggg | 6300 |
| cctatacacc cccgcttcct tatgctatag gtgatggtat agcttagcct ataggtgtgg | 6360 |
| gttattgacc attattgacc actcccctat tggtgacgat actttccatt actaatccat | 6420 |
| aacatgctc tttgccacaa ctatctctat tggctatatg ccaatactct gtccttcaga | 6480 |
| gactgacacg gactctgtat ttttacagga tggggtccca tttattattt acaaattcac | 6540 |
| atatacaaca acgccgtccc ccgtgccgc agttttatt aaacatagcg tgggatctcc | 6600 |
| acgcgaatct cgggtacgtg ttccggacat gggctcttct ccggtagcgg cggagcttcc | 6660 |
| acatccgagc cctggtccca tgcctccagc ggctcatggt cgctcggcag ctccttgctc | 6720 |
| ctaacagtgg aggccagact taggcacagc acaatgccca ccaccaccag tgtgccgcac | 6780 |
| aaggccgtgg cggtagggta tgtgtctgaa aatgagcgtg gagattgggc tcgcacggct | 6840 |
| gacgcagatg gaagacttaa ggcagcggca aagaagatg caggcagctg agttgttgta | 6900 |
| ttctgataag agtcagaggt aactcccgtt gcggtgctgt taacggtgga gggcagtgta | 6960 |
| gtctgagcag tactcgttgc tgccgcgcgc gccaccagac ataatagctg acagactaac | 7020 |
| agactgttcc tttccatggg tcttttctgc agtcaccgtc gtcgacacgt gtgatcagat | 7080 |

<210> SEQ ID NO 9
<211> LENGTH: 1023
<212> TYPE: DNA
<213> ORGANISM: herpes simplex virus 2   gD

<400> SEQUENCE: 9

| | |
|---|---|
| atgggcagac tgactagcgg agtgggcaca gccgccctgc tcgtggtggc tgtgggcctg | 60 |
| agagtggtgt gtgctaagta cgccctggct gaccctagcc tgaagatggc tgatcctaat | 120 |
| aggtttaggg gcaagaacct gcccgtgctg accagctga ctgaccccc tggcgtgaag | 180 |
| agagtgtacc acatccagcc tagcctggag gaccccttcc agcccctag catccctatc | 240 |
| accgtgtact acgccgtgct ggagagagcc tgtagaagcg tgctgctgca cgcccctagt | 300 |
| gaggcccctc agattgtgag aggcgctagt gacgaggcta ggaagcacac ctataacctg | 360 |
| accatcgcct ggtataggat gggcgataac tgcgccatcc ccatcacagt gatggagtac | 420 |

| | |
|---|---|
| actgagtgcc cctataataa gagcctgggc gtgtgtccca ttaggaccca gcctaggtgg | 480 |
| agctactacg atagctttag cgccgtgagt gaggataacc tgggcttcct gatgcacgcc | 540 |
| ccagcctttg agaccgccgg cacctacctg agactggtga agattaacga ctggactgag | 600 |
| atcacccagt tcatcctgga gcatagggct agggctagct gtaaatacgc cctgcccctg | 660 |
| agaatccccc ctgccgcctg cctgactagt aaggcctacc agcaaggcgt gaccgtggat | 720 |
| agcatcggca tgctgcctag attcatccct gagaaccaga gaaccgtggc cctgtatagc | 780 |
| ctgaaaatcg ccggctggca cggccctaag cctccttaca ctagcaccct gctgcccct | 840 |
| gagctgagtg ataccactaa cgccacccag cctgagctgg tgcctgagga ccctgaggat | 900 |
| agcgctctgc tggaagatcc tgccggcacc gtgagtagcc agatcccccc taactggcac | 960 |
| atccctagca ttcaggacgt ggccccccac cacgcccctg ccgctcctag taaccctggc | 1020 |
| tga | 1023 |

```
<210> SEQ ID NO 10
<211> LENGTH: 900
<212> TYPE: DNA
<213> ORGANISM: herpes simplex virus 2  UL49

<400> SEQUENCE: 10
```

| | |
|---|---|
| atgacctcta ggcggagcgt gaagagctgc cctagagagg cccctagagg cacccacgag | 60 |
| gagctgtact acgccctgt gtccctgcc gaccctgaga gccctagaga tgactttaga | 120 |
| cggggagccg gccctatgag agccagacct agaggcgaag tgagattcct gcactacgac | 180 |
| gaggccggct acgccctgta tcgggatagc agctctgacg acgacgagtc tagggatacc | 240 |
| gccaggccta agaagcgc cagcgtggcc ggcagccacg gccctggccc tgccagagcc | 300 |
| cccctcctc ctggcggccc tgtgggagcc ggcggaagaa gccacgcccc tcccgcccgg | 360 |
| accctaaga tgaccagagg cgcccctaag gccagcgcca cccccgccac cgatcccgcc | 420 |
| agaggcagga gaccgcccca ggcgatagc gccgtgctgc tggacgcccc tgcccccacc | 480 |
| gcctccggca gaaccaagac ccctgcccag ggcctggcca agaagctgca ctttagcacc | 540 |
| gcccctcctt ccccaccgc ccctggacc ctagagtgg ccggctttaa taagcgcgtg | 600 |
| ttctgtgccg ctgtgggcag actggccgcc acccacgcca ggctggccgc cgtgcagctg | 660 |
| tgggatatga gcagacccca caccgacgag gacctgaacg agctgctgga cctgaccaca | 720 |
| attagagtga ccgtgtgtga gggcaagaac ctgctgcaga gggccaacga gctggtgaac | 780 |
| cctgacgccg cccaggacgt ggacgccacc gccgccgcca gggcagacc tgccggcaga | 840 |
| gccgccgcca cagccagggc ccctgccaga agcgcctcta ggccaagacg gcccctggag | 900 |

```
<210> SEQ ID NO 11
<211> LENGTH: 2088
<212> TYPE: DNA
<213> ORGANISM: herpes simplex virus 2  UL47

<400> SEQUENCE: 11
```

| | |
|---|---|
| atgtctgtga gaggccacgc tgtgagaaga agaagggcta gcaccagaag ccacgcccct | 60 |
| agcgcccaca gagccgatag ccctgtggag gatgagcctg agggcggagg aggggggcctg | 120 |
| atgggctacc tgagggccgt gtttaacgtg gacgacgata gcgaagtgga agccgccgga | 180 |
| gagatggcct ctgaggagcc ccctcctaga aggagaagag aggccagagg ccaccccggc | 240 |
| tctaggagag cctctgaggc cagagccgcc gccccaccta agagagccag cttccctaga | 300 |

| | |
|---|---|
| cctagaagcg tgaccgccag aagccagtct gtgcgcggca ggagggatag cgctatcacc | 360 |
| agagccccta gaggcggcta cctgggccct atggaccctc gcgacgtgct gggcagagtg | 420 |
| ggcggctcta gggtggtgcc tagcccctg ttcctggatg agctgagcta cgaggaggac | 480 |
| gactaccctg ccgccgtggc ccacgacgac ggagccggag ccagaccccc tgccaccgtg | 540 |
| gagatcctgg ccggcagagt gagcggacct gagctgcaag ccgccttccc cctggatcgg | 600 |
| ctgaccctc gggtggccgc ctgggatgag tctgtgagga gcgccctggc cctgggccac | 660 |
| cctgccggct ctaccctg ccctgattcc gccttcggcc tgagcagagt gggagtgatg | 720 |
| cacttcgcca gccctgccga ccctaaagtg ttcttccggc aaacactgca gcagggcgag | 780 |
| gccctcgcat ggtacatcac cggcgacgcc atcctggatc tgaccgatag acgggccaag | 840 |
| accagcccta gcagagctat gggctttctg gtggacgcta ttgtgagagt ggctattaac | 900 |
| ggctgggtgt gcggcaccag actgcacacc gagggcagag gctctgagct ggatgataga | 960 |
| gccgccgagc tgaggagaca gttcgccagc ctgaccgccc tgagacctgt gggcgccgct | 1020 |
| gccgtgcccc tgctgagcgc cggaggagcc gcccctcccc accctggccc tgacgccgcc | 1080 |
| gtgtttcggt ctagcctggg cagcctgctg tactggcccg gagtgagagc cctgctgggc | 1140 |
| agggactgta gagtggctgc cagatacgcc ggcaggatga cctacatcgc caccggcgcc | 1200 |
| ctgctggcca gatttaaccc tggcgccgtg aaatgcgtgc tgcctagaga agccgccttc | 1260 |
| gccggaagag tgctggacgt cctggccgtg ctggctgagc agaccgtgca gtggctgagc | 1320 |
| gtggttgtgg gcgccaggct gcaccctcac agcgcccacc ctgccttcgc cgacgtggag | 1380 |
| caggaggccc tgtttagagc cctgcctctg gcagccctg gcgtggtggc cgccgagcac | 1440 |
| gaagccctgg gcgacaccgc tgccaggaga ctgctcgcca agcggcct gaacgccgtg | 1500 |
| ctgggagccc ccgtgtacgc cctgcacacc gccctggcca ccgtgaccct gaaatacgcc | 1560 |
| ctggcctgcg gcgacgcccg cagacgccgc gacgacgccg ctgcagccag agccgtcctg | 1620 |
| gccaccggcc tgatcctgca gaggctgctg ggcctggcc acaccgtggt ggcctgcgtg | 1680 |
| gccctggccg cctttgacgg cggcagcacc gcccctgaag tgggcaccta caccctctg | 1740 |
| agatacgcct gcgtgctgag agccacccag cctctgtacg ccagaaccac ccctgccaag | 1800 |
| ttctggggccg atgtgagggc cgccgccgaa cacgtggacc tgagaccgc ctctagcgcc | 1860 |
| ccaagggccc ctgtgagcgg caccgccgac cccgccttcc tgctggagga tctgccgct | 1920 |
| ttccctcccg cccctctgaa tagcgagagc gtgctgggc ctagagtgag agtggtggat | 1980 |
| attatgcccc agtttagaaa gctgctgatg ggcgacgagg aaacagccgc cctgagggcc | 2040 |
| cacgtgtctg gcagaagagc cacaggcctg ggcggacctc ctagacct | 2088 |

<210> SEQ ID NO 12
<211> LENGTH: 2163
<212> TYPE: DNA
<213> ORGANISM: herpes simplex virus 2 UL46

<400> SEQUENCE: 12

| | |
|---|---|
| atgcagcgga gagccagagg cgcctctagc ctgagactgg cccggtgcct gaccccgcc | 60 |
| aatctgatta gaggcgccaa cgccggcgtg cctgagagaa gaatcttcgc cggctgcctg | 120 |
| ctgcctaccc ctgagggcct gctgagcgcc gctgtgggcg tgctgagaca gagggccgat | 180 |
| gacctgcagc ccgccttcct gaccggcgcc gatagatctg tgaggctggc cgccagacac | 240 |
| cacaacaccg tgcctgagtc cctgatcgtg gacggcctgg cctctgaccc ccactacgac | 300 |
| tacattaggc actacgccag cgccgccaag caggccctgg gcgaagtgga gctgagcggc | 360 |

```
ggacagctga gcagagccat cctggcccag tactggaagt acctgcagac cgtggtgcct    420
agcggcctgg acatccctga tgatcctgcc ggcgactgtg accctagcct gcacgtgctg    480
ctgagaccca cactgctgcc taagctgctt gtgagggccc cctttaagag cggcgctgcc    540
gccgccaaat acgccgccgc cgtggccggc ctgagggacg ccgcccacag actgcagcag    600
tatatgttct ttatgagacc cgccgaccct agcagaccta gcaccgacac cgccctgaga    660
ctgagcgagc tgctggccta tgtgagcgtg ctgtaccact gggccagctg gatgctgtgg    720
accgccgata aatacgtgtg taggcggctg ggccctgccg atagaagatt cgtggccctg    780
agcggcagcc tggaggcccc tgccgagacc tttgcccggc acctggatag aggccctagc    840
ggcaccaccg gctctatgca gtgtatggcc ctgagagccg ccgtgtctga cgtgctgggc    900
cacctgacca gactggccca cctgtgggag accggcaaga gaagcggcgg cacctacggc    960
atcgtggacg ccattgtgag caccgtggaa gtgctgagca tcgtgcacca ccacgcccag   1020
tacatcatta acgccaccct gaccggctac gttgtgtggg cctctgatag cctgaataat   1080
gagtacctga gggctgccgt cgatagccag gagcggttct gtagaacagc cgcccctctg   1140
ttccccacca tgaccgcccc ttcctgggcc agaatggaac tgagcattaa gagctggttc   1200
ggagccgccc tggcccctga cctgctgaga agcggcaccc ctagccctca ctacgagagc   1260
atcctgcgcc tggctgccag cggccctcct ggcggcagag gagctgtggg cggcagctgt   1320
agggataaga tccagcggac ccggagagat aacgcccctc cccccctgcc tcgggccaga   1380
ccccacagca cccctgctgc ccctcggcgg tttagacggc acagagagga cctgcctgag   1440 cctcccacg tggacgccgc cgatagggc cctgagccct gcgccggcag acccgccacc   1500
tactacaccc acatggccgg agccccccct cggctgcccc ctcggaaccc tgcccctcct   1560
gagcagagac ctgccgccgc tgcccggcct ctggccgccc agagagaagc cgccggagtg   1620
tatgacgctg tgagaacctg gggccctgac gccgaggccg agcctgatca gatggagaac   1680
acctacctgc tgcctgacga cgacgccgcc atgcctgccg gagtgggcct gggcgccacc   1740
ccagccgccg ataccacagc cgccgcctgg cccgccaaga gccacgcccc tagagcccct   1800
agcgaggacg ccgatagcat ctacgaaagc gtgtctgagg acggcggcag agtgtatgag   1860
gagatcccct gggtgcgggt gtacgaaaac atctgcctga ggagacagga cgccggagga   1920
gccgccccac ccggcgacgc ccctgatagc ccttacattg aggccgagaa ccccctgtac   1980
gactggggcg gcagcgccct gtttagcccc cctggcgcca ccagagcccc tgacccggc   2040 ctgagcctga gccccatgcc cgccagacct agaaccaacg ccctgccaa tgacggcccc   2100 accaacgtgg ccgccctgag cgccctgctg accaagctga agaggggcag acaccagagc   2160
cac                                                                  2163
```